US011034980B2

(12) United States Patent
Edgar et al.

(10) Patent No.: US 11,034,980 B2
(45) Date of Patent: Jun. 15, 2021

(54) MICROBIAL ENGINEERING FOR THE PRODUCTION OF ISOPRENOIDS

(71) Applicant: Massachusetts Institute of Technology, Cambridge, MA (US)

(72) Inventors: Steven McBride Edgar, Cambridge, MA (US); Alkiviadis Orfefs Chatzivasileiou, Cambridge, MA (US); Valerie Ward, Kitchener (CA); Gregory Stephanopoulos, Winchester, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/425,373

(22) Filed: May 29, 2019

(65) Prior Publication Data

US 2019/0367950 A1 Dec. 5, 2019

Related U.S. Application Data

(60) Provisional application No. 62/677,421, filed on May 29, 2018.

(51) Int. Cl.
| | |
|---|---|
| *C12N 1/15* | (2006.01) |
| *C12N 1/19* | (2006.01) |
| *C12N 1/21* | (2006.01) |
| *C12N 9/12* | (2006.01) |
| *C12N 9/90* | (2006.01) |
| *C12P 5/00* | (2006.01) |
| *C12N 9/10* | (2006.01) |
| *C12N 15/70* | (2006.01) |

(52) U.S. Cl.
CPC ............ *C12P 5/007* (2013.01); *C12N 9/1085* (2013.01); *C12N 9/1229* (2013.01); *C12N 15/70* (2013.01); *C12P 5/002* (2013.01); *C12Y 207/04026* (2015.07); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 2003/0233675 A1 | 12/2003 | Cao et al. | |
| 2010/0192985 A1* | 8/2010 | Aehle | C11D 3/38645 134/26 |
| 2018/0334692 A1* | 11/2018 | Barr | C12Y 602/01 |

FOREIGN PATENT DOCUMENTS

| | | |
|---|---|---|
| CN | 104774799 A | 7/2015 |
| WO | WO 2011/009132 A2 | 1/2011 |
| WO | WO 2016/134381 A1 | 8/2016 |
| WO | WO 2017/161041 A1 | 9/2017 |
| WO | WO-2017161041 A1 * | 9/2017 ............... C12P 7/26 |

OTHER PUBLICATIONS

Wang et al., Cell Chemical Biology 25:560-570, 2018 (Year: 2018).*
Clomburg et al., PNAS 116:12810-12815, Jun. 2019 (Year: 2019).*
UniProt Database Accession No. P20485, May 23, 2018, 4 pages (Year: 2018).*
Chatzivasileiou et al., PNAS 116:506-511, Jan. 2019 (Year: 2019).*
UniProt Database Accession No. Q8H1F7, May 23, 2018, 4 pages (Year: 2018).*
Ajikumaretal., Science 30:70-74, 2010 (Year: 2010).*
Lange et al., PNAS 96:13714-13719, 1999 (Year: 1999).*
Rico et al., Microb. Cell Fact. 18:23, Feb. 2019, 10 pages (Year: 2019).*
Edgar, Metabolic engineering for the production of functionalized terpenoids in heterologous hosts. MIT Thesis. Doctor of Philosophy in Chemical Engineering. Jan. 1, 2017:3-259. Available to the public Jun. 6, 2017.
Zheng et al., Metabolic engineering of *Escherichia coli* for high-specificity production of isoprenol and prenol as next generation of biofuels. Biotechnol Biofuels. Apr. 2013;6(1):57, 14 pages.
PCT/US2019/034365, Sep. 3, 2019, Invitation to Pay Additional Fees.
PCT/US2019/034365, Nov. 25, 2019, International Search Report and Written Opinion.

* cited by examiner

*Primary Examiner* — David Steadman
(74) *Attorney, Agent, or Firm* — Wolf, Greenfield & Sacks, P.C.

(57) ABSTRACT

Disclosed herein are engineered cells and cell-free systems, compositions, and methods for conversion of isopentenols to isoprenoid precursors.

14 Claims, 58 Drawing Sheets

Specification includes a Sequence Listing.

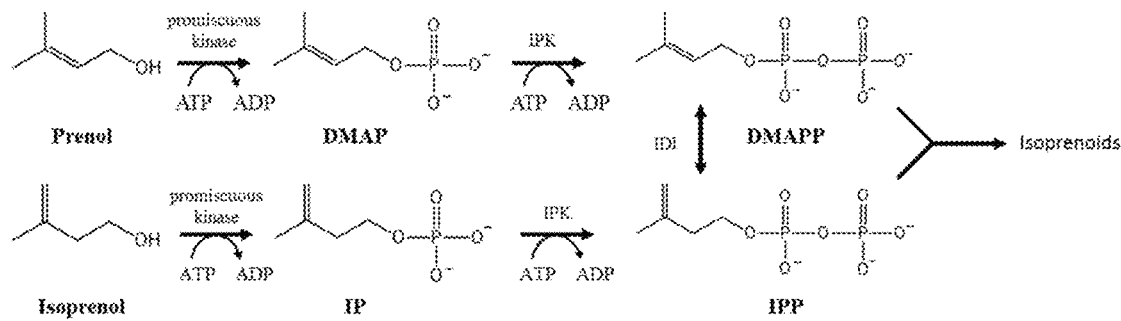

FIG. 9A

| Enzyme candidate | Source | Abbrev. |
|---|---|---|
| Isopentenyl Phosphate Kinase | H. volcanii | HvIPK |
| Isopentenyl Phosphate Kinase | M. thermoautotrophicus | MtIPK |
| Isopentenyl Phosphate Kinase | M. janaschii | MjIPK |
| Isopentenyl Phosphate Kinase | T. acidophilium | TaIPK |
| Isopentenyl Phosphate Kinase | T. acidophilium – V73I + Y141V + K204G | TaIPK-3m |
| Mevalonate Kinase | S. cerevisiae | ScMK |
| Glycerol Kinase | E. coli | EcGK |
| Homoserine Kinase | E. coli | EcHK |
| Choline Kinase | S. cerevisiae | ScCK |

FIG. 9B

| Level | Enzyme Concentrations (μg/mL) | | | | |
|---|---|---|---|---|---|
| | CK | IPK | IDI | IspA | GGPPS |
| Low | 25 | 0.61 | 25 | 25 | 0.33 |
| Medium | 125 | 3.03 | 125 | 125 | 1.64 |
| High | 625 | 15.2 | 625 | 625 | 8.18 |

| | Enzyme Concentrations (μg/mL) | | | | |
|---|---|---|---|---|---|
| Level | CK | IPK | IDI | IspA | GGPPS |
| Low | 25 | 0.61 | 25 | 25 | 0.33 |
| Medium | 125 | 3.03 | 125 | 125 | 1.64 |
| High | 625 | 15.2 | 625 | 625 | 8.18 |

SEQUENCE LISTING

```
<160> NUMBER OF SEQ ID NOS: 110

<210> SEQ ID NO 1
<211> LENGTH: 1749
<212> TYPE: DNA
<213> ORGANISM: Artificial Sequence
<220> FEATURE:
<223> OTHER INFORMATION: codon-optimized sequence

<400> SEQUENCE: 1
atggtgcagg agtcccgccc cggctcggtc cggtcgtatt ccgtgggcta ccaggcccgg      60
tcgcggtcgt cgtcccagcg ccgccattcg ctcacgcggc agcgcagcag ccagcggctc     120
atccggacga tctccatcga gagcgatgtg agcaatatca cggacgatga tgatctgcgg     180
gcggtgaatg aagggggtggc cggggtccag ctcgacgtct ccgagacggc gaacaaaggg     240
ccacgccggg ccagtgccac cgatgtcacc gactcgctgg gctccacgtc cagcgaatat     300
atcgagatcc ccttcgtgaa agagacgctg gacgcgagcc tccctcgga ttacctcaaa     360 caagacatcc tgaacctgat ccaatccctg aagatctcga aatggtacaa taacaaaaag     420
atccagcccg tcgcccagga catgaacctc gtcaaaatct ccggcgcgat gaccaatgcg     480
```

-continued

```
atcttcaagg tggagtaccc gaaactgccg tccctcctgc tgcggatcta tggcccgaat    540
atcgataaca tcatcgaccg cgaatatgaa ctccagatcc tcgcgcggct ctcgctgaaa    600
aacatcgggc cgtccctgta cggctgcttc gtgaatgggc gcttcgagca gttcctcgaa    660
aactccaaaa cgctgaccaa ggatgatatc cggaactgga aaaactcgca acggatcgcc    720
cgccgcatga aggagctgca tgtgggcgtg cccctcctct cgtcggagcg aagaatggg    780
agcgcctgct ggcaaaaaat caaccaatgg ctccgcacga tcgagaaggt ggatcagtgg    840
gtcggggacc cgaagaacat cgagaacagc ctcctctgcg aaaattggtc caaattcatg    900
gacatcgtcg atcggtacca aagtggctg atcagccaag aacaagggat cgagcaagtc     960
aacaaaaatc tgatcttctg ccataatgat gcccaatacg ggaatctcct cttcaccgcg   1020
cccgtcatga acaccccctc cctgtatacc gcgccgagct cgacctccct gacgtcccaa   1080
agcagcagcc tcttcccctc gtccagcaac gtgatcgtcg atgatatcat caatcccccg   1140
aagcaagaac aatcccaaga ttccaaactc gtggtcatcg atttcgaata cgccggggcc   1200
aatcccgccg cgtacgatct cgccaatcac ctctcggaat ggatgtacga ctataataac   1260
gccaaagccc cgcaccagtg ccacgccgac cggtaccccg acaaggagca agtgctcaac   1320
ttcctgtatt cgtatgtcag ccatctccgc ggcggggcca aagagcccat cgatgaagaa   1380
gtccagcgcc tctataaatc gatcatccag tggcgcccca cggtgcagct cttctggtcg   1440
ctgtgggcga tcctgcaaag cggcaagctg gaaaaaaaag aagccagcac cgccatcacc   1500
cgcgaagaaa tcgggcccaa tgggaaaaag tatatcatca agacggagcc cgagtcgccc   1560
gaagaggact tcgtcgaaaa tgacgacgaa cccgaagccg gcgtgtcgat cgataccttc   1620
gactacatgg cctacgggcg ggacaagatc gcggtgttct gggggacct gatcgggctg   1680
ggcatcatca cggaggagga atgcaagaac ttctcgagct tcaaattcct cgacaccagc   1740
tacctgtaa                                                           1749
```

<210> SEQ ID NO 2
<211> LENGTH: 28
<212> TYPE: DNA
<213> ORGANISM: Artificial Sequence
<220> FEATURE:
<223> OTHER INFORMATION: primer

<400> SEQUENCE: 2

```
atggtatatc tccttattaa agttaaac                                        28
```

<210> SEQ ID NO 3
<211> LENGTH: 29
<212> TYPE: DNA
<213> ORGANISM: Artificial Sequence
<220> FEATURE:
<223> OTHER INFORMATION: primer

<400> SEQUENCE: 3

```
tattagttaa gtataagaag gagatatac                                       29
```

<210> SEQ ID NO 4
<211> LENGTH: 43
<212> TYPE: DNA
<213> ORGANISM: Artificial Sequence
<220> FEATURE:
<223> OTHER INFORMATION: primer

<400> SEQUENCE: 4

-continued taataaggag ataccata tggaatttga cttcaacaaa tac                43

<210> SEQ ID NO 5
<211> LENGTH: 39
<212> TYPE: DNA
<213> ORGANISM: Artificial Sequence
<220> FEATURE:
<223> OTHER INFORMATION: primer

<400> SEQUENCE: 5
cttcttatac ttaactaata cgaggaagcg gaatatatc                39

<210> SEQ ID NO 6
<211> LENGTH: 38
<212> TYPE: DNA
<213> ORGANISM: Artificial Sequence
<220> FEATURE:
<223> OTHER INFORMATION: primer

<400> SEQUENCE: 6
taataaggag ataccata tggactttcc gcagcaac                38

<210> SEQ ID NO 7
<211> LENGTH: 46
<212> TYPE: DNA
<213> ORGANISM: Artificial Sequence
<220> FEATURE:
<223> OTHER INFORMATION: primer

<400> SEQUENCE: 7
ctccttctta aaagatcctt tatttattac gctggatgat gtagtc                46

<210> SEQ ID NO 8
<211> LENGTH: 54
<212> TYPE: DNA
<213> ORGANISM: Artificial Sequence
<220> FEATURE:
<223> OTHER INFORMATION: primer

<400> SEQUENCE: 8
gtaataaata aggatctttt taagaaggag atatacatgg ccctgaccga agag                54

<210> SEQ ID NO 9
<211> LENGTH: 41
<212> TYPE: DNA
<213> ORGANISM: Artificial Sequence
<220> FEATURE:
<223> OTHER INFORMATION: primer

<400> SEQUENCE: 9
cttcttatac ttaactaata tcagatggac atcgggtaaa c                41

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
cagttattgg tgcccttaaa cg                22

<210> SEQ ID NO 11
<211> LENGTH: 26
<212> TYPE: DNA
<213> ORGANISM: Artificial Sequence

```
<220> FEATURE:
<223> OTHER INFORMATION: primer

<400> SEQUENCE: 11
taagctttaa tgcggtagtt tatcac                                          26

<210> SEQ ID NO 12
<211> LENGTH: 36
<212> TYPE: DNA
<213> ORGANISM: Artificial Sequence
<220> FEATURE:
<223> OTHER INFORMATION: primer

<400> SEQUENCE: 12
agggcaccaa taactgggtg aacactatcc catatc                               36

<210> SEQ ID NO 13
<211> LENGTH: 29
<212> TYPE: DNA
<213> ORGANISM: Artificial Sequence
<220> FEATURE:
<223> OTHER INFORMATION: primer

<400> SEQUENCE: 13
taaccgtata atcatggcaa ttctggaag                                       29

<210> SEQ ID NO 14
<211> LENGTH: 29
<212> TYPE: DNA
<213> ORGANISM: Artificial Sequence
<220> FEATURE:
<223> OTHER INFORMATION: primer

<400> SEQUENCE: 14
gccatgatta tacggttatc cacagaatc                                       29

<210> SEQ ID NO 15
<211> LENGTH: 36
<212> TYPE: DNA
<213> ORGANISM: Artificial Sequence
<220> FEATURE:
<223> OTHER INFORMATION: primer

<400> SEQUENCE: 15
ctaccgcatt aaagcttaag gatctaggtg aagatc                               36

<210> SEQ ID NO 16
<211> LENGTH: 33
<212> TYPE: DNA
<213> ORGANISM: Artificial Sequence
<220> FEATURE:
<223> OTHER INFORMATION: primer

<400> SEQUENCE: 16
attgccatga ttccccttgt attactgttt atg                                  33

<210> SEQ ID NO 17
<211> LENGTH: 36
<212> TYPE: DNA
<213> ORGANISM: Artificial Sequence
<220> FEATURE:
<223> OTHER INFORMATION: primer

<400> SEQUENCE: 17
ctaccgcatt aaagcttaac tcaaaggcgg taatac                               36
```

<210> SEQ ID NO 18
<211> LENGTH: 46
<212> TYPE: DNA
<213> ORGANISM: Artificial Sequence
<220> FEATURE:
<223> OTHER INFORMATION: primer

<400> SEQUENCE: 18
atggtatatc tccttattaa agttaaacaa aattatttct acaggg        46

<210> SEQ ID NO 19
<211> LENGTH: 40
<212> TYPE: DNA
<213> ORGANISM: Artificial Sequence
<220> FEATURE:
<223> OTHER INFORMATION: primer

<400> SEQUENCE: 19
ttaataagga gataccat atggtgagtg gcagtaaagc        40

<210> SEQ ID NO 20
<211> LENGTH: 41
<212> TYPE: DNA
<213> ORGANISM: Artificial Sequence
<220> FEATURE:
<223> OTHER INFORMATION: primer

<400> SEQUENCE: 20
ctccttctta tacttaacta atactgcgtg aacgtcatgg c        41

<210> SEQ ID NO 21
<211> LENGTH: 29
<212> TYPE: DNA
<213> ORGANISM: Artificial Sequence
<220> FEATURE:
<223> OTHER INFORMATION: primer

<400> SEQUENCE: 21
tattagttaa gtataagaag gagatatac        29

<210> SEQ ID NO 22
<211> LENGTH: 18
<212> TYPE: DNA
<213> ORGANISM: Artificial Sequence
<220> FEATURE:
<223> OTHER INFORMATION: primer

<400> SEQUENCE: 22
caccaccacc accaccac        18

<210> SEQ ID NO 23
<211> LENGTH: 38
<212> TYPE: DNA
<213> ORGANISM: Artificial Sequence
<220> FEATURE:
<223> OTHER INFORMATION: primer

<400> SEQUENCE: 23
cggtatatct ccttcttaaa gttaaacaaa attatttc        38

<210> SEQ ID NO 24
<211> LENGTH: 36
<212> TYPE: DNA
<213> ORGANISM: Artificial Sequence
<220> FEATURE:
<223> OTHER INFORMATION: primer -continued

<400> SEQUENCE: 24
aagaaggaga taccgatg gtacaagaat cacgtc                          36

<210> SEQ ID NO 25
<211> LENGTH: 43
<212> TYPE: DNA
<213> ORGANISM: Artificial Sequence
<220> FEATURE:
<223> OTHER INFORMATION: primer

<400> SEQUENCE: 25
tcagtggtgg tggtggtggt gcaaataact agtatcgagg aac               43

<210> SEQ ID NO 26
<211> LENGTH: 43
<212> TYPE: DNA
<213> ORGANISM: Artificial Sequence
<220> FEATURE:
<223> OTHER INFORMATION: primer

<400> SEQUENCE: 26
aagaaggaga taccgatg actgaaaaaa aatatatcgt tgc                 43

<210> SEQ ID NO 27
<211> LENGTH: 40
<212> TYPE: DNA
<213> ORGANISM: Artificial Sequence
<220> FEATURE:
<223> OTHER INFORMATION: primer

<400> SEQUENCE: 27
tcagtggtgg tggtggtggt gttcgtcgtg ttcttcccac                    40

<210> SEQ ID NO 28
<211> LENGTH: 37
<212> TYPE: DNA
<213> ORGANISM: Artificial Sequence
<220> FEATURE:
<223> OTHER INFORMATION: primer

<400> SEQUENCE: 28
aagaaggaga taccgatg gttaaagttt atgcccc                        37

<210> SEQ ID NO 29
<211> LENGTH: 39
<212> TYPE: DNA
<213> ORGANISM: Artificial Sequence
<220> FEATURE:
<223> OTHER INFORMATION: primer

<400> SEQUENCE: 29
tcagtggtgg tggtggtggt ggttttccag tactcgtgc                    39

<210> SEQ ID NO 30
<211> LENGTH: 39
<212> TYPE: DNA
<213> ORGANISM: Artificial Sequence
<220> FEATURE:
<223> OTHER INFORMATION: primer

<400> SEQUENCE: 30
aagaaggaga taccgatg atgattctga aaatcggag                      39

<210> SEQ ID NO 31

```
<211> LENGTH: 40
<212> TYPE: DNA
<213> ORGANISM: Artificial Sequence
<220> FEATURE:
<223> OTHER INFORMATION: primer

<400> SEQUENCE: 31
tcagtggtgg tggtggtggt gtcgaatgac agtaccgatg                              40

<210> SEQ ID NO 32
<211> LENGTH: 39
<212> TYPE: DNA
<213> ORGANISM: Artificial Sequence
<220> FEATURE:
<223> OTHER INFORMATION: primer

<400> SEQUENCE: 32
aagaaggaga tataccgatg ctgaccatcc tgaaattag                               39

<210> SEQ ID NO 33
<211> LENGTH: 39
<212> TYPE: DNA
<213> ORGANISM: Artificial Sequence
<220> FEATURE:
<223> OTHER INFORMATION: primer

<400> SEQUENCE: 33
tcagtggtgg tggtggtggt gttcgctaaa gtcgatctc                               39

<210> SEQ ID NO 34
<211> LENGTH: 40
<212> TYPE: DNA
<213> ORGANISM: Artificial Sequence
<220> FEATURE:
<223> OTHER INFORMATION: primer

<400> SEQUENCE: 34
aagaaggaga tataccgatg atgattctta agataggggg                              40

<210> SEQ ID NO 35
<211> LENGTH: 40
<212> TYPE: DNA
<213> ORGANISM: Artificial Sequence
<220> FEATURE:
<223> OTHER INFORMATION: primer

<400> SEQUENCE: 35
tcagtggtgg tggtggtggt gacgaatgac ggttccgatg                              40

<210> SEQ ID NO 36
<211> LENGTH: 37
<212> TYPE: DNA
<213> ORGANISM: Artificial Sequence
<220> FEATURE:
<223> OTHER INFORMATION: primer

<400> SEQUENCE: 36
aagaaggaga tataccgatg atcattctga aactggg                                 37

<210> SEQ ID NO 37
<211> LENGTH: 40
<212> TYPE: DNA
<213> ORGANISM: Artificial Sequence
<220> FEATURE:
<223> OTHER INFORMATION: primer

<400> SEQUENCE: 37
```
tcagtggtgg tggtggtggt gatgttttcc tgtgatacgc                              40

<210> SEQ ID NO 38
<211> LENGTH: 38
<212> TYPE: DNA
<213> ORGANISM: Artificial Sequence
<220> FEATURE:
<223> OTHER INFORMATION: primer

<400> SEQUENCE: 38
aagaaggaga tataccgatg tccctggtgg tccttaaa                                38

<210> SEQ ID NO 39
<211> LENGTH: 39
<212> TYPE: DNA
<213> ORGANISM: Artificial Sequence
<220> FEATURE:
<223> OTHER INFORMATION: primer

<400> SEQUENCE: 39
tcagtggtgg tggtggtggt gttccccgcg aatgactgt                               39

<210> SEQ ID NO 40
<211> LENGTH: 40
<212> TYPE: DNA
<213> ORGANISM: Artificial Sequence
<220> FEATURE:
<223> OTHER INFORMATION: primer

<400> SEQUENCE: 40
tttaagaagg agatataccg atgtcattac cgttcttaac                              40

<210> SEQ ID NO 41
<211> LENGTH: 42
<212> TYPE: DNA
<213> ORGANISM: Artificial Sequence
<220> FEATURE:
<223> OTHER INFORMATION: primer

<400> SEQUENCE: 41
cagtggtggt ggtggtggtg ctatgaagtc catggtaaat tc                           42

<210> SEQ ID NO 42
<211> LENGTH: 18
<212> TYPE: DNA
<213> ORGANISM: Artificial Sequence
<220> FEATURE:
<223> OTHER INFORMATION: primer

<400> SEQUENCE: 42
atgacccacc tgaacatc                                                      18

<210> SEQ ID NO 43
<211> LENGTH: 21
<212> TYPE: DNA
<213> ORGANISM: Artificial Sequence
<220> FEATURE:
<223> OTHER INFORMATION: primer

<400> SEQUENCE: 43
gcgcaacgca attaatgtaa g                                                  21

<210> SEQ ID NO 44
<211> LENGTH: 44
<212> TYPE: DNA

<213> ORGANISM: Artificial Sequence
<220> FEATURE:
<223> OTHER INFORMATION: primer

<400> SEQUENCE: 44
ttacattaat tgcgttgcgc ttaagaccca ctttcacatt taag                44

<210> SEQ ID NO 45
<211> LENGTH: 45
<212> TYPE: DNA
<213> ORGANISM: Artificial Sequence
<220> FEATURE:
<223> OTHER INFORMATION: primer

<400> SEQUENCE: 45
gcgatgttca ggtgggtcat atgtatatct ccttcttaaa agatc               45

<210> SEQ ID NO 46
<211> LENGTH: 38
<212> TYPE: DNA
<213> ORGANISM: Artificial Sequence
<220> FEATURE:
<223> OTHER INFORMATION: primer

<400> SEQUENCE: 46
tttaagaagg agatatacat atggtgcagg agtcccgc                       38

<210> SEQ ID NO 47
<211> LENGTH: 45
<212> TYPE: DNA
<213> ORGANISM: Artificial Sequence
<220> FEATURE:
<223> OTHER INFORMATION: primer

<400> SEQUENCE: 47
gtcgacggag ctcgaattcg ttatttgctg aagcggatga tggtc               45

<210> SEQ ID NO 48
<211> LENGTH: 18
<212> TYPE: DNA
<213> ORGANISM: Artificial Sequence
<220> FEATURE:
<223> OTHER INFORMATION: primer

<400> SEQUENCE: 48
cgaattcgag ctccgtcg                                             18

<210> SEQ ID NO 49
<211> LENGTH: 35
<212> TYPE: DNA
<213> ORGANISM: Artificial Sequence
<220> FEATURE:
<223> OTHER INFORMATION: primer

<400> SEQUENCE: 49
atgtatatct ccttcttaaa agatcttttg aattc                          35

<210> SEQ ID NO 50
<211> LENGTH: 39
<212> TYPE: DNA
<213> ORGANISM: Artificial Sequence
<220> FEATURE:
<223> OTHER INFORMATION: primer

<400> SEQUENCE: 50
gggcatgcat aaggctcgga tgatatattc agggagacc                      39

```
<210> SEQ ID NO 51
<211> LENGTH: 18
<212> TYPE: DNA
<213> ORGANISM: Artificial Sequence
<220> FEATURE:
<223> OTHER INFORMATION: primer

<400> SEQUENCE: 51
cgagccttat gcatgccc                                                       18

<210> SEQ ID NO 52
<211> LENGTH: 18
<212> TYPE: DNA
<213> ORGANISM: Artificial Sequence
<220> FEATURE:
<223> OTHER INFORMATION: primer

<400> SEQUENCE: 52
gggtccccaa taattacg                                                       18

<210> SEQ ID NO 53
<211> LENGTH: 18
<212> TYPE: DNA
<213> ORGANISM: Artificial Sequence
<220> FEATURE:
<223> OTHER INFORMATION: primer

<400> SEQUENCE: 53
cagctgggcg cgccgtag                                                       18

<210> SEQ ID NO 54
<211> LENGTH: 40
<212> TYPE: DNA
<213> ORGANISM: Artificial Sequence
<220> FEATURE:
<223> OTHER INFORMATION: primer

<400> SEQUENCE: 54
ttctacggcg cgcccagctg ttctagagca cagctaacac                               40

<210> SEQ ID NO 55
<211> LENGTH: 28
<212> TYPE: DNA
<213> ORGANISM: Artificial Sequence
<220> FEATURE:
<223> OTHER INFORMATION: primer

<400> SEQUENCE: 55
tccttgcgtt gaaaccgttg tggtctcc                                            28

<210> SEQ ID NO 56
<211> LENGTH: 31
<212> TYPE: DNA
<213> ORGANISM: Artificial Sequence
<220> FEATURE:
<223> OTHER INFORMATION: primer

<400> SEQUENCE: 56
caacggtttc aacgcaagga aacacattaa g                                        31

<210> SEQ ID NO 57
<211> LENGTH: 28
<212> TYPE: DNA
<213> ORGANISM: Artificial Sequence
<220> FEATURE:
```

<223> OTHER INFORMATION: primer

<400> SEQUENCE: 57
tttcttgtac ttacaggtag ctggtgtc                                    28

<210> SEQ ID NO 58
<211> LENGTH: 31
<212> TYPE: DNA
<213> ORGANISM: Artificial Sequence
<220> FEATURE:
<223> OTHER INFORMATION: primer

<400> SEQUENCE: 58
ctacctgtaa gtacaagaaa agtcagtagt c                                31

<210> SEQ ID NO 59
<211> LENGTH: 29
<212> TYPE: DNA
<213> ORGANISM: Artificial Sequence
<220> FEATURE:
<223> OTHER INFORMATION: primer

<400> SEQUENCE: 59
ctccttagtt ttatttgctg aagcggatg                                   29

<210> SEQ ID NO 60
<211> LENGTH: 30
<212> TYPE: DNA
<213> ORGANISM: Artificial Sequence
<220> FEATURE:
<223> OTHER INFORMATION: primer

<400> SEQUENCE: 60
cagcaaataa aactaaggag gtctatatgc                                  30

<210> SEQ ID NO 61
<211> LENGTH: 40
<212> TYPE: DNA
<213> ORGANISM: Artificial Sequence
<220> FEATURE:
<223> OTHER INFORMATION: primer

<400> SEQUENCE: 61
atcgtaatta ttggggaccc gatatagttc ctcctttcag                       40

<210> SEQ ID NO 62
<211> LENGTH: 30
<212> TYPE: DNA
<213> ORGANISM: Artificial Sequence
<220> FEATURE:
<223> OTHER INFORMATION: primer

<400> SEQUENCE: 62
ctacctgtaa aactaaggag gtctatatgc                                  30

<210> SEQ ID NO 63
<211> LENGTH: 28
<212> TYPE: DNA
<213> ORGANISM: Artificial Sequence
<220> FEATURE:
<223> OTHER INFORMATION: primer

<400> SEQUENCE: 63
ctccttagtt ttacaggtag ctggtgtc                                    28

<210> SEQ ID NO 64
<211> LENGTH: 21
<212> TYPE: DNA
<213> ORGANISM: Artificial Sequence
<220> FEATURE:
<223> OTHER INFORMATION: primer

<400> SEQUENCE: 64
gcgacattga agaagataag g                                              21

<210> SEQ ID NO 65
<211> LENGTH: 20
<212> TYPE: DNA
<213> ORGANISM: Artificial Sequence
<220> FEATURE:
<223> OTHER INFORMATION: primer

<400> SEQUENCE: 65
gtttacggtg taagcgatcc                                                20

<210> SEQ ID NO 66
<211> LENGTH: 20
<212> TYPE: DNA
<213> ORGANISM: Artificial Sequence
<220> FEATURE:
<223> OTHER INFORMATION: primer

<400> SEQUENCE: 66
gattgctggc tggaggtcac                                                20

<210> SEQ ID NO 67
<211> LENGTH: 60
<212> TYPE: DNA
<213> ORGANISM: Artificial Sequence
<220> FEATURE:
<223> OTHER INFORMATION: primer

<400> SEQUENCE: 67
gtcctaggta taatactagt cgctgcgtat ccgttcgcga gttttagagc tagaaatagc    60

<210> SEQ ID NO 68
<211> LENGTH: 24
<212> TYPE: DNA
<213> ORGANISM: Artificial Sequence
<220> FEATURE:
<223> OTHER INFORMATION: primer

<400> SEQUENCE: 68
actagtatta tacctaggac tgag                                           24

<210> SEQ ID NO 69
<211> LENGTH: 20
<212> TYPE: DNA
<213> ORGANISM: Artificial Sequence
<220> FEATURE:
<223> OTHER INFORMATION: primer

<400> SEQUENCE: 69
caccaccgac tatttgcaac                                                20

<210> SEQ ID NO 70
<211> LENGTH: 22
<212> TYPE: DNA
<213> ORGANISM: Artificial Sequence
<220> FEATURE:
<223> OTHER INFORMATION: primer

<400> SEQUENCE: 70
ctcgagtagg gataacaggg ta                                                      22

<210> SEQ ID NO 71
<211> LENGTH: 41
<212> TYPE: DNA
<213> ORGANISM: Artificial Sequence
<220> FEATURE:
<223> OTHER INFORMATION: primer

<400> SEQUENCE: 71
ccctgttatc cctactcgag ccagcgtctg tggatactac c                                 41

<210> SEQ ID NO 72
<211> LENGTH: 28
<212> TYPE: DNA
<213> ORGANISM: Artificial Sequence
<220> FEATURE:
<223> OTHER INFORMATION: primer

<400> SEQUENCE: 72
tcccatcacg tctcccgcgt tacccgtc                                                28

<210> SEQ ID NO 73
<211> LENGTH: 28
<212> TYPE: DNA
<213> ORGANISM: Artificial Sequence
<220> FEATURE:
<223> OTHER INFORMATION: primer

<400> SEQUENCE: 73
acgcgggaga cgtgatggga agcgcctc                                                28

<210> SEQ ID NO 74
<211> LENGTH: 39
<212> TYPE: DNA
<213> ORGANISM: Artificial Sequence
<220> FEATURE:
<223> OTHER INFORMATION: primer

<400> SEQUENCE: 74
gttgcaaata gtcggtggtg cttcgcagcc caactgatg                                    39

<210> SEQ ID NO 75
<211> LENGTH: 38
<212> TYPE: DNA
<213> ORGANISM: Artificial Sequence
<220> FEATURE:
<223> OTHER INFORMATION: primer

<400> SEQUENCE: 75
ttaataagga gatataccat atgttcgact tcaacgag                                     38

<210> SEQ ID NO 76
<211> LENGTH: 38
<212> TYPE: DNA
<213> ORGANISM: Artificial Sequence
<220> FEATURE:
<223> OTHER INFORMATION: primer

<400> SEQUENCE: 76
ttgaacccaa aagggcggta ttagttttga cgaaaggc                                     38

<210> SEQ ID NO 77
<211> LENGTH: 18

```
<212> TYPE: DNA
<213> ORGANISM: Artificial Sequence
<220> FEATURE:
<223> OTHER INFORMATION: primer

<400> SEQUENCE: 77
taccgccctt ttgggttc                                                18

<210> SEQ ID NO 78
<211> LENGTH: 28
<212> TYPE: DNA
<213> ORGANISM: Artificial Sequence
<220> FEATURE:
<223> OTHER INFORMATION: primer

<400> SEQUENCE: 78
atggtatatc tccttattaa agttaaac                                     28

<210> SEQ ID NO 79
<211> LENGTH: 38
<212> TYPE: DNA
<213> ORGANISM: Artificial Sequence
<220> FEATURE:
<223> OTHER INFORMATION: primer

<400> SEQUENCE: 79
gaaagaggag aaatactagt atgagcaagg gcgaagag                          38

<210> SEQ ID NO 80
<211> LENGTH: 44
<212> TYPE: DNA
<213> ORGANISM: Artificial Sequence
<220> FEATURE:
<223> OTHER INFORMATION: primer

<400> SEQUENCE: 80
caagcttgtc gacggagctc ttacttatag agttcatcca tgcc                   44

<210> SEQ ID NO 81
<211> LENGTH: 20
<212> TYPE: DNA
<213> ORGANISM: Artificial Sequence
<220> FEATURE:
<223> OTHER INFORMATION: primer

<400> SEQUENCE: 81
gagctccgtc gacaagcttg                                              20

<210> SEQ ID NO 82
<211> LENGTH: 37
<212> TYPE: DNA
<213> ORGANISM: Artificial Sequence
<220> FEATURE:
<223> OTHER INFORMATION: primer

<400> SEQUENCE: 82
actagtattt ctcctctttc tctagtaaaa gttaaac                           37

<210> SEQ ID NO 83
<211> LENGTH: 38
<212> TYPE: DNA
<213> ORGANISM: Artificial Sequence
<220> FEATURE:
<223> OTHER INFORMATION: primer

<400> SEQUENCE: 83
```

-continued tttaagaagg agatatacat atgagcaagg gcgaagag					38

<210> SEQ ID NO 84
<211> LENGTH: 44
<212> TYPE: DNA
<213> ORGANISM: Artificial Sequence
<220> FEATURE:
<223> OTHER INFORMATION: primer

<400> SEQUENCE: 84
gtcgacggag ctcgaattcg ttacttatag agttcatcca tgcc					44

<210> SEQ ID NO 85
<211> LENGTH: 18
<212> TYPE: DNA
<213> ORGANISM: Artificial Sequence
<220> FEATURE:
<223> OTHER INFORMATION: primer

<400> SEQUENCE: 85
cgaattcgag ctccgtcg					18

<210> SEQ ID NO 86
<211> LENGTH: 35
<212> TYPE: DNA
<213> ORGANISM: Artificial Sequence
<220> FEATURE:
<223> OTHER INFORMATION: primer

<400> SEQUENCE: 86
atgtatatct ccttcttaaa agatcttttg aattc					35

<210> SEQ ID NO 87
<211> LENGTH: 18
<212> TYPE: DNA
<213> ORGANISM: Artificial Sequence
<220> FEATURE:
<223> OTHER INFORMATION: primer

<400> SEQUENCE: 87
gagctccgtc gacaagct					18

<210> SEQ ID NO 88
<211> LENGTH: 31
<212> TYPE: DNA
<213> ORGANISM: Artificial Sequence
<220> FEATURE:
<223> OTHER INFORMATION: primer

<400> SEQUENCE: 88
actagtattt ctcctctttc tctagtaaaa g					31

<210> SEQ ID NO 89
<211> LENGTH: 48
<212> TYPE: DNA
<213> ORGANISM: Artificial Sequence
<220> FEATURE:
<223> OTHER INFORMATION: primer

<400> SEQUENCE: 89
ctagagaaag aggagaaata ctagtatgtc attaccgttc ttaacttc					48

<210> SEQ ID NO 90
<211> LENGTH: 40
<212> TYPE: DNA
<213> ORGANISM: Artificial Sequence
<220> FEATURE:
<223> OTHER INFORMATION: primer

<400> SEQUENCE: 90
caagcttgtc gacggagctc ttattccttt ggtagaccag            40

<210> SEQ ID NO 91
<211> LENGTH: 125
<212> TYPE: DNA
<213> ORGANISM: Artificial Sequence
<220> FEATURE:
<223> OTHER INFORMATION: Promoter sequence

<400> SEQUENCE: 91
ttctagagca cagctaacac cacgtcgtcc ctatctgctg ccctaggtct atgagtggtt     60
gctggataac tttacgggca tgcataaggc tcgtataata tattcaggga gaccacaacg   120
gtttc                                                              125

<210> SEQ ID NO 92
<211> LENGTH: 30
<212> TYPE: DNA
<213> ORGANISM: Artificial Sequence
<220> FEATURE:
<223> OTHER INFORMATION: RBS for ck

<400> SEQUENCE: 92
aacgcaagga aacacattaa ggaggtttaa                       30

<210> SEQ ID NO 93
<211> LENGTH: 34
<212> TYPE: DNA
<213> ORGANISM: Artificial Sequence
<220> FEATURE:
<223> OTHER INFORMATION: RBS for ipk

<400> SEQUENCE: 93
gtacaagaaa agtcagtagt ctaaggaggt aagc                  34

<210> SEQ ID NO 94
<211> LENGTH: 16
<212> TYPE: DNA
<213> ORGANISM: Artificial Sequence
<220> FEATURE:
<223> OTHER INFORMATION: RBS for idi

<400> SEQUENCE: 94
aactaaggag gtctat                                      16

<210> SEQ ID NO 95
<211> LENGTH: 122
<212> TYPE: DNA
<213> ORGANISM: Artificial Sequence
<220> FEATURE:
<223> OTHER INFORMATION: T7 terminator region

<400> SEQUENCE: 95
gctaacaaag cccgaaagga agctgagttg gctgctgcca ccgctgagca ataactagca     60
taaccccttg gggcctctaa acgggtcttg aggggttttt tgctgaaagg aggaactata   120
tc                                                                 122

<210> SEQ ID NO 96
<211> LENGTH: 582
<212> TYPE: PRT

<213> ORGANISM: Artificial Sequence
<220> FEATURE:
<223> OTHER INFORMATION: Synthetic Polypeptide

<400> SEQUENCE: 96

```
Met Val Gln Glu Ser Arg Pro Gly Ser Val Arg Ser Tyr Ser Val Gly
1               5                   10                  15

Tyr Gln Ala Arg Ser Arg Ser Ser Gln Arg Arg His Ser Leu Thr
            20                  25                  30

Arg Gln Arg Ser Ser Gln Arg Leu Ile Arg Thr Ile Ser Ile Glu Ser
        35                  40                  45

Asp Val Ser Asn Ile Thr Asp Asp Asp Leu Arg Ala Val Asn Glu
    50                  55                  60

Gly Val Ala Gly Val Gln Leu Asp Val Ser Glu Thr Ala Asn Lys Gly
65                  70                  75                  80

Pro Arg Arg Ala Ser Ala Thr Asp Val Thr Asp Ser Leu Gly Ser Thr
                85                  90                  95

Ser Ser Glu Tyr Ile Glu Ile Pro Phe Val Lys Glu Thr Leu Asp Ala
            100                 105                 110

Ser Leu Pro Ser Asp Tyr Leu Lys Gln Asp Ile Leu Asn Leu Ile Gln
        115                 120                 125

Ser Leu Lys Ile Ser Lys Trp Tyr Asn Asn Lys Lys Ile Gln Pro Val
130                 135                 140

Ala Gln Asp Met Asn Leu Val Lys Ile Ser Gly Ala Met Thr Asn Ala
145                 150                 155                 160

Ile Phe Lys Val Glu Tyr Pro Lys Leu Pro Ser Leu Leu Leu Arg Ile
                165                 170                 175

Tyr Gly Pro Asn Ile Asp Asn Ile Ile Asp Arg Glu Tyr Glu Leu Gln
            180                 185                 190

Ile Leu Ala Arg Leu Ser Leu Lys Asn Ile Gly Pro Ser Leu Tyr Gly
        195                 200                 205

Cys Phe Val Asn Gly Arg Phe Glu Gln Phe Leu Glu Asn Ser Lys Thr
    210                 215                 220

Leu Thr Lys Asp Asp Ile Arg Asn Trp Lys Asn Ser Gln Arg Ile Ala
225                 230                 235                 240

Arg Arg Met Lys Glu Leu His Val Gly Val Pro Leu Leu Ser Ser Glu
                245                 250                 255

Arg Lys Asn Gly Ser Ala Cys Trp Gln Lys Ile Asn Gln Trp Leu Arg
            260                 265                 270

Thr Ile Glu Lys Val Asp Gln Trp Val Gly Asp Pro Lys Asn Ile Glu
        275                 280                 285

Asn Ser Leu Leu Cys Glu Asn Trp Ser Lys Phe Met Asp Ile Val Asp
    290                 295                 300

Arg Tyr His Lys Trp Leu Ile Ser Gln Glu Gln Gly Ile Glu Gln Val
305                 310                 315                 320

Asn Lys Asn Leu Ile Phe Cys His Asn Asp Ala Gln Tyr Gly Asn Leu
                325                 330                 335

Leu Phe Thr Ala Pro Val Met Asn Thr Pro Ser Leu Tyr Thr Ala Pro
            340                 345                 350

Ser Ser Thr Ser Leu Thr Ser Gln Ser Ser Leu Phe Pro Ser Ser
        355                 360                 365

Ser Asn Val Ile Val Asp Asp Ile Ile Asn Pro Pro Lys Gln Glu Gln
    370                 375                 380

Ser Gln Asp Ser Lys Leu Val Val Ile Asp Phe Glu Tyr Ala Gly Ala
```

```
               385                 390                 395                 400
Asn Pro Ala Ala Tyr Asp Leu Ala Asn His Leu Ser Glu Trp Met Tyr
                    405                 410                 415

Asp Tyr Asn Asn Ala Lys Ala Pro His Gln Cys His Ala Asp Arg Tyr
                    420                 425                 430

Pro Asp Lys Glu Gln Val Leu Asn Phe Leu Tyr Ser Tyr Val Ser His
                    435                 440                 445

Leu Arg Gly Gly Ala Lys Glu Pro Ile Asp Glu Val Gln Arg Leu
            450                 455                 460

Tyr Lys Ser Ile Ile Gln Trp Arg Pro Thr Val Gln Leu Phe Trp Ser
465                 470                 475                 480

Leu Trp Ala Ile Leu Gln Ser Gly Lys Leu Glu Lys Lys Glu Ala Ser
                    485                 490                 495

Thr Ala Ile Thr Arg Glu Glu Ile Gly Pro Asn Gly Lys Lys Tyr Ile
                    500                 505                 510

Ile Lys Thr Glu Pro Glu Ser Pro Glu Glu Asp Phe Val Glu Asn Asp
                    515                 520                 525

Asp Glu Pro Glu Ala Gly Val Ser Ile Asp Thr Phe Asp Tyr Met Ala
            530                 535                 540

Tyr Gly Arg Asp Lys Ile Ala Val Phe Trp Gly Asp Leu Ile Gly Leu
545                 550                 555                 560

Gly Ile Ile Thr Glu Glu Glu Cys Lys Asn Phe Ser Ser Phe Lys Phe
                    565                 570                 575

Leu Asp Thr Ser Tyr Leu
                580

<210> SEQ ID NO 97
<211> LENGTH: 332
<212> TYPE: PRT
<213> ORGANISM: Artificial Sequence
<220> FEATURE:
<223> OTHER INFORMATION: Synthetic Polypeptide

<400> SEQUENCE: 97

Met Glu Leu Asn Ile Ser Glu Ser Arg Ser Arg Ser Ile Arg Cys Ile
1               5                   10                  15

Val Lys Leu Gly Gly Ala Ala Ile Thr Cys Lys Asn Glu Leu Glu Lys
                20                  25                  30

Ile His Asp Glu Asn Leu Glu Val Val Ala Cys Gln Leu Arg Gln Ala
            35                  40                  45

Met Leu Glu Gly Ser Ala Pro Ser Lys Val Ile Gly Met Asp Trp Ser
        50                  55                  60

Lys Arg Pro Gly Ser Ser Glu Ile Ser Cys Asp Val Asp Asp Ile Gly
65                  70                  75                  80

Asp Gln Lys Ser Ser Glu Phe Ser Lys Phe Val Val His Gly Ala
                85                  90                  95

Gly Ser Phe Gly His Phe Gln Ala Ser Arg Ser Gly Val His Lys Gly
                100                 105                 110

Gly Leu Glu Lys Pro Ile Val Lys Ala Gly Phe Val Ala Thr Arg Ile
            115                 120                 125

Ser Val Thr Asn Leu Asn Leu Glu Ile Val Arg Ala Leu Ala Arg Glu
        130                 135                 140

Gly Ile Pro Thr Ile Gly Met Ser Pro Phe Ser Cys Gly Trp Ser Thr
145                 150                 155                 160

Ser Lys Arg Asp Val Ala Ser Ala Asp Leu Ala Thr Val Ala Lys Thr
```

```
                    165                 170                 175
Ile Asp Ser Gly Phe Val Pro Val Leu His Gly Asp Ala Val Leu Asp
                180                 185                 190

Asn Ile Leu Gly Cys Thr Ile Leu Ser Gly Asp Val Ile Ile Arg His
            195                 200                 205

Leu Ala Asp His Leu Lys Pro Glu Tyr Val Val Phe Leu Thr Asp Val
        210                 215                 220

Leu Gly Val Tyr Asp Arg Pro Pro Ser Pro Ser Glu Pro Asp Ala Val
225                 230                 235                 240

Leu Leu Lys Glu Ile Ala Val Gly Glu Asp Gly Ser Trp Lys Val Val
                245                 250                 255

Asn Pro Leu Leu Glu His Thr Asp Lys Lys Val Asp Tyr Ser Val Ala
            260                 265                 270

Ala His Asp Thr Thr Gly Gly Met Glu Thr Lys Ile Ser Glu Ala Ala
        275                 280                 285

Met Ile Ala Lys Leu Gly Val Asp Val Tyr Ile Val Lys Ala Ala Thr
290                 295                 300

Thr His Ser Gln Arg Ala Leu Asn Gly Asp Leu Arg Asp Ser Val Pro
305                 310                 315                 320

Glu Asp Trp Leu Gly Thr Ile Ile Arg Phe Ser Lys
                325                 330
```

<210> SEQ ID NO 98
<211> LENGTH: 182
<212> TYPE: PRT
<213> ORGANISM: Artificial Sequence
<220> FEATURE:
<223> OTHER INFORMATION: Synthetic Polypeptide

<400> SEQUENCE: 98

```
Met Gln Thr Glu His Val Ile Leu Leu Asn Ala Gln Gly Val Pro Thr
1               5                   10                  15

Gly Thr Leu Glu Lys Tyr Ala Ala His Thr Ala Asp Thr Arg Leu His
                20                  25                  30

Leu Ala Phe Ser Ser Trp Leu Phe Asn Ala Lys Gly Gln Leu Leu Val
            35                  40                  45

Thr Arg Arg Ala Leu Ser Lys Lys Ala Trp Pro Gly Val Trp Thr Asn
        50                  55                  60

Ser Val Cys Gly His Pro Gln Leu Gly Glu Ser Asn Glu Asp Ala Val
65                  70                  75                  80

Ile Arg Arg Cys Arg Tyr Glu Leu Gly Val Glu Ile Thr Pro Pro Glu
                85                  90                  95

Ser Ile Tyr Pro Asp Phe Arg Tyr Arg Ala Thr Asp Pro Ser Gly Ile
            100                 105                 110

Val Glu Asn Glu Val Cys Pro Val Phe Ala Ala Arg Thr Thr Ser Ala
        115                 120                 125

Leu Gln Ile Asn Asp Asp Glu Val Met Asp Tyr Gln Trp Cys Asp Leu
    130                 135                 140

Ala Asp Val Leu His Gly Ile Asp Ala Thr Pro Trp Ala Phe Ser Pro
145                 150                 155                 160

Trp Met Val Met Gln Ala Thr Asn Arg Glu Ala Arg Lys Arg Leu Ser
                165                 170                 175

Ala Phe Thr Gln Leu Lys
            180
```

```
<210> SEQ ID NO 99
<211> LENGTH: 74
<212> TYPE: DNA
<213> ORGANISM: Artificial Sequence
<220> FEATURE:
<223> OTHER INFORMATION: Synthetic polynucleotide

<400> SEQUENCE: 99
caccaccacc accaccactg agatccggct gctaaccggt atatctcctt cttaaagtta    60
aacaaaatta tttc                                                      74

<210> SEQ ID NO 100
<211> LENGTH: 95
<212> TYPE: DNA
<213> ORGANISM: Artificial Sequence
<220> FEATURE:
<223> OTHER INFORMATION: Synthetic polynucleotide

<400> SEQUENCE: 100
tttaagaagg agatataccg atggtgcagg agtcccgctt gttagcagcc ggatctcagt    60
ggtggtggtg gtggtgcagg tagctggtgt cgagg                               95

<210> SEQ ID NO 101
<211> LENGTH: 91
<212> TYPE: DNA
<213> ORGANISM: Artificial Sequence
<220> FEATURE:
<223> OTHER INFORMATION: Synthetic polynucleotide

<400> SEQUENCE: 101
aagaaggaga taccgatgg gaactcaata tcagcggtta gcagccggat ctcagtggtg     60
gtggtggtgg tgtttgctga agcggatgat g                                   91

<210> SEQ ID NO 102
<211> LENGTH: 91
<212> TYPE: DNA
<213> ORGANISM: Artificial Sequence
<220> FEATURE:
<223> OTHER INFORMATION: Synthetic polynucleotide

<400> SEQUENCE: 102
aagaaggaga taccgatgg caaacggaac acgtcgttag cagccggatc tcagtggtgg     60
tggtggtggt gtttaagctg ggtaaatgca g                                   91

<210> SEQ ID NO 103
<211> LENGTH: 96
<212> TYPE: DNA
<213> ORGANISM: Artificial Sequence
<220> FEATURE:
<223> OTHER INFORMATION: Synthetic polynucleotide

<400> SEQUENCE: 103
aagaaggaga taccgatgg gactttccgc agcaacgtta gcagccggat ctcagtggtg     60
gtggtggtgg tgtttattac gctggatgat gtagtc                              96

<210> SEQ ID NO 104
<211> LENGTH: 95
<212> TYPE: DNA
<213> ORGANISM: Artificial Sequence
<220> FEATURE:
<223> OTHER INFORMATION: Synthetic polynucleotide

<400> SEQUENCE: 104
```
aagaaggaga tataccgatg ttcgacttca acgaggttag cagccggatc tcagtggtgg    60
tggtggtggt ggttttgacg aaaggcaata taatc                              95

<210> SEQ ID NO 105
<211> LENGTH: 92
<212> TYPE: DNA
<213> ORGANISM: Artificial Sequence
<220> FEATURE:
<223> OTHER INFORMATION: Synthetic polynucleotide

<400> SEQUENCE: 105
aagaaggaga tataccgatg tctagctcta cgggtacgtt agcagccgga tctcagtggt    60
ggtggtggtg gtggacctgg attggatcga tg                                 92

<210> SEQ ID NO 106
<211> LENGTH: 90
<212> TYPE: DNA
<213> ORGANISM: Artificial Sequence
<220> FEATURE:
<223> OTHER INFORMATION: Synthetic polynucleotide

<400> SEQUENCE: 106
aagaaggaga tataccgatg gccgagatgt tcaacggtta gcagccggat ctcagtggtg    60
gtggtggtgg tgggggatga tgggctcgac                                    90

<210> SEQ ID NO 107
<211> LENGTH: 92
<212> TYPE: DNA
<213> ORGANISM: Artificial Sequence
<220> FEATURE:
<223> OTHER INFORMATION: Synthetic polynucleotide

<400> SEQUENCE: 107
aagaaggaga tataccgatg cgtcgcagtg gtaattacgt tagcagccgg atctcagtgg    60
tggtggtggt ggtgggcgaa aggtgcaaac ag                                 92

<210> SEQ ID NO 108
<211> LENGTH: 90
<212> TYPE: DNA
<213> ORGANISM: Artificial Sequence
<220> FEATURE:
<223> OTHER INFORMATION: Synthetic polynucleotide

<400> SEQUENCE: 108
aagaaggaga tataccgatg gccctgaccg aagaggttag cagccggatc tcagtggtgg    60
tggtggtggt ggatggacat cgggtaaacc                                    90

<210> SEQ ID NO 109
<211> LENGTH: 299
<212> TYPE: PRT
<213> ORGANISM: Escherichia coli

<400> SEQUENCE: 109

Met Asp Phe Pro Gln Gln Leu Glu Ala Cys Val Lys Gln Ala Asn Gln
1               5                   10                  15

Ala Leu Ser Arg Phe Ile Ala Pro Leu Pro Phe Gln Asn Thr Pro Val
            20                  25                  30

Val Glu Thr Met Gln Tyr Gly Ala Leu Leu Gly Gly Lys Arg Leu Arg
        35                  40                  45

Pro Phe Leu Val Tyr Ala Thr Gly His Met Phe Gly Val Ser Thr Asn
    50                  55                  60

```
Thr Leu Asp Ala Pro Ala Ala Val Glu Cys Ile His Ala Tyr Ser
 65                  70                  75                  80

Leu Ile His Asp Asp Leu Pro Ala Met Asp Asp Asp Leu Arg Arg
                 85                  90                  95

Gly Leu Pro Thr Cys His Val Lys Phe Gly Glu Ala Asn Ala Ile Leu
            100                 105                 110

Ala Gly Asp Ala Leu Gln Thr Leu Ala Phe Ser Ile Leu Ser Asp Ala
        115                 120                 125

Asp Met Pro Glu Val Ser Asp Arg Asp Arg Ile Ser Met Ile Ser Glu
    130                 135                 140

Leu Ala Ser Ala Ser Gly Ile Ala Gly Met Cys Gly Gly Gln Ala Leu
145                 150                 155                 160

Asp Leu Asp Ala Glu Gly Lys His Val Pro Leu Asp Ala Leu Glu Arg
                165                 170                 175

Ile His Arg His Lys Thr Gly Ala Leu Ile Arg Ala Ala Val Arg Leu
            180                 185                 190

Gly Ala Leu Ser Ala Gly Asp Lys Gly Arg Arg Ala Leu Pro Val Leu
        195                 200                 205

Asp Lys Tyr Ala Glu Ser Ile Gly Leu Ala Phe Gln Val Gln Asp Asp
    210                 215                 220

Ile Leu Asp Val Val Gly Asp Thr Ala Thr Leu Gly Lys Arg Gln Gly
225                 230                 235                 240

Ala Asp Gln Gln Leu Gly Lys Ser Thr Tyr Pro Ala Leu Leu Gly Leu
                245                 250                 255

Glu Gln Ala Arg Lys Lys Ala Arg Glu Leu Ile Asp Asp Ala Arg Gln
            260                 265                 270

Ser Leu Lys Gln Leu Ala Glu Gln Ser Leu Asp Thr Ser Ala Leu Glu
        275                 280                 285

Ala Leu Ala Asp Tyr Ile Ile Gln Arg Asn Lys
    290                 295

<210> SEQ ID NO 110
<211> LENGTH: 393
<212> TYPE: PRT
<213> ORGANISM: Taxus canadensis

<400> SEQUENCE: 110

Met Ala Tyr Thr Ala Met Ala Ala Gly Thr Gln Ser Leu Gln Leu Arg
 1               5                  10                  15

Thr Val Ala Ser Tyr Gln Glu Cys Asn Ser Met Arg Ser Cys Phe Lys
                20                  25                  30

Leu Thr Pro Phe Lys Ser Phe His Gly Val Asn Phe Asn Val Pro Ser
            35                  40                  45

Leu Gly Ala Ala Asn Cys Glu Ile Met Gly His Leu Lys Leu Gly Ser
        50                  55                  60

Leu Pro Tyr Lys Gln Cys Ser Val Ser Ser Lys Ser Thr Lys Thr Met
 65                  70                  75                  80

Ala Gln Leu Val Asp Leu Ala Glu Thr Glu Lys Ala Glu Gly Lys Asp
                 85                  90                  95

Ile Glu Phe Asp Phe Asn Glu Tyr Met Lys Ser Lys Ala Val Ala Val
            100                 105                 110

Asp Ala Ala Leu Asp Lys Ala Ile Pro Leu Glu Tyr Pro Glu Lys Ile
        115                 120                 125

His Glu Ser Met Arg Tyr Ser Leu Leu Ala Gly Gly Lys Arg Val Arg
```

-continued

```
                130                 135                 140
Pro Ala Leu Cys Ile Ala Ala Cys Glu Leu Val Gly Gly Ser Gln Asp
145                 150                 155                 160

Leu Ala Met Pro Thr Ala Cys Ala Met Glu Met Ile His Thr Met Ser
                165                 170                 175

Leu Ile His Asp Asp Leu Pro Cys Met Asp Asn Asp Asp Phe Arg Arg
            180                 185                 190

Gly Lys Pro Thr Asn His Lys Val Phe Gly Glu Asp Thr Ala Val Leu
            195                 200                 205

Ala Gly Asp Ala Leu Leu Ser Phe Ala Phe Glu His Ile Ala Val Ala
            210                 215                 220

Thr Ser Lys Thr Val Pro Ser Asp Arg Thr Leu Arg Val Ile Ser Glu
225                 230                 235                 240

Leu Gly Lys Thr Ile Gly Ser Gln Gly Leu Val Gly Gly Gln Val Val
                245                 250                 255

Asp Ile Thr Ser Glu Gly Asp Ala Asn Val Asp Leu Lys Thr Leu Glu
            260                 265                 270

Trp Ile His Ile His Lys Thr Ala Val Leu Leu Glu Cys Ser Val Val
            275                 280                 285

Ser Gly Gly Ile Leu Gly Gly Ala Thr Glu Asp Glu Ile Ala Arg Ile
            290                 295                 300

Arg Arg Tyr Ala Arg Cys Val Gly Leu Leu Phe Gln Val Val Asp Asp
305                 310                 315                 320

Ile Leu Asp Val Thr Lys Ser Ser Glu Glu Leu Gly Lys Thr Ala Gly
                325                 330                 335

Lys Asp Leu Leu Thr Asp Lys Ala Thr Tyr Pro Lys Leu Met Gly Leu
            340                 345                 350

Glu Lys Ala Lys Glu Phe Ala Ala Glu Leu Ala Thr Arg Ala Lys Glu
            355                 360                 365

Glu Leu Ser Ser Phe Asp Gln Ile Lys Ala Ala Pro Leu Leu Gly Leu
            370                 375                 380

Ala Asp Tyr Ile Ala Phe Arg Gln Asn
385                 390
```

MICROBIAL ENGINEERING FOR THE PRODUCTION OF ISOPRENOIDS

RELATED APPLICATION

This application claims the benefit under 35 U.S.C. § 119(e) of U.S. Provisional Application No. 62/677,421, filed on May 29, 2018, and entitled "MICROBIAL ENGINEERING FOR THE PRODUCTION OF ISOPRENOIDS," which is incorporated herein by reference in its entirety for all purposes.

GOVERNMENT INTEREST

This invention was made with Government support under Grant No. DE-SC0008744 and DE-EE0007531 awarded by the Department of Energy. The Government has certain rights in the invention.

FIELD

Disclosed herein are cells, compositions and methods for the production of isoprenoid precursors and isoprenoids through biosynthesis.

BACKGROUND

Isoprenoids, or terpenoids/terpenes, are a class of natural products found in almost all living organisms, comprising of more than 50,000 molecules.[1] Isoprenoids have uses such as pharmaceuticals, pigments, flavors, aromas, nutraceuticals and biofuels.[1] Due to their many and varied applications, isoprenoids are a family of molecules of great industrial significance.

Isoprenoids exist in nature in only small quantities, thus making their extraction and purification in sufficient quantities difficult. Furthermore, their chemical synthesis is complicated and costly.

SUMMARY

Isoprenoid biosynthesis has thus far been dependent on pathways inextricably linked to glucose metabolism. These pathways suffer from inherent limitations due to their length, complex regulation and extensive cofactor requirements. Disclosed herein is a novel, synthetic isoprenoid pathway that overcomes these limitations. This Isopentenol Utilization Pathway (IUP) can produce isopentenyl diphosphate or dimethylallyl diphosphate, the main precursors to isoprenoid synthesis, through sequential phosphorylation of isopentenol isomers isoprenol or prenol.

Disclosed herein are cells engineered to produce isoprenoid precursors and/or isoprenoids. These cells include one or more recombinantly expressed enzymes that phosphorylate isoprenol and/or prenol to produce isopentenyl monophosphate (IP) and/or dimethylallyl monophosphate (DMAP). Any enzyme that phosphorylates prenol and/or isoprenol may be used. Amino-alcohol kinases, amide-alcohol kinases, kinases that phosphorylate short-chain alcohols, and/or phosphotransferases with a phosphate group as an acceptor (enzyme class 2.7.4) can all be used to phosphorylate isoprenol and/or prenol. Non-limiting examples of recombinantly expressed enzymes that can phosphorylate prenol and/or isoprenol include choline kinase, isopentenyl phosphate kinase, glycerol kinase, mevalonate kinase, homoserine kinase, pantoate kinase, ceramide kinase, ethanolamine kinase, undecaprenol kinase, phosphomevalonate kinase, farnesyl-diphosphate kinase, and farnesyl-phosphate kinase.

The recombinantly expressed enzyme may also be a heterologous enzyme. In one embodiment, the recombinantly expressed enzyme that phosphorylates isoprenol and prenol is choline kinase. In some embodiments, the choline kinase is from S. cerevisiae. In some embodiments, the isopentenyl phosphate kinase is from H. volcanii, M. thermoautotrophicus, M. janaschii, A. thaliana, or T. acidophilium. In some embodiments, the glycerol kinase is from E. coli. In some embodiments, the mevalonate kinase is from S. cerevisiae, and/or the homoserine kinase is from S. cerevisiae.

The recombinantly expressed enzyme can be a bacterial enzyme, an archaeal enzyme, a yeast enzyme, and/or a mammalian enzyme. In some embodiments, the recombinantly expressed enzyme is an enzyme from S. cerevisiae, Y. lipolytica, and/or E. coli.

The enzymes disclosed herein may be expressed in any prokaryotic or eukaryotic cell. Non-limiting examples include bacterial cells, archaeal cells, insect cells, yeast cells, and mammalian cells. In some embodiments, the recombinantly expressed enzymes are expressed in S. cerevisiae, Y. lipolytica, and/or E. coli.

The engineered cells described herein can produce isoprenoid precursors, for example, isopentenyl pyrophosphate (IPP) and/or dimethylallyl pyrophosphate (DMAPP). IP can be converted to IPP by choline kinase, isopentenyl phosphate kinase, glycerol kinase, mevalonate kinase, homoserine kinase, pantoate kinase, ceramide kinase, ethanolamine kinase, undecaprenol kinase, phosphomevalonate kinase, farnesyl-diphosphate kinase, and/or farnesyl-phosphate kinase. DMAP can be converted to DMAPP by choline kinase, isopentenyl phosphate kinase, glycerol kinase, mevalonate kinase, homoserine kinase, pantoate kinase, ceramide kinase, ethanolamine kinase, undecaprenol kinase, phosphomevalonate kinase, farnesyl-diphosphate kinase, and/or farnesyl-phosphate kinase. In some embodiments, IP is converted to IPP by choline kinase or isopentenyl phosphate kinase (IPK). In some embodiments, DMAP is converted to DMAPP by choline kinase or IPK.

The engineered cells disclosed herein may also express an isomerization enzyme that converts IPP to DMAPP and vice versa. Isopentenyl pyrophosphate isomerase (IDI) is an example of an isomerization enzyme that can be used to convert IPP to DMAPP and vice versa.

In other embodiments, the isoprenol and the prenol are present at a ratio that produces IPP and/or DMAPP in a two-step phosphorylation, so that isomerization of IPP and/or DMAPP is not required for further isoprenoid production. In some embodiments, the ratio of isoprenol to prenol is between 1:10 and 10:1.

In some embodiments, the engineered cells disclosed herein may include one or more enzymes that convert the IP, DMAP, IPP and/or DMAPP to an isoprenoid product.

Also disclosed herein are methods for producing an isoprenoid precursor. The method includes culturing any of the engineered cells described herein under conditions that result in the production of an isoprenoid precursor.

Further disclosed herein are synthetic, in vitro, compositions for the production of isoprenoid precursors such as, for example, IPP and/or DMAPP. These compositions include prenol and/or isoprenol, and one or more enzymes that convert isoprenol to IP, and/or convert prenol to DMAP. Enzymes that can be used in the composition to convert isoprenol and prenol to IP and DMAP, respectively, include amino-alcohol kinases, amide-alcohol kinases, kinases that phosphorylate short-chain alcohols, and phosphotransferases with a phosphate group as an acceptor (enzyme class 2.7.4). Non-limiting examples include choline kinase, isopentenyl phosphate kinase, glycerol kinase, mevalonate kinase, homoserine kinase, pantoate kinase, ceramide kinase, ethanolamine kinase, undecaprenol kinase, phosphomevalonate kinase, farnesyl-diphosphate kinase, and farnesyl-phosphate kinase. In some embodiments, the choline kinase is from *S. cerevisiae*; the isopentenyl phosphate kinase is from *H. volcanii, M. thermoautotrophicus, M. janaschii, A. thaliana*, or *T. acidophilium*; the glycerol kinase is from *E. coli*; the mevalonate kinase is from *S. cerevisiae*; and/or the homoserine kinase is from *S. cerevisiae*.

The enzymes can be bacterial enzymes, archaeal enzymes, yeast enzymes, and/or mammalian enzymes. In some embodiments, the enzyme is choline kinase is from *S. cerevisiae, Y. lipolytica*, and/or *E. coli*. The enzymes of the synthetic composition described herein can be in liquid solution or suspension and/or immobilized in or on the surface of a gel or solid.

In some embodiments of the synthetic, in vitro, composition disclosed herein, IP is converted to IPP by choline kinase, isopentenyl phosphate kinase, glycerol kinase, mevalonate kinase, homoserine kinase, pantoate kinase, ceramide kinase, ethanolamine kinase, undecaprenol kinase, phosphomevalonate kinase, farnesyl-diphosphate kinase, and/or farnesyl-phosphate kinase. In some embodiments, DMAP is converted to DMAPP by choline kinase, isopentenyl phosphate kinase, glycerol kinase, mevalonate kinase, homoserine kinase, pantoate kinase, ceramide kinase, ethanolamine kinase, undecaprenol kinase, phosphomevalonate kinase, farnesyl-diphosphate kinase, and/or farnesyl-phosphate kinase. In some embodiments, IP is converted to IPP by choline kinase or IPK and/or DMAP is converted to DMAPP by choline kinase or IPK.

The synthetic, in vitro compositions disclosed herein may also include one or more isomerization enzymes. A non-limiting example of an isomerization enzyme that can be used in the composition is isopentenyl pyrophosphate isomerase (IDI). The synthetic, in vitro, compositions can also produce isoprenoid precursors in the absence of an isomerization enzyme. In some embodiments of the synthetic composition, the isoprenol and the prenol are present at a ratio that produces IPP and/or DMAPP in a two-step phosphorylation, and isomerization of IPP and/or DMAPP is not required for further isoprenoid production. The ratio of isoprenol to prenol can be anywhere between 1:10 and 10:1. In some embodiments, the synthetic, in vitro compositions include one or more enzymes that converts the IP, DMAP, IPP and/or DMAPP to an isoprenoid product.

Also disclosed herein are nucleic acids encoding a choline kinase. In some embodiments, the nucleotide sequence is at least 90%, 91%, 92%, 93%, 94%, 95%, 96%, 97%, 98%, 99% or 100% identical to the codon optimized nucleotide sequence set forth in SEQ ID NO: 1.

In addition, methods of producing an isoprenoid precursor or isoprenoid are provided. In some embodiments, the method includes the introduction of isoprenol and/or prenol into a cell culture containing any of the engineered cells disclosed herein, under conditions that result in the production of an isoprenoid precursor or isoprenoid. In some embodiments, the cell expresses an isoprenoid synthesis pathway that converts the IP, DMAP, IPP and/or DMAPP to an isoprenoid product. Further disclosed are methods of producing an isoprenoid precursor or isoprenoid comprising contacting any engineered cell disclosed herein with isoprenol and/or prenol under conditions that result in the production of an isoprenoid precursor or isoprenoid. In some embodiments, the cell expresses an isoprenoid synthesis pathway that converts the IP, DMAP, IPP and/or DMAPP to an isoprenoid product.

Also provided are methods of producing an isoprenoid precursor or isoprenoid in vitro. This method includes incubating a synthetic, in vitro, composition described herein under conditions that result in the production of an isoprenoid precursor or isoprenoid. In some embodiments, the composition includes enzymes of an isoprenoid synthesis pathway that convert the IP, DMAP, IPP and/or DMAPP to an isoprenoid product.

The synthetic, in vitro compositions disclosed herein may also include one or more isomerization enzymes. A non-limiting example of an isomerization enzyme that can be used in the composition is isopentenyl pyrophosphate isomerase (IDI). The synthetic, in vitro, compositions can also produce isoprenoid precursors in the absence of an isomerization enzyme. In some embodiments of the synthetic composition, the isoprenol and the prenol are present at a ratio that produces IPP and/or DMAPP in a two-step phosphorylation, and isomerization of IPP and/or DMAPP is not required for further isoprenoid production. The ratio of isoprenol to prenol can be anywhere between 1:10 and 10:1. In some embodiments, the synthetic, in vitro compositions include one or more enzymes that converts the IP, DMAP, IPP and/or DMAPP to an isoprenoid product.

Also provided are cells engineered to produce an isoprenoid precursor. In some embodiments, the cell expresses one or more recombinantly expressed enzymes that phosphorylate isoprenol and/or prenol to produce isopentenyl diphosphate (IPP) and/or dimethylallyl diphosphate (DMAPP). In some embodiments the cell is a microbial cell. In some embodiments, the one or more recombinantly expressed enzymes includes an amino acid sequence that is at least 50% identical to the amino acid sequence of SEQ ID NO: 96 and capable of catalyzing the synthesis of IPP and DMAPP from isoprenol and/or prenol.

In some embodiments, the enzyme capable of catalyzing the synthesis of IPP and DMAPP from isoprenol and/or prenol includes from 1 to about 20 amino acid modifications with respect to SEQ ID NO: 96, the amino acid modifications increasing enzyme productivity for synthesis of IPP and DMAPP from isoprenol and/or prenol. In some embodiments, the enzyme capable of catalyzing the synthesis of IPP and DMAPP from isoprenol and/or prenol includes from 1 to about 10 amino acid modifications with respect to SEQ ID NO: 96, the amino acid modifications increasing enzyme productivity for synthesis of IPP and DMAPP from isoprenol and/or prenol.

In some embodiments, the enzyme capable of catalyzing the synthesis of IPP and DMAPP from isoprenol and/or prenol includes an amino acid sequence that is at least 70% identical to SEQ ID NO: 96. In some embodiments, the enzyme capable of catalyzing the synthesis of IPP and DMAPP from isoprenol and/or prenol includes an amino acid sequence that is at least 80% identical to SEQ ID NO: 96. In some embodiments, the enzyme capable of catalyzing the synthesis of IPP and DMAPP from isoprenol and/or prenol includes an amino acid sequence that is at least 90% identical to SEQ ID NO: 96.

In some embodiments, the cell further expresses a recombinant isopentenyl phosphate kinase. In some embodiments, the isopentenyl phosphate kinase includes an amino acid sequence that is at least 70% identical to the amino acid sequence of SEQ ID NO: 97.

In some embodiments, the isopentenyl phosphate kinase includes from 1 to about 20 amino acid modifications with respect to SEQ ID NO: 97, the amino acid modifications increasing enzyme productivity for synthesis of IPP and DMAPP from IP and DMAP. In some embodiments, the isopentenyl phosphate kinase includes from 1 to about 10 amino acid modifications with respect to SEQ ID NO: 97, the amino acid modifications increasing enzyme productivity for synthesis of IPP and DMAPP from IP and DMAP.

In some embodiments, the isopentenyl phosphate kinase includes an amino acid sequence that is at least 80% identical to the amino acid sequence of SEQ ID NO: 97. In some embodiments, the isopentenyl phosphate kinase includes an amino acid sequence that is at least 90% identical to the amino acid sequence of SEQ ID NO: 97.

In some embodiments, the cell further includes an overexpression of isopentenyl pyrophosphate isomerase (IDI).

In some embodiments, the microbial cell is a prokaryotic cell or eukaryotic cell. In some embodiments, the microbial cell is a bacterial cell. In some embodiments, the microbial cell is *Escherichia* spp., *Bacillus* spp., *Corynebacterium* spp., *Rhodobacter* spp., *Zymomonas* spp., *Vibrio* spp., *Pseudomonas* spp., *Agrobacterium* spp., *Brevibacterium* spp., and *Paracoccus* spp. In some embodiments, the microbial cell is *Escherichia coli* or *Corynebacterium glutamicum*. In some embodiments, the microbial cell is a yeast. In some embodiments, the yeast is selected from *S. cerevisiae* and *Y. lipolytica*.

In some embodiments, the cell further includes one or more enzymes that converts the IPP and/or DMAPP to an isoprenoid product.

In some embodiments, the cell expresses a recombinant prenyl transferase enzyme. In some embodiments, the prenyl transferase is geranyldiphosphate synthase (GPPS), farnesyldiphosphate synthase (FPPS), or geranylgeranyldiphosphate synthase (GGPPS).

In some embodiments, the cell further includes an overexpression of one or more MEP pathway genes or MVA pathway genes.

In some embodiments, the cell further expresses a terpenoid synthase enzyme.

In some embodiments, the cell produces a terpenoid selected from: Farnesene, Amorphadiene, Artemisinic acid, Artemisinin, Bisabolol, Bisabolene, alpha-Sinensal, beta-Thujone, Camphor, Carveol, Carvone, Cineole, Citral, Citronellal, Cubebol, Geraniol, Limonene, Menthol, Menthone, Myrcene, Nootkatone, Nootkatol, Patchouli, Piperitone, Rose oxide, Sabinene, Steviol, Steviol glycoside, Taxadiene, Thymol, and Valencene.

Also provided are methods of producing an isoprenoid precursor or downstream product thereof. In some embodiments, the method includes a cell disclosed herein and culturing the cell with fed prenol or isoprenol under conditions that result in production of the isoprenoid precursor or downstream product thereof.

In some embodiments, the microbial cell is cultured with a C1, C2, C3, C4, C5, or C6 carbon source. In some embodiments, the carbon source is glucose or glycerol.

In some embodiments, the microbial cell is cultured at a temperature of from about 22° to about 37° C. In some embodiments, the microbial cell is cultured at a temperature of from about 30° to about 37° C.

In some embodiments, the culturing step is a fed-batch process including a first phase where bacterial biomass is created, followed by a production phase. In some embodiments, the prenol and/or isoprenol is added at the production phase.

In some embodiments, the culture is at least about 100 L. In some embodiments, the culture is at least about 1,000 L. In some embodiments, the culture is at least about 10,000 L. In some embodiments, the culture is at least about 100,000 L.

In some embodiments, the culture is maintained under aerobic or microaerobic conditions.

In some embodiments, the production phase includes feeding a nitrogen source and a carbon source.

In some embodiments, the method further includes recovering the isoprenoid precursor or downstream product thereof.

Also provided are methods for making an industrial or consumer product. In some embodiments, the method includes incorporating the downstream product made according to a method disclosed herein into said industrial or consumer product. In some embodiments, the industrial or consumer product is a flavor product, a fragrance product, a sweetener, a cosmetic, a cleaning product, a detergent or soap, or a pest control product. In some embodiments, the industrial or consumer product is a food, beverage, texturant, pharmaceutical, tobacco product, nutraceutical, oral hygiene product, or cosmetic product.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

(FIG. 3A) Time-courses to determine the linear region of the enzyme, (FIG. 3B) Determination of the optimum pH, (FIG. 3C) Determination of the optimum temperature. Reaction rates in (FIG. 3B) & (FIG. 3C) are reported as means±SD (n=3). Isoprenol is indicated by smaller filled circles (and in most cases presents the upper line in these figures), while prenol is represented by larger filled circles (and in most cases presents the lower line in these figures).

FIGS. 9A-9E. Development of the Isopentenol Utilization Pathway and in vitro characterization of choline kinase. (FIG. 9A) The IUP can produce the basic isoprenoid metabolic intermediates, IPP and DMAPP in two steps using isoprenol or prenol respectively as feedstock. The steps are catalyzed by a promiscuous kinase and isopentenyl phosphate kinase (IPK). IPP and DMAPP can then be interconverted via isopentenyl-diphosphate isomerase (idi). IPP and DMAPP act as the precursor molecules for larger prenyl diphosphates and eventually isoprenoids. (FIG. 9B) Enzymes screened in this work. (FIGS. 9C & 9D) Results of overnight screen to identify a suitable promiscuous kinase using isoprenol or prenol as a substrate respectively. (FIG. 9E) Kinetic analysis of choline kinase from *Saccharomyces cerevisiae* (scCK) at a fixed ATP concentration for the determination of kcat and Km with regards to isopentenol substrate. Reaction rates are reported as means±SD (n=3). In FIG. 9C, the left bar in each set of bars represents IP, and the right bar in each set of bars represents IPP. In FIG. 9D, the left bar in each set of bars represents DMAP, and the right bar in each set of bars represents DMAPP. In FIG. 9E, the upper line shows results with prenol, and the lower line shows results with isoprenol.

(FIG. 10A) Lycopene content in strains containing the IUP under the control of a low strength constitutive promoter (pro4) or a strong inducible promoter (pTET) induced with 20 ng/mL of aTc. This was compared to the control strain containing only the lycopene production plasmid (pAC-LYCipi), without the IUP plasmid or addition of either isopentenol (FIG. 10B) The effect of ipk gene on the synthesis of lycopene. (FIG. 10C) The effect of the pro4IUP pathway on intracellular levels of IPP/DMAPP compared to the control strain containing only pAC-LYCipi. In FIG. 10A, the left bar in each set of bars (other than control) represents pro4, and the right bar in each set of bars (other than control) represents pTET.

(FIG. 11A) Levels of unlabeled MEC, (FIG. 11B) Levels of labeled IPP/DMAPP, (FIG. 11C) Levels of unlabeled IP/DMAP, (FIG. 11D) Levels of unlabeled IPP/DMAPP, (FIG. 11E)&(FIG. 11F) Labeling patterns for 3-phosphoglycerate (3PG) and phosphoenolpyruvate (PEP) respectively in the pro4IUPi strain over the first 60 min. All experimental values are normalized to dry cell weight and represent the mean±SD of three biological replicates. In FIG. 11E and FIG. 11F, the portions of each stacked bar are, from bottom to top: M0, M+1, M+2, and M+3.

(FIG. 12A) Isoprenoid product titers after culturing for 48 h expressing the IUP under the control of the pro4 or pTET promoters, along with a control expressing only the downstream cassette. Concentrations are expressed as equivalents of the internal standard caryophyllene (FIG. 12B) Lycopene content in strains using an endogenous constitutive promoter with various copy number plasmids (pAC-LYCipi ~15, p20-LYCipi ~20, pUC-LYCipi >100) and under the control of a strong inducible promoter in a plasmid with copy number ~5 (p5T7-LYCipi). (FIG. 12C)&(FIG. 12D) Concentrations of metabolic intermediates for strains expressing the IU pathway along with a plasmid for the production of (FIG. 12C) lycopene (p5T7-LYCipi) or (FIG. 12D) taxadiene (p5T7tds-ggpps) respectively. All metabolite and product concentrations are reported as means±SD of three biological replicates. In FIG. 12A and FIG. 12B, the left bar in each set of bars represents control, the middle bar in each set of bars represents pro4, and the right bar in each set of bars represents pTET.

(FIG. 13F) Titers of taxadiene produced after 48 h, (FIG. 13G) Labeled taxadiene mass spectrum, (FIG. 13H) Unlabeled taxadiene mass spectrum. All metabolite and product concentrations are reported as means±SD of three biological replicates. In FIG. 13A and FIG. 13B, the portions of each stacked bar are, from bottom to top: M1, M2, M3, M4, and M5. FIG. 13C, the portions of each stacked bar are, from bottom to top: M3, M4, M5, M6, M7, M8, M9, and M10. FIG. 13D, the portions of each stacked bar are, from bottom to top: M0, M1, M2, M3, M4, M5, M6, M7, M8, M9, M10, M11, M12, M13, M14, and M15. FIG. 13E, the portions of each stacked bar are, from bottom to top: M0, M1, M2, M3, M4, M5, M6, M7, M8, M9, M10, M11, M12, M13, M14, M15, M16, M17, M18, M19 and M20.

(FIG. 14A) Glucose concentration and optical density over time. (FIG. 14B) Lycopene content over time. (FIG. 14C) Cumulative IPP flux calculated from lycopene productivity and comparison to some of the highest reported isoprenoid fluxes in the literature. (FIG. 14D) Cell pellets taken from one CrtE bioreactor at different time points. All values represent the mean±SD based on samples taken from 3 bioreactor runs.

(FIG. 16A) IPK activity towards IP (dark) and DMAP (light) was measured by monitoring ATP consumption coupled to the PK-LDH NADH assay in the presence of 10 mM ATP. (FIG. 16B) Activity towards ATP in the presence of 200 uM IP (dark) or DMAP (light). (FIG. 16C) Activity of GGPPS towards FPP and IPP as measured by the liberation of pyrophosphate. Referencing the legend from top to bottom, are: 50, 25, 12.5, 6.25, 3.1, 1.6 µM FPP. In FIG. 16C, at the IPP concentration 50 µM mark, the top line represents 3.1 µM FPP and the bottom line represents 50 µM FPP. (FIG. 16D) Activity of TDS towards GGPP as measured by the pyrophosphate assay.

(FIG. 17A) Isoprenoid titers reported as normalized to the area and concentration of the internal standard β-caryophyllene. All of the systems used the enzymes CK, IPK, IDI, and IspA. In the case of taxadiene, GGPPS and TDS were included. In the case of valencene, amorphadiene, and limonene only their respective synthases was added. Each protein was mixed together at 50 µg/mL with 10 mM $MgCl_2$, 2 mM $MnCl_2$, 2 mM DTT, 10 mM ATP, and 25 mM isopentenol composed of either pure isoprenol, pure prenol, or a mixture of isoprenol and prenol at a 3:1 mole ratio. Enzyme systems were all incubated at 30° C. at pH 7.4 for 24 h. (FIG. 17B) Intermediates from the taxadiene run using 5 µg/mL of each enzyme and pure isoprenol. (FIG. 17C-17F). Electron Ionization mass spectra for each product as detected in panel FIG. 17A. In FIG. 17A, from left to right, the bars in each set of bars represent taxadiene (left), amorphadiene (second from left), valencene (third from left), and limonene (right). In FIG. 17B, at the 4 hour mark, from top to bottom, the lines represent IPP/DMAPP (top), FPP (second from top), GPP (third from top), IP (fourth from top), and GGPP (bottom).

FIG. 18A. Enzyme concentrations used at each level. FIG. 18. B-F. Intermediate concentrations as a single enzyme concentration was changed: FIG. 18B. CK, FIG. 18C. IPK, FIG. 18D. IDI, FIG. 18E. IspA, FIG. 18F. GGPPS. In FIGS. 18B-18F, the left bar in each set of bars (dark) represents low enzyme concentration, the middle bar in each set of bars represents medium enzyme concentration, and the right bar in each set of bars (light) represents high enzyme concentration.

FIG. 20B. Optimization of TDS concentration.

FIG. 21A. Inhibition by ATP and ADP. FIG. 21B. Metal ion dependence. FIG. 21C. Reducing agent. FIG. 21D. Addition of pyruvate kinase (PK) and phosphoenolpyruvate (PEP) ATP recycling system with 1 mM ATP, or inorganic pyrophosphatase (IPPase), or both. In FIG. 21A, the left bar in each set of bars represents ATP, and the right bar in each set of bars represents ADP.

FIG. 22A. The effect of the molar ratio of isoprenol to prenol using the taxadiene producing multi-enzyme system without IDI. FIG. 22B. The production of alternative isoprenoids using the optimized multi-enzyme system with IDI and isoprenol only.

FIG. 23A. Time profiles were constructed for taxadiene production using the optimized enzyme system (1×) and multiples of each enzymes concentration (e.g., all enzyme concentrations were doubled for 2×). From top to both, 10×, 5×, 2×, 1×. FIG. 23B. The linear relationship between the rate of taxadiene formation and the enzyme concentration.

In FIGS. 25B-25F, the left bar in each set of bars represents low enzyme concentration, the middle bar in each set of bars represents medium enzyme concentration, and the right bar in each set of bars represents high enzyme concentration.

FIG. 26A. GGPPS flux compared to relative enzyme level. Midpoint concentration of each enzyme is scaled to 1. FIGS. 26B-26F. Elasticities calculated for the multi-system pathway using lin-log kinetics in reference to state 3 using the maximum connectivity assumption. All experiments were performed in triplicate (error bars 1σ). In FIG. 26A, at relative enzyme concentration mark 5, from top to bottom, the lines represent IspA (top), CK (second from top), IDI (third from top), GGPPS (fourth from top), and IPK (bottom).

FIG. 27B. Optimization of TDS concentration. All experiments were performed in triplicate (error bars 1σ).

FIG. 28A. Inhibition by ATP or ADP. ATP concentration was varied from 0-20 mM. ADP concentration was varied from 0-20 mM in the presence of 10 mM ATP FIG. 28B. The dependence of the reaction on the metal ion, Magnesium or on the reducing agent, DTT. FIG. 28C. Varying of the isoprenol to prenol molar ratio in the multi-enzyme system without IDI. FIG. 28D. The production of various isoprenoids using the optimized enzyme system. All experiments were performed in triplicate (error bars 1σ). In FIG. 28A, the left bar in each set of bars represents ATP, and the right bar in each set of bars represents ADP. In FIG. 28B, the left bar in each set of bars represents magnesium (Mg), and the right bar in each set of bars represents DTT.

FIG. 29A. Time profiles over 9 h for taxadiene production. Enzymes were resuspended at either 1× (the optimized concentration), or every enzyme was resuspended at 2, 5, or 10 fold the original concentration. FIG. 29B. The linear response of enzyme concentration to taxadiene flux. All experiments were performed in triplicate (error bars 1σ).

FIG. 30A. IPK activity towards IP (dark) and DMAP (light) was measured by monitoring ATP consumption coupled to the PK-LDH NADH assay in the presence of 10 mM ATP. FIG. 30B. Activity towards ATP in the presence of 200 uM IP (dark) or DMAP (light). FIG. 30C. Activity of GGPPS towards FPP and IPP as measured by the liberation of pyrophosphate. The legend indicates FPP concentration. Referencing the legend from top to bottom, are: 50, 25, 12.5, 6.25, 3.1, 1.6 µM FPP. In FIG. 30C, at the IPP concentration 50 µM mark, the top line represents 3.1 µM FPP and the bottom line represents 50 µM FPP. FIG. 30D. Activity of TDS towards GGPP measured by the pyrophosphate assay. All experiments were performed in triplicate (error bars 1σ).

FIG. 31A. Isoprenoid titers compared to the internal standard β-caryophyllene. All of the systems used CK, IPK, IDI, and IspA. In the case of taxadiene, GGPPS and TDS were included. In the case of valencene, amorphadiene, and limonene only their respective synthases was added. Each protein was mixed together at 50 µg/mL with 10 mM ATP, and 5 mM isopentenol composed of either pure isoprenol, pure prenol, or a mixture of isoprenol and prenol at a 3:1 mole ratio. Enzyme systems were incubated at 30° C. at pH 7.4 for 24 h. FIG. 31B. Intermediates from the taxadiene run using 5 µg/mL of each enzyme and pure isoprenol. FIG. 31C-31F. Electron Ionization mass spectra for each product as detected in FIG. 31A. The mass of major ions are indicated. In FIG. 31A, from left to right, the bars in each set of bars represent taxadiene (left), amorphadiene (second from left), valencene (third from left), and limonene (right). In FIG. 31B, at the 4 hour mark, from top to bottom, the lines represent IPP/DMAPP (top), FPP (second from top), GPP (third from top), IP (fourth from top), and GGPP (bottom).

FIG. 33A. Glucose concentration and optical density over time. FIG. 33B. Lycopene content over time. FIG. 33C. Cumulative IPP flux calculated from lycopene productivity and comparison to some of the highest reported isoprenoid fluxes in the literature. FIG. 33D. Cell pellets taken from one CrtE bioreactor at different time points. All values represent the mean±SD based on samples taken from 3 bioreactor runs.

DETAILED DESCRIPTION

Figure 1:
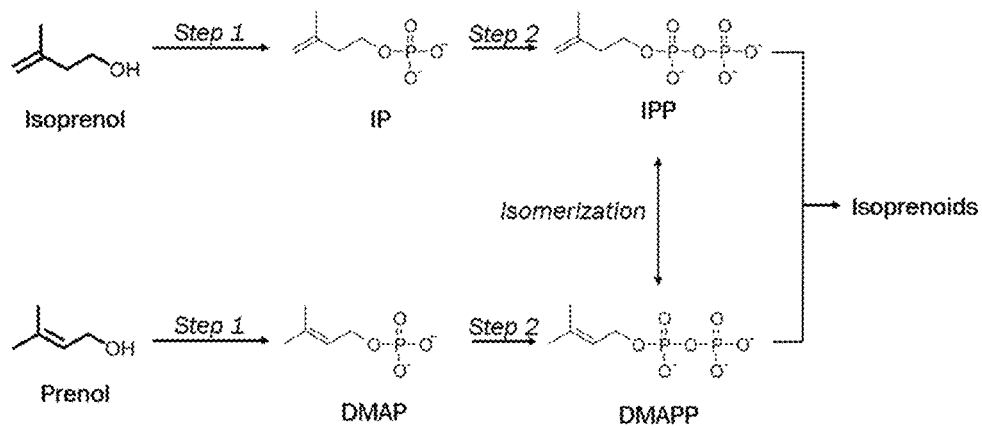
FIG. 1. The production of isoprenoid precursors (IPP and DMAPP) and subsequently all isoprenoids through the Isopentenol Utilization Pathway, starting from isoprenol or prenol.
Figure 2:
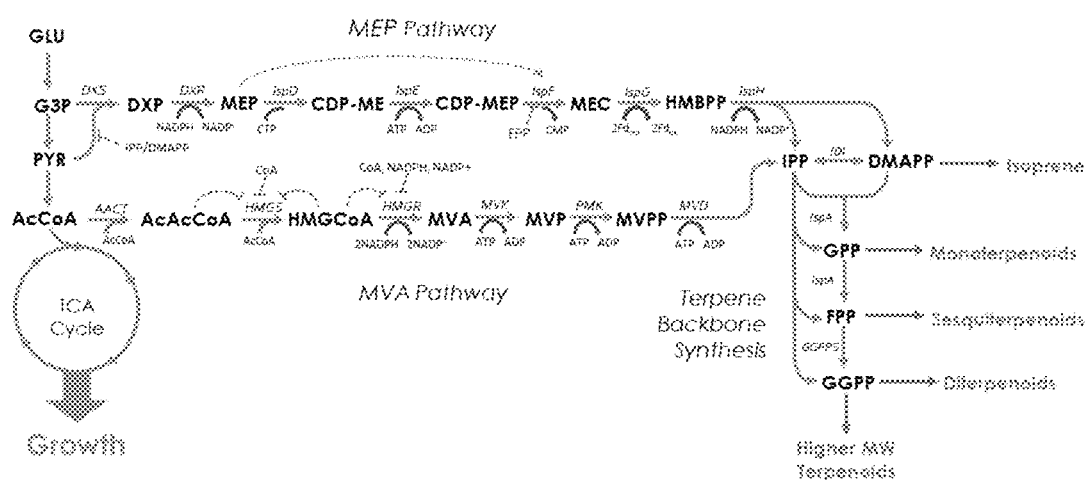
FIG. 2. The production of isoprenoid precursors (IPP and DMAPP) and subsequently all isoprenoids through one of the two natural isoprenoid pathways (MEP or MVA), starting from glucose. Intermediates in are bold font. Catalytic steps are signified using arrows, with the enzymes that catalyze each reaction in italics. The use of cofactors in reactions is indicated by curved arrows at specific reaction steps. Inhibitory (negative) effects on enzymes are shown by dashed lines ending in a "T", whereas positive effects are shown by dashed lines ending in an arrowhead.

All biologically-produced isoprenoids ultimately descend from two isoprenoid precursor molecules, isopentenyl pyrophosphate (IPP) and dimethylallyl pyrophosphate (DMAPP), both of which are $C_5$ molecules. Once IPP and DMAPP are produced, they can be used to create the backbones of higher isoprenoids, which can then be cyclized and decorated. In nature, IPP and DMAPP are produced from one of two main pathways, as shown in FIG. 2.[2] The first pathway, the mevalonate (MVA) pathway, produces them by utilizing acetyl-CoA as its starting point, whereas the second pathway, the methyl-erythritol phosphate or "non-mevalonate" (MEP or DXP) pathway, starts from the condensation of equimolar quantities of pyruvate and acetyl-CoAglyceraldehyde 3-phosphate (G3P). The MVA pathway requires 6 or 7 reaction steps to produce IPP and DMAPP respectively, while the MEP pathway produces both DMAPP and IPP at a ratio of approximately 5:1 after 7 reactions.[2,3]

These natural pathways have many limitations that must be overcome for them to perform optimally. Concerning the MEP pathway, imbalances in the supply of G3P and pyruvate can create bottlenecks leading to decreased pathway performance.[4] Furthermore, the iron-sulfur enzymes IspG and IspH are sensitive to oxygen.[5] Their inactivation leads to carbon loss, due to accumulation and excretion of metabolic intermediates, such as 2-C-methyl-D-erythritol 2,4-cyclodiphosphate (MEC).[6] Pathway intermediates or downstream products have been shown to inhibit 'gate keeper' enzymes in both the MEP and the MVA pathways, with IPP inhibiting 1-deoxy-D-xylulose 5-phosphate (DXP) synthase.[7]

Coenzyme A, acetylacetyl-CoA and HMG-CoA inhibit HMG-CoA synthase[8]; HMG, free CoA and NAD(P)+/NADPH inhibit HMG-CoA reductase[9, 10]; and IPP, DMAPP, GPP, and FPP inhibit mevalonate kinase.[11] This complex regulation can hinder attempts to up-regulate either pathway. Finally, at a system level, both the MVA and the MEP pathways require precursors and cofactors for IPP synthesis from central carbon metabolism, therefore competing with other cellular processes for resources, which can complicate attempts to further increase isoprenoid pathway flux.

Described herein is a two-step pathway for the bioconversion of isopentenols (isoprenol, also known as 3-methyl-3-buten-1-ol; and prenol, also known as 3-methyl-2-buten-1-ol) to isoprenoid precursors. All biologically-produced isoprenoids ultimately descend from two isoprenoid precursor molecules, isopentenyl pyrophosphate (IPP) and dimethylallyl pyrophosphate (DMAPP), both of which are $C_5$ molecules. Once IPP and DMAPP are produced, they can be used to create the backbones of higher isoprenoids, which can then be cyclized and decorated. For example, IPP and DMAPP may be condensed through sequential addition to generate larger precursor molecules, such as such as geranyl diphosphate (GPP, C10), farnesyl diphosphate (FPP, C15) and geranylgeranyl diphosphate (GGPP, C20). These prenyl diphosphate backbones can be further functionalized by terpene synthases and cytochrome P450 monooxygenases to produce a variety of isoprenoids.

The novel, two-step pathway disclosed herein can be used both in vivo (pathway in living cells) or in vitro (e.g., as purified or isolated enzymes in aqueous solution or immobilized on a support). IPP and DMAPP can be produced by phosphorylating isoprenol or prenol twice, respectively. Once either one has been produced, the other can be produced through an isomerization step. Once IPP and DMAPP are produced, they can be used to create the backbones of higher isoprenoids, which can then be cyclized and decorated.

In the first step of the two-step IUP, isoprenol or prenol is phosphorylated to form isopentenyl monophosphate (IP) or dimethylallyl monophosphate (DMAP), respectively. This first phosphorylation does not occur in nature. In the second step, IP or DMAP is phosphorylated again to form IPP or DMAPP, respectively. The second step of the pathway can be catalyzed by, for example, isopentenyl phosphate kinase (IPK), which is a part of the archaeal mevalonate pathway.[12]

Described herein is the construction of a novel engineered pathway for the bioconversion of isopentenols, isoprenol or prenol, to IPP or DMAPP, the main isoprenoid intermediates. In some embodiments, this pathway uses the previously unknown promiscuous activity of choline kinase for the efficient phosphorylation of isoprenol or prenol. After minimal optimization of the downstream isoprenoid pathways, an IPP/DMAPP flux comparable to some of the highest reported demonstrates the competitiveness of this new alternative pathway. Optimization of the combined IUP and downstream product-forming pathway should be simpler than the current MVA or MEP alternatives. Whereas the latter pathways require multiple unique cofactors and comprise multiple steps, the IUP is much simpler, since it only requires a single cofactor (ATP) and is comprised of only two reaction steps. The IUP does not appear to exchange carbon with central metabolism, meaning that it does not have to compete with the rest of the cell for carbon flux. Further, the downstream cassettes used in this work were unable to accommodate the flux generated by the IUP, shown by large intermediate accumulation, indicating untapped potential. As such, the Isopentenol Utilization Pathway is an important advancement in the field of isoprenoid biosynthesis.

In one aspect, described herein is a microbial cell engineered to produce an isoprenoid precursor. In some embodiments, the microbial cell expresses one or more recombinantly expressed enzymes that phosphorylate isoprenol and/or prenol to produce isopentenyl diphosphate (IPP) and/or dimethylallyl diphosphate (DMAPP). In some embodiments, the recombinantly expressed enzyme catalyzes a first phosphorylation step.

In some embodiments, the cell expresses a recombinant enzyme comprising an amino acid sequence that is 50% to 100% identical to the amino acid sequence of SEQ ID NO: 96 (*Saccharomyces cerevisiae* choline kinase) and capable of catalyzing the synthesis of IPP and/or DMAPP from isoprenol and/or prenol. In some embodiments, the recombinant enzyme is 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98%, 99%, or 100%, or any range or combination thereof, identical to the amino acid sequence of SEQ ID NO: 96 and capable of catalyzing the synthesis of IPP and DMAPP from isoprenol and/or prenol. In some embodiments, the recombinant enzyme is at least 55%, at least 60%, at least 65%, at least 70%, at least 75%, at least 76%, at least 77%, at least 70%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence of SEQ ID NO: 96 and capable of catalyzing the synthesis of IPP and DMAPP from isoprenol and/or prenol. In some embodiments, the recombinant enzyme is at least 50% identical to the amino acid sequence of SEQ ID NO: 96 and capable of catalyzing the synthesis of IPP and DMAPP from isoprenol and/or prenol.

In some embodiments, the recombinant enzyme comprises one or more amino acid modifications that increase productivity for synthesis of IPP and/or DMAPP from isoprenol and/or prenol relative to a recombinant enzyme in which the amino acids have not been modified or relative to a wildtype control. In some embodiments, the recombinant enzyme comprises from 1 to about 20 or from 1 to 10 amino acid modifications with respect to SEQ ID NO: 96. In some embodiments, the recombinant enzyme comprises from 1 to 5 amino acid modifications with respect to the amino acid sequence of SEQ ID NO: 96. In some embodiments, the recombinant enzyme comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 amino acid modifications with respect to the amino acid sequence of SEQ ID NO: 96. In some embodiments, the recombinant enzyme comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 35, at least 40, or at least 45, amino acid modifications with respect to the amino acid sequence of SEQ ID NO: 96. Amino acid modifications can be independently selected from amino acid substitutions, insertions, and deletions.

Amino acid modifications to the amino acid sequence of SEQ ID NO: 96 can be guided by enzyme structures available to one of ordinary skill in the art and/or construction of homology models. Exemplary structures are described in, e.g., Peisach et al. *Structure* 11.6 (2003): 703-13; and Malito, et al. *J Mol Biol* 364.2 (2006): 136-51. The publicly available crystal structures for choline kinase (ScCK; PDB entry: 1NW1 and 2CKO) may be used to inform amino acid modifications. For example, one or more amino acid modifications can be made to the active site or in the vicinity of the active site of the enzyme to improve the binding of a prenol, isoprenol, IP and/or DMAP substrate, and/or to improve reaction geometries of one or more of the substrates with catalytic side chains. Modification of one or more amino acids in the amino acid sequence of SEQ ID NO: 96 increases productivity for synthesis of IPP and/or DMAPP from isoprenol and/or prenol relative to a recombinant enzyme in which the amino acids have not been modified or relative to a wildtype control.

In some embodiments, the cell expresses a recombinant isopentenyl phosphate kinase. In some embodiments, the recombinant isopentenyl phosphate kinase phosphorylates IP and/or DMAP in a second phosphorylation step. While several isopentenyl phosphate kinases are disclosed herein, in some embodiments, the recombinant isopentenyl phosphate kinase comprises an amino acid sequence that is at least 70% identical to the amino acid sequence of SEQ ID NO: 97 (*Arabidopsis thaliana* IPK). In some embodiments, the recombinant isopentenyl phosphate kinase is 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98%, 99%, or 100%, or any range or combination thereof, identical to the amino acid sequence of SEQ ID NO: 97. In some embodiments, the recombinant enzyme is at least 55%, at least 60%, at least 65%, at least 70%, at least 75%, at least 76%, at least 77%, at least 70%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence of SEQ ID NO: 97. In some embodiments, the recombinant enzyme is at least 50% identical to the amino acid sequence of SEQ ID NO: 97.

In some embodiments, the recombinant isopentenyl phosphate kinase comprises one or more amino acid modifications that increase productivity for synthesis of IPP and/or DMAPP from IP and/or DMAP relative to a recombinant enzyme in which the amino acids have not been modified or relative to a wildtype control. In some embodiments, the recombinant isopentenyl phosphate kinase comprises from 1 to about 20 or from 1 to about 10 amino acid modifications with respect to SEQ ID NO: 97. In some embodiments, the recombinant isopentenyl phosphate kinase comprises from 1 to 5 amino acid modifications with respect to SEQ ID NO: 97. In some embodiments, the recombinant isopentenyl phosphate kinase comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 35, 40, 45, 50, or more than 50 amino acid modifications with respect to the amino acid sequence of SEQ ID NO: 97. In some embodiments, the recombinant isopentenyl phosphate kinase comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 35, at least 40, or at least 45, amino acid modifications with respect to the amino acid sequence of SEQ ID NO: 97. Amino acid modifications can be independently selected from amino acid substitutions, insertions, and deletions.

Amino acid modifications to the amino acid sequence of SEQ ID NO: 97, can be guided by available enzyme structures available to one of ordinary skill in the art and/or construction of homology models. Exemplary structures are described in, e.g., Mabanglo et al. *ACS Chem Biol* 5.5 (2010): 517-27 and Dellas, et al. *ACS Chem Biol* 5.6 (2010): 589-601. The publicly available crystal structure for isopentenyl kinase (PDB entry: 3LKK, 3LL9, and 3K4O) may be used to inform amino acid modifications. For example, one or more amino acid modifications can be made to the active site or in the vicinity of the active site to improve the binding of a substrate, and/or to improve reaction geometries of the substrate with catalytic side chains. Modification of one or more amino acids in the amino acid sequence of SEQ ID NO: 97 increases productivity for synthesis of IPP and/or DMAPP from isoprenol and/or prenol relative to a recombinant enzyme in which the amino acids have not been modified or relative to a wildtype control.

In some embodiments, the cell overexpresses an isopentenyl pyrophosphate isomerase (IDI), including a bacterial IDI or yeast IDI, to facilitate isomerization of one or more isoprenoid precursors. In some embodiments, IDI isomerizes IPP to DMAPP and/or DMAPP to IPP. The level of IDI is increased by overexpression of an endogenous enzyme (e.g., through gene complementation), or by overexpression of a heterologous IDI. While several isopentenyl pyrophosphate isomerases are disclosed herein, in some embodiments, the isopentenyl pyrophosphate isomerase comprises an amino acid sequence that is at least 70% identical to the amino acid sequence of SEQ ID NO: 98 (*Escherichia coli* IDI). In some embodiments, the isopentenyl pyrophosphate isomerase is 50%, 55%, 60%, 65%, 70%, 75%, 76%, 77%, 70%, 79%, 80%, 81%, 82%, 83%, 84%, 85%, 86%, 87%, 88%, 89%, 90%, 91%, 92%, 93%, 94%, 95% 96%, 97%, 98%, 99%, or 100%, or any range or combination thereof, identical to the amino acid sequence of SEQ ID NO: 98. In some embodiments, the isopentenyl pyrophosphate isomerase is at least 50%, at least 55%, at least 60%, at least 65%, at least 70%, at least 75%, at least 76%, at least 77%, at least 70%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence of SEQ ID NO: 98.

In some embodiments, the isopentenyl pyrophosphate isomerase comprises from 1 to about 20 or from 1 to about 10 amino acid modifications with respect to SEQ ID NO: 98. In some embodiments, the isopentenyl pyrophosphate isomerase comprises from 1 to 5 amino acid modifications with respect to SEQ ID NO: 98. In some embodiments, the isopentenyl pyrophosphate isomerase comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 amino acid modifications with respect to the amino acid sequence of SEQ ID NO: 98. In some embodiments, the isopentenyl pyrophosphate isomerase comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 35, at least 40, or at least 45, amino acid modifications with respect to the amino acid sequence of SEQ ID NO: 98. Amino acid modifications can be independently selected from amino acid substitutions, insertions, and deletions.

Amino acid modifications to the amino acid sequence of SEQ ID NO: 98 can be guided by available enzyme structures available to one of ordinary skill in the art and/or construction of homology models. For example, one or more amino acid modifications can be made to the active site or in the vicinity of the active site to improve the binding of substrate, and/or to improve reaction geometries of the substrate with catalytic side chains.

Modification of one or more amino acids in the amino acid sequence of SEQ ID NO: 98 increases productivity for synthesis of IPP and/or DMAPP from isoprenol and/or prenol relative to a recombinant enzyme in which the amino acids have not been modified or relative to a wildtype control.

In some embodiments, the cell comprises one or more enzymes that converts the IPP and/or DMAPP to an isoprenoid product. For example, the cell may express a recombinant prenyltransferase enzyme, such as but not limited to geranyldiphosphate synthase (GPPS), farnesyldiphosphate synthase (FPPS), or geranylgeranyldiphosphate synthase (GGPPS).

In various embodiments, the microbial cell expresses a downstream biosynthetic pathway, including but not limited to a terpenoid biosynthesis pathway.

In some embodiments, the cell expresses a downstream terpenoid synthesis pathway, e.g., comprising a terpenoid synthase enzyme. Such pathways may produce a terpenoid selected from: Farnesene, Amorphadiene, Artemisinic acid, Artemisinin, Bisabolol, Bisabolene, alpha-Sinensal, beta-Thujone, Camphor, Carveol, Carvone, Cineole, Citral, Citronellal, Cubebol, Geraniol, Limonene, Menthol, Menthone, Myrcene, Nootkatone, Nootkatol, Patchouli, Piperitone, Rose oxide, Sabinene, Steviol, Steviol glycoside, Taxadiene, Thymol, and Valencene. Other terpenoids and pathways are described in U.S. Pat. No. 9,404,130, which is hereby incorporated by reference in its entirety.

Other non-limiting aspects and embodiments of the invention are described below.

Cells Engineered to Produce an Isoprenoid Precursor

As used herein, a "cell engineered to produce an isoprenoid precursor" is a cell engineered to recombinantly express one or more enzymes that phosphorylate isoprenol and/or prenol to produce prenol to produce isopentenyl monophosphate (IP) and/or dimethylallyl monophosphate (DMAP). A recombinantly expressed enzyme, in some embodiments, can be one or more of amino-alcohol kinases, amide-alcohol kinases, kinases that phosphorylate short-chain alcohols, and phosphotransferases with a phosphate group as an acceptor (enzyme class 2.7.4). Examples of amino-alcohol kinases include ethanolamine kinase (EC 2.7.1.82). Examples of amide-alcohol kinases include ceramide kinase (EC 2.7.1.138). Examples of kinases phosphorylating short-chain alcohols include pantoate kinase (EC 2.7.1.169) and undecaprenol kinase (EC 2.7.1.66). Examples of phosphotransferases with a phosphate group as an acceptor (enzyme class 2.7.4) include polyphosphate kinase, phosphomevalonate kinase, adenylate kinase, nucleoside-phosphate kinase, deoxycytidylate kinase, nucleoside-diphosphate kinase, phosphomethylpyrimidine kinase, guanylate kinase, dTMP kinase, nucleoside-triphosphate-adenylate kinase, (deoxy)adenylate kinase, T2-induced deoxynucleotide kinase, (deoxy)nucleoside-phosphate kinase, UMP/CMP kinase, thiamine-diphosphate kinase, thiamine-phosphate kinase, 3-phosphoglyceroyl-phosphate-polyphosphate phosphotransferase, farnesyl-diphosphate kinase, 5-methyldeoxycytidine-5'-phosphate kinase, dolichyl-diphosphate-polyphosphate phosphotransferase, inositol-hexakisphosphate kinase, UMP kinase, ribose 1,5-bisphosphate phosphokinase, diphosphoinositol-pentakisphosphate kinase, (d)CMP kinase, isopentenyl phosphate kinase, [pyruvate, phosphate dikinase]-phosphate phosphotransferase, [pyruvate, water dikinase]-phosphate phosphotransferase, Kdo2-lipid A phosphotransferase, lipid A phosphoethanolamine transferase, [5-(aminomethyl)furan-3-yl]methyl phosphate kinase, farnesyl phosphate kinase, yeast UMP kinase, polyphosphate-AMP phosphotransferase, and geranylgeranyl phosphate kinase.

A cell engineered to produce an isoprenoid precursor comprises at least one engineered (e.g., recombinant or synthetic) nucleic acid, or is otherwise modified such that it is structurally and/or functionally distinct from its naturally-occurring counterparts. A "nucleic acid" is at least two nucleotides covalently linked together, and in some instances, may contain phosphodiester bonds (e.g., a phosphodiester "backbone"). Nucleic acids (e.g., components, or portions, of nucleic acids) may be naturally occurring or engineered. "Naturally occurring" nucleic acids are present in a cell that exists in nature in the absence of human intervention. "Engineered nucleic acids" include recombinant nucleic acids and synthetic nucleic acids. A "recombinant nucleic acid" refers to a molecule that is constructed by joining nucleic acid molecules (e.g., from the same species or from different species) and, typically, can replicate in a living cell. A "synthetic nucleic acid" refers to a molecule that is biologically synthesized, chemically synthesized, or by other means synthesized or amplified. A synthetic nucleic acid includes nucleic acids that are chemically modified or otherwise modified but can base pair with naturally-occurring nucleic acid molecules. Recombinant and synthetic nucleic acids also include those molecules that result from the replication of either of the foregoing. Engineered nucleic acids may contain portions of nucleic acids that are naturally occurring, but as a whole, engineered nucleic acids do not occur naturally and require human intervention. In some embodiments, a nucleic acid encoding a product of the present disclosure is a recombinant nucleic acid or a synthetic nucleic acid. In other embodiments, a nucleic acid encoding a product is naturally occurring. Thus, a cell that contains an engineered nucleic acid is considered a "cell engineered to produce an isoprenoid precursor."

Engineered or recombinant nucleic acids may be introduced into host cells using any means known in the art, including, without limitation, transformation, transfection (e.g., chemical (e.g., calcium phosphate, cationic polymers, or liposomes) or non-chemical (e.g., electroporation, sonoporation, impalefection, optical transfection, hydrodynamic transfection)), and transduction (e.g., viral transduction). Enzymes encoded by a naturally-occurring, intracellular nucleic acid may be referred to as "endogenous enzymes."

Typically, engineered cells are cultured. "Culturing" refers to the process by which cells are grown under controlled conditions. For example, engineered cells, such as engineered bacterial cells, may be grown as a cell suspension in liquid nutrient broth, also referred to as liquid "culture medium."

Examples of commonly used bacterial *Escherichia coli* growth media include, without limitation, LB (Lysogeny Broth) Miller broth (1% NaCl): 1% peptone, 0.5% yeast extract, and 1% NaCl; LB (Lysogeny Broth) Lennox Broth (0.5% NaCl): 1% peptone, 0.5% yeast extract, and 0.5% NaCl; SOB medium (Super Optimal Broth): 2% peptone, 0.5% Yeast extract, 10 mM NaCl, 2.5 mM KCl, 10 mM $MgCl_2$, 10 mM MgSO4; SOC medium (Super Optimal broth with Catabolic repressor): SOB+20 mM glucose; 2×YT broth (2× Yeast extract and Tryptone): 1.6% peptone, 1% yeast extract, and 0.5% NaCl; TB (Terrific Broth) medium: 1.2% peptone, 2.4% yeast extract, 72 mM $K_2HPO_4$, 17 mM $KH_2PO_4$ and 0.4% glycerol; and SB (Super Broth) medium: 3.2% peptone, 2% yeast extract, and 0.5% NaCl and or Korz medium (Korz, D J et al. 1995).

Examples of high density bacterial *Escherichia coli* growth media include, but are not limited to, DNAGro™ medium, ProGro™ medium, AutoX™ medium, DetoX™ medium, InduX™ medium, and SecPro™ medium.

In some embodiments, engineered cells are cultured under conditions that result in expression of enzymes. Such culture conditions may depend on the particular product being expressed and the desired amount of the product.

In some embodiments, engineered cells are cultured at a temperature of 28° C. to 40° C. For example, engineered cells may be cultured at a temperature of 28° C., 29° C., 30° C., 31° C., 32° C., 33° C., 34° C., 35° C., 36° C., 37° C., 38° C., 39° C. or 40° C., or any range or combination thereof. In some embodiments, a cell (e.g., microbial cell) is cultured at a temperature of from about 22° C. to about 37° C. In some embodiments, the microbial cell is cultured at a temperature of from about 30° to about 37° C. Typically, engineered cells, such as engineered *E. coli* cells, are cultured at a temperature of 37° C.

In some embodiments, engineered cells are cultured for a period of time of 12 hours to 72 hours, or more. For example, engineered cells may be cultured for a period of time of 12, 18, 24, 30, 36, 42, 48, 54, 60, 66, or 72 hours. Typically, engineered cells, such as engineered bacterial cells, are cultured for a period of time of 12 to 24 hours. In some embodiments, engineered cells are cultured for 12 to 24 hours at a temperature of 37° C.

In some embodiments, engineered cells are cultured (e.g., in liquid cell culture medium) to an optical density, measured at a wavelength of 600 nm (OD600), of 5 to 200. In some embodiments, engineered cells are cultured to an $OD_{600}$ of 5, 10, 15, 20, 25, 50, 75, 100, 150, or 200. In some embodiments, engineered cells are cultured to a density of $1×10^8$ (OD<1) to $2×10^{11}$ (OD ~200) viable cells/ml cell culture medium. In some embodiments, engineered cells are cultured to a density of $1×10^8$, $2×10^8$, $3×10^8$, $4×10^8$, $5×10^8$, $6×10^8$, $7×10^8$, $8×10^8$, $9×10^8$, $1×10^9$, $2×10^9$, $3×10^9$, $4×10^9$, $5×10^9$, $6×10^9$, $7×10^9$, $8×10^9$, $9×10^9$, $1×10^{10}$, $2×10^{10}$, $3×10^{10}$, $4×10^{10}$, $5×10^{10}$, $6×10^{10}$, $7×10^{10}$, $8×10^{10}$, $9×10^{10}$, $1×10^{11}$, or $2×10^{11}$ viable cells/ml. (Conversion factor: OD 1=$8×10^8$ cells/ml).

In some embodiments, the cell (e.g., microbial cell) is cultured with various carbon substrates, including a C1, C2, C3, C4, C5, or C6 carbon source. Exemplary carbon sources include glucose or glycerol.

In some embodiments, the cell (e.g., microbial cell) overexpresses one or more MEP pathway genes or MVA pathway genes. In such embodiments, the cell can create isoprenoid precursors from carbon sources such as glucose or glycerol, as well as from prenol and/or isoprenol supplemented in the culture media.

In some embodiments, the culture conditions are aerobic or anaerobic. In some embodiments, the culture is maintained under aerobic or microaerobic conditions.

In some embodiments, the method further comprises recovering the isoprenoid precursor or downstream product thereof. In some embodiments, the isoprenoid precursor or downstream product thereof can be recovered from the culture media (or organic overlayer, such as 10% dodecane) or can be recovered from the cell.

In some embodiments, a cell disclosed herein is an engineered cell.

In some embodiments, the cell (e.g., microbial cell) overexpresses one or more of a MEP pathway gene and/or a MVA pathway gene. In such embodiments, the cell can create isoprenoid precursors from carbon sources such as glucose or glycerol, as well as from prenol and/or isoprenol supplemented in the culture media.

In some embodiments, engineered cells are cultured in a bioreactor. A bioreactor refers simply to a container in which cells are cultured, such as a culture flask, a dish, or a bag that may be single-use (disposable), autoclavable, or sterilizable. The bioreactor may be made of glass, or it may be polymer-based, or it may be made of other materials.

Examples of bioreactors include, without limitation, stirred tank (e.g., well mixed) bioreactors and tubular (e.g., plug flow) bioreactors, airlift bioreactors, membrane stirred tanks, spin filter stirred tanks, vibromixers, fluidized bed reactors, and membrane bioreactors. The mode of operating the bioreactor may be a batch or a continuous process and will depend on the engineered cells being cultured. A bioreactor is continuous when the feed and product streams are continuously being fed and withdrawn from the system. A batch bioreactor may have a continuous recirculating flow, but no continuous feeding of nutrient or product harvest. For intermittent-harvest and fed-batch (or batch fed) cultures, cells are inoculated at a lower viable cell density in a medium that is similar in composition to a batch medium. Cells are allowed to grow exponentially with essentially no external manipulation until nutrients are somewhat depleted and cells are approaching stationary growth phase. At this point, for an intermittent harvest batch-fed process, a portion of the cells and product may be harvested, and the removed culture medium is replenished with fresh medium. This process may be repeated several times. For production of recombinant enzymes, a fed-batch process may be used. While cells are growing exponentially, but nutrients are becoming depleted, concentrated feed medium (e.g., 10-15 times concentrated basal medium) is added either continuously or intermittently to supply additional nutrients, allowing for further increase in cell concentration and the length of the production phase. Fresh medium may be added proportionally to cell concentration without removal of culture medium (broth). To accommodate the addition of medium, a fed batch culture is started in a volume much lower that the full capacity of the bioreactor (e.g., approximately 40% to 50% of the maximum volume).

The culturing step can be a batch or continuous fermentation process. In some embodiments, the culturing is a fed-batch process comprising a first phase where bacterial biomass is created followed by a production phase. Prenol and/or isoprenol are added at the production phase. The production phase further includes feeding a nitrogen source and a carbon source.

In some embodiments, the culture can be conducted at large scale. In some embodiments, the culture is about 100 L, about 500 L, about 1,000 L, about 1,500 L, about 2,000 L, about 3,000 L, about 4,000 L, about 5,000 L, about 6,000 L, about 7,000 L, about 8,000 L, about 9,000, about 10,000 L, about 20,000 L, about 30,000 L, about 40,000 L, about 50,000 L, about 60,000 L, about 70,000 L, about 80,000 L, about 90,000 L, or about 100,000 L. In some embodiments, the culture is at least about 100 L, at least about 500 L, at least about 1,000 L, at least about 1,500 L, at least about 2,000 L, at least about 3,000 L, at least about 4,000 L, at least about 5,000 L, at least about 6,000 L, at least about 7,000 L, at least about 8,000 L, at least about 9,000 L, at least about 10,000 L, at least about 20,000 L, at least about 30,000 L, at least about 40,000 L, at least about 50,000 L, at least about 60,000 L, at least about 70,000 L, at least about 80,000 L, at least about 90,000 L, or at least about 100,000 L.

In other aspects, the invention provides a method for producing an isoprenoid precursor or downstream product thereof. The method comprises providing the microbial cell described herein, and culturing the cell with fed prenol or isoprenol under conditions that result in production of the isoprenoid precursor or downstream product thereof.

Aspects of the disclosure relate to expression of recombinant genes in engineered cells. The disclosure encompasses any type of cell that recombinantly expresses genes associated with the disclosure, including prokaryotic and eukaryotic cells. A cell engineered to produce an isoprenoid precursor of the present disclosure may be a prokaryotic cell or an eukaryotic cell. In some embodiments the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp. and *Pantoea* spp. The bacterial cell can be a Gram-negative cell such as an *Escherichia coli* (*E. coli*) cell, or a Gram-positive cell such as a species of *Bacillus* or *Corynebacterium glutamicum*. In other embodiments the cell is an archaeal cell, such as *Methanosphaera* spp., *Methanothermus* spp., *Methanomicrobium* spp., *Methanohalobium* spp., *Methanimicrococcus* spp., *Methanocalculus* spp., *Haloferax* spp., *Halobacterium* spp., *Halococcus* spp., *Halorubrum* spp., *Haloterrigena* spp., *Thermoplasma* spp., *Thermoproteus* spp., *Chaetomium* spp., *Thermomyces* spp., *Brevibacillus* spp., and *Sulfolobus* spp. In other embodiments, the cell is a fungal cell such as a yeast cell, e.g., *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp., and industrial polyploid yeast strains. Preferably the yeast strain is a *S. cerevisiae* strain or a *Yarrowia* spp. strain. Other examples of fungi include *Aspergillus* spp., *Pennicilium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp. In other embodiments, the cell is a mammalian cell, an algal cell, or a plant cell. It should be appreciated that some cells may express an endogenous copy of one or more of the genes disclosed herein as well as a recombinant copy. In some embodiments, if a cell has an endogenous copy of one or more of the genes then the methods will not necessarily require adding a recombinant copy of the gene(s) that are endogenously expressed. In some embodiments the cell may endogenously express one or more enzymes from the pathways described herein and may recombinantly express one or more other enzymes from the pathways described herein for efficient production of an isoprenoid precursor and/or an isoprenoid.

In some embodiments, the microbial cell is a prokaryotic or eukaryotic cell. Exemplary bacterial cells include *Escherichia* spp., *Bacillus* spp., *Corynebacterium* spp., *Rhodobacter* spp., *Zymomonas* spp., *Vibrio* spp., *Pseudomonas* spp., *Agrobacterium* spp., *Brevibacterium* spp., and *Paracoccus* spp. In some embodiments, the microbial cell is *E. coli*. In other embodiments, the microbial cell is a yeast, such as *S. cerevisiae* or *Y. lipolytica*. Other exemplary microbial cell species are described herein.

A cell engineered to produce an isoprenoid precursor of the present disclosure, in some embodiments, expresses selectable markers.

Recombinantly Expressed and Synthetic Enzymes

A "recombinantly expressed enzyme" as used herein, is any enzyme derived from a recombinant nucleic acid that is expressed from a plasmid inserted into a cell or a gene integrated into the genome of the cell. A cell "expresses" a recombinant enzyme if the recombinant enzyme, encoded by a nucleic acid (e.g., an engineered nucleic acid), is produced in the cell. It is known in the art that gene expression refers to the process by which genetic instructions in the form of a nucleic acid are used to synthesize a product, such as a protein (e.g., an enzyme).

In some aspects of the disclosure, enzymes (such as those used in the IUP) are synthetic enzymes. A "synthetic enzyme" as used herein is any molecule or particle that has or mimics the activity or active site of any one or more of the enzymes disclosed herein, including but not limited to, for example, choline kinase or IPK. A synthetic enzyme can be a chemically-synthesized enzyme, and/or can be produced from naturally-occurring, or non-naturally occurring molecules (e.g., artificial enzymes).

Enzymes purified from natural sources (e.g., from cells of an organism) also can be used in the methods, cells, and compositions described herein.

Recombinantly expressed and/or synthetic enzymes that can be used for step 1 of the IUP (the phosphorylation of isoprenol and/or prenol to produce IP and/or DMAP) include choline kinase, isopentenyl phosphate kinase, glycerol kinase, mevalonate kinase, homoserine kinase, pantoate kinase, ceramide kinase, ethanolamine kinase, undecaprenol kinase, phosphomevalonate kinase, farnesyl-diphosphate kinase, and farnesyl-phosphate kinase. In some embodiments, choline kinase is used to phosphorylate isoprenol and/or prenol to produce IP and/or DMAP. As used herein, "choline kinase" is any enzyme that phosphorylates choline. Amino acid modifications to the choline kinase can be made to improve the reaction with prenol and/or isoprenol substrate, as disclosed herein.

Recombinantly expressed and/or synthetic enzymes that can be used for step 2 of the IUP (the phosphorylation of IP and/or DMAP to form IPP and/or DMAPP) include choline kinase, isopentenyl phosphate kinase, glycerol kinase, mevalonate kinase, homoserine kinase, pantoate kinase, ceramide kinase, ethanolamine kinase, undecaprenol kinase, phosphomevalonate kinase, farnesyl-diphosphate kinase, and farnesyl-phosphate kinase. In some embodiments, choline kinase is used to phosphorylate IP and/or DMAP to form IPP and/or DMAPP. In some embodiments IPK is used to convert IP and/or DMAP to IPP and/or DMAPP. In certain embodiments, the choline kinase is from *S. cerevisiae*; the isopentenyl phosphate kinase is from *H. volcanii, M. thermoautotrophicus, M. janaschii, A. thaliana*, or *T. acidophilium*; the glycerol kinase is from *E. coli*; the mevalonate kinase is from *S. cerevisiae*; and/or the homoserine kinase is from *S. cerevisiae*.

A recombinantly expressed enzyme of the present disclosure can be a heterologous enzyme. As used herein, a "heterologous enzyme" is one that is not from the same cell as it is expressed in. For example, a choline kinase from *S. cerevisiae* expressed in an *E. coli* cell is a heterologous enzyme. A recombinantly expressed enzyme can be a prokaryotic or eukaryotic enzyme, such as a bacterial enzyme, an archaeal enzyme, a yeast enzyme, and/or a mammalian enzyme.

In some embodiments, the engineered cell expresses an isomerization enzyme that converts IP to DMAP, and/or IPP to DMAPP or vice versa, such as isopentenyl pyrophosphate isomerase (IDI) or another enzyme that catalyzes the same reaction through promiscuous activity. In some embodiments, isomerization of IPP and/or DMAPP is not required for further isoprenoid production. In some aspects, isoprenol and/or prenol are present at a ratio that produces isopentenyl pyrophosphate (IPP) and/or dimethylallyl pyrophosphate (DMAPP) in a two-step phosphorylation, such that isomerization of IPP and/or DMAPP is not required for further isoprenoid production. The ratio of prenol to isoprenol can be any ratio between 1:10 and 10:1. For example, the ratio of prenol to isoprenol can be 1:1, 1:2, 1:3, 1:4, 1:5, 1:6, 1:7, 1:8, 1:9, 1:10, 2:1, 2:3, 2:5, 2:7, 2:9, 3:1, 3:2, 3:4, 3:5, 3:7, 3:8, 3:10, 4:1, 4:3, 4:5, 4:7, 4:9, 5:1, 5:2, 5:3, 5:4, 6:1, 6:5, 7:1, 7:2, 7:3, 7:4, 7:5, 7:6, 8:1, 8:3, 8:5, 8:7, 9:1, 9:2, 9:4, 9:5, 9:7, 9:8, 10:1, 10:3, 10:7, or 10:9.

Production of Isoprenoid precursors and Isoprenoids

Aspects of the present disclosure also include methods for producing an isoprenoid precursor comprising culturing any of the engineered cells described herein under conditions that result in the production of an isoprenoid precursor. As used herein, an "isoprenoid precursor" is a five-carbon isoprene unit that can be converted into an isoprenoid. In some embodiments the isoprenoid precursor is IPP and/or DMAPP.

Also provided are methods of producing an isoprenoid precursor or isoprenoid comprising introducing isoprenol and/or prenol into a cell culture comprising any of the engineered cells described herein under conditions that result in the production of an isoprenoid precursor or isoprenoid. In some embodiments, the cell expresses an isoprenoid synthesis pathway that converts the IP, DMAP, IPP and/or DMAPP to an isoprenoid product, as described extensively above.

Further disclosed are methods of producing an isoprenoid precursor or isoprenoid comprising contacting any of the engineered cells disclosed herein with isoprenol and/or prenol under conditions that result in the production of an isoprenoid precursor or isoprenoid. In some embodiments, the cell expresses an isoprenoid synthesis pathway that converts the IP, DMAP, IPP and/or DMAPP to an isoprenoid product.

Aspects of the disclosure relate to the production of isoprenoids. As used herein, a isoprenoid, also referred to as a terpenoid, is an organic chemical derived from an isoprenoid precursor. The terms terpenoid and isoprenoid are used interchangeably throughout this disclosure. Several non-limiting examples of isoprenoids, classified based on the number of isoprene units that they contain, include: hemiterpenoids (1 isoprene unit), monoterpenoids (2 isoprene units), sesquiterpenoids (3 isoprene units), diterpenoids (4 Isoprene units), sesterterpenoids (5 isoprene units), triterpenoids (6 isoprene units), tetraterpenoids (8 isoprene units), and polyterpenoids with a larger number of isoprene units. In some embodiments, the isoprenoid that is produced is taxadiene; amorphadiene; valencene; miltiradiene; lycopene; citronellol; cubebol; nootkatone; cineol; limonene; eleutherobin; sarcodictyin; pseudopterosins; ginkgolides; kaurene; a steviol such as stevioside or steviobioside; a steviol glycoside such as rebaudioside M, rebaudioside A, rebaudioside B, rebaudioside C, rebaudioside D, rebaudioside E, rebaudioside F, or dulcoside A; sclareol; labdenediol; levopimaradiene; sandracopimaradiene; or isopemaradiene. In some embodiments, the isoprenoid is a mogroside (e.g., Mog V).

Aspects of the disclosure relate to methods that include measuring the amount or concentration of an isoprenoid in a cell that produces one or more isoprenoids, or in a culture of the cells that produce one or more isoprenoids. The methods can include measuring the amount or concentration of an isoprenoid two or more times. In some embodiments, the measured amount or concentration of an isoprenoid in the cell or cells is used to guide a process of producing one or more isoprenoids. In some embodiments, the measured amount or concentration of an isoprenoid is used to guide strain construction.

In other aspects, methods are provided for making a product containing an isoprenoid. The method comprises increasing isoprenoid production in a cell that produces one or more isoprenoids by controlling the accumulation of isoprenoid in the cell or in a culture of the cells. The isoprenoid is recovered from the cell(s), and optionally, one or more chemical or enzymatic steps may be performed to produce the desired compound. The recovered isoprenoid or the isoprenoid prepared through one or more chemical or enzymatic steps, is incorporated into a product to thereby make the product containing an isoprenoid. In various embodiments, the product is a food product or beverage.

In some embodiments, a method disclosed herein produces a product, such as an industrial product or consumer product. In some embodiments, the product, such as an industrial product or consumer product, is a flavor product, a fragrance product, a sweetener, a cosmetic, a cleaning product, a detergent, or a pest control product. In some embodiments, the industrial product or consumer product is a food, beverage, texturant, pharmaceutical, tobacco product, nutraceutical, oral hygiene product, or cosmetic product.

In some embodiments, the engineered cells disclosed herein may comprise one or more enzymes that convert IPP and/or DMAPP to an isoprenoid.

Described herein are methods and compositions for producing and optimizing production of isoprenoid precursors and/or isoprenoids in cells by controlling expression of genes or proteins participating in a two-step upstream pathway and a downstream pathway. The upstream pathway (IUP) involves production of IP, DMAP, IPP, and/or DMAPP.

The downstream pathway is a synthetic pathway that leads to production of an isoprenoid and involves recombinant gene expression of a terpenoid synthase (also referred to as terpene cyclase) enzyme, and a geranylgeranyl diphosphate synthase (GGPPS) enzyme. In some embodiments, a terpenoid synthase enzyme is a diterpenoid synthase enzyme. Several non-limiting examples of diterpenoid synthase enzymes include casbene synthase, taxadiene synthase, levopimaradiene synthase, abietadiene synthase, isopimaradiene synthase, ent-copalyl diphosphate synthase, syn-stemar-13-ene synthase, syn-stemod-13(17)-ene synthase, syn-pimara-7,15-diene synthase, ent-sandaracopimaradiene synthase, ent-cassa-12,15-diene synthase, ent-pimara-8(14), 15-diene synthase, ent-kaur-15-ene synthase, ent-kaur-16-ene synthase, aphidicolan-16β-ol synthase, phyllocladan-16α-ol synthase, fusicocca-2,10(14)-diene synthase, and terpentetriene cyclase. In some embodiments, the cell further expresses a kaurene oxidase (KO), a P450 mono-oxygenase, a kaurenoic acid 13-hydroxylase (KAH), and/or a cytochrome P450. Additional enzymes of the downstream pathway, and aspects of their use, can be found in U.S. Pat. Nos. 8,512,988, 8,927,241, 9,359,624, 9,404,130, 9,796,980, and 9,957,527, and PCT published application WO2012/075030, each of which is hereby incorporated by reference in its entirety.

Expression of genes and proteins within the downstream synthetic isoprenoid synthesis pathway can also be regulated in order to optimize isoprenoid production. The synthetic downstream isoprenoid synthesis pathway involves recombinant expression of an isoprenoid synthase enzyme and a GGPPS enzyme. Any terpenoid synthase enzyme, as discussed above, can be expressed with GGPPS depending on the downstream product to be produced. For example, taxadiene synthase is used for the production of taxadiene. Recombinant expression of the taxadiene synthase enzyme and the GGPPS enzyme can be regulated independently or together. In some embodiments the two enzymes are regulated together in a modular fashion. For example the two enzymes can be expressed in an operon in either order (GGPPS-TS, referred to as "GT," or TS-GGPPS, referred to as "TG").

Manipulation of the expression of genes and/or proteins, including modules such as the Isopentenol Utilization Pathway (IUP), and the TS-GGPPS operon, can be achieved through methods known to one of ordinary skill in the art. For example, expression of the genes or operons can be regulated through selection of promoters, such as inducible promoters, with different strengths. Several non-limiting examples of promoters include Trc, T5 and T7. Additionally, expression of genes or operons can be regulated through manipulation of the copy number of the gene or operon in the cell. For example, in certain embodiments, a strain containing an additional copy of the IUP on its chromosome under Trc promoter control produces an increased amount of isoprenoid relative to one overexpressing only the synthetic downstream pathway. In some embodiments, expression of genes or operons can be regulated through manipulating the order of the genes within a module. In some embodiments, expression of genes or operons is regulated through integration of one or more genes or operons into a chromosome. For example, in certain embodiments, integration of the IUP into the chromosome of a cell can result in increased isoprenoid production.

It should be appreciated that the genes that express enzymes used in the disclosed cells, compositions and methods disclosed herein can be obtained from a variety of sources. In some embodiments, the genes in the Isopentenol Utilization Pathway (IUP), such as choline kinase, isopentenyl phosphate kinase, glycerol kinase, mevalonate kinase, homoserine kinase, pantoate kinase, ceramide kinase, ethanolamine kinase, undecaprenol kinase, phosphomevalonate kinase, farnesyl-diphosphate kinase, and farnesyl-phosphate kinase, are prokaryotic genes or eukaryotic genes. In some specific embodiments, the choline kinase is from S. cerevisiae; the isopentenyl phosphate kinase is from H. volcanii, M. thermoautotrophicus, M. janaschii, A. thaliana, or T. acidophilium; the glycerol kinase is from E. coli; the mevalonate kinase is from S. cerevisiae; and/or the homoserine kinase is from S. cerevisiae. In some embodiments, the gene encoding for GGPPS is a plant gene. For example, the gene encoding for GGPPS can be from a species of Taxus such as Taxus canadensis (T. canadensis). In some embodiments, the gene encoding for taxadiene synthase is a plant gene. For example, the gene encoding for taxadiene synthase can be from a species of Taxus such as Taxus brevifolia (T. brevifolia). Representative GenBank Accession numbers for T. canadensis GGPPS and T. brevifolia taxadiene synthase are provided by AF081514 and U48796.

As one of ordinary skill in the art would be aware, homologous genes for use in the disclosed cells, compositions and methods can be obtained from other species and can be identified by homology searches, for example through a protein BLAST search, available at the National Center for Biotechnology Information (NCBI) internet site (ncbi.nlm.nih.gov). Genes and/or operons associated with the disclosed cells, compositions and methods can be cloned, for example by PCR amplification and/or restriction digestion, from DNA from any source of DNA which contains the given gene. In some embodiments, a gene and/or operon associated with the disclosed cells, compositions and methods is synthetic.

In some embodiments, further optimization of isoprenoid production is achieved by modifying a gene before it is recombinantly expressed in a cell. In some embodiments, the GGPPS enzyme has one or more of the follow mutations: A162V, G140C, L182M, F218Y, D160G, C184S, K367R, A151T, M185I, D264Y, E368D, C184R, L331I, G262V, R365S, A114D, S239C, G295D, I276V, K343N, P183S, I172T, D267G, I149V, T234I, E153D and T259A. In some embodiments, the GGPPS enzyme has a mutation in residue S239 and/or residue G295. In certain embodiments, the GGPPS enzyme has the mutation S239C and/or G295D.

In some embodiments, modification of a gene before it is recombinantly expressed in a cell involves codon optimization for expression in a bacterial cell. Codon usages for a variety of organisms can be accessed in the Codon Usage Database (kazusa.or.jp/codon/). Codon optimization, including identification of optimal codons for a variety of organisms, and methods for achieving codon optimization, are familiar to one of ordinary skill in the art, and can be achieved using standard methods.

The present disclosure provides a novel nucleic acid sequence for choline kinase from S. cerevisiae which has been codon optimized for expression in E. coli, as set forth in SEQ ID NO: 1:

```
ATGGTGCAGGAGTCCCGCCCCGGCTCGGTCCGGTCGTATTCCGTGGGCTA
CCAGGCCCGGTCGCGGTCGTCGTCCCAGCGCCGCCATTCGCTCACGCGGC
AGCGCAGCAGCCAGCGGCTCATCCGGACGATCTCCATCGAGAGCGATGTG
AGCAATATCACGGACGATGATGATCTGCGGGCGGTGAATGAAGGGGTGGC
CGGGGTCCAGCTCGACGTCTCCGAGACGGCGAACAAAGGGCCaCGCCGGG
CCAGtGCCACCGATGTCACCGACTCGCTGGGCTCCACGTCCAGCGAATAT
ATCGAGATCCCCTTCGTGAAAGAGACGCTGGACGCGAGCCTCCCCTCGGA
TTACCTCAAACAAGACATCCTGAACCTGATCCAATCCCTGAAGATCTCGA
AATGGTACAATAACAAAAAGATCCAGCCCGTCGCCCAGGACATGAACCTC
```

```
GTCAAAATCTCCGGCGCGATGACCAATGCGATCTTCAAGGTGGAGTACCC

GAAACTGCCGTCCCTCCTGCTGCGGATCTATGGCCCGAATATCGATAACA

TCATCGACCGCGAATATGAACTCCAGATCCTCGCGCGGCTCTCGCTGAAA

AACATCGGGCCGTCCCTGTACGGCTGCTTCGTGAATGGGCGCTTCGAGCA

GTTCCTCGAAAACTCCAAAACGCTGACCAAGGATGATATCCGGAACTGGA

AAAACTCGCAACGGATCGCCCGCCGCATGAAGGAGCTGCATGTGGGCGTG

CCCCTCCTCTCGTCGGAGCGGAAGAATGGGAGCGCCTGCTGGCAAAAAAT

CAACCAATGGCTCCGCACGATCGAGAAGGTGGATCAGTGGGTCGGGGACC

CGAAGAACATCGAGAACAGCCTCCTCTGCGAAAATTGGTCCAAATTCATG

GACATCGTCGATCGGTACCACAAGTGGCTGATCAGCCAAGAACAAGGGAT

CGAGCAAGTCAACAAAAATCTGATCTTCTGCCATAATGATGCCCAATACG

GGAATCTCCTCTTCACCGCGCCCGTCATGAACACCCCCTCCCTGTATACC

GCGCCGAGCTCGACCTCCCTGACGTCCCAAAGCAGCAGCCTCTTCCCCTC

GTCCAGCAACGTGATCGTCGATGATATCATCAATCCCCCGAAGCAAGAAC

AATCCCAAGATTCCAAACTCGTGGTCATCGATTTCGAATACGCCGGGGCC

AATCCCGCCGCGTACGATCTCGCCAATCACCTCTCGGAATGGATGTACGA

CTATAATAACGCCAAAGCCCCGCACCAGTGCCACGCCGACCGGTACCCCG

ACAAGGAGCAAGTGCTCAACTTCCTGTATTCGTATGTCAGCCATCTCCGC

GGCGGGGCCAAAGAGCCCATCGATGAAGAGTCCAGCGCCTCTATAAATC

GATCATCCAGTGGCGCCCCACGGTGCAGCTCTTCTGGTCGCTGTGGGCGA

TCCTGCAAAGCGGCAAGCTGGAAAAAAAAGAAGCCAGCACCGCCATCACC

CGCGAAGAAATCGGGCCCAATGGGAAAAAGTATATCATCAAGACGGAGCC

CGAGTCGCCCGAAGAGGACTTCGTCGAAAATGACGACGAACCCGAAGCCG

GCGTGTCGATCGATACCTTCGACTACATGGCCTACGGGCGGGACAAGATC

GCGGTGTTCTGGGGGGACCTGATCGGGCTGGGCATCATCACGGAGGAGGA

ATGCAAGAACTTCTCGAGCTTCAAATTCCTCGACACCAGCTACCTGTAA.
```

As noted, SEQ ID NO: 1 has been optimized for expression in *E. coli* and expresses choline kinase from *S. cerevisiae*, which has accession number NP 01324.1, and in *S. cerevisiae* is produced from the gene with accession number CP020134.1.

In some embodiments, modifying a gene before it is recombinantly expressed in a cell involves making one or more mutations in the gene before it is recombinantly expressed in a cell. For example, a mutation can involve a substitution or deletion of a single nucleotide or multiple nucleotides. In some embodiments, a mutation of one or more nucleotides in a gene will result in a mutation in the protein produced from the gene, such as a substitution or deletion of one or more amino acids.

In some embodiments, it may be advantageous to use a cell that has been optimized for production of an isoprenoid. For example, in some embodiments, a cell that overexpresses one or more components of the IUP is used, at least in part, to produce greater quantities of isopentenyl diphosphate (IPP) and dimethylallyl diphosphate (DMAPP), substrates of GPPS, GGPPS, and FPPS, for example. In some embodiments, overexpression of one or more components of the IUP is achieved by increasing the copy number of one or more components of the IUP.

In some embodiments "rational design" is involved in constructing specific mutations in proteins such as enzymes. As used herein, "rational design" refers to incorporating knowledge of the enzyme, or related enzymes, such as its three dimensional structure, its active site(s), its substrate(s) and/or the interaction between the enzyme and substrate, into the design of the specific mutation. Based on a rational design approach, mutations can be created in an enzyme which can then be screened for increased production of an isoprenoid relative to control levels. In some embodiments, mutations can be rationally designed based on homology modeling. As used herein, "homology modeling" refers to the process of constructing an atomic resolution model of one protein from its amino acid sequence and a three-dimensional structure of a related homologous protein.

In some embodiments, random mutations can be made in a gene, such as a gene encoding for an enzyme, and these mutations can be screened for increased production of an isoprenoid relative to control levels. For example, screening for mutations in components of the IUP, or components of other pathways, that lead to enhanced production of an isoprenoid or isoprenoid precursor may be conducted through a random mutagenesis screen, or through screening of known mutations. In some embodiments, shotgun cloning of genomic fragments could be used to identify genomic regions that lead to an increase in production of an isoprenoid or isoprenoid precursor, through screening cells or organisms that have these fragments for increased production of an isoprenoid or isoprenoid precursor. In some cases one or more mutations may be combined in the same cell or organism.

In some embodiments, production of an isoprenoid or isoprenoid precursor in a cell can be increased through manipulation of enzymes that act in the same pathway as the enzymes associated with the disclosed cells, compositions and methods. For example, in some embodiments it may be advantageous to increase expression of an enzyme or other factor that acts upstream of a target enzyme such as an enzyme associated with the disclosed cells, compositions and methods. This could be achieved by over-expressing the upstream factor using any standard method.

Optimization of protein expression can also be achieved through selection of appropriate promoters and ribosome binding sites. In some embodiments, this may include the selection of high-copy number plasmids, or low or medium-copy number plasmids. The step of transcription termination can also be targeted for regulation of gene expression, through the introduction or elimination of structures such as stem-loops.

As used herein, the terms "protein" and "polypeptide" are used interchangeably and thus the term polypeptide may be used to refer to a full-length polypeptide and may also be used to refer to a fragment of a full-length polypeptide. As used herein with respect to polypeptides, proteins, or fragments thereof, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. The term "substantially pure" means that the proteins or polypeptides are essentially free of other substances with which they may be found in production, nature, or in vivo systems to an extent practical and appropriate for their intended use. Substantially pure polypeptides may be obtained naturally or produced using methods described herein and may be purified with techniques well known in the art. Because an isolated protein may be admixed with other components in a preparation, the protein may comprise only a small percentage by weight of the preparation. The protein is nonetheless isolated in that it has been separated from the substances with which it may be associated in living systems, i.e. isolated from other proteins.

The disclosure also encompasses nucleic acids that encode for any of the polypeptides described herein, libraries that contain any of the nucleic acids and/or polypeptides described herein, and compositions that contain any of the nucleic acids and/or polypeptides described herein.

In some embodiments, one or more of the genes associated with the disclosed cells, compositions and methods is expressed in a recombinant expression vector. As used herein, a "vector" may be any of a number of nucleic acids into which a desired sequence or sequences may be inserted by restriction and ligation for transport between different genetic environments or for expression in a host cell. Vectors are typically composed of DNA, although RNA vectors are also available. Vectors include, but are not limited to: plasmids, fosmids, phagemids, virus genomes and artificial chromosomes.

A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host cell such as a host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule that encodes any of the enzymes of the disclosed cells, compositions and methods is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors used in the disclosed cells, compositions and methods may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., Molecular Cloning: A Laboratory Manual, Second Edition, Cold Spring Harbor Laboratory Press, 1989. Cells are genetically engineered by the introduction into the cells of heterologous DNA (RNA). That heterologous DNA (RNA) is placed under operable control of transcriptional elements to permit the expression of the heterologous DNA in the host cell. Heterologous expression of genes associated with the disclosed cells, compositions and methods, for production of a isoprenoid, is demonstrated in the Examples section using *E. coli*. The novel method for producing terpenoids can also be expressed in other bacterial cells, fungi (including yeast cells), plant cells, etc.

A nucleic acid molecule that encodes an enzyme associated with the disclosed cells, compositions and methods can be introduced into a cell or cells using methods and techniques that are standard in the art. For example, nucleic acid molecules can be introduced by standard protocols such as transformation including chemical transformation and electroporation, transduction, particle bombardment, etc. Expressing the nucleic acid molecule encoding the enzymes also may be accomplished by integrating the nucleic acid molecule into the genome.

In some embodiments one or more genes associated with the disclosed cells, compositions and methods is expressed recombinantly in a bacterial cell. Bacterial cells can be cultured in media of any type (rich or minimal) and any composition. As would be understood by one of ordinary skill in the art, routine optimization would allow for use of a variety of types of media. The selected medium can be supplemented with various additional components. Some non-limiting examples of supplemental components include glucose, antibiotics, IPTG for gene induction, ATCC Trace Mineral Supplement, and glycolate. Similarly, other aspects of the medium, and growth conditions of the cells may be optimized through routine experimentation. For example, pH and temperature are non-limiting examples of factors which can be optimized. In some embodiments, factors such as choice of media, media supplements, and temperature can influence production levels of isoprenoids, such as taxadiene. In some embodiments the concentration and amount of a supplemental component may be optimized. In some embodiments, how often the media is supplemented with one or more supplemental components, and the amount of time that the media is cultured before harvesting a isoprenoid, such as taxadiene, is optimized.

According to an aspect of the disclosure, high titers of a isoprenoid are produced through the recombinant expression of genes in a cell. According to another aspect of the disclosure, high titers of an isoprenoid are produced using a synthetic, in vitro, composition disclosed herein.

As used herein "high titer" refers to a titer in the grams per liter (g $L^{-1}$) scale. The titer produced for a given product will be influenced by multiple factors including choice of media. In some embodiments, the total isoprenoid titer is at least 1 mg $L^{-1}$. In some embodiments, the total isoprenoid titer is at least 10 mg $L^{-1}$. In some embodiments, the total isoprenoid titer is at least 250 mg $L^{-1}$. For example, the total isoprenoid titer can be at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 75, 80, 85, 90, 95, 100, 125, 150, 175, 200, 205, 210, 215, 220, 225, 230, 235, 240, 245, 250, 275, 300, 325, 350, 375, 400, 425, 450, 475, 500, 525, 550, 575, 600, 625, 650, 675, 700, 725, 750, 775, 800, 825, 850, 875, 900 or more than 900 mg $L^{-1}$ including any intermediate values, or any ranges or combinations thereof. In some embodiments, the total isoprenoid titer can be at least 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or more than 5.0 g $L^{-1}$ including any intermediate values, or any ranges or combinations thereof. In some embodiments, the total isoprenoid titer is at least 1 g $L^{-1}$. In some embodiments, the total isoprenoid titer is at least 10 g $L^{-1}$. In some embodiments, the total isoprenoid titer is at least 250 g $L^{-1}$. For example, the total isoprenoid titer can be at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more than 50 g $L^{-1}$ including any intermediate values, or any ranges or combinations thereof. In some embodiments, the total isoprenoid titer can be at least 10.0, 10.1, 10.2, 10.3, 10.4, 10.5, 10.6, 10.7, 10.8, 10.9, 20.0, 20.1, 20.2, 20.3, 20.4, 20.5, 20.6, 20.7, 20.8, 20.9, 30.0, 30.1, 30.2, 30.3, 30.4, 30.5, 30.6, 30.7, 30.8, 30.9, 40.0, 40.1, 40.2, 40.3, 40.4, 40.5, 40.6, 40.7, 40.8, or 40.9 g $L^{-1}$, including any intermediate values, or any ranges or combinations thereof.

In some embodiments, the isoprenoid is produced at a rate of 24.4 mg/L/h. In some embodiments, the isoprenoid is produced at a rate of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more than 50 mg/L/h, including any intermediate values, or any ranges or combinations thereof. In some embodiments, the isoprenoid is produced at a rate of 10.0, 10.1, 10.2, 10.3, 10.4, 10.5, 10.6, 10.7, 10.8, 10.9, 20.0, 20.1, 20.2, 20.3, 20.4, 20.5, 20.6, 20.7, 20.8, 20.9, 30.0, 30.1, 30.2, 30.3, 30.4, 30.5, 30.6, 30.7, 30.8, 30.9, 40.0, 40.1, 40.2, 40.3, 40.4, 40.5, 40.6, 40.7, 40.8, or 40.9 mg/L/h, including any intermediate values, or any ranges or combinations thereof. In some embodiments, the isoprenoid is produced at said rate through the recombinant expression of genes in a cell. In some embodiments, the isoprenoid is produced at said rate using a synthetic, in vitro, composition disclosed herein.

The liquid cultures used to grow cells can be housed in any of the culture vessels known and used in the art. In some embodiments large scale production in an aerated reaction vessel such as a stirred tank reactor can be used to produce large quantities of isoprenoids that can be recovered from the cell culture. In some embodiments, the isoprenoid is recovered from the gas phase of the cell culture, for example by adding an organic layer such as dodecane to the cell culture and recovering the isoprenoid from the organic layer.

Terpenoids or isoprenoids, such as taxadiene; amorphadiene; valencene; miltiradiene; lycopene; citronellol; cubebol; nootkatone; cineol; limonene; eleutherobin; sarcodictyin; pseudopterosins; ginkgolides; kaurene; steviols such as stevioside or steviobioside; steviol glycosides such as rebaudioside M, rebaudioside A, rebaudioside B, rebaudioside C, rebaudioside D, rebaudioside E, rebaudioside F, or dulcoside A; sclareol; labdenediol; levopimaradiene; sandracopimaradiene; or isopemaradiene, produced through methods described herein have widespread applications including pharmaceuticals such as paclitaxel (Taxol), artemisinin, ginkgolides, eleutherobin and pseudopterosins, and many other potential pharmaceutical compounds. Further applications include compounds used in flavors and cosmetics such as geraniol, farnesol, geranylgeraniol, linalool, limonene, pinene, cineol and isoprene. Further applications include compounds for use as biofuels such as alcohols of 5, 10, and 15-carbon atom length. It is noted that the above compounds are presently produced as extracts of various plants. Plant extract-based methods are tedious, yield very small amounts and are limited as to the actual molecules that can be so obtained, namely, they do not allow the easy production of derivatives that may possess far superior properties than the original compounds.

Synthetic, In Vitro, Composition for Production of an Isoprenoid Precursor

In some aspects, the disclosure relates to synthetic, in vitro, compositions for the production of isoprenoid precursors. The compositions comprise isoprenol and/or prenol, as well as one or more enzymes that convert the isoprenol to IP and/or convert the prenol to DMAP. This enzyme can be an amino-alcohol kinase, amide-alcohol kinase, kinase that phosphorylates short-chain alcohols, and/or a phosphotransferase with a phosphate group as an acceptor (enzyme class 2.7.4). Non-limiting examples of enzymes that convert isoprenol to IP and/or convert prenol to DMAP include choline kinase, isopentenyl phosphate kinase, glycerol kinase, mevalonate kinase, homoserine kinase, pantoate kinase, ceramide kinase, ethanolamine kinase, undecaprenol kinase, phosphomevalonate kinase, farnesyl-diphosphate kinase, and farnesyl-phosphate kinase. In some embodiments, the choline kinase is from *S. cerevisiae*; the isopentenyl phosphate kinase is from *H. volcanii, M. thermoautotrophicus, M. janaschii, A. thaliana,* or *T. acidophilium*; the glycerol kinase is from *E. coli*; the mevalonate kinase is from *S. cerevisiae*; and/or the homoserine kinase is from *S. cerevisiae*. The enzyme can be a prokaryotic enzyme such as a bacterial enzyme or an archaeal enzyme, or a eukaryotic enzyme such as a yeast enzyme or a mammalian enzyme. Numerous examples of enzymes are provided above. In some embodiments, the enzyme is choline kinase is from *S. cerevisiae*, *Y. lipolytica*, and/or *E. coli*.

In some aspects, the one or more enzymes that convert isoprenol and/or prenol to IP and/or DMAP are in liquid solution or suspension and/or immobilized in or on the surface of a support, such as a gel or a solid. Examples of liquid solutions or suspensions include aqueous solutions or suspensions, such as buffered aqueous solutions or suspensions, where the pH of the buffered aqueous solution or suspension is selected to facilitate enzymatic activity. Examples of suitable supports include agarose, cellulose, dextran, Sephadex, Sepharose, liposomes, carboxymethyl cellulose, polystyrene, filter paper, ion-exchange resin, plastic film, plastic tube, glass beads, polyamine-methyl vinyl ether-maleic acid copolymer, amino acid copolymer, ethylene-maleic acid copolymer, nylon, silk, magnetic materials, etc. The support may be in the shape of, for example, a tube, test plate, well, beads, disc, sphere, etc. The support may be porous or non-porous, and may be placed in an aqueous solution as described above. The immobilized enzyme(s) may be prepared by reacting it with a suitable support using known chemical or physical methods, for example, cyanogen bromide coupling, coupling via linkers, antibody-based coupling, etc.

In some embodiments, the synthetic, in vitro, composition is used to produce isopentenyl pyrophosphate (IPP) and/or dimethylallyl pyrophosphate (DMAPP). As described above, IP can be converted to IPP by choline kinase, isopentenyl phosphate kinase, glycerol kinase, mevalonate kinase, homoserine kinase, pantoate kinase, ceramide kinase, ethanolamine kinase, undecaprenol kinase, phosphomevalonate kinase, farnesyl-diphosphate kinase, and/or farnesyl-phosphate kinase. Likewise, DMAP can be converted to DMAPP by choline kinase, isopentenyl phosphate kinase, glycerol kinase, mevalonate kinase, homoserine kinase, pantoate kinase, ceramide kinase, ethanolamine kinase, undecaprenol kinase, phosphomevalonate kinase, farnesyl-diphosphate kinase, and/or farnesyl-phosphate kinase. In some embodiments, IP is converted to IPP by choline kinase or isopentenyl phosphate kinase (IPK) and/or DMAP is converted to DMAPP by choline kinase or IPK.

In some aspects of the disclosure, the synthetic, in vitro, compositions also include an isomerization enzyme. In some embodiments, the isomerization enzyme is isopentenyl pyrophosphate isomerase (IDI). Such an isomerization enzyme serves to convert IP to DMAP, and/or IPP to DMAPP or vice versa. In some embodiments, isomerization of IPP and/or DMAPP is not required for further isoprenoid production. In some aspects of the disclosure, isoprenol and/or prenol are present at a ratio that produces isopentenyl pyrophosphate (IPP) and/or dimethylallyl pyrophosphate (DMAPP) in a two-step phosphorylation, such that isomerization of IPP and/or DMAPP is not required for further isoprenoid production. The ratio of prenol to isoprenol can be any ratio between 1:10 and 10:1. For example, the ratio of prenol to isoprenol can be 1:1, 1:2, 1:3, 1:4, 1:5, 1:6, 1:7, 1:8, 1:9, 1:10, 2:1, 2:3, 2:5, 2:7, 2:9, 3:1, 3:2, 3:4, 3:5, 3:7, 3:8, 3:10, 4:1, 4:3, 4:5, 4:7, 4:9, 5:1, 5:2, 5:3, 5:4, 6:1, 6:5, 7:1, 7:2, 7:3, 7:4, 7:5, 7:6, 8:1, 8:3, 8:5, 8:7, 9:1, 9:2, 9:4, 9:5, 9:7, 9:8, 10:1, 10:3, 10:7, or 10:9.

In yet another embodiment, the synthetic, in vitro, compositions may include one or more enzymes that convert the IP, DMAP, IPP and/or DMAPP to an isoprenoid product. This downstream pathway, in which an isoprenoid precursor such as IPP and/or DMAPP is converted into an isoprenoid is described extensively above.

Aspects of the present disclosure also include methods of producing an isoprenoid precursor or isoprenoid comprising incubating any of the synthetic, in vitro, compositions described herein under conditions that result in the production of an isoprenoid precursor or isoprenoid. In some aspects, the composition includes enzymes of an isoprenoid synthesis pathway that convert the IP, DMAP, IPP and/or DMAPP to an isoprenoid product.

In some embodiments, the synthetic, in vitro, composition includes any of the enzymes disclosed herein. In some embodiments, the synthetic, in vitro, composition includes a CK, IPK, ispA or a variant thereof disclosed herein and/or monoterpene synthase. In some embodiments, the monoterpene synthase is (4S)-limonene synthase (EC 4.2.3.16); (R)-limonene synthase (EC 4.2.3.20); sabinene-hydrate synthase (EC 4.2.3.11); myrcene synthase (EC 4.2.3.15); S-linalool synthase (EC 4.2.3.25); R-linalool synthase (EC 4.2.3.26); tricyclene synthase (EC 4.2.3.105); (E)-beta-ocimene synthase (EC 4.2.3.106); 1,8-cineole synthase (EC 4.2.3.108); (−)-sabinene synthase (EC 4.2.3.109); (+)-sabinene synthase (EC 4.2.3.110); (−)-alpha-terpineol synthase (EC 4.2.3.111); (+)-alpha-terpineol synthase (EC 4.2.3.112); terpinolene synthase (EC 4.2.3.113); gamma-terpinene synthase (EC 4.2.3.114); alpha-terpinene synthase (EC 4.2.3.115); (+)-camphene synthase (EC 4.2.3.116); (−)-camphene synthase (EC 4.2.3.117); (−)-alpha-pinene synthase (EC 4.2.3.119); (−)-beta-pinene synthase (EC 4.2.3.120); (+)-alpha-pinene synthase (EC 4.2.3.121); (+)-beta-pinene synthase (EC 4.2.3.122); (+)-bornyl diphosphate synthase (EC 5.5.1.8) and/or (−)-bornyl diphosphate synthase (EC 5.5.1.22).

In some embodiments, the synthetic, in vitro, composition includes ATP. In some embodiments, the concentration of ATP is 10 mM. In some embodiments, the concentration of ATP is 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, or more than 20 mM, or any ranges or combinations thereof.

In some embodiments, the synthetic, in vitro, composition includes magnesium. In some embodiments, the concentration of magnesium is 2 mM. In some embodiments, the concentration of magnesium is 0.1 mM, 0.2 mM, 0.3 mM, 0.4 mM, 0.5 mM, 0.6 mM, 0.7 mM, 0.8 mM, 0.9 mM, 1.0 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.1 mM, 3.2 mM, 3.3 mM, 3.4 mM, 3.5 mM, 3.6 mM, 3.7 mM, 3.8 mM, 3.9 mM, 4.0 mM, or more than 4.0 mM, or any range or combination thereof.

In some embodiments, the productivity of the synthetic, in vitro, composition is optimized by adjusting the ratio, amount or concentration of one or more enzymes used in the composition. In some embodiments, the enzyme is choline kinase, such as a choline kinase disclosed herein. In some embodiments, choline kinase is at a concentration of 25 µg/mL. In some embodiments, the choline kinase is at a concentration of 1 or about 1 µg/mL, 2 or about 2 µg/mL, 3 or about 3 µg/mL, 4 or about 4 µg/mL, 5 or about 5 µg/mL, 6 or about 6 µg/mL, 7 or about 7 µg/mL, 8 or about 8 µg/mL, 9 or about 9 µg/mL, 10 or about 10 µg/mL, 11 or about 11 µg/mL, 12 or about 12 µg/mL, 13 or about 13 µg/mL, 14 or about 14 µg/mL, 15 or about 15 µg/mL, 16 or about 16 µg/mL, 17 or about 17 µg/mL, 18 or about 18 µg/mL, 19 or about 19 µg/mL, 20 or about 20 µg/mL, 21 or about 21 µg/mL, 22 or about 22 µg/mL, 23 or about 23 µg/mL, 24 or about 24 µg/mL, about 25 µg/mL, 26 or about 26 µg/mL, 27 or about 27 µg/mL, 28 or about 28 µg/mL, 29 or about 29

μg/mL, 30 or about 30 μg/mL, 31 or about 31 μg/mL, 32 or about 32 μg/mL, 33 or about 33 μg/mL, 34 or about 34 μg/mL, 35 or about 35 μg/mL, 36 or about 36 μg/mL, 37 or about 37 μg/mL, 38 or about 38 μg/mL, 39 or about 39 μg/mL, 40 or about 40 μg/mL, 41 or about 41 μg/mL, 42 or about 42 μg/mL, 43 or about 43 μg/mL, 44 or about 44 μg/mL, 45 or about 45 μg/mL, 46 or about 46 μg/mL, 47 or about 47 μg/mL, 48 or about 48 μg/mL, 49 or about 49 μg/mL, 50 or about 50 μg/mL, 55 or about 55 μg/mL, 60 or about 60 μg/mL, 65 or about 65 μg/mL, 70 or about 70 μg/mL, 75 or about 75 μg/mL, 80 or about 80 μg/mL, 85 or about 85 μg/mL, 90 or about 90 μg/mL, 95 or about 95 μg/mL, 100 or about 100 μg/mL, or more than 100 μg/mL or any range or combination thereof.

In some embodiments, the enzyme is IPK, such as an IPK disclosed herein. In some embodiments, IPK is at a concentration of 15 μg/mL. In some embodiments, IPK is at a concentration of 1 or about 1 μg/mL, 2 or about 2 μg/mL, 3 or about 3 μg/mL, 4 or about 4 μg/mL, 5 or about 5 μg/mL, 6 or about 6 μg/mL, 7 or about 7 μg/mL, 8 or about 8 μg/mL, 9 or about 9 μg/mL, 10 or about 10 μg/mL, 11 or about 11 μg/mL, 12 or about 12 μg/mL, 13 or about 13 μg/mL, 14 or about 14 μg/mL, about 15 μg/mL, 16 or about 16 μg/mL, 17 or about 17 μg/mL, 18 or about 18 μg/mL, 19 or about 19 μg/mL, 20 or about 20 μg/mL, 21 or about 21 μg/mL, 22 or about 22 μg/mL, 23 or about 23 μg/mL, 24 or about 24 μg/mL, 25 or about 25 μg/mL, 26 or about 26 μg/mL, 27 or about 27 μg/mL, 28 or about 28 μg/mL, 29 or about 29 μg/mL, 30 or about 30 μg/mL, 31 or about 31 μg/mL, 32 or about 32 μg/mL, 33 or about 33 μg/mL, 34 or about 34 μg/mL, 35 or about 35 μg/mL, 36 or about 36 μg/mL, 37 or about 37 μg/mL, 38 or about 38 μg/mL, 39 or about 39 μg/mL, 40 or about 40 μg/mL, 41 or about 41 μg/mL, 42 or about 42 μg/mL, 43 or about 43 μg/mL, 44 or about 44 μg/mL, 45 or about 45 μg/mL, 46 or about 46 μg/mL, 47 or about 47 μg/mL, 48 or about 48 μg/mL, 49 or about 49 μg/mL, 50 or about 50 μg/mL, 55 or about 55 μg/mL, 60 or about 60 μg/mL, 65 or about 65 μg/mL, 70 or about 70 μg/mL, 75 or about 75 μg/mL, 80 or about 80 μg/mL, 85 or about 85 μg/mL, 90 or about 90 μg/mL, 95 or about 95 μg/mL, 100 or about 100 μg/mL, or more than 100 μg/mL or any range or combination thereof.

In some embodiments, the enzyme is IDI, such as an IDI disclosed herein. In some embodiments, IDI is at a concentration of 25 μg/mL. In some embodiments, IDI is at a concentration of 1 or about 1 μg/mL, 2 or about 2 μg/mL, 3 or about 3 μg/mL, 4 or about 4 μg/mL, 5 or about 5 μg/mL, 6 or about 6 μg/mL, 7 or about 7 μg/mL, 8 or about 8 μg/mL, 9 or about 9 μg/mL, 10 or about 10 μg/mL, 11 or about 11 μg/mL, 12 or about 12 μg/mL, 13 or about 13 μg/mL, 14 or about 14 μg/mL, 15 or about 15 μg/mL, 16 or about 16 μg/mL, 17 or about 17 μg/mL, 18 or about 18 μg/mL, 19 or about 19 μg/mL, 20 or about 20 μg/mL, 21 or about 21 μg/mL, 22 or about 22 μg/mL, 23 or about 23 μg/mL, 24 or about 24 μg/mL, about 25 μg/mL, 26 or about 26 μg/mL, 27 or about 27 μg/mL, 28 or about 28 μg/mL, 29 or about 29 μg/mL, 30 or about 30 μg/mL, 31 or about 31 μg/mL, 32 or about 32 μg/mL, 33 or about 33 μg/mL, 34 or about 34 μg/mL, 35 or about 35 μg/mL, 36 or about 36 μg/mL, 37 or about 37 μg/mL, 38 or about 38 μg/mL, 39 or about 39 μg/mL, 40 or about 40 μg/mL, 41 or about 41 μg/mL, 42 or about 42 μg/mL, 43 or about 43 μg/mL, 44 or about 44 μg/mL, 45 or about 45 μg/mL, 46 or about 46 μg/mL, 47 or about 47 μg/mL, 48 or about 48 μg/mL, 49 or about 49 μg/mL, 50 or about 50 μg/mL, 55 or about 55 μg/mL, 60 or about 60 μg/mL, 65 or about 65 μg/mL, 70 or about 70 μg/mL, 75 or about 75 μg/mL, 80 or about 80 μg/mL, 85 or about 85 μg/mL, 90 or about 90 μg/mL, 95 or about 95 μg/mL, 100 or about 100 μg/mL, or more than 100 μg/mL or any range or combination thereof.

In some embodiments, the enzyme is IspA, such as an IspA disclosed herein. In some embodiments, IspA is at a concentration of 37 μg/mL. In some embodiments, the choline kinase is at a concentration of 1 or about 1 μg/mL, 2 or about 2 μg/mL, 3 or about 3 μg/mL, 4 or about 4 μg/mL, 5 or about 5 μg/mL, 6 or about 6 μg/mL, 7 or about 7 μg/mL, 8 or about 8 μg/mL, 9 or about 9 μg/mL, 10 or about 10 μg/mL, 11 or about 11 μg/mL, 12 or about 12 μg/mL, 13 or about 13 μg/mL, 14 or about 14 μg/mL, 15 or about 15 μg/mL, 16 or about 16 μg/mL, 17 or about 17 μg/mL, 18 or about 18 μg/mL, 19 or about 19 μg/mL, 20 or about 20 μg/mL, 21 or about 21 μg/mL, 22 or about 22 μg/mL, 23 or about 23 μg/mL, 24 or about 24 μg/mL, 25 or about 25 μg/mL, 26 or about 26 μg/mL, 27 or about 27 μg/mL, 28 or about 28 μg/mL, 29 or about 29 μg/mL, 30 or about 30 μg/mL, 31 or about 31 μg/mL, 32 or about 32 μg/mL, 33 or about 33 μg/mL, 34 or about 34 μg/mL, 35 or about 35 μg/mL, 36 or about 36 μg/mL, about 37 μg/mL, 38 or about 38 μg/mL, 39 or about 39 μg/mL, 40 or about 40 μg/mL, 41 or about 41 μg/mL, 42 or about 42 μg/mL, 43 or about 43 μg/mL, 44 or about 44 μg/mL, 45 or about 45 μg/mL, 46 or about 46 μg/mL, 47 or about 47 μg/mL, 48 or about 48 μg/mL, 49 or about 49 μg/mL, 50 or about 50 μg/mL, 55 or about 55 μg/mL, 60 or about 60 μg/mL, 65 or about 65 μg/mL, 70 or about 70 μg/mL, 75 or about 75 μg/mL, 80 or about 80 μg/mL, 85 or about 85 μg/mL, 90 or about 90 μg/mL, 95 or about 95 μg/mL, 100 or about 100 μg/mL, or more than 100 μg/mL or any range or combination thereof.

In some embodiments, the enzyme is GGPPS, such as a GGPPS disclosed herein. In some embodiments, GGPPS is at a concentration of 8.2 μg/mL. In some embodiments, GGPPS is at a concentration of 1 or about 1 μg/mL, 2 or about 2 μg/mL, 3 or about 3 μg/mL, 4 or about 4 μg/mL, 5 or about 5 μg/mL, 6 or about 6 μg/mL, 7 or about 7 μg/mL, 8 or about 8 μg/mL, 9 or about 9 μg/mL, 10 or about 10 μg/mL, 11 or about 11 μg/mL, 12 or about 12 μg/mL, 13 or about 13 μg/mL, 14 or about 14 μg/mL, 15 or about 15 μg/mL, 16 or about 16 μg/mL, 17 or about 17 μg/mL, 18 or about 18 μg/mL, 19 or about 19 μg/mL, 20 or about 20 μg/mL, 21 or about 21 μg/mL, 22 or about 22 μg/mL, 23 or about 23 μg/mL, 24 or about 24 μg/mL, 25 or about 25 μg/mL, 26 or about 26 μg/mL, 27 or about 27 μg/mL, 28 or about 28 μg/mL, 29 or about 29 μg/mL, 30 or about 30 μg/mL, 31 or about 31 μg/mL, 32 or about 32 μg/mL, 33 or about 33 μg/mL, 34 or about 34 μg/mL, 35 or about 35 μg/mL, 36 or about 36 μg/mL, 37 or about 37 μg/mL, 38 or about 38 μg/mL, 39 or about 39 μg/mL, 40 or about 40 μg/mL, 41 or about 41 μg/mL, 42 or about 42 μg/mL, 43 or about 43 μg/mL, 44 or about 44 μg/mL, 45 or about 45 μg/mL, 46 or about 46 μg/mL, 47 or about 47 μg/mL, 48 or about 48 μg/mL, 49 or about 49 μg/mL, 50 or about 50 μg/mL, 55 or about 55 μg/mL, 60 or about 60 μg/mL, 65 or about 65 μg/mL, 70 or about 70 μg/mL, 75 or about 75 μg/mL, 80 or about 80 μg/mL, 85 or about 85 μg/mL, 90 or about 90 μg/mL, 95 or about 95 μg/mL, 100 or about 100 μg/mL, or more than 100 μg/mL or any range or combination thereof.

In some embodiments, the enzyme is taxadiene synthase. In some embodiments, taxadiene synthase is at a concentration of 30 μg/mL. In some embodiments, taxadiene synthase is at a concentration of 1 or about 1 μg/mL, 2 or about 2 μg/mL, 3 or about 3 μg/mL, 4 or about 4 μg/mL, 5 or about 5 μg/mL, 6 or about 6 μg/mL, 7 or about 7 μg/mL, 8 or about 8 μg/mL, 9 or about 9 μg/mL, 10 or about 10 μg/mL, 11 or about 11 µg/mL, 12 or about 12 µg/mL, 13 or about 13 µg/mL, 14 or about 14 µg/mL, 15 or about 15 µg/mL, 16 or about 16 µg/mL, 17 or about 17 µg/mL, 18 or about 18 µg/mL, 19 or about 19 µg/mL, 20 or about 20 µg/mL, 21 or about 21 µg/mL, 22 or about 22 µg/mL, 23 or about 23 µg/mL, 24 or about 24 µg/mL, 25 or about 25 µg/mL, 26 or about 26 µg/mL, 27 or about 27 µg/mL, 28 or about 28 µg/mL, 29 or about 29 µg/mL, about 30 µg/mL, 31 or about 31 µg/mL, 32 or about 32 µg/mL, 33 or about 33 µg/mL, 34 or about 34 µg/mL, 35 or about 35 µg/mL, 36 or about 36 µg/mL, 37 or about 37 µg/mL, 38 or about 38 µg/mL, 39 or about 39 µg/mL, 40 or about 40 µg/mL, 41 or about 41 µg/mL, 42 or about 42 µg/mL, 43 or about 43 µg/mL, 44 or about 44 µg/mL, 45 or about 45 µg/mL, 46 or about 46 µg/mL, 47 or about 47 µg/mL, 48 or about 48 µg/mL, 49 or about 49 µg/mL, 50 or about 50 µg/mL, 55 or about 55 µg/mL, 60 or about 60 µg/mL, 65 or about 65 µg/mL, 70 or about 70 µg/mL, 75 or about 75 µg/mL, 80 or about 80 µg/mL, 85 or about 85 µg/mL, 90 or about 90 µg/mL, 95 or about 95 µg/mL, 100 or about 100 µg/mL, or more than 100 µg/mL or any range or combination thereof. In some embodiments, the taxadiene synthase produces taxadiene.

In some embodiments, choline kinase is at a concentration of between 15 and 35 µg/mL, IPK is at a concentration of between 5 and 25 µg/mL, IDI is at a concentration of between 15 and 35 µg/mL, IspA is at a concentration of between 25 and 45 µg/mL, GGPPS is at a concentration of between 5 and 15 µg/mL, and/or taxadiene synthase is at a concentration of between 20 and 40 µg/mL. In some embodiments, choline kinase is at a concentration of 25 µg/mL, IPK is at a concentration of 15 µg/mL, IDI is at a concentration of 25 µg/mL, IspA is at a concentration of 37 µg/mL, GGPPS is at a concentration of 8.2 µg/mL, and/or taxadiene synthase is at a concentration of 30 µg/mL.

EXAMPLES

Materials and Methods

Strains, Plasmids and Genes

*E. coli* K12 MG1655(DE3) was used at the parent strain for all metabolic pathway expression studies, while DH5α (New England Biolabs-NEB) was used for routine cloning purposes, and BL21 (DE3) (NEB) was used for the expression of proteins for purification. Genotypes are listed in Table 1. Plasmids used as templates for the construction of the Isopentenol Utilization Pathway (IUP) vector and the downstream vectors are also listed in Table 1. The genes listed in Table 1 were custom synthesized, and codon optimized for *E. coli* MG1655 (Integrated DNA Technologies-IDT) where indicated, otherwise they were amplified from an existing plasmid or from genomic DNA. Genomic DNA was purified using the Wizard Genomic DNA Purification Kit (Promega Corporation).

TABLE 1

List of strains and plasmids

| Host/Strain | Description | Reference |
|---|---|---|
| MG1655 (DE3) | ΔendA ΔrecA (λ DE3) | |
| DH5α | fhuA2 Δ(argF-lacZ)U169 phoA glnV44 Φ80 Δ(lacZ)M15 gyrA96 recA1 relA1 endA1 thi-1 hsdR17 | NEB |
| BL21 (DE3) | fhuA2 [lon] ompT gal (λ DE3) [dcm] ΔhsdS λ DE3 = λ sBamHIo ΔEcoRI-B int::(lacI::PlacUV5::T7 gene1) i21 Δnin5 | NEB |
| KO1 | MG1655 (DE3), ΔispG, pBad33-proA-MEVI | This study |
| KO2 | MG1655 (DE3), ΔispG, pBad33-proA-MEVI, pSEVA228pro4IUPi | This study |
| KO3 | MG1655 (DE3), ΔispG, pBad33-proA-MEVI, pTETIUPi | This study |

| Plasmids | Description (origin, antibiotic marker, promoter, operon) | Reference |
|---|---|---|
| pET28a(+) | pBR322, $Kn^R$, $P_{T7lacUV}$, enzymes from Table 1 with N terminal 6 x his tag | Novagen |
| pADS | pTrc99A derivative containing the ADS gene; $Ap^R$ | (19) |
| pJBEI-6409 | p15A, $Cm^R$, $P_{lacUV5}$, atoB, hmgs, hmgr, $P_{lacUV5}$, mvk, pmk, pmd, idi, $P_{trc}$, trGPPS, ls | (36) |
| pAC-LYCipi | p15A, $Cm^R$, crtE, ipi, crtI, crtB, endogenous promoter | (26) |
| pSEVA228 | RK2, $Kn^R$, xlyS-Pm | (20) |
| pBbS2k-RFP | SC101, $Kn^R$, $P_{TET}$, rfp | (22) |
| pETMEOH500 | pBR322, $Kn^R$, $P_{T7lacUV}$, mdh | This study |
| pTETmdh | pBR322, $Kn^R$, $P_{TET}$, mdh | This study |
| pMBIS | RK2, $Tc^R$, $P_{trc}$, erg12, erg8, mvd1, idi, ispA | (19) |
| pBad33-proA-MEVI | p15A, $Cm^R$, $P_{proA}$, erg12, erg8, mvd1 | This study |
| pCas9 | pSC101 ori RepA101ts, $Kn^R$, $P_{araC}$, cas9 | (18) |
| pTargetF | pij23119, pMB1, $Sp^R$ | (18) |
| pTargetF-ispG | pij23119, pMB1, $Sp^R$ | This study |
| p20-LYCipi | pBR322, $Sp^R$, crtE, ipi, crtI, crtB, endogenous promoter | This study |
| pUC-LYCipi | pUC19, $Sp^R$, crtE, ipi, crtI, crtB, endogenous promoter | This study |
| p5T7-LYCipi | pSC101, $Sp^R$, $P_{T7lacUV}$, crtE, ipi, crtI, crtB | This study |
| p5T7-LYCipi-ggpps | pSC101, $Sp^R$, $P_{T7lacUV}$, ggpps, ipi, crtI, crtB | This study |
| p5T7tds-ggpps | pSC101, $Sp^R$, $P_{T7lacUV}$, tds, ggpps | (27) |
| p5T7ksl-ggpps | pSC101, $Sp^R$, $P_{T7lacUV}$, ksl, ggpps | (37) |
| p5T7vs-ispA | pSC101, $Sp^R$, $P_{T7lacUV}$, vs, ispA | (37) |
| p5T7ggps-ls | pSC101, $Sp^R$, $P_{T7lacUV}$, gpps, ls | This study |
| p5T7ispA-ads | pSC101, $Sp^R$, $P_{T7lacUV}$, ispA, ads | This study |
| pSEVA228-pro4IUPi | RK2, $Kn^R$, $P_{proA}$, ck, ipk, idi | This study |
| pSEVA228-proDIUPi | RK2, $Kn^R$, $P_{proD}$, ck, ipk, idi | This study |

TABLE 1-continued

List of strains and plasmids

| | | |
|---|---|---|
| pTET-IUPi | pBR322, Kn$^R$, P$_{TET}$, ck, ipk, idi | This study |
| pTrcsGFP | pBR322, Amp$^R$, P$_{trc}$, sgfp | (32) |
| pSEVA228pro4-gfp | RK2, Kn$^R$, P$_{pro4}$, sgfp | This study |
| pTET-gfp | pBR322, Kn$^R$, P$_{TET}$, sgfp | This study |
| pSEVA228pro4-ck-idi | RK2, Kn$^R$, P$_{pro4}$, ck, idi | This study |

Ap$^R$ = ampicillin
Kn$^R$ = kanamycin
Tc$^R$ = Tetracyclin
Sp$^R$ = Spectinomycin

TABLE 2

List of genes and their origins used in this study

| Genes | Origin (Accession Number) |
|---|---|
| tds | *Taxus brevifolia* (AAC49310.1), codon optimized, truncated first 60 amino acids, methionine added |
| ggpps | *Taxus canadensis* (AAD16018.1), codon optimized, truncated first 98 amino acids, methionine added |
| crtE, crtI, crtB, ipi | *Pantoea agglomerans*, crtE (AAA21260.1), crtB (AFZ89043.1), crtI (AFZ89042.1), ipi (AAA64978.1) |
| ksl | *Salvia miltiorrhiza*, codon optimized, methionine added, (ABV08817.1) |
| vs | *Callitropsis nootkatensis*, codon optimized, methionine added (AFN21429.1) |
| ls | *Mentha spicata* (AAC37366.1), codon optimized |
| gpps | *Abies grandis* (AAN01134.1), codon optimized |
| ads | *Artemisia annua* (AEQ63683.1), codon optimized |
| ispA | *E. coli* (WP_097750737.1) |
| ipk | *Arabidopsis thaliana* (AAN12957.1), codon optimized |
| Scck | *S. cerevisiae* (AAA34499.1), codon optimized |
| Hvipk | *Haloferax volcanii* (ADE04091.1), codon optimized |
| Mtipk | *Methanothermobacter thermautotrophicus* (AAB84554.1), codon optimized |
| Mjipk | *Methanocaldococcus jannaschii* (AAB98024.1), codon optimized |
| Taipk | *Thermoplasma acidophilum* (CAC11251.1), codon optimized |
| Taipk-3m | *Thermoplasma acidophilum* (CAC11251.1), codon optimized, three mutations (V72I, Y140V, K203G) |
| Ecgk | *E. coli* (AAA23913.1) |
| erg12/Scmk | *S. cerevisiae* (CAA29487.1) |
| Echk | *E. coli* (AAC73114.1) |
| idi | *E. coli* (AAD26812.1) |

TABLE 3

List of primers used in this study

| Name | SEQ ID NO | Sequence |
|---|---|---|
| GB_p5t7tds-ggpps_r | 2 | ATGGTATATCTCCTTATTAAAGTTAAAC |
| GB_p5t7tds-ggpps_f | 3 | TATTAGTTAAGTATAAGAAGGAGATATAC |
| GB_gpps_ls_f | 4 | TAATAAGGAGATATACCATATGGAATTTGACTTCAACAAATAC |
| GB_gpps_ls_r | 5 | CTTCTTATACTTAACTAATACGAGGAAGCGGAATATATC |
| GB_ispA_f | 6 | TAATAAGGAGATATACCATATGGACTTTCCGCAGCAAC |
| GB_ispA_r | 7 | CTCCTTCTTAAAAGATCCTTTATTTATTACGCTGGATGATGTAGTC |
| GB_ads_f | 8 | GTAATAAATAAAGGATCTTTTAAGAAGGAGATATACATGGCCCTGACCGAAGAG |
| GB_ads_r | 9 | CTTCTTATACTTAACTAATATCAGATGGACATCGGGTAAAC |
| GB_pAC-LYCipi_r | 10 | CAGTTATTGGTGCCCTTAAACG |
| GB_pAC-LYCipi_f | 11 | TAAGCTTTAATGCGGTAGTTTATCAC |
| GB_aadA1_f | 12 | AGGGCACCAATAACTGGGTGAACACTATCCCATATC |
| GB_aadA1_r | 13 | TAACCGTATAATCATGGCAATTCTGGAAG |
| GB_pUC19_f | 14 | GCCATGATTATACGGTTATCCACAGAATC |
| GB_pUC19_r | 15 | CTACCGCATTAAAGCTTAAGGATCTAGGTGAAGATC |
| GB_pBR322_f | 16 | ATTGCCATGATTCCCCTTGTATTACTGTTTATG |
| GB_pBR322_r | 17 | CTACCGCATTAAAGCTTAACTCAAAGGCGGTAATAC |
| GB_p5T7_r | 18 | ATGGTATATCTCCTTATTAAAGTTAAACAAAATTATTTCTACAGGG |
| GB_p5T7_f | 19 | TTAATAAGGAGATATACCATATGGTGAGTGGCAGTAAAGC |
| GB_p20-LYCipi_f | 20 | CTCCTTCTTATACTTAACTAATACTGCGTGAACGTCATGGC |
| GB_p20-LYCipi_r | 21 | TATTAGTTAAGTATAAGAAGGAGATATAC |
| GB-pET28-HisT-vec f | 22 | CACCACCACCACCACCAC |
| GB-pET28-HisT-vec r | 23 | CGGTATATCTCCTTCTTAAAGTTAAACAAAATTATTTC |
| GB-pET28-ScCK_f | 24 | AAGAAGGAGATATACCGATGGTACAAGAATCACGTC |
| GB-pET28-ScCK_r | 25 | TCAGTGGTGGTGGTGGTGGTGCAAATAACTAGTATCGAGGAAC |
| GB-pET28-EcGK f | 26 | AAGAAGGAGATATACCGATGACTGAAAAAAAATATATCGTTGC |
| GB-pET28-EcGK r | 27 | TCAGTGGTGGTGGTGGTGGTGTTCGTCGTGTTCTTCCCAC |

TABLE 3-continued

List of primers used in this study

| Name | SEQ ID NO | Sequence |
|---|---|---|
| GB-pET28-EcHK_f | 28 | AAGAAGGAGATATACCGATGGTTAAAGTTTATGCCCC |
| GB-pET28-EcHK_r | 29 | TCAGTGGTGGTGGTGGTGGTTTTCCAGTACTCGTGC |
| GB-pET28-TaIPK-3m_f | 30 | AAGAAGGAGATATACCGATGATGATTCTGAAAATCGGAG |
| GB-pET28-TaIPK-3m_r | 31 | TCAGTGGTGGTGGTGGTGGTGTCGAATGACAGTACCGATG |
| GB-pET28-MjIPK_f | 32 | AAGAAGGAGATATACCGATGCTGACCATCCTGAAATTAG |
| GB-pET28-MjIPK_r | 33 | TCAGTGGTGGTGGTGGTGGTGTTCGCTAAAGTCGATCTC |
| GB-pET28-TaIPK_f | 34 | AAGAAGGAGATATACCGATGATGATTCTTAAGATAGGGGG |
| GB-pET28-TaIPK_r | 35 | TCAGTGGTGGTGGTGGTGGTGACGAATGACGGTTCCGATG |
| GB-pET28-Mtipk_f | 36 | AAGAAGGAGATATACCGATGATCATTCTGAAACTGGG |
| GB-pET28-Mtipk_r | 37 | TCAGTGGTGGTGGTGGTGGTGATGTTTTCCTGTGATACGC |
| GB-pET28-HvIPK_f | 38 | AAGAAGGAGATATACCGATGTCCCTGGTGGTCCTTAAA |
| GB-pET28-HvIPK_r | 39 | TCAGTGGTGGTGGTGGTGGTGTTCCCCGCGAATGACTGT |
| GB-pET28-ScMK_f | 40 | TTTAAGAAGGAGATATACCGATGTCATTACCGTTCTTAAC |
| GB-pET28-ScMK_r | 41 | CAGTGGTGGTGGTGGTGGTGCTATGAAGTCCATGGTAAATTC |
| GB-pETMeOH500_f | 42 | ATGACCCACCTGAACATC |
| GB-pETMeOH500_r | 43 | GCGCAACGCAATTAATGTAAG |
| GB-pBBS2k-rfp_f | 44 | TTACATTAATTGCGTTGCGCTTAAGACCCACTTTCACATTTAAG |
| GB-pBBS2k-rfp_r | 45 | GCGATGTTCAGGTGGGTCATATGTATATCTCCTTCTTAAAAGATC |
| GB-pTet-IUP-Ins_f | 46 | TTTAAGAAGGAGATATACATATGGTGCAGGAGTCCCGC |
| GB-pTet-IUP-Ins_r | 47 | GTCGACGGAGCTCGAATTCGTTATTTGCTGAAGCGGATGATGGTC |
| GB-pTet-Vec_f | 48 | CGAATTCGAGCTCCGTCG |
| GB-pTet-Vec_r | 49 | ATGTATATCTCCTTCTTAAAAGATCTTTTGAATTC |
| Pro4_Mut_f | 50 | GGGCATGCATAAGGCTCGGATGATATATTCAGGGAGACC |
| ProLibrary_Mut_r | 51 | CGAGCCTTATGCATGCCC |
| GB-SEVA228_f | 52 | GGGTCCCCAATAATTACG |
| GB-SEVA228_r | 53 | CAGCTGGGCGCGCCGTAG |
| GB-proD_f | 54 | TTCTACGGCGCGCCCAGCTGTTCTAGAGCACAGCTAACAC |
| GB-proD_r | 55 | TCCTTGCGTTGAAACCGTTGTGGTCTCC |
| GB-chk_f | 56 | CAACGGTTTCAACGCAAGGAAACACATTAAG |
| GB-chk_r | 57 | TTTCTTGTACTTACAGGTAGCTGGTGTC |
| GB-atipk_f | 58 | CTACCTGTAAGTACAAGAAAAGTCAGTAGTC |
| GB-atipk_r | 59 | CTCCTTAGTTTTATTTGCTGAAGCGGATG |
| GB-iditerm_f | 60 | CAGCAAATAAAACTAAGGAGGTCTATATGC |
| GB-iditerm_r | 61 | ATCGTAATTATTGGGGACCCGATATAGTTCCTCCTTTCAG |
| GB-IUPnoIPK_f | 62 | CTACCTGTAAAACTAAGGAGGTCTATATGC |
| GB-IUPnoIPK_r | 63 | CTCCTTAGTTTTACAGGTAGCTGGTGTC |
| pCas9-ispG_f | 64 | GCGACATTGAAGAAGATAAGG |
| pCas9-ispG_r | 65 | GTTTACGGTGTAAGCGATCC |
| pCas9-ispG-seq_f | 66 | GATTGCTGGCTGGAGGTCAC |
| GB-pTargetF-ispGN20_f | 67 | GTCCTAGGTATAATACTAGTCGCTGCGTATCCGTTCGCGAGTTTTAGAGCTAGAAATAGC |
| GB-ptargetF-N20_r | 68 | ACTAGTATTATACCTAGGACTGAG |
| GB-pTargetF-vec_f | 69 | CACCACCGACTATTTGCAAC |
| GB-pTargetF-vec_r | 70 | CTCGAGTAGGGATAACAGGGTA |
| GB-ispG-H1_f | 71 | CCCTGTTATCCCTACTCGAGCCAGCGTCTGTGGATACTACC |
| GB-ispG-H1_r | 72 | TCCCATCACGTCTCCCGCGTTACCCGTC |
| GB-ispG-H2_f | 73 | ACGCGGGAGACGTGATGGGAAGCGCCTC |
| GB-ispG-H2_r | 74 | GTTGCAAATAGTCGGTGGTGCTTCGCAGCCCAACTGATG |
| p5T7Lyc-ggpps_f | 75 | TTAATAAGGAGATATACCATATGTTCGACTTCAACGAG |
| p5T7Lyc-ggpps_r | 76 | TTGAACCCAAAAGGCGGTATTAGTTTTGACGAAAGGC |
| p5T7Lyc-back_f | 77 | TACCGCCCTTTTGGGTTC |
| p5T7Lyc-back_r | 78 | ATGGTATATCTCCTTATTAAAGTTAAAC |
| GB-sGFP-pSEVA F | 79 | GAAAGAGGAGAAATACTAGTATGAGCAAGGGCGAAGAG |
| GB-sGFP-pSEVA R | 80 | CAAGCTTGTCGACGGAGCTCTTACTTATAGAGTTCATCCATGCC |
| GB-pSEVA-back F | 81 | GAGCTCCGTCGACAAGCTTG |

TABLE 3-continued

List of primers used in this study

| Name | SEQ ID NO | Sequence |
|---|---|---|
| GB-pSEVA-back R | 82 | ACTAGTATTTCTCCTCTTTCTCTAGTAAA AGTTAAAC |
| GB-sGFP-pTET F | 83 | TTTAAGAAGGAGATATACATATGAGCAAG GGCGAAGAG |
| GB-sGFP-pTET R | 84 | GTCGACGGAGCTCGAATTCGTTACTTATA GAGTTCATCCATGCC |
| GB-pTET-back F | 85 | CGAATTCGAGCTCCGTCG |
| GB-pTET-back R | 86 | ATGTATATCTCCTTCTTAAAAGATCTTTT GAATTC |
| GB-pBro IAI Vec F | 87 | GAGCTCCGTCGACAAGCT |
| GB-pBro IAI Vec R | 88 | ACTAGTATTTCTCCTCTTTCTCTAGTAAA AG |
| GB-proX-Mevi Ins F | 89 | CTAGAGAAAGAGGAGAAATACTAGTATGT CATTACCGTTCTTAACTTC |
| GB-proX-Mevi Ins R | 90 | CAAGCTTGTCGACGGAGCTCTTATTCCTT TGGTAGACCAG |

Routine Cloning Protocol

A standard protocol was used for the cloning of all plasmids described in this work. First primers were designed for Gibson assembly using the NEBuilder online tool (NEB), and primers were purchased from Sigma-Aldrich. PCR reactions were performed in a Bio-rad C1000 Touch Dual Block thermocycler using 2×Q5 polymerase master mix (NEB) according to manufacturer's recommendations. The products were digested with DpnI (NEB) enzyme for 1 h at 37° C. to digest the template DNA. The PCR products were then run on a 1% agarose gel using a Mini or Sub Cell and a Powerpac Basic power supply (Bio-rad). Fragments were gel extracted using a Zymoclean Gel DNA recovery kit (Zymo Research) according to the manufacturer's recommendation. Fragments were ligated using the Gibson Assembly Master Mix (NEB) for 1 h at 50° C. and transformed into DH5α (NEB) high efficiency chemical competent cells (NEB) according to standard protocol. Transformants were screened by PCR using colonies boiled in water for 10 min as the template. Two to three positive transformants were cultured overnight in LB media and the plasmid was purified using a Mini-prep kit (Qiagen). Overlapping regions of the new construct were sequenced to confirm the sequence of the new plasmid (Quintara Biosciences, Boston). Plasmids with confirmed sequences for protein purification were transformed into BL21(DE3) using heat-shock, otherwise, plasmids were transformed into MG1655(DE3) for further study by electroporation using a MicroPulser (Bio-rad). Electrocompetent cells were made by a standard glycerol washing of mid-log phase cells (Bio-rad) and stored at −80° C. until future use. For electroporation, 1 μL of purified plasmid in water was added to 50 μL of electrocompetent cells using 1. kV and electroporated in 1 mm pathlength cuvettes (Bulldog Bio).

Construction of Enzyme Expression Vectors

All enzyme expression vectors were based on the pET-28 vector, into which the genes for enzyme expression were inserted. Backbone fragments were amplified from pET-28 a (+) vector using the primer pair GB pET28-HisT-vec_f/r.

The insert fragments were amplified as follows: the fragments containing the genes for ScCK or ScMK expression were amplified from S. cerevisiae genomic DNA using the primer pairs GB-pET28-CHOLKIN_f/r or GB-pET28-MEVKIN_f/r respectively, the fragments containing the gene for EcGK or EcGK expression were amplified from E. coli genomic DNA using the primer pairs GB-pET28-GLYCKIN_f/r or GB-pET28-HSERKIN_f/r respectively, whereas the fragments the genes for HvIPK, MtIPK, MjIPK, TaIPK or TaIPK-3m expression were amplified from custom synthesized, and codon optimized DNA using the primer pairs GB-pET28-HV_f/r, GB-pET28-MTH_f/r, GB-pET28-MJ_f/r, GB-pET28-THA_f/r, or GB-pET28-THA3m_f/r respectively. The backbone and insert fragments were then assembled to give the respective plasmids.

Construction of the Isopentenol Utilization Pathway (IUP)

The plasmid pSEVA228-proDIUPi was generated by amplifying the backbone pSEVA228 with the primers GB-SEVA228_f/r and inserting a custom-synthesized promoter sequence, shown in Table 4, which incorporates the proD promoter system,[21] which was amplified using the primer pairs GB-proD_f/r, along with the IUP operon, consisting of the genes ck, ipk and idi. Each of the three operon elements was amplified from custom synthesized DNA fragments (IDT) using the primer pairs GB-chk_f/r, GB-atipk_f/r and GB-iditerm_f/r respectively. In all three cases, the codon-optimized gene coding sequence was preceded by a corresponding optimized RBS (shown in Table 4) and in the case of idi, it was followed by a T7 terminator derived from pET-28(+) (shown in Table 4). The RBSs were optimized using the Salis lab RBS optimization tool.[30, 31] The PCR fragments were assembled to give pSEVA228-proDIUPi. The plasmid pSEVA228-pro4IUPi was created by replacing the 6 nucleotides in the proD promoter sequence of pSEVA228-proDIUPi with the primer pairs GB-pro4_Mut_f/GB-ProLibrary_Mut_r to amplify the whole plasmid and then subsequently assembling the amplification product. The plasmid pSEVA228pro4-ck-idi, which carries a reduced version of the IUP operon, lacking ipk, was created by amplifying pSEVA228-pro4IUPi using the primer pair GB-IUPnoIPK_f/r and then subsequently assembling the amplification product. The pTET-IUPi plasmid was created as follows: The pTET backbone was created by replacing the T7/lac promoter region of pET-28a carrying a methanol utilization operon (pETMeOH500) with the androtetracycline repressor and promoter region of pBbS2k-rfp by Gibson assembly using primers GB-pETMeOH500-f/r and GB-pBbS2k-rfp-f/r. Then, the methanol utilization operon was replaced with the IUP operon from pSEVA228-pro4IUPi by Gibson assembly using the primers pTet-IUP-ins_f/r, and pTet-IUP-ins_f/r, to produce plasmid pTET-IUPi. pSEVA228 was a gift from Jason King. pETMeOH500 was a gift from Benjamin Woolston. pBbS2k-RFP was a gift from Jay Keasling (Addgene plasmid #35330).

TABLE 4

Custom promoter and RBS Sequences used for the creation of pSEVA228-proDIUPi vector

| SEQ ID NO | |
|---|---|
| 91 | Promoter sequence TTCTAGAGCACAGCTAACACCACGTCGTCCCTATCTGCTGCCCT AGGTCTATGAGTGGTTGCTGGATAACTTTACGGGCATGCATAAG GCTCGTATAATATATTCAGGGAGACCACAACGGTTTC |

TABLE 4-continued

Custom promoter and RBS Sequences used
for the creation of pSEVA228-proDIUPi vector

| SEQ ID NO | |
|---|---|
| 92 | RBS for ck<br>AACGCAAGGAAACACATTAAGGAGGTTTAA |
| 93 | RBS for ipk<br>GTACAAGAAAAGTCAGTAGTCTAAGGAGGTAAGC |
| 94 | RBS for idi<br>AACTAAGGAGGTCTAT |
| 95 | T7 terminator region<br>GCTAACAAAGCCCGAAAGGAAGCTGAGTTGGCTGCTGCCACCGC<br>TGAGCAATAACTAGCATAACCCCTTGGGGCCTCTAAACGGGTCT<br>TGAGGGGTTTTTTGCTGAAAGGAGGAACTATATC |

Estimation of IUP Expression Strength

The expression strength for both IUP expression vectors (either pSEVA228-proDIUPi or pTET-IUPi) was approximated through characterization using superfolded GFP (sGFP), as reported in C. N. S. Santos, M. Koffas, G. Stephanopoulos, Optimization of a heterologous pathway for the production of flavonoids from glucose. *Metab. Eng.* 13, 392-400 (2011), as a reporter gene. Variants of both IUP expression vectors containing the sGFP ORF instead of the IUP genes were created by first PCR amplifying the vector backbone from pSEVA228-proDIUPi using the primer pair GB-pSEVA-back F/R or from pTET-IUPi using the primer pair GB-pTET-back F/R respectively, then PCR amplifying PCR amplifying the insert fragment containing sGFP from plasmid pTrcsGFP[32] using the primer pairs GB-sGFP-pSEVA F/R or GB-sGFP-pTET F/R respectively and then assembling the respective fragments to give plasmids pSEVA228pro4-gfp and pTET-gfp.

In order to assess the strength of the expression systems, we use a GFP-based assay, adapted from J. H. Davis, A. J. Rubin, R. T. Sauer, Design, construction and characterization of a set of insulated bacterial promoters. *Nucleic Acids Res.* 39, 1131-1141 (2011). *E. coli* MG1655 DE3 transformed with either plasmid were grown at 37° C. until reaching mid-log phase, at which point GFP fluorescence and $OD_{600}$ was measured (time point 1; tp1). After a further 1.25 h of growth (time point 2; tp2), GFP fluorescence and OD600 was again assayed and the GFP synthesis rate, which we used as a proxy for promoter strength, was calculated using the equation: Synthesis rate=$(GFP_{tp2}-GFP_{tp1})/OD_{600,average}$.

Knockout of the Native MEP Pathway

The MEP pathway was knocked out by deleting ispG using the CRISPR-cas9 system, in a procedure adapted from Y. Jiang et al., Multigene editing in the *Escherichia coli* genome using the CRISPR-Cas9 system. *Appl. Environ. Microbiol.* 81, 2506-2514 (2015); V. J. J. Martin, D. J. Pitera, S. T. Withers, J. D. Newman, J. D. Keasling, Engineering a mevalonate pathway in *Escherichia coli* for production of terpenoids. *Nat. Biotechnol.* 21, 796-802 (2003). First, pBad33-proA-MEVI was created by Gibson assembly after PCR amplification of the pBAD33 backbone using primer GB-pBro IAI Vec F/R and the amplification of the lower mevalonate pathway from the pMBIS plasmid using primers GB-proX-Mevi F/R. The resulting plasmid pBAD33-proA-MEV was created to act as a rescue mechanism for the knockout of ispG which is normally non-viable. The targeting plasmid, pTargetF-ispG was created by first altering the N20 targeting sequence of the pTargetF plasmid using the primer pair GB-pTargetF-ispGN20_f and GB-ptargetF_N20_r to amplify pTargetF and circularizing the resulting PCR product with Gibson assembly. The vector was then amplified using the primer pair GB-pTargetF-vec_f/r and the homology regions H1 and H2 were inserted. H1 was designed to encompass the 494 base pairs preceding the ispG gene and H2 was designed to encompass the 501 base pairs after the ispG gene. The homology regions were amplified using GB-ispG-H1_f/r and GB-ispG-H2_f/r respectively. The resulting fragments were then ligated using Gibson Assembly. pMBIS was a gift from Jay Keasling (Addgene plasmid #17817). pTargetF was a gift from Sheng Yang (Addgene plasmid #62226).

*E. coli* MG1655 (DE3) was then transformed with the plasmids pBAD33-proA-MEV and pCas9 and plated on a chloramphenicol and kanamycin LB-agar plate overnight. The resulting double transformant was then grown at 30° C. in LB media, which was supplemented with 1 mM D-arabinose at $OD_{600}$=0.03. Upon reaching mid-log phase, the cells were harvested and washed with glycerol to make them electrocompetent which were then transformed with the plasmid pTargetF-ispG and plated overnight at 30° C. on LB-agar plates supplemented with kanamycin, chloramphenicol, spectinomycin, and 1 mM mevalonate. Deletion of ispG was confirmed by amplification of the area surrounding ispG in the genome using primer pair pCas9-ispG_f/r and sequencing the fragment using primer pCas9-ispG-seq_f. Strain KO1 was obtained by curing the cells of pTargetF-ispG by growth in LB media supplemented with 1 mM IPTG and subsequently curing the cells of pCas9 by growth overnight at 42° C. Strain KO2 was obtained by making KO1 electrocompetent and transforming with pSEVA-pro4IUPi plasmid. pCas was a gift from Sheng Yang (Addgene plasmid #62225)

Mevalonate used in this experiment was produced using the process described in V. J. J. Martin, D. J. Pitera, S. T. Withers, J. D. Newman, J. D. Keasling, Engineering a mevalonate pathway in *Escherichia coli* for production of terpenoids. *Nat. Biotechnol.* 21, 796-802 (2003) by mixing 1.02 volumes of 2 mM KOH with 1 volume of 2 mM DL-mevalonolactone (sigma-Aldrich) and incubating at 37° C. for 30 min.

Construction of Downstream Isoprenoid Pathways

The copy number of the lycopene plasmids were varied by first amplification of the genes crtEIB and ipi as well as the endogenous lycopene promoter using primers GB_pAC-LYCipi_f/r from the pAC-LYCipi plasmid. The fragment containing the gene aadA1 (spectinomycin resistance) was amplified using GB_aadA1_f/r from p5T7tds-ggpps and the origins pUC19 and pBR322 were amplified using GB_pUC19_f/r and GB_pBR322_f/r from pUC19 and pET28a respectively. These fragments were assembled with the appropriate origin to create pUC-LYCipi and p20-LYCipi. To create p5T7-LYCipi, the backbone of p5T7tds-ggpps was amplified using GB_p5T7_f/r and the lycopene synthesis genes were amplified from p20-LYCipi using the primers GB_p20-LYCipi_f/r and then assembled. To make p5T7-LYCipi-ggpps, the backbone of p5T7-LYCipi was amplified using primers p5T7Lyc-back_f/r and the ggpps was amplified from p5T7tds-ggpps using p5T7Lyc-ggpps_f/r and then assembled. p5T7gpps-1s and P5T7ispA-ads were created by PCR amplification of the p5T7tds-ggpps vector using primers GB_p5t7ggppstds_f/r to create the backbone from the T7 terminator to the T7 promoter. The primers GB_gpps_ls_f/r were used to amplify the gpps-ls operon from JBEI-6409 for Gibson Assembly in this backbone created the p5T7-gpps-ls vector. Primers GB_ispA_f/r and GB_ads_f/r (with RBS encoded on the primer) were used to amplify ispA from p5T7vs-ispA and ads from pADS respectively. These two fragments were assembled into the same backbone as gpps-ls to create the p5T7-ispA-ads vector. pAC-LYCipi was a gift from Francis X Cunningham Jr (Addgene plasmid #53279) pADS was a gift from Jay Keasling (Addgene plasmid #19040). JBEI-6409 was a gift from Taek Soon Lee (Addgene plasmid #47048).

Enzyme Expression and Purification

Figure 9C:
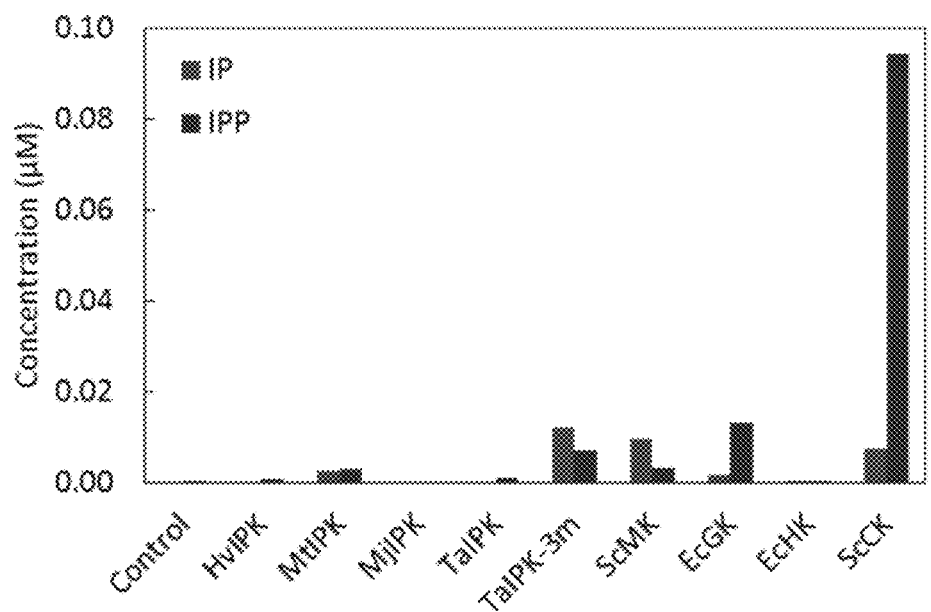

BL21 harboring a pET-28 vector for the expression of proteins in FIG. 9B was revived from a glycerol stock by inoculating into LB media and growing at 37° C. overnight. Two hundred milliliters of SOB media (Amresco) in a baffled 1 L flask was inoculated at 1% with the overnight culture and grown until an OD of 0.5 at 30° C. The culture then induced with IPTG at a final concentration of 100 uM. Cultures were incubated for 3-4 h at 30° C. for protein synthesis after which they were centrifuged in an Allegra X12R centrifuge (Beckman-Coulter) at 3273×g for 15 min. The supernatant was removed, and the cell pellets were stored at −20° C. until purification. Proteins were purified using the following protocol and at all stages proteins were keep on ice. First, cells were lysed using 5 mL of ice-cold NPI-10 buffer (50 mM $NaH_2PO_4$, 300 mM NaCl, 10 mM imidazole, pH 8.0) using a gas driven high-pressure homogenizer, the EmulsiFlex-C5 (Avestin). After disruption, 100 μM PMSF was added to the lysate. The lysate was centrifuged at 15 000×g for 10 min at 4° C. Ni-NTA resin purchased from Qiagen was equilibrated using 10 column volumes (CV) of NPI-10 buffer in gravity column (Fisher-Scientific). The clarified supernatant was loaded to the column and allowed to drip through by gravity. After all of the lysate was loaded, the column was washed with 10 CV of NPI-20 buffer (20 mM imidazole). Then the protein was eluted from the column using 3 CV of NPI-250 buffer (250 mM imidazole). Protein purification was confirmed by protein gel electrophoresis using a Mini-protean system (Bio-rad) using precast 4-20% acrylamide gels (Bio-rad), Kalidescope Prestained Protein Ladder (Bio-rad), and Tris-glycine, SDS buffer (Bio-rad) at 200V for 20 min. Gels were stained with InstantBlue (Expedeon).

In Vitro Enzyme Assays

Enzyme assays for screening of isopentenol kinase activity was performed as follows. The purified enzymes were added to the enzyme assay master mix for a final concentration of 2 mM ATP, 10 mM $MgCl_2$, 50 mM $NH_4HCO_3$ pH 7.5, and 600 μM isoprenol or prenol. They were incubated overnight at 37° C. The reactions were stopped using 5 volumes of ice-cold acetonitrile and centrifuged to remove precipitated proteins using a plate adaptor at 3273×g for 15 min. The supernatant was transferred to a new microplate and frozen at −80° C. The liquid was removed by a 4.5 L lyophilizer (Labconco) and the samples were resuspended in an equal volume of water and centrifuged again prior to quantification using LC-MS/MS.

Figure 3A:
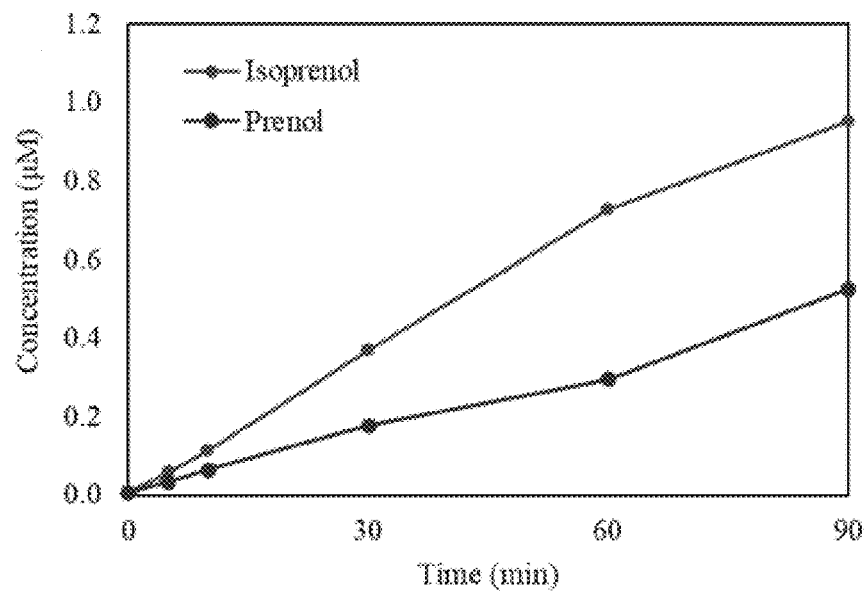
FIGS. 3A-3C. In vitro protein assays on scCK.
Figure 3B:
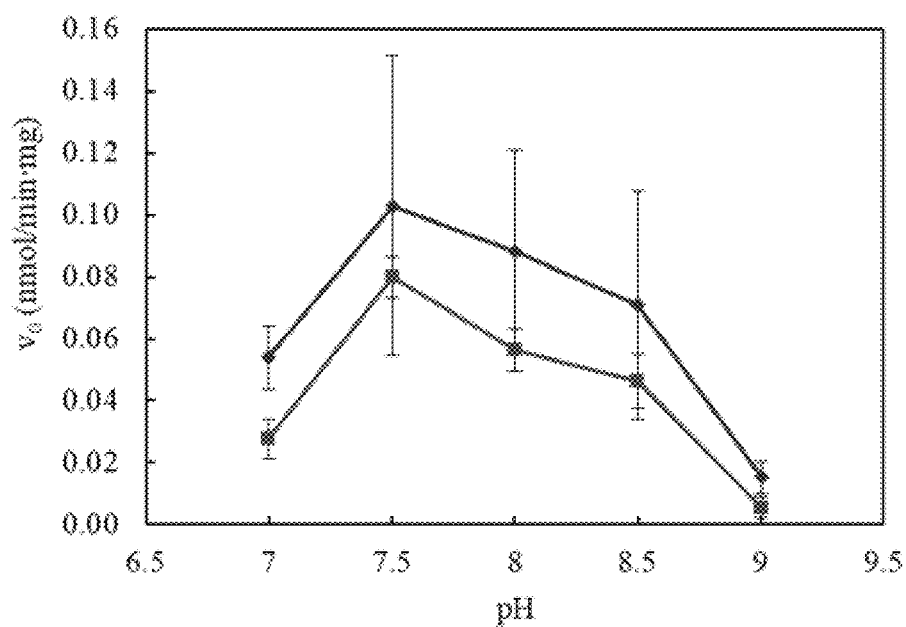
Figure 3C:
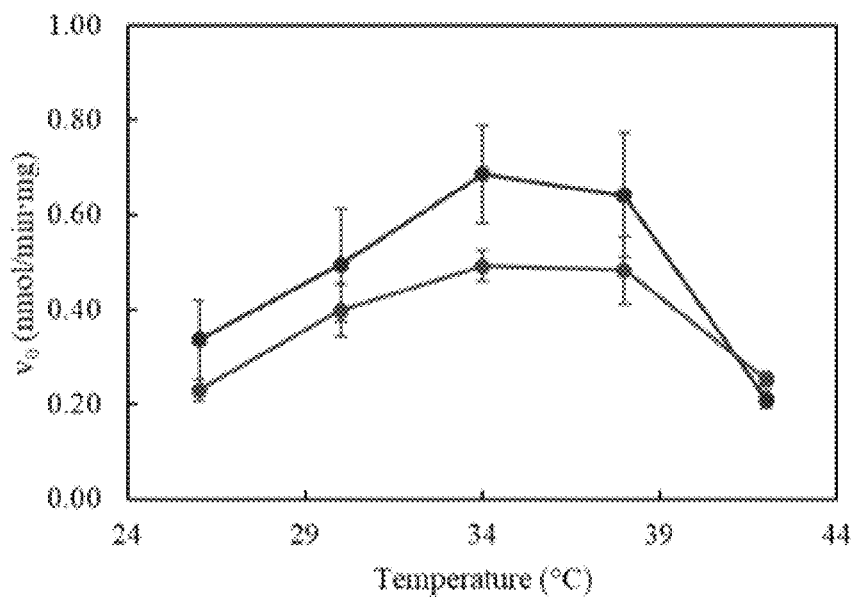

Kinetic enzyme assays were conducted using the standard assay conditions described above with the following changes. First, the linear range of the assay was determined over a 90 min period (FIG. 3). Initial velocity appeared linear over this period. Therefore, kinetic assays were quenched after 30 min. For assays at different temperatures, the standard reaction mixture was used while the temperature was varied using a water bath. For pH optimum, enzymes were buffer exchanged into 50 mM Tris-HCl at the appropriate pH using 10 kDa nanoseps (Millipore) by exchanging the buffer 5 times which resulted in a dilution factor of over 10 000. Afterwards, reactions were performed in the standard reaction mixture with $NH_4HCO_3$ buffer was adjusted to the appropriate pH. For Michaelis-Menten kinetics, only the concentration of isoprenol or prenol was varied between 1.5-50 μM.

Cultivation in Serum Bottles

In general, all media and media additives were prepared according to manufacturer's recommendations and autoclaved or sterile filtered (when casamino acids were supplemented) prior to use. Antibiotics and inducers were filter sterilized and stored as 1000× solutions at −20° C. until use. Strains were revived in LB media (BD) from glycerol stocks by culturing overnight at 37° C. containing the appropriate antibiotic. Overnight cultures were then inoculated at 1% (v/v) into 20 mL of M9 media (US Biological Life Sciences) containing 0.32% w/v glucose, 0.5% w/v casamino acids (Tecknova) and ATCC trace minerals. When they reached and OD of 0.5, if necessary, IPTG was added to a final concentration of 100 μM to induce the downstream plasmid expression, 10 ng/mL of anhydrotetracycline was added to induce the $P_{TET}$ IUP operon, and 25 mM isoprenol was added (or the specified concentration) as a substrate for the IUP. In the case of pro4IUP strains, isoprenol was present from the beginning of cultivation. Strains were cultured in 110 mL serum bottles with rubber closured to prevent the evaporation of isoprenol. When strains containing downstream operons for limonene, amorphadiene, valencene, miltiradiene, and taxadiene were used, 100 μL of C18 flash resin (VWR) was added to the cultures at the induction time to capture these products. Strains for lycopene and amorphadiene production were grown as 37° C., otherwise all cultures were performed at 30° C.

Labeling Experiments

Stains used in the pro4 and pTET IUP labeling studies were revived in M9 media with 3.2% w/v U-$C^{13}$ glucose. They were then subcultured in the same media and grown until early stationary phase at 37° C. Samples were taken prior to the start of the pulse by pipetting 5 mL of culture onto a vacuum filter flask with a 25 mm 0.2 um nylon filter. The cells were washed with 10 mL of water and the filter was submerged in ice cold 80% acetonitrile. At this point, 25 mM isoprenol was added to each culture and the cultures were sampled at approximately 1, 5, 10, 15, 30, 60 and 120 min. Times and optical densities for each point were recorded. IP and IPP levels were quantified as described above by LC-MS/MS. All trials were performed using three biological replicates. For taxadiene labeling experiments, the cultures were prepared similarly except they were incubated at 30° C. for 48 h after induction and a C18 flash resin was added. At 48 h, the metabolites were extracted and determined by LC-MS/MS as described above. Taxadiene was eluted from the resin and quantified using the GCMS method described above.

IUP Flux Estimation Through Metabolite Measurements

In order to have a first-order estimate of IPP flux through the IUP a simple model was developed that utilizes the results of the pulse labeling experiment (see FIG. 11). The basis of the model lies on Eq 1, which states that in our experiment, IPP is being produced through either the MEP pathway ($r_{MEP}$) or through the IUP ($r_{IUP}$) and is consumed at a rate $r_C$.

$$\frac{d[IPP_{TOT}]}{dt} = r_{MEP} + r_{IUP} - r_C \quad (1)$$

IPP can be either labeled or unlabeled, with labeled IPP being produced from the MEP pathway and unlabeled IPP being produced from the IUP, that is:

$$\frac{d[IPP_L]}{dt} = r_{MEP} - \lambda r_C \quad (2)$$

$$\frac{d[IPP_{UL}]}{dt} = r_{IUP} - (1-\lambda)r_C \quad (3)$$

In the above λ indicated the fraction of IPP that is labeled, i.e:

$$\lambda = \frac{[IPP_L]}{[IPP_{TOT}]} \Rightarrow 1 - \lambda = \frac{[IPP_{UL}]}{[IPP_{TOT}]} \quad (4)$$

Using the definition of λ, we can rework Eq. 3 as follows:

$$(1-\lambda)\frac{d[IPP_{TOT}]}{dt} = \frac{d\lambda}{dt}[IPP_{TOT}] + r_{IUP} - (1-\lambda)r_C \quad (5)$$

Figure 11A:
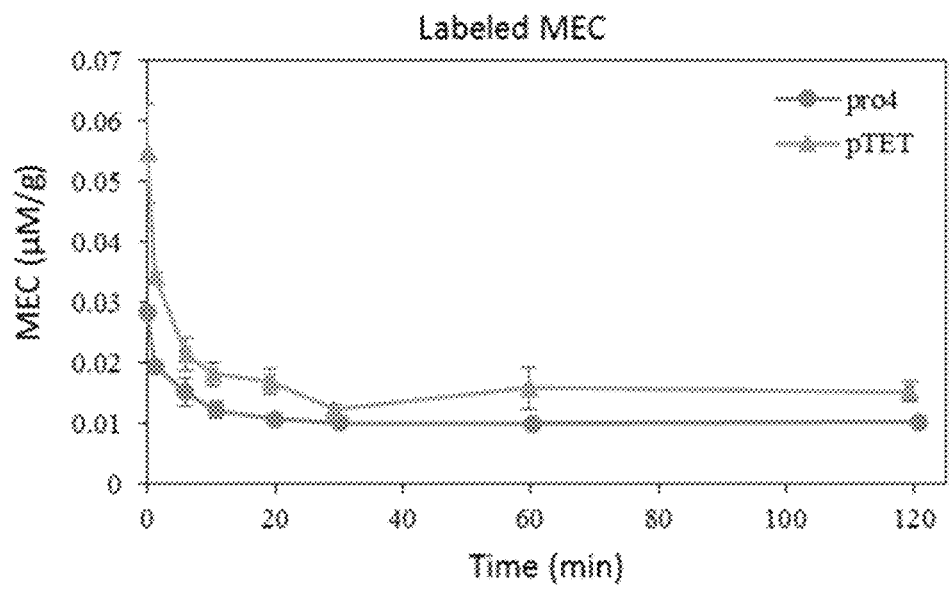
FIGS. 11A-11F. Isoprenol pulse-in experiment for metabolite monitoring.
Figure 11B:
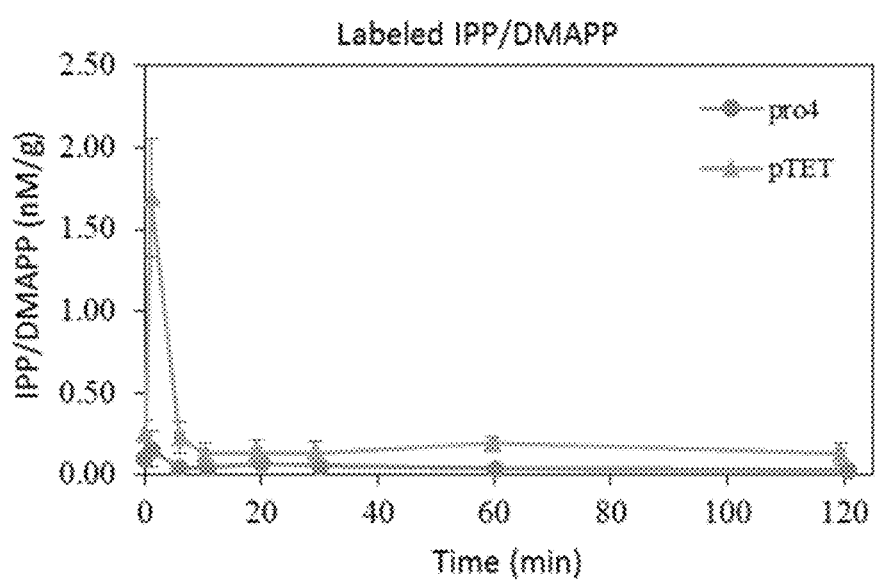

We then make the following assumptions. First we assume that in the cell, as an aggregate, IPP consumption follows a $1^{st}$ order rate law. Secondly, we assume that the fraction of labeled IPP is very small, something that is corroborated by our data (FIGS. 11A & 11B). Therefore:

$$r_C = k[IPP_{TOT}]$$

$$1 - \lambda \approx 1$$

This leads to Eq. 5 being transformed as follows:

$$\frac{d[IPP_{TOT}]}{dt} = \left(\frac{d\lambda}{dt} - k\right)[IPP_{TOT}] + r_{IUP} \quad (6)$$

If it is assumed that for at least the first 30 mins of the experiment we have a quasi-steady state, meaning that the terms $$\left(\frac{d\lambda}{dt} - k\right)$$

and $r_{IUP}$ will remain relatively constant. Thus, Eq. 6 can be integrated. Using $IPP_{TOT,0} = IPP_0$ (IPP at t=0, which is measured) as its initial condition, we get:

$$[IPP_{TOT}] = \frac{e^{At}(B + A \cdot IPP_0) - B}{A} \quad (7)$$

By least-square fitting our data on total IPP concentration (which is calculated by summing the measured values of $IPP_L$ and $IPP_{UL}$ against Eq. 7, we can then estimate a value for $r_{IUP}$.

Cultivation in Bioreactors

The strains p5T7-LYCipi, p5T7-LYCipi-ggpps, and p5T7tds-ggpps with pro4IUP were cultivated in a 3-L Bioflo 110 bioreactor (New Brunswick) with aeration, agitation, and pH control. One and a half liters of defined media (M9 salts, 5 g/L casamino acids, ATCC trace elements solution, 100 µL of antifoam 204, and 50 µg/mL spectinomycin and kanamycin) was inoculated at 1% v/v with an overnight culture (12 h) grown in LB media. Aeration (0.3-1 vvm) and agitation (250-1250 rpm) was controlled by a cascade to maintain dissolved oxygen at 40% of saturation. pH was controlled by the addition of 25% v/v $NH_4OH$. The temperature was controlled at 37° C. for lycopene cultures and 30° C. for taxadiene cultures. When an OD of 0.5 was reached, 1.5 mL of 0.1 M IPTG and 3.75 mL of isoprenol were added. For taxadiene cultures the temperature was reduced to 22° C. after induction. Cell density was monitored by UV/Vis spectroscopy at 600 nm, while glucose consumption was determined by HPLC using a Aminex HPX-87H column (300×7.8 mm) (Bio-rad) on an Infinity 1260 series HPLC (Agilent) at a flow rate of 0.7 mL/min with 14 mM $H_2SO_4$, at room temperature using a refractive index detector set at 50° C. C18 flash resin was added to taxadiene bioreactors to capture taxadiene and eluted in acetonitrile for purification by semi-preparative HPLC as previously described.

Synthesis of IP and DMAP

Isopentenyl monophosphate (IP) and dimethylallyl monophosphate (DMAP) were chemically synthesized using isoprenol or prenol respectively as they are not commercially available. The synthesis process was adapted from L. M. Lira, D. Vasilev, R. A. Pilli, L. A. Wessjohann, One-pot synthesis of organophosphate monoesters from alcohols. *Tetrahedron Lett.* 54, 1690-1692 (2013); Y. Wang, H. Xu, M. K. Jones, R. H. White, Identification of the final two genes functioning in methanofuran biosynthesis in *Methanocaldococcus jannaschii*. *J. Bacteriol.* 197, 2850-2858 (2015). All chemicals and solvents were used as supplied without further purification. Trichloroacetonitrile (2.26 equiv.) tetrabutylammonium phosphate (1.66 equiv.) was added to a solution of the appropriate isopentenol (1 equiv.) in acetonitrile and stirred for 4 h. The acetonitrile was evaporated, and the synthesized isopentenyl phosphate was resuspended in water and cooled for 6h at 4° C. This caused the crystallization and precipitation of the trichloroamide which was removed by filtration. The isopentenyl phosphate was purified by flash chromatography using a DOWEX 50WX8 ion-exchange column by percolation using $NH_4HCO_3$ (0.025 M) then eluted using isopropanol/$NH_4OH$/$H_2O$ 7:2:1. The resulting product was recovered as a solid by lyophilization.

The structure of the resulting IP and DMAP were confirmed by $^1H$ and $^{31}P$-NMR. Spectra were recorded on a Varian Mercury-300 NMR Spectrometer in deuterated water (Sigma-Aldrich) at 300 MHz and chemical shifts (δ) are reported in parts per million (ppm) downfield from the internal standard, tetramethylsilane (TMS). The resulting spectra for IP were $^1H$ NMR (300 MHz, $D_2O$): δ: 4.71 (s, 1H), 3.80 (q, 2H), 2.21 (t, 2H), 1.61 (s, 3H) and $^{31}P$ NMR (300 MHz, $D_2O$): δ 2.38. The resulting spectra for DMAP were $^1H$ NMR (300 MHz, $D_2O$): δ 5.26 (t, 1H), 4.17 (t, 2H), 1.61 (s, 3H), 1.56 (s, 3H) and $^{31}P$ NMR (300 MHz, $D_2O$): δ 2.96.

Quantification of Metabolites

IP/DMAP and IPP/DMAPP were quantified by LC-MS/MS by comparison to synthetic IP/DMAP made in house according to the procedure described above and IPP and DMAPP standards purchased from Sigma-Aldrich. Liquid Chromatography was conducted using an Agilent 1100 Series HPLC (Agilent Technologies) and the MS/MS was conducted using an API 4000 triple quadrupole mass spectrometer (SCIEX) with ESI running in negative MRM mode. Mobile phases consisted of LCMS grade 10 mM tributylammonium (TBA) (Sigma-Aldrich), 15 mM acetic acid (Sigma) in water (A) and 100% acetonitrile (B). A EC18 column (2.7 m, 2.1 mm, 50 mm length) (Agilent) was used to separate 20 µL of sample with a flow rate of 0.3 mL/min and linear gradient program: 0-3 min 0% B, 3-10 min 0-50% B, 10-12 min 50-100% B, 12-18 min 100% B, 18-18.5 min 100-0% B, 0% B until 25 min. Metabolite specific ionization and fragmentation voltages were obtained from a 1 M standard solution of each metabolite using the Analyst software (v 1.6) and monitored during the chromatography. Peaks were integrated using the Analyst software and compared to a standard curve generated for each metabolite.

GPP, FPP, and GGPP were quantified using an alternative method using the same instrumentation described above. An Xbridge C18 column (150 mm, 3.5 µm, 2.1 mm) (Waters) was operated with a mobile phase of 0.1% v/v TBA, 0.12% v/v acetic acid, and titrated with ~0.5% v/v 5N $NH_4OH$ until a pH of 8.5 was reached (A). The elutant was 100% acetonitrile (B). A series of linear gradients: 0-5 min 0% B, 5-20 min 0-65% B, 20-25 min 65% B, 25-30 min 100% B, 30-35 min 100% B, 35-36 min 100-0% B, 0% B until 45 min, was used to separate these analytes which were then compared to standard curves generated using standards purchased from Sigma-Aldrich and/or Cayman Chemicals. Samples were resuspended in the aqueous mobile phases described above.

Quantification of Lycopene

Figure 7:
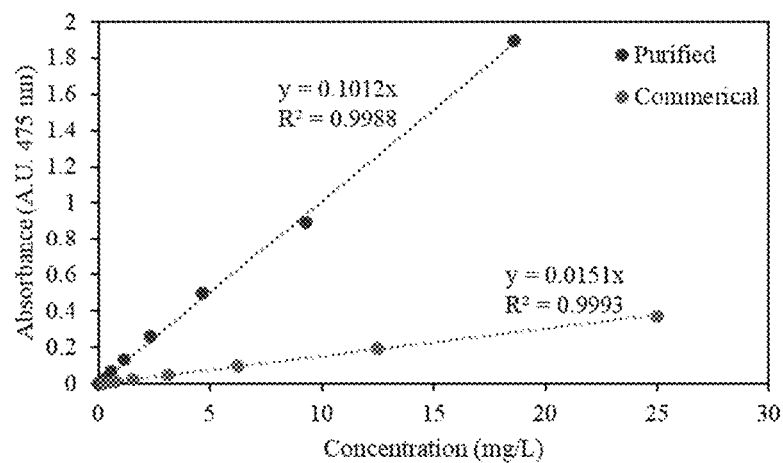
FIG. 7. Standard Curve for lycopene quantification. Lycopene purchased from a commercial source (lower line) is compared to lycopene freshly purified (upper line) in house (n=3).
Figure 8A:
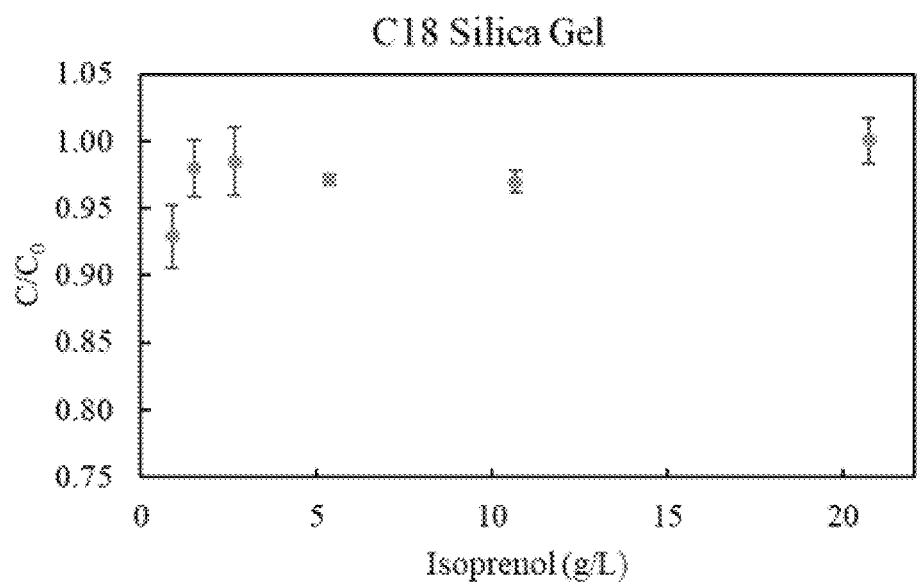
FIGS. 8A and 8B. Isoprenol adsorption isotherms (FIG. 8A) for C18 silica gel, (FIG. 8B) for dodecane.
Figure 8B:
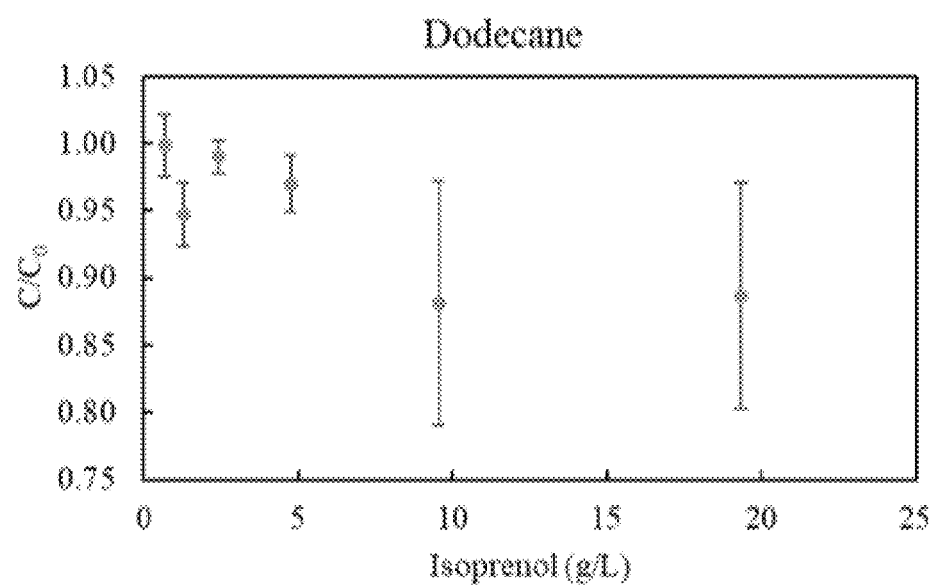

Lycopene content was assessed by UV-Vis spectroscopy. First, 1 mL of cells was transferred to an amber microtube and centrifuged at 16 000×g for 2 min. The cell pellet was then resuspended in 1 mL of a 50% ethanol, 50% acetone solution and vortexed for 30 min (VWR). The solution was centrifuged to remove particulates and 200 L was transferred to a microplate and the absorbance at 475 nm was recorded. This was compared to a standard curve generated using a standard freshly purified in-house as the commercial standards purchased from three different companies (Indofine Chemical Company, Inc., Carbosynth, Santa Cruz Biotechnology) were found to be overestimating the lycopene content by about 10-fold, presumably due to degradation and bleaching of these standards during storage.[25] Therefore, a fresh standard was prepared according to a standard protocol[24] from E. coli biomass expressing the lycopene synthesis genes. First, E. coli biomass was centrifuged, then resuspended in acetone in the dark and left to stir for 1 h. This solution was then filtered, and a small amount of acetone was added to wash residual lycopene from the cells. The filtrate was then chilled at −20° C. to induce crystallization of the lycopene. Crystals were recovered by filtration and the crystallization process was repeated twice to purify the lycopene. The resulting lycopene was dried, weighed and subjected to UV/VIS spectroscopy to confirm its authenticity. It was compared to a commercially available standard from Indofine in FIG. 7. It was then resuspended in 50% ethanol, 50% acetone solution to create a standard curve for quantification. Lycopene content was calculated using the cell density of the culture calculated from the optical density at 600 nm using a correlation of 0.33 g/A.U.

Quantification of Volatile Isoprenoids

Volatile isoprenoids were quantified using GC-MS using ultra-pure helium as the carrier gas. First, the C18 resin used to capture the isoprenoids was vacuum-filtered from the cells and culture media using BioSpin columns (Bio-rad). The resin was then spun at 1000×g to remove residual water, then eluted in ethyl acetate containing 36 mg/L caryophyllene as an internal standard which allowed a 20-fold concentration of the isoprenoid for quantification. The 1 µL of the eluted isoprenoid was quantified on a HP-5 MS UI capillary column (30 m, 250 µm, 0.25 µm) (Agilent Technologies) using a 7890B Series GC and a 5977B MS. Chromatography was performed under the following conditions: splitless injection, inlet temperature 280° C., constant inlet pressure 115.8 kPa, valve temperature 300° C., and MS transfer line 300° C. A oven program of 100° C., hold 1 min, 15° C./min until 200° C., hold 2 min, 30° C./min until 250° C., hold 1 min, and 30° C./min until 290° C., hold 2 min was used for determination of taxadiene, miltiradiene, valencene, and amorphadiene. Limonene was separated using an oven program of 80° C., hold 3 min, 10° C./min until 140° C., hold 2 min, 45° C./min until 290° C., hold 1 min. The MS was operated at an ion source temperature of 280° C., and a quadrupole temperature of 180° C. Ions were scanned between a mass of 40 to 400 at 1.562 u/s. Taxadiene was quantified using a standard curve based on the m/z 122 ion which has the greatest abundance in unlabeled taxadiene. The 131 m/z ion was used to quantify labeled taxadiene using the same standard curve generated from purified unlabeled taxadiene. Taxadiene was purified using a semi-preparative HPLC using a Supelco Discovery C18 (25 cm, 10 mm, 5 um) column under isocratic conditions, 89% acetonitrile in water at 8 mL/min on a Shimazu LC-2AD HPLC[35] equipped with a SPD-M20A diode array set at 210 nm. The fractions containing taxadiene as confirmed by GCMS were collected using a fraction collector, pooled and recovered by rotary evaporation on a Buchi Rotavapor R-210. The purified taxadiene was weighed and resuspended for generation of the standard curve.

Example 1—Screening Enzymes

Although the first phosphorylation does not occur in nature, some phosphokinases exhibit promiscuous activity.[13, 14] Several kinases were screened for isopentenol kinase activity, including IPK homologs, as a recent report suggested that some IPK variants can convert prenol to DMAP through promiscuous activity,[15] along with other kinases selected based on the similarity of their natural substrates to isoprenol or prenol (FIG. 9B). After purification, these enzymes were screened for isopentenol kinase activity in vitro.[16]

Figure 9D:
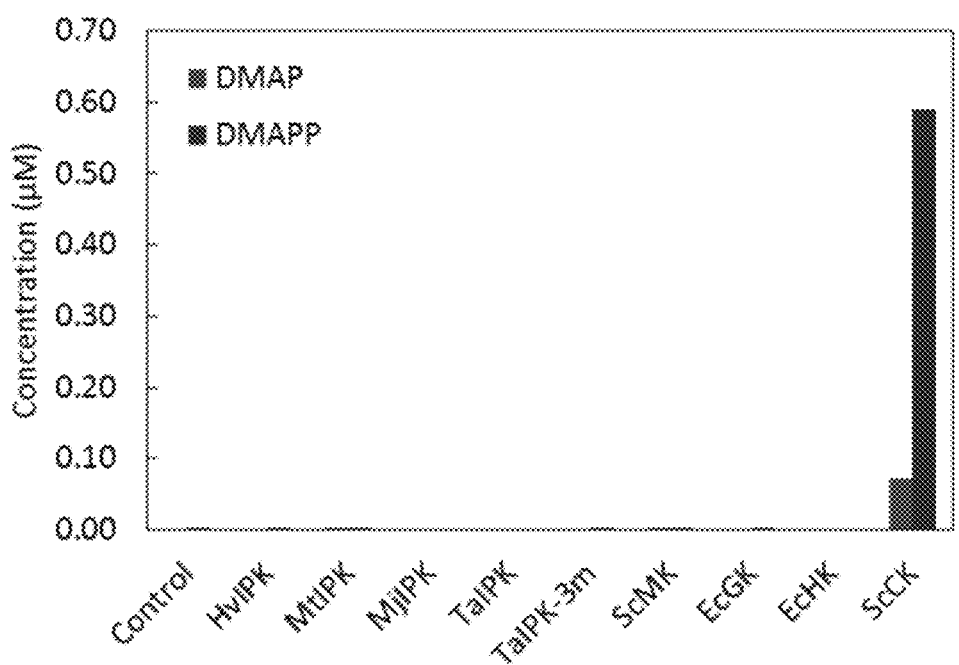
Figure 9E:
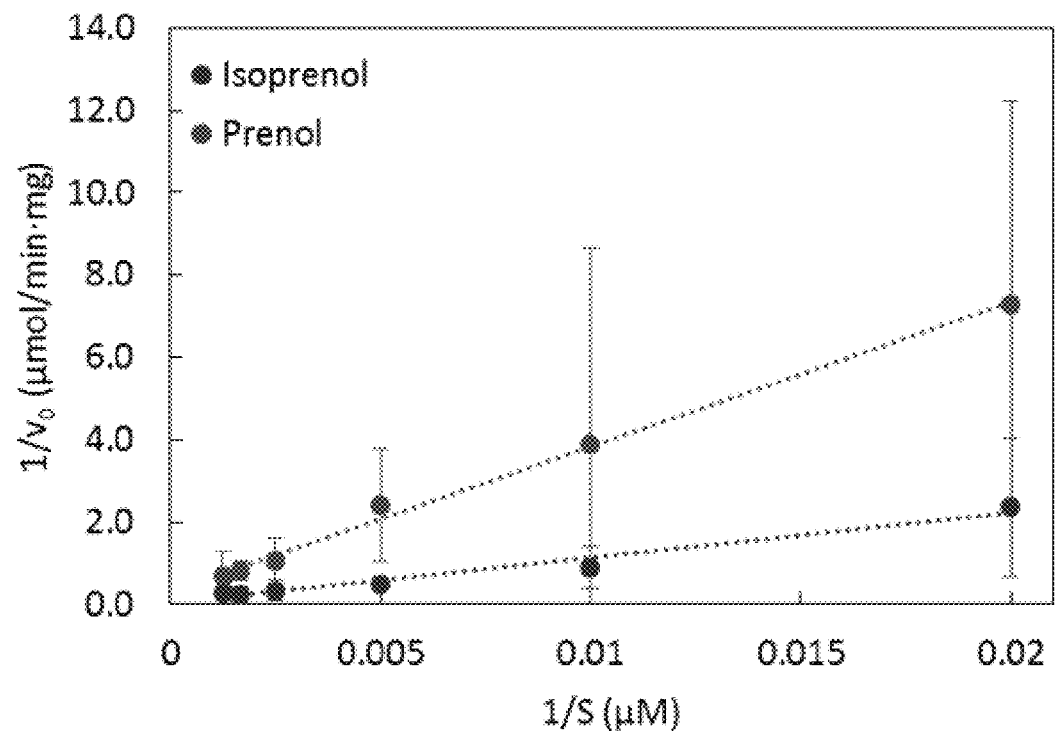

While several enzymes were capable of converting isoprenol to IP after an overnight incubation period (FIGS. 9C & 9D), only choline kinase from S. cerevisiae (ScCK) was capable of producing appreciable amounts of both IP and DMAP. Interestingly, ScCK was also able to catalyze the second phosphorylation step, forming IPP and DMAPP. However, very little IPP or DMAPP was detected after a shorter incubation (~90 min), suggesting a preference for the first step of the pathway (FIG. 3). Kinetic studies using the purified enzyme revealed that ScCK operates at an optimal pH of 7.5 and an optimal temperature of 34-38° C. (FIG. 3). The enzyme displayed a Michaelis-Menten constant (KM) of 4539 or 1113 µM and kcat of 14.7 or 1.1 s−1 at 37° C. when the substrate was isoprenol or prenol, respectively (FIG. 9E). ScCK was paired with an IPK from A. thaliana (AtIPK) to catalyze the second step of the pathway as it had the highest reported KM/kcat.[12] To balance the ratio of IPP and DMAPP, an IDI was included. The complete isopentenyl utilization pathway (IUP) is thus composed of the enzymes ScCK, AtIPK and IDI and requires ATP as its sole cofactor.

Figure 4:
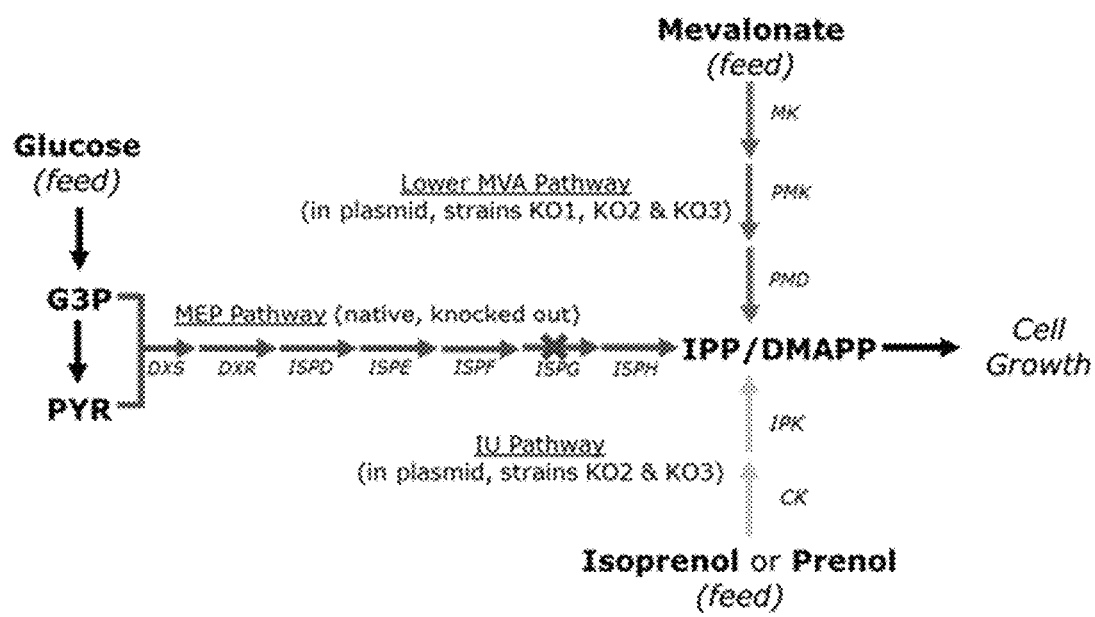
FIG. 4. Isoprenoid pathways of the MEP knockout strains KO1, KO2 and KO3. In these strains, the native MEP pathway has been knocked out through a deletion in ISPG, rendering them unable to produce isoprenoids required for their growth. Growth in strains KO1, KO2 and KO3 can be recovered through the lower MVA pathway, by supplementing the media with mevalonate. In strains KO2 and KO3, growth can be recovered by using the IUP to produce isoprenoids from isoprenol or prenol feed.
Figure 5:
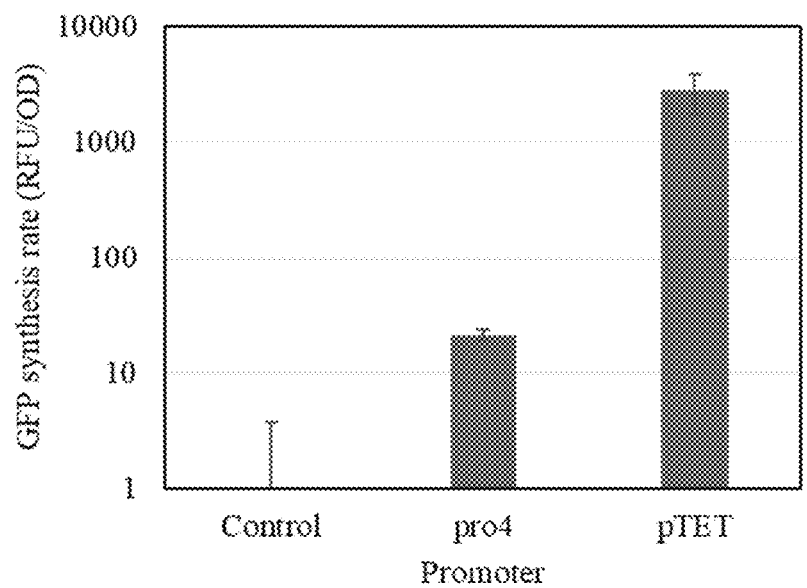
FIG. 5. Initial characterization of expression system strength. Characterization of expression plasmids using GFP as a reporter protein, with either the pSEVA228pro4-gfp plasmid (pro4), the pTET-gfp plasmid (pTET) or no plasmid (control). All values represent the means±SD of 3 biological replicates.
Figure 6:
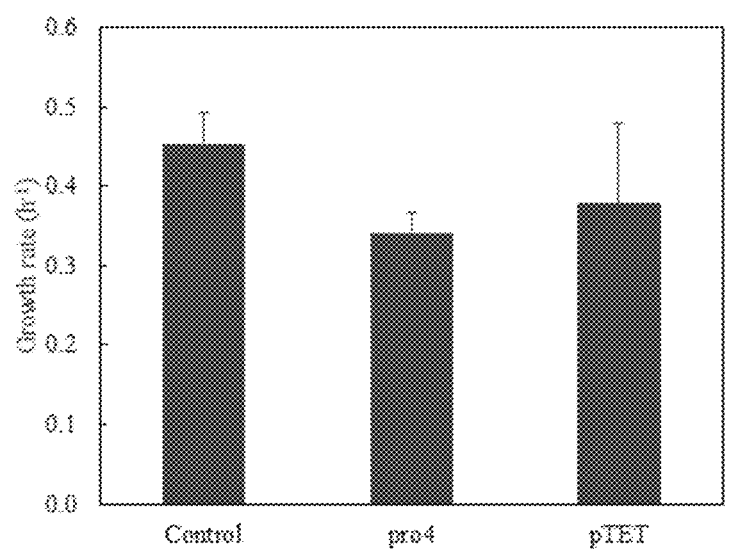
FIG. 6. Growth rates of the ΔispG MEP knockout strains. The control, wild-type MG1655 (DE3), strain KO2 containing the pro4IUP and KO3 containing the pTETIUP were grown in M9 minimal media. The culture media was supplemented with 25 mM isoprenol.

Isoprenoids are necessary for cell survival and perform essential cellular functions, including electron transport and maintenance of membrane fluidity.[17] In order to create an in vivo proof of concept, the ability of the IUP to rescue a non-viable MEP-knockout strain incapable of producing isoprenoids via its native MEP pathway was tested. Using the CRISPR-Cas9 system (Y. Jiang et al., Multigene editing in the *Escherichia coli* genome using the CRISPR-Cas9 system. *Appl. Environ. Microbiol.* 81, 2506-2514 (2015); V. J. J. Martin, D. J. Pitera, S. T. Withers, J. D. Newman, J. D. Keasling, Engineering a mevalonate pathway in *Escherichia coli* for production of terpenoids. *Nat. Biotechnol.* 21, 796-802 (2003)), an MEP-knockout strain, KO1, was created, in which the ispG gene is removed, rendering it unable to synthesize the MEP pathway intermediate (E)-4-Hydroxy-3-methyl-but-2-enyl pyrophosphate (HMBPP). Growth can be rescued via the lower mevalonate pathway encoded by the genes erg12, erg8 and mvd1 on the plasmid pBad33-proA-MEVI when mevalonate is supplied in minimal media (FIG. 4). Two plasmids were created for the expression of the IUP to test its ability to act as a sole provider of isoprenoids. The first used the Standard European Vector Architecture[20] to clone the IUP operon under the control of the constitutive promoter Ppro4[21], creating the plasmid pSEVA228-pro4IUPi (herein called "pro4IUP"). The second, pTET-IUPi, herein called "pTETIUP", places control of the IUP under the strong inducible anhydrotetracycline promoter (PTET).[22] The difference in strength of these expression systems was confirmed by green fluorescent protein expression (FIG. 5). KO1 was transformed with either pro4IUP or pTETIUP plasmids to create strains KO2 or KO3 respectively. As expected, strain KO1 was not viable in minimal media unless supplemented with 1 mM mevalonate. When supplemented with 0.6 mM isoprenol in the absence of mevalonate or HMBPP, both KO2 and KO3 grew after lag periods of 36 h, compared with wild-type *E. coli* which exhibited a lag period of 2 h, and exponential growth rate shown in FIG. 6. IUP is thus sufficiently expressed in *E. coli* to be used as the sole isoprenoid pathway and an alternative to the MEP or the MVA pathways. All subsequent experiments expressed the IUP in wild-type *E. coli*.

Figure 10A:
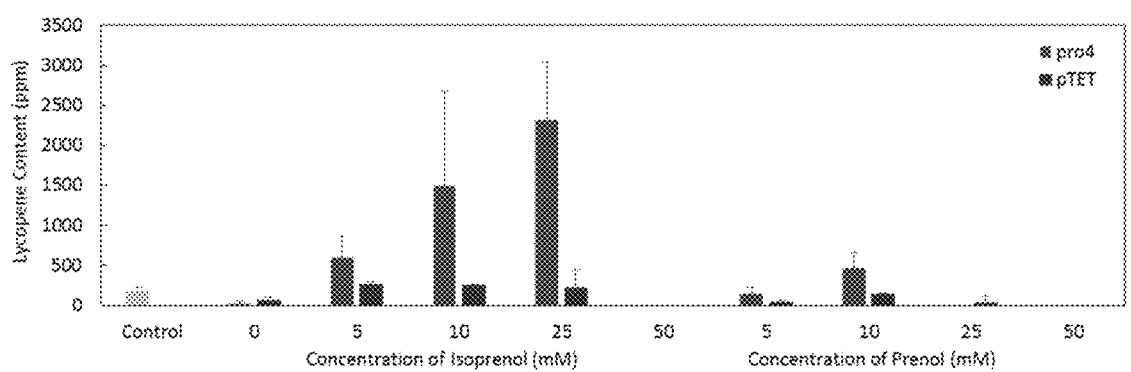
FIGS. 10A-10C. Characterization of the IUP using the lycopene pathway encoded by pAC-LYCipi in M9 media.
Figure 10B:
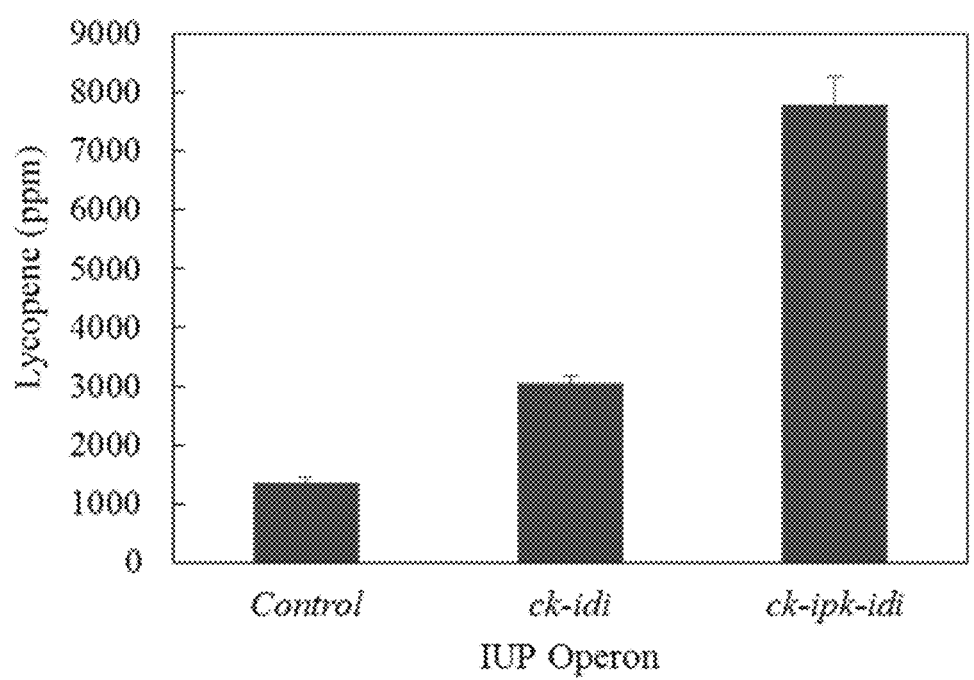

Example 2—Characterization of IUP Strength by Combining IUP with Downstream Module for Lycopene Synthesis Lycopene is the C40 isoprenoid responsible for the coloration of tomatoes[23], and can be readily quantified using UV/Vis spectroscopy. For quantification purposes, a fresh lycopene standard was generated in lab using a standard procedure[24], as lycopene is known to degrade rapidly due to oxidation, heat, and/or light during storage[25], leading to bleaching of the standard and over-estimation of lycopene titers. The upstream (IUP) and downstream (lycopene synthesis) genes were partitioned into two operons carried on separate plasmids. The lycopene plasmid, pAC-LYCipi, encoded genes required for the production of lycopene (crtE, crtB and crtI) and a copy of idi from *Enterobacter agglomerans*[26]. The lycopene plasmid was transformed alone (control) or in combination with the pro4IUP or pTETIUP plasmids. After culturing in different concentrations of prenol or isoprenol in M9 media for 48 h, lycopene content was quantified. The highest lycopene titer was observed using 25 mM isoprenol (FIG. 10A).

Figure 10C:
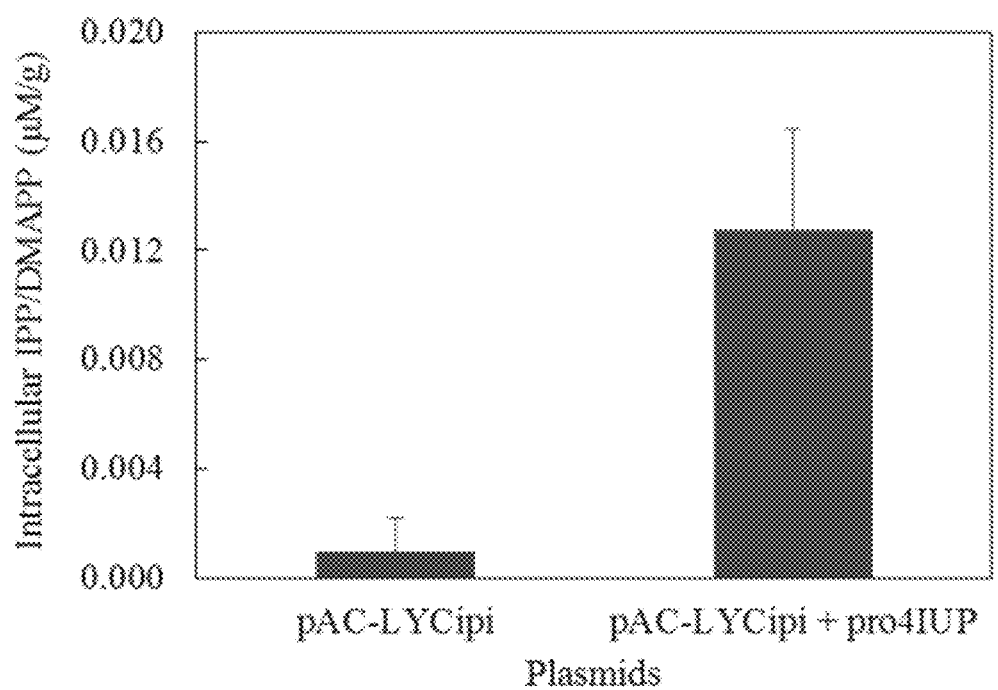

Removing the ipk gene from the IUP operon was found to significantly decrease lycopene titers (FIG. 2B). There was still a significant pool of IPP/DMAPP in the pro4IUP strain, despite the expression of the lycopene genes, suggesting a mismatch in flux generated by IUP and converted into lycopene (FIG. 10C). In order to estimate the flux generated by pro4 and pTET IUP strains lacking a downstream cassette, the strains were grown at 37° C. in M9 media using uniformly $^{13}$C-labeled glucose as the sole carbon source. During stationary phase, unlabeled isoprenol was pulsed in and pTETIUP cultures were induced to start production of the IUP enzymes (FIG. 11).

Figure 11C:
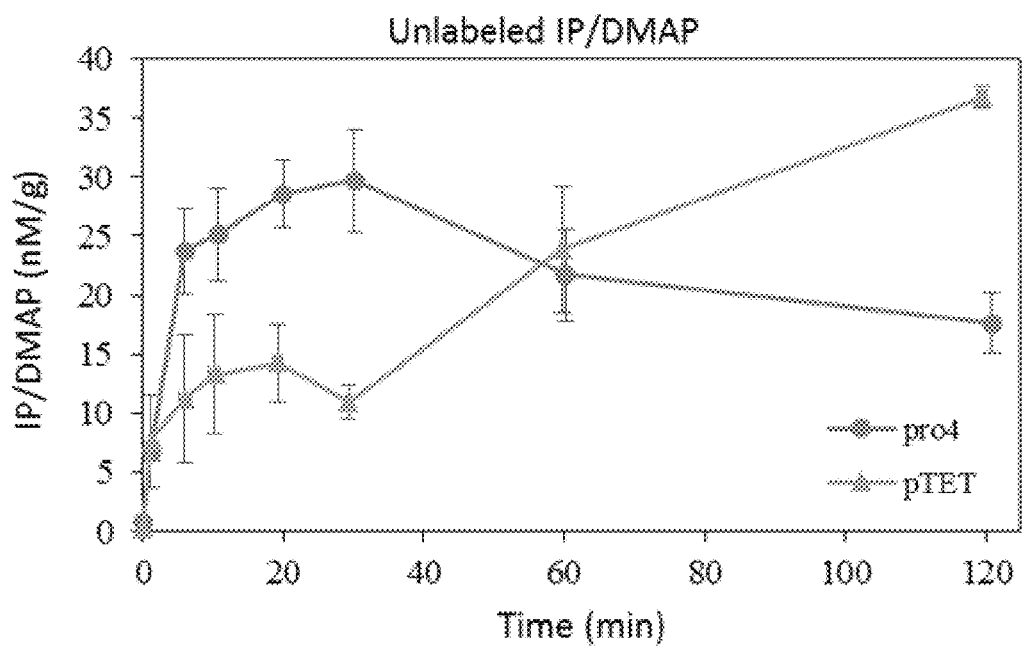
Figure 11D:
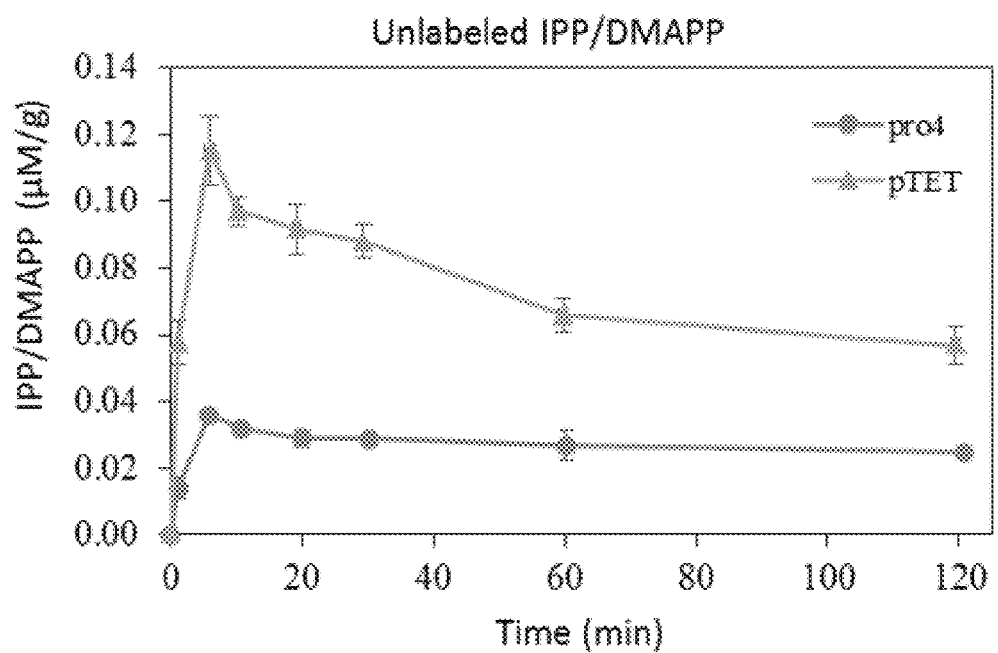
Figure 11E:
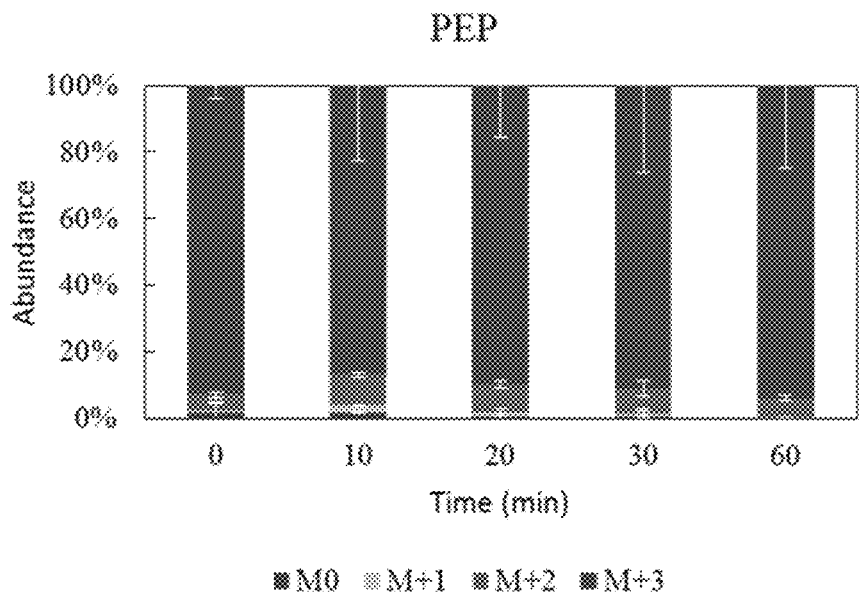
Figure 11F:
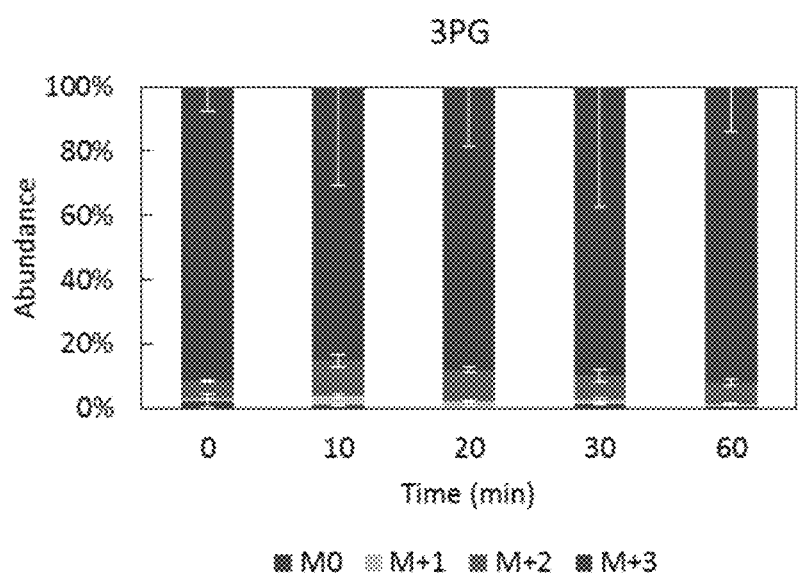

Immediately prior to the addition of unlabeled isoprenol, fully-labeled MEC was detected. MEC is an MEP-pathway metabolite that is known to accumulate in *E. coli*[6] (FIG. 11A), as well as a small amount of fully-labeled isopentenyl pyrophosphate (FIG. 11B). No unlabeled isopentenyl monophosphate (IP) or pyrophosphate (IPP) was detected (FIGS. 11C & 11D). Within minutes of isoprenol addition, concentrations of unlabeled IP and IPP rapidly increased to levels significantly higher than those of the native MEP pathway (Labeled IPP/DMAPP at t=0) (FIGS. 11C & 11D). The concentration of labeled IPP quickly dropped to barely detectable levels while the concentration of labeled MEC also decreased (FIGS. 11A & 11B), indicating possible feedback inhibition of the MEP pathway by high concentrations of IPP, as previously reported.[7] By fitting a simple first-order mathematical model (described in supplementary text) to the total measured concentrations of IPP, IPP flux generated by the IUP was estimated. The largest IPP flux (4.93 µM/(gdcw·h); SSR=4.7·10−4 µM2/gdcw2) occurred under the control of the pTET promoter (induced with 10 ng/mL aTC). It was also observed that the labeling patterns of the glycolytic intermediates phosphoenolpyruvate (PEP) and 3-phosphoglyceric acid (3PG) remained unchanged after the isoprenol pulse (FIGS. 11E & 11F), suggesting that the IUP is uncoupled from main glycolysis.

Thus, it was established that expression of the IUP can lead to IPP accumulation higher than that produced by the MEP pathway. Furthermore, even in cells harboring the (high flux) lycopene pathway, significant accumulation of precursors IPP/DMAPP was observed. These observations suggest a high flux through the IUP.

Example 3—IUP Flux Through the Synthesis of Other Isoprenoid Compounds

Figure 12A:
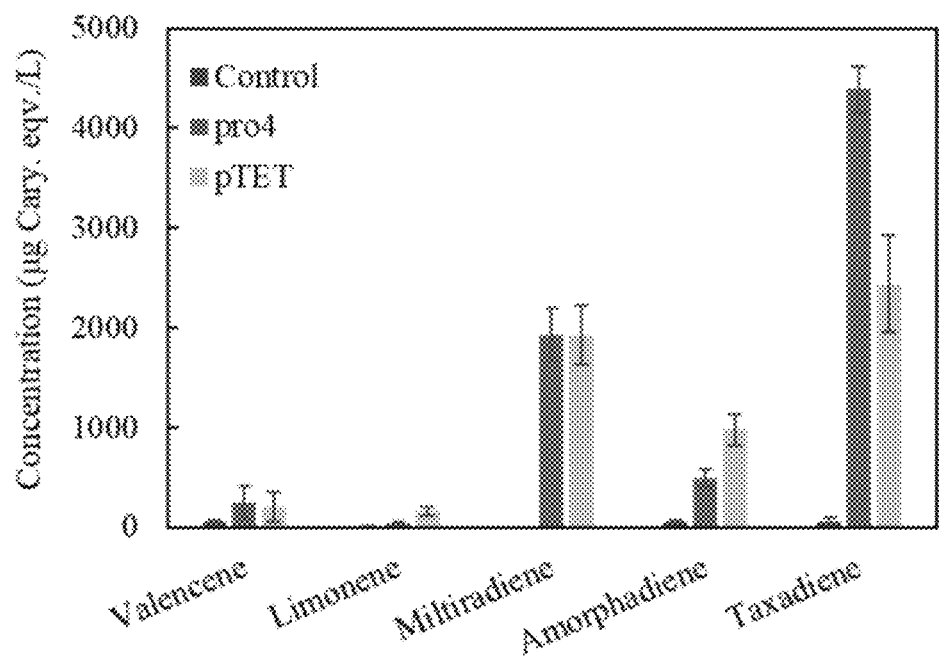
FIGS. 12A-12D. Use of the Isopentenol Utilization Pathway for the production of isoprenoids.

Both the IUP plasmids, along with plasmids containing downstream operons for the production of valencene, limonene, miltiradiene, amorphadiene, and taxadiene, were transformed (Table 1). In all cases except valencene, addition of the IUP led to significantly higher isoprenoid titers (p<0.01) (FIG. 12A).

Figure 12B:
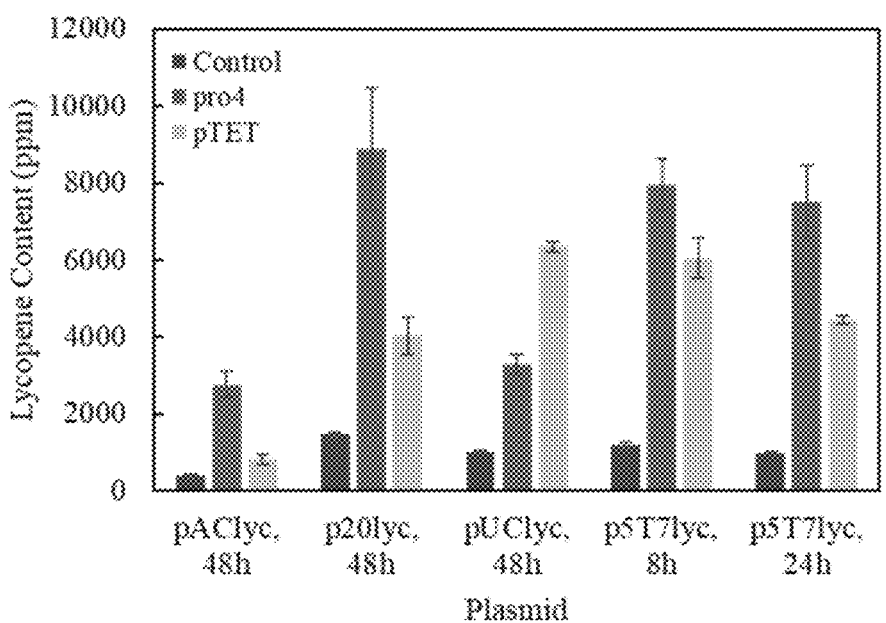
Figure 12C:
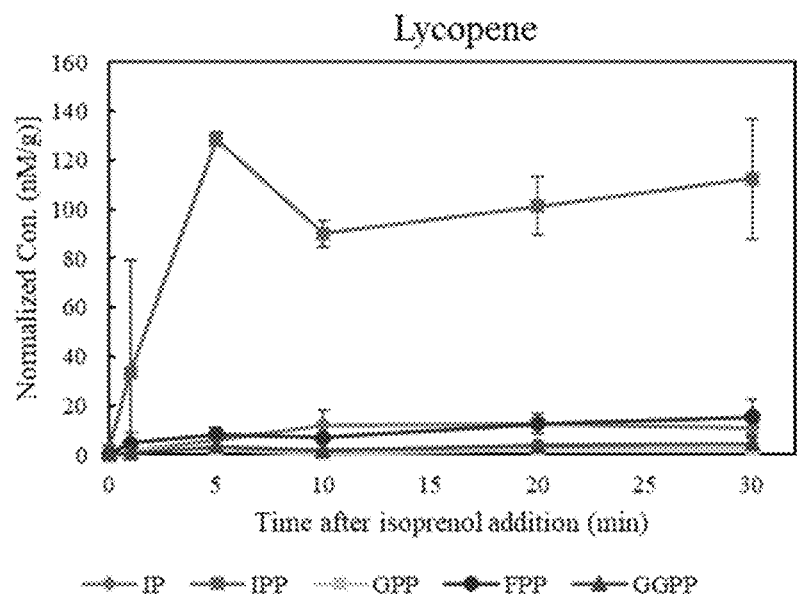
Figure 12D:
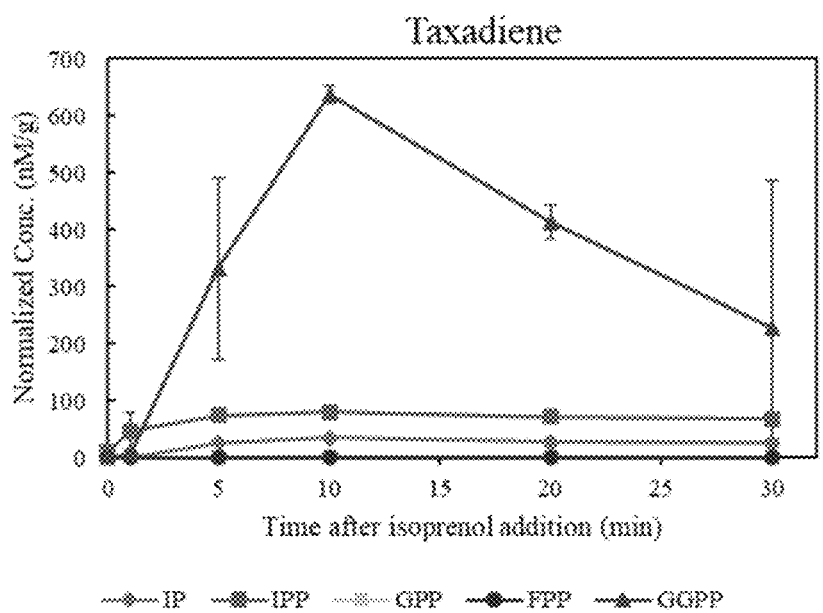

Previous results indicated that the lycopene operon from pAC-LYCipi was not sufficient to completely utilize the flux from the pro4IUP plasmid (FIG. 10C). Therefore, variants were created with different copy numbers (p5T7-LYCipi ~5, pAC-LYCipi ~15, p20-LYCipi ~20, pUC-LYCipi >100) and promoter strengths (endogenous constitutive promoter vs T7 inducible promoter) and transformed alone or in combination with either pro4IUP or pTETIUP. Cells were cultured in M9 media supplemented with 0.5% (w/v) casamino acids in serum bottles and lycopene production was monitored until a maximum lycopene content was reached (FIG. 12B). When the endogenous constitutive promoter was used, cells took 48 hours to reach their maximum lycopene content. However, increasing the plasmid copy number to approximately 20 using the pBR322 origin of replication increased lycopene content more than 3-fold. When the T7 promoter was used, lycopene productivity was increased by over 17-fold in the pro4 strain from the original pAC-LYCipi pro4IUP stain, reaching maximum lycopene content within 8 h. To establish whether the IUP or the downstream operons were the limiting factor in the production of these isoprenoids, an LC-MS/MS method was developed for the detection of intermediates IP, IPP, GPP, FPP, and GGPP, and the intracellular metabolites for the pro4IUP taxadiene strain and the pro4IUP p5T7-LYCipi (lycopene) strain using the same type of pulse-chase experiment described earlier were assessed. The results indicated that the downstream lycopene flux was still limiting, and optimization of downstream isoprenoid production is necessary to achieve higher titers using the IUP. Even in our highest productivity vector, p5T7-LYCipi, the lycopene cultures were still accumulating significant amounts of IPP (FIG. 12C) suggesting IspA, CrtE (GGPP synthase), CrtB (phytoene synthase), or CrtI (phytoene desaturase) may be limiting enzymes in lycopene synthesis. In taxadiene cultures (FIG. 12D), very high levels of GGPP were found to accumulate in the cell, suggesting taxadiene synthase activity was insufficient to accommodate the high flux generated by the IUP and terpenoid backbone synthesis.

Example 4—Internal Metabolites and Quantification of the Contributions of IUP and MEP to Taxadiene Production Using Pulse-in Labeling Experiments (FIG. 13)

Figure 13A:
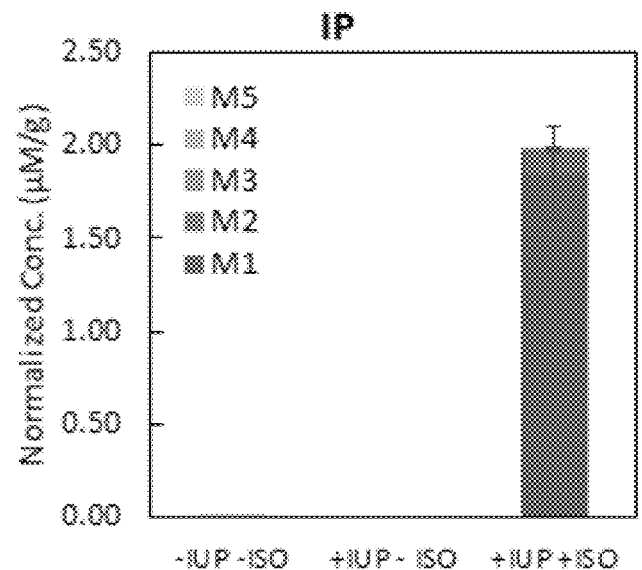
FIGS. 13A-13H. Metabolite levels and products from cultures with taxadiene-producing strains growing in U-$^{13}$C labeled glucose. The cultures differ on whether they express the IU pathway (+/−IUP) and on whether the culture media was supplemented with unlabeled isoprenol at t=0 (+/−ISO). Taxadiene and metabolic intermediate pools are analyzed after 48 h of culture. Concentrations and labeling patterns for metabolic intermediates (FIG. 13A) IP, (FIG. 13B) IPP/DMAPP, (FIG. 13C) GPP, (FIG. 13D) FPP and (FIG. 13E) GGPP respectively.
Figure 13B:
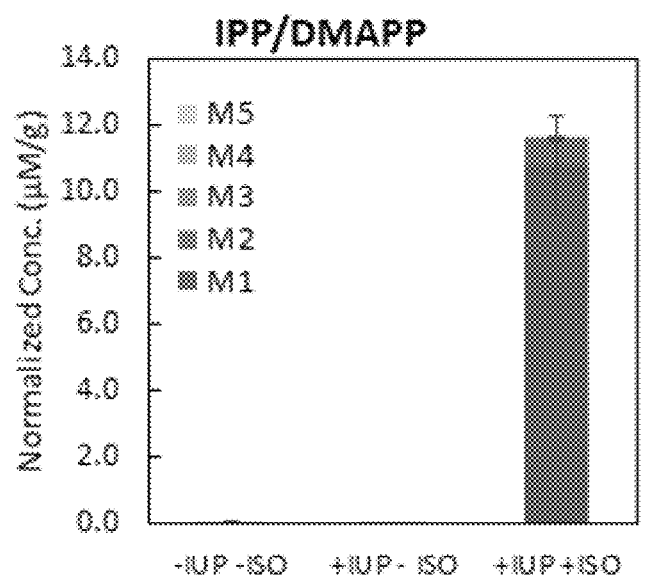
Figure 13C:
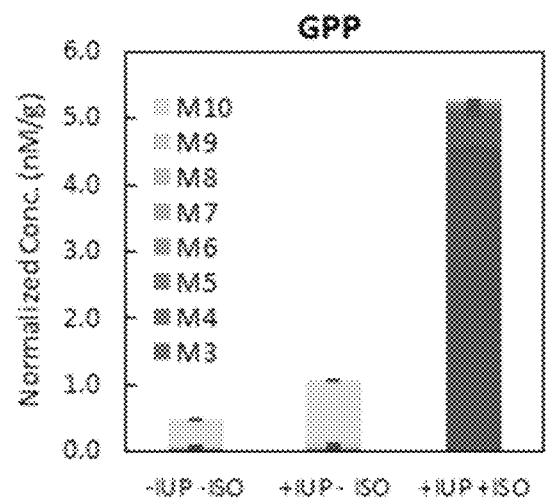
Figure 13D:
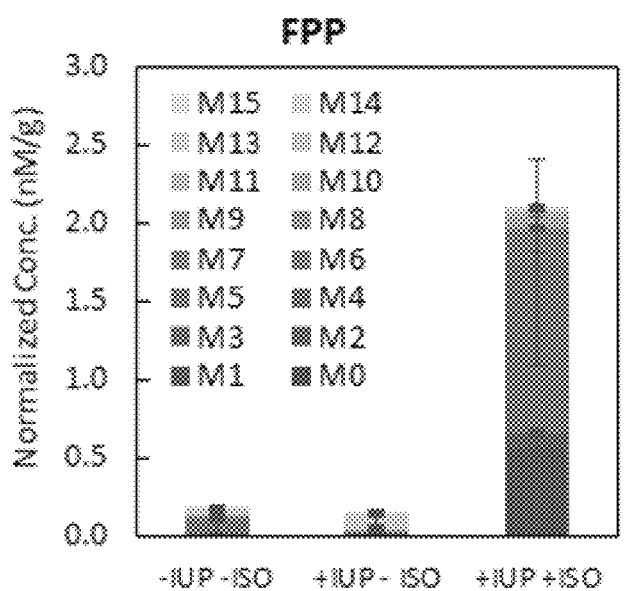
Figure 13E:
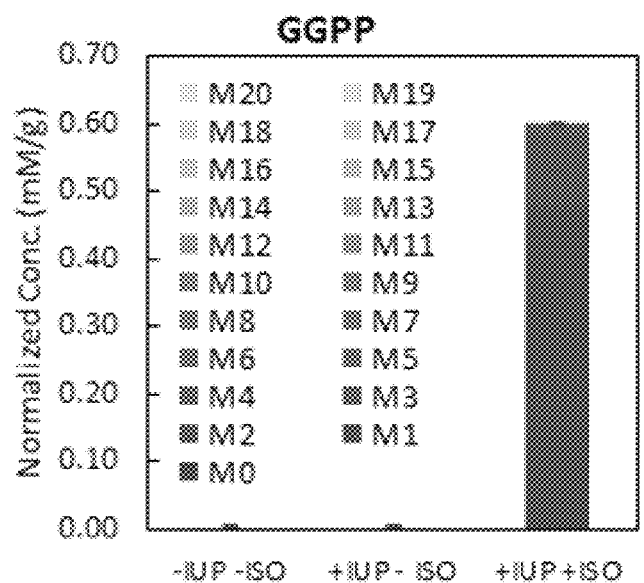
Figure 13F:
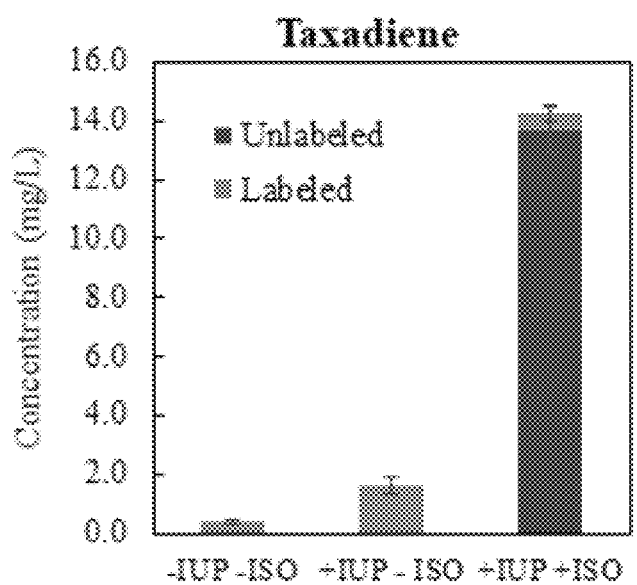
Figure 13G:
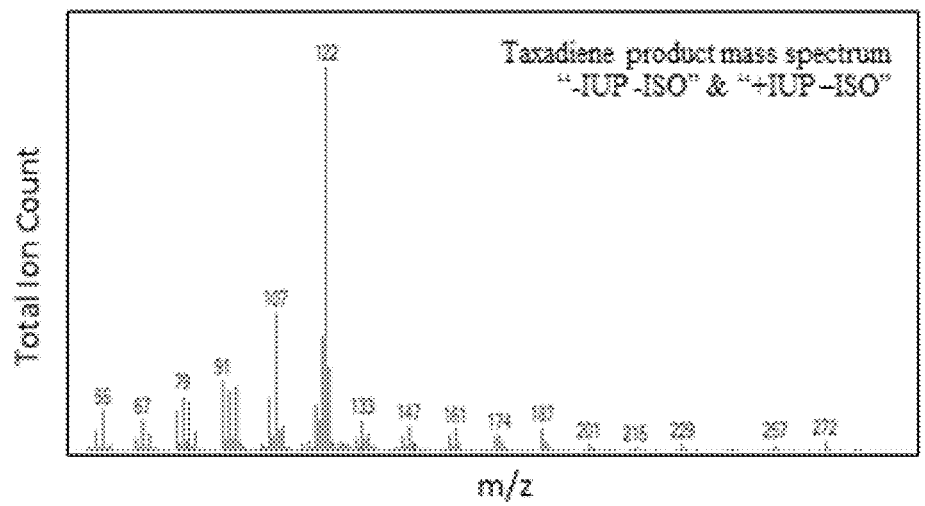
Figure 13H:
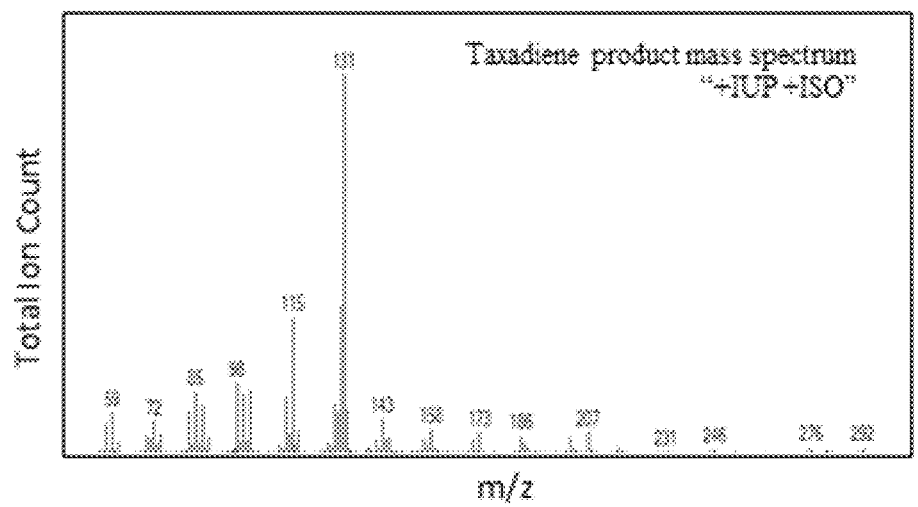
Figure 14A:
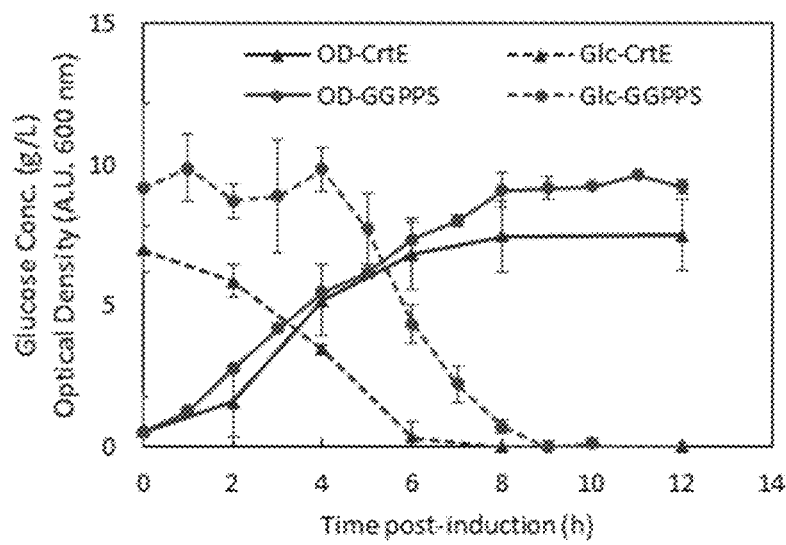
FIGS. 14A-14D. Batch bioreactor cultivation of lycopene production utilizing the IUP. The IUP was expressed under the control of the pro4 promoter along with a p5T7-LYC vector containing either crtE or ggpps.
Figure 14B:
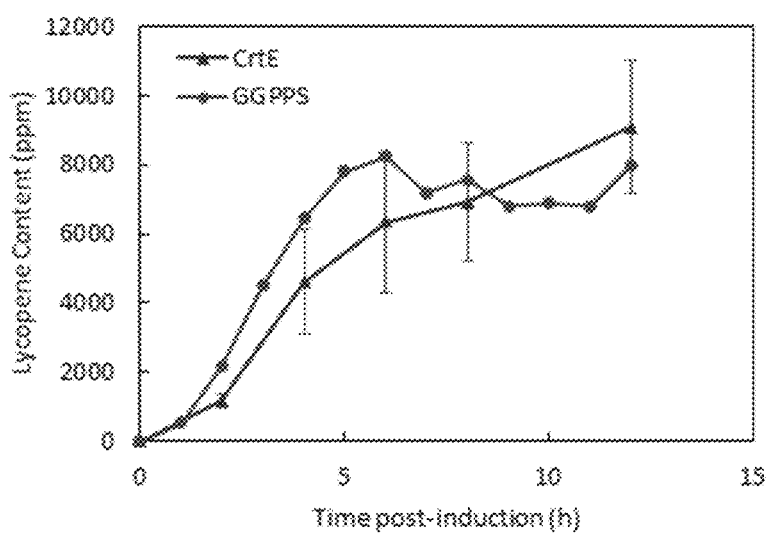
Figure 14C:
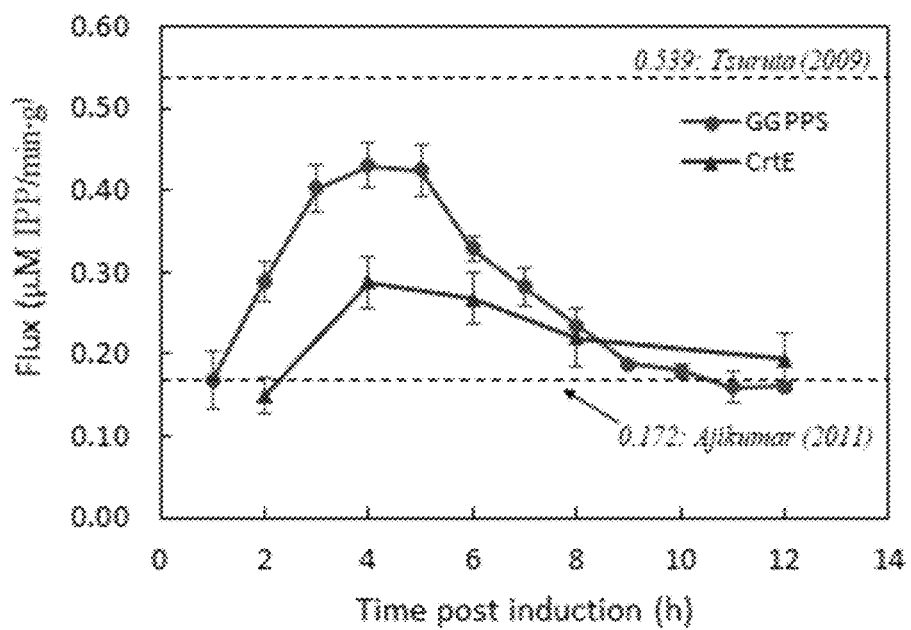
Figure 14D:
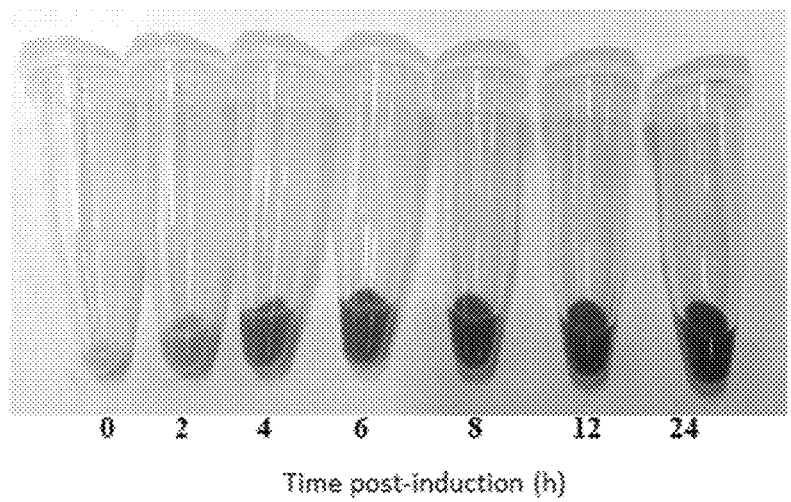
Figure 15:
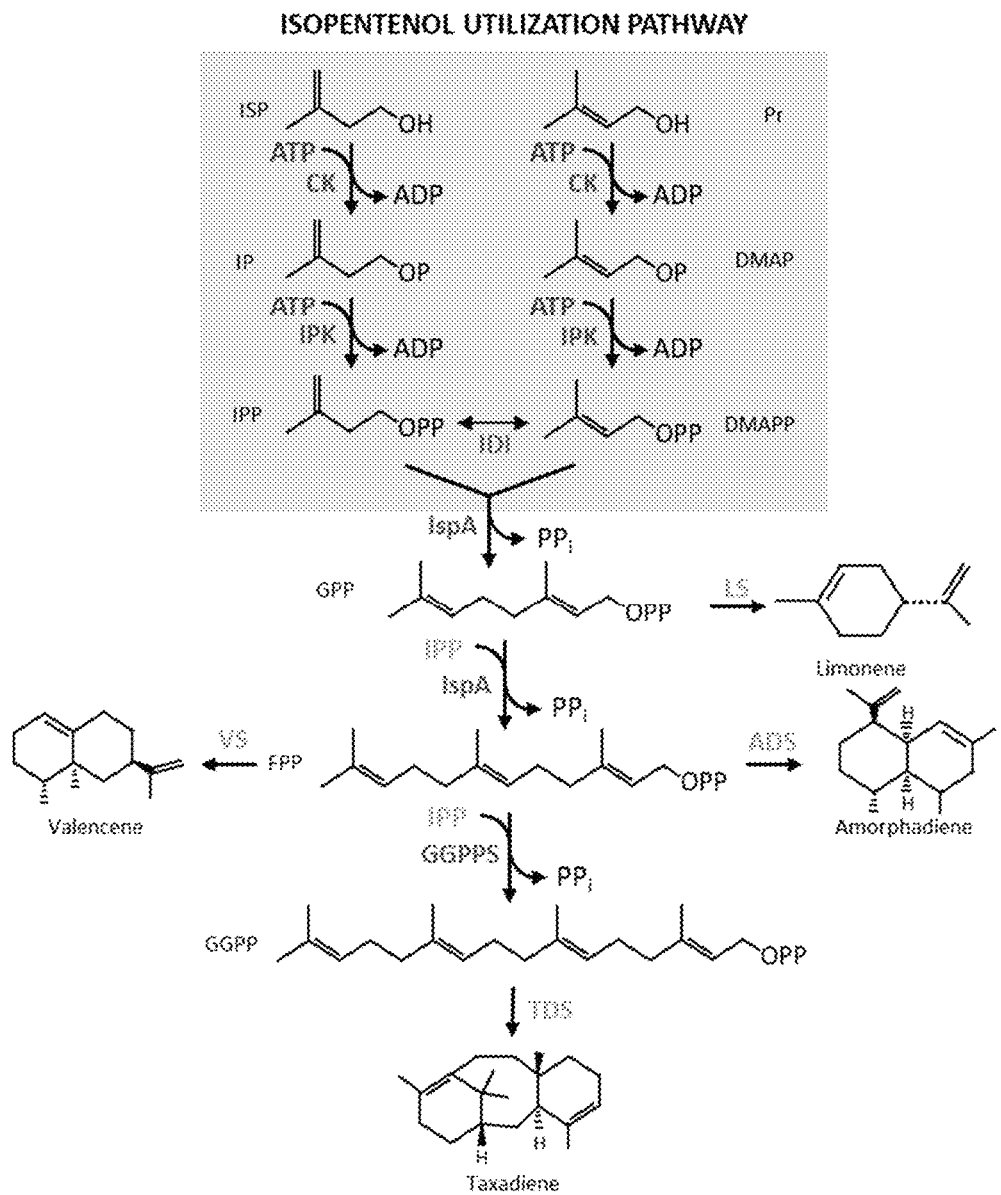
FIG. 15. Reaction scheme for the in vitro synthesis pathway for taxadiene, valencene, amorphadiene, and limonene. Enzymes involved in the formation of the prenyl precursors are shown and include choline kinase (CK), isopentenyl phosphate kinase (IPK), isopentenyl pyrophosphate isomerase (IDI), farnesyl pyrophosphate synthase (IspA), and geranylgeranyl pyrophosphate synthase (GGPPS). Terpene synthases used in this work include limonene synthase (LS), valencene synthase (VS), amorphadiene synthase (ADS), and taxadiene synthase (TDS). Metabolites structures are shown and include: isoprenol (ISP), prenol (Pr), isoprenyl phosphate (IP), dimethylallyl phosphate (DMAP), isoprenyl pyrophosphate (IPP), dimethylallylpyrophosphate (DMAPP), geranyl pyrophosphate (GPP), farnesyl pyrophosphate (FPP), and geranylgeranyl pyrophosphate (GGPP).

Taxadiene cultures were grown in M9 media with $^{13}C$ uniformly labeled glucose as the sole carbon source. Upon reaching OD 0.5, taxadiene production was induced with IPTG, and, if applicable, isoprenol was added to the media. In these cultures, the IUP plasmid was present or not present (+IUP or –IUP, respectively) and either no isoprenol or 25 mM isoprenol was added (–ISO or +ISO, respectively). After 48 h, the intermediates were extracted and quantified using LC-MS/MS, and taxadiene produced was quantified by GC-MS. As expected, in cultures without isoprenol, no IP (FIG. 13A) and very low or undetectable levels of pathway intermediates IPP/DMAPP, GPP, FPP, and GGPP (FIGS. 13B-13E) were found. When isoprenol was supplied to the IUP strain, there was a marked increase in all pathway metabolites, with GGPP accumulating to extremely high levels (600 mM±1.89), like previously observed, after 48 h of growth (FIG. 13E). The taxadiene produced by the pro4IUP strain supplemented with isoprenol was 96.3% unlabeled (FIG. 13F), as confirmed by its mass spectrum (FIGS. 13G & 13H). Therefore, taxadiene was mostly produced by the IUP from unlabeled isoprenol, and the conversion of GGPP to taxadiene is the rate limiting step.

Example 5—Impact of the Different GGPP Synthases

Since the lycopene and taxadiene strains, which showed different metabolite accumulation profiles (FIGS. 12C-12D), were identical except for their GGPP synthases and downstream product-synthesis cassettes, the impact of the different GGPP synthases was explored. Whereas lycopene cultures used CrtE derived from *Enterobacter agglomerans*, taxadiene cultures employed the homolog GGPPS from *Taxus canadensis*. A new lycopene vector was created, replacing crtE with ggpps from *T. canadensis*. The original (CrtE) pro4IUP p5T7-LYCipi strain and the new (GGPPS) pro4IUP p5T7-LYCipi-ggpps strain were cultured in batch bioreactors (FIG. 14).

Glucose was depleted within 6 h for the CrtE reactors and 9 h in the GGPPS reactors, however the GGPPS reactors started with slightly higher glucose at the time of induction (FIG. 6A). Lycopene content increased until glucose was depleted (FIG. 14B), suggesting that lycopene flux is tied to active growth. The flux observed in the GGPPS reactors was higher than in the CrtE reactors and reached a maximum of 0.430 μM IPP/min-g DCW, comparable to some of the best reported isoprenoid fluxes (FIG. 14C).[27, 28] The maximum lycopene content reached was similar for both cultures and consistent with that observed in serum bottles (FIG. 12B). This may suggest that lycopene production from the IUP is limited by the capacity of *E. coli* to store this hydrophobic molecule, which is thought to accumulate in the cell membrane.[29]

Example 6—Batch Bioreactor Cultivation of Lycopene Production Utilizing the IUP

The lycopene and taxadiene strains studied above differed only in their GGPP synthases and downstream product-synthesis cassettes. Given the GGPP accumulation in the taxadiene strain, indicating that the GGPP synthase used is in said strain is exceptionally active, a lycopene vector was created, replacing the original GGPP synthase it used, crtE from *Enterobacter agglomerans*, with ggpps from *Taxus canadensis*. Both the original (CrtE) pro4IUP p5T7-LYCipi strain and the new (GGPPS) pro4IUP p5T7-LYCipi-ggpps strain were then cultured in batch bioreactors (FIG. 33). A marked increase in flux was observed, with the flux observed in GGPPS reactors approaching a maximum of maximum of 0.430 Mm IPP/min·$g_{DCW}$ (FIG. 33C), comparable to some of the best reported isoprenoid fluxes. The maximum lycopene content reached was similar for both cultures and consistent with that observed in serum bottles (FIG. 12B). This may suggest that lycopene production from the IUP is limited by the capacity of *E. coli* to store this hydrophobic molecule, which is thought to accumulate in the cell membrane.

The effect that substituting crtE from *Enterobacter agglomerans*, with ggpps from *Taxus canadensis* had on the metabolite profile was also investigated. While the IPP levels remained relatively constant, switching from crtE to ggpps led to a decrease in the concentrations of GPP, FPP and GGPP in the case of the weaker expression of the IUP (i.e., under the pro4 expression system). Precursor concentrations (especially IPP) are still high, indicating room for further improvements once bottlenecks are overcome.

Example 7—In Vitro Reconstitution of the Isopentenol Utilization Pathway for the Production of Isoprenoids Methods and Materials
Strains and Cultivation Conditions
The gene for choline kinase (ck) from *Saccharomyces cerevisiae* was previously codon optimized, 6× his-tagged and cloned under the control of the T7lacUV promoter in pET28a(+) for overexpression in *E. coli* BL21 (DE3). The following genes were also cloned into pET28a(+) and his-tagged for overexpression and purification: isopentenyl kinase (ipk) from *Arabidopsis thaliana*, isopentenyl pyrophosphate isomerase (idi) from *E. coli*, farnesyl pyrophosphate synthase (ispA) from *E. coli*, geranylgeranyl pyrophosphate synthase (ggpps) from *Taxus canadensis*, a truncated taxadiene synthase (tds) from *Taxus brevifolia*, a codon optimized amorphadiene synthase (ads) from *Artemisia annua*, a valencene synthase (vs) from *Callitropsis nootkatensis*, and a limonene synthase (ls) from *Mentha spicata*. All plasmids were constructed using a standard workflow for Gibson Assembly described above. Confirmed plasmids were transformed by heat-shocked into BL21 (DE3) accordingly to manufacturer's recommendation (NEB) plated on kanamycin plates (50 µg/L) overnight at 37° C.

Cultivation, Protein Expression, and Quantification

A single colony from each strain containing one plasmid for the expression of a single enzyme was inoculated into 5 mL of sterile LB media (BD Sciences) with kanamycin and grown overnight at 37° C. One milliliter was then inoculated into a 1 L flask containing 200 mL of sterile SOB media (AMERSCO) with kanamycin. The culture was grown at 30° C. until an optical density (OD) of 0.4-0.6 ($\lambda$=600 nm). At this point protein production was induced by the addition of IPTG for a final concentration of 0.1 mM and continued at 30° C. for 3 h. Cells were harvested by centrifugation at 3750 rpm in an Allegra X12R centrifuge (Beckman-Coulter). The supernatant was removed and the cell pellets were frozen at −20° C. until purification. Proteins were visualized by SDS-PAGE performed accordingly to the manufacturer's guidelines (Bio-rad). Gradient (4-20%) gels were purchased from Biorad, as were the Kaleidoscope pre-stained protein ladder, Laemmli 4x sample buffer, Tris-glycine-SDS buffer, and mini-protean electrophoresis chambers. Gels were stained using Instant-Blue (Expedeon). Protein concentrations were very roughly estimated from the gel using Image J (NIH) in order to determine an appropriate amount of resin for purification.

Protein Purification

All purification steps were performed in a single day on ice and in a cold room when possible. Cell pellets were thawed and resuspended in 30 mL of NPI-10 buffer (50 mM $NaH_2PO_4$, 300 mM NaCl, 10 mM imidazole, pH 8.0) and supplemented with 0.5 mM PMSF immediately prior to cell lysis. Cells were lysed by 2-3 passages through an Emulsi-Flex-C5 high-pressure homogenizer (Avestin). Lysates were then centrifuged at 4 C for 15 min to remove cellular debris. The clarified lysate was loaded onto a Ni-NTA resin (Gold Bio, capacity 50 mg/mL) which was housed in a gravity column (Thermofisher) and was pre-equilibrated with 10 column volumes (CV) of NPI-10 buffer. The column was then washed with 10 CV of NPI-20 buffer (20 mM imidazole). The enzyme was then eluted from the column by 3 CV using NPI-250 buffer (250 mM imidazole). Enzymes were then exchanged into 50 mM Tris-HCl pH 7.5 using 10 kDa Microseps (Millipore) by centrifugation and repeated buffer exchanges until the imidazole was calculated to be under 1 mM. Buffer exchange of IDI was performed by using a 10 kDa Float-a-lyzer device (Spectrum Labs) for dialysis as the solution would not exchange through the Microsep. In this case, the IDI solution was added to the Float-a-lyzer and the solution was topped up to 10 mL using 50 mM Tris (pH 7.5). The device was then place fully submerged in a beaker of 50 mM Tris (pH 7.5) and the buffer was completely changed at 2, 6 and 16 h. Dialysis was allowed to proceed for 24 h. Enzyme concentration was determined using a bicin-choninic acid (BCA) assay kit from Pierce using bovine serum albumin as a standard (BSA). Proteins were then diluted in Tris buffer if necessary and aliquoted into microtubes, which were flash frozen in liquid nitrogen and stored at −80° C. until use.

Individual Enzyme Assays

Figure 16A:
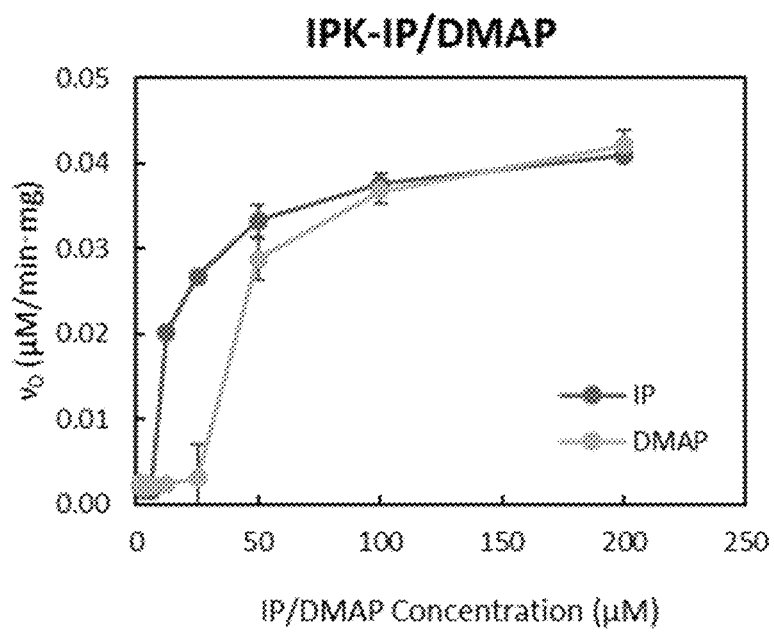
FIGS. 16A-16D. Enzyme kinetics for IUP and terpenoid backbone biosynthesis enzymes. Enzyme assays were conducted at 30° C., at pH 7.4 in ammonium bicarbonate buffer with 10 mM $MgCl_2$, 2 mM $MnCl_2$, and 2 mM DTT. Error bars (1σ) are presented for assays performed in triplicate.
Figure 16B:
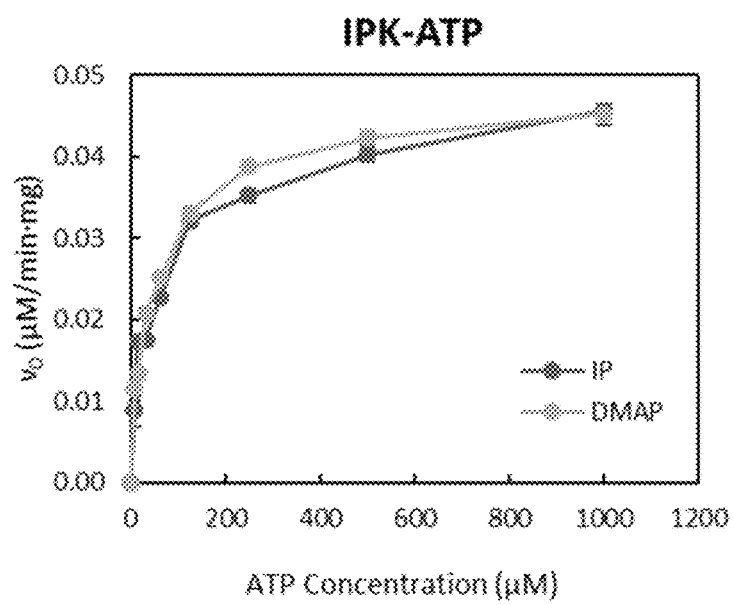
Figure 16C:
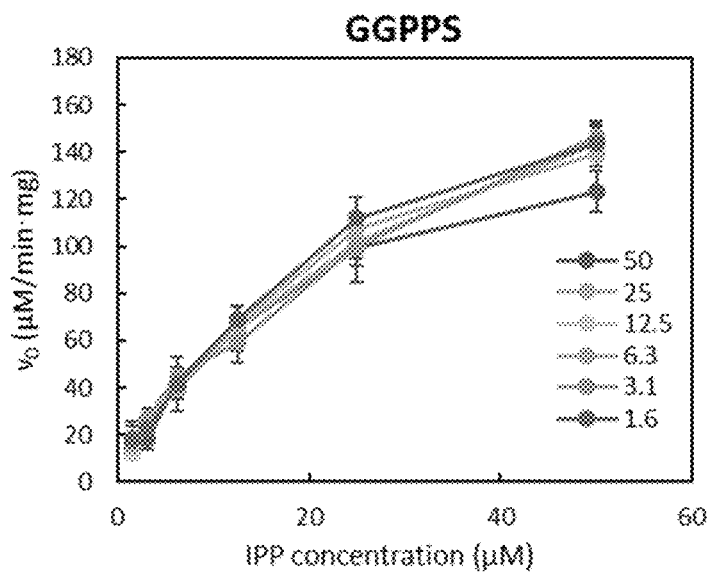
Figure 16D:
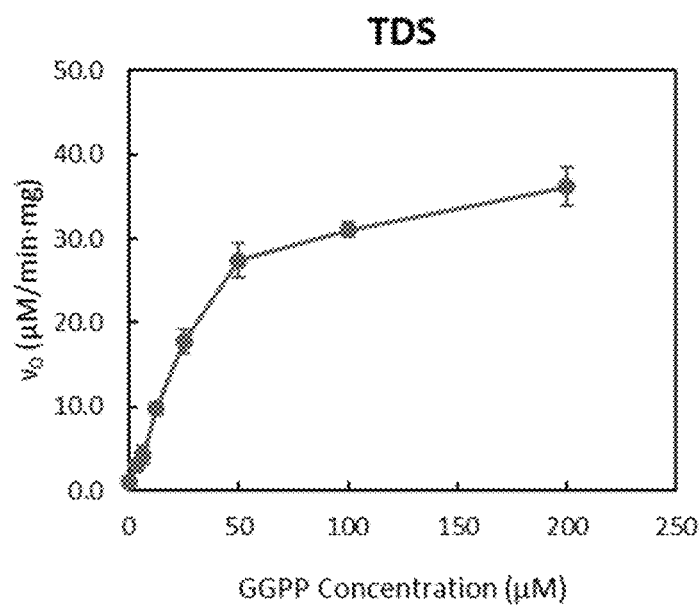

In order to estimate the best ratio of pathway enzymes, each enzyme was individually assayed using a kinetic assay to determine the Michaelis-Menten constant and the specific velocity/catalytic constant of each enzyme. The kinetics for CK were previously determined as described. The kinetics for IPK were determined by ATP consumption using a pyruvate kinase (PK) lactate dehydrogenase (LDH) coupled assay (FIGS. 16A & 16B). The following components were added into a single solution then distributed into a 96 well microplate for continuous monitoring at 340 nm: 10 mM ATP, 10 mM $MgCl_2$, 50 mM ammonium bicarbonate pH 7.4, 10 mM phosphoenolpyruvate (pH 7.4), 0.6 mM NADH, and 1 U of PK, and 1.4 U LDH (PK-LDH solution from Sigma Aldrich), and IPK (10 ug/mL). NADH was made fresh each time and the appropriate concentration was determined by constructing a standard curve using a SpectraMax M3 and selecting the highest value in the linear range. This curve was also used to determine the adsorption coefficient of NADH for calculation of the reaction rate. The reactions were monitored prior to the addition of the substrate to determine if any rate non-specific hydrolysis of ATP was present, however it was found to be none for purified enzymes. Pyruvate and ADP (Sigma-Aldrich) were used to determine the appropriate amount of PK-LDH solution (Sigma-Aldrich) and to confirm the assay was working appropriately. No substrate/enzyme only and no enzyme/substrate only controls were also included but no activity was detected. The substrates (IP or DMAP) were diluted in a 2 log standard curve which were then added to the microplate using a multichannel pipette and NADH oxidation to NAD+ was monitored at 340 nm. Assays were done in triplicate. The rate of IPP or DMAPP formation was equivalent to the negative rate of ATP consumption. The activity of GGPPS was determined for the conversion of IPP and FPP to GFPP by monitoring pyrophosphate (PPi) formation using the EnzChek pyrophosphate assay kit (Invitrogen) (FIG. 16C). The activity of TDS was also monitored using the PPi assay but only used GGPP as the substrate (FIG. 16D). The assays were performed as described for IPK using the same controls as above: TDS was added to 50 mM Tris-HCl pH 7.5, with 10 mM $MgCl_2$, 20 mM 2-amino-6-mercapto-7-pethylpurine (MESG), 1 U of purine nucleoside phosphatase (PNP), and 0.03 U of inorganic pyrophosphatase (IPPase). The substrates for GGPPS, IPP and FPP were each diluted in a microplate so that all combinations of each level were assayed in triplicate. The substrates were added to the appropriate well and the reaction was monitored for the fluorescence of MESG-phosphate. A standard curve was constructed using sodium pyrophosphate provided in the kit and was used to calculate the rate for each reaction. The rate of IDI was not determined as the isomerization of IPP to/from DMAPP cannot be measured using a kinetic assay and was not found to be a necessary component of the enzyme system.

Multienzyme Reactions in Solution

The multienzyme system assays were carried out in 50 mM ammonium bicarbonate (pH 7.4) with 10 mM $MgCl_2$, 2 mM $MnCl_2$, $_{0.05}$% (w/v) Tween 20, 10 mM ATP, and 5 mM isoprenol at 30° C. unless otherwise stated. The solution in glass GC vials (Agilent) were overlaid with 1/10 volume of dodecane to entrap the volatile isoprenoids. The enzyme concentrations used in the large perturbation experiments are reported in Table 5. An estimated optimal concentration of each enzyme was calculated using the rates determined by individual enzyme assays.

Time profiles were constructed by dividing up three separately prepared reaction master mixes into 100 µL aliquots in a deep-well microplate after the addition of ATP to start the reaction. The reactions were stopped in at different times by the addition of 1 mL of −20° C. acetonitrile which was then transferred into a microtube and centrifuged at 16,000×g for 10 min to remove the precipitated enzymes. The supernatant was dried using a Reacti-Therm III with filtered air in glass test tubes. The dried precipitate was resuspended in 100 µL of LC-MS/MS mobile phases as described below. The samples were vortexed and then centrifuged at 16,000×g a second time. Samples were analysed using LC-MS/MS and/or GC-MS.

column (30 m, 250 µm, 0.25 µm) (Agilent Technologies) using a 7890B Series GC and a 5977B MS. Chromatography was performed under the following conditions: 1 uL splitless injection, inlet temperature 280° C., constant inlet pressure 115.8 kPa, valve temperature 300° C., and MS transfer line 300° C. A oven program of 100° C., hold 1 min, 15° C./min

TABLE 5

Enzyme perturbation experiments

| | Enzyme Concentration (ug/mL) | | | | Metabolite Concentration (µM) | | | | Flux (µM/h) |
|---|---|---|---|---|---|---|---|---|---|
| Run | CK | IPK | IDI | ISPA | GGPPS | IP | IPP/DMAPP | GPP | FPP | GGPP |
| 1 | 5.0 | 15.0 | 25.4 | 37.2 | 8.2 | 0.03 ± 0.01 | 0.37 ±0.15 | 0.24 ± 0.07 | 0.15 ± 0.09 | 4.77 ± 2.97 |
| 2 | 12.5 | 15.0 | 25.4 | 37.2 | 8.2 | 0.11 ± 0.02 | 0.62 ± 0.28 | 0.47 ± 0.16 | 0.26 ± 0.20 | 7.23 ± 1.18 |
| 3 | 25.0 | 15.0 | 25.4 | 37.2 | 8.2 | 0.21 ± 0.05 | 0.82 ± 0.21 | 0.48 ± 0.13 | 0.57 ± 0.59 | 9.48 ± 3.80 |
| 4 | 50.0 | 15.0 | 25.4 | 37.2 | 8.2 | 0.98 ± 0.04 | 1.36 ± 0.43 | 1.03 ± 0.09 | 0.99 ± 0.30 | 9.32 ± 1.87 |
| 5 | 125.0 | 15.0 | 25.4 | 37.2 | 8.2 | 7.82 ± 0.00 | 0.98 ± 0.50 | 0.76 ± 0.18 | 1.25 ± 0.74 | 9.95 ± 2.37 |
| 6 | 25.0 | 3.0 | 25.4 | 37.2 | 8.2 | 1.58 ± 0.24 | 0.36 ± 0.21 | 0.23 ± 0.16 | 0.17 ± 0.16 | 4.58 ± 2.77 |
| 7 | 25.0 | 7.5 | 25.4 | 37.2 | 8.2 | 0.34 ± 0.20 | 0.83 ± 0.53 | 0.28 ± 0.19 | 0.64 ± 0.42 | 8.93 ± 1.39 |
| 8 | 25.0 | 15.0 | 25.4 | 37.2 | 8.2 | 0.09 ± 0.07 | 0.70 ± 0.43 | 0.28 ± 0.26 | 0.86 ± 0.42 | 9.89 ± 2.91 |
| 9 | 25.0 | 30.0 | 25.4 | 37.2 | 8.2 | 0.04 ± 0.00 | 1.12 ± 0.01 | 0.73 ± 0.04 | 0.42 ± 0.12 | 8.30 ± 1.29 |
| 10 | 25.0 | 75.0 | 25.4 | 37.2 | 8.2 | 0.03 ± 0.00 | 0.89 ± 0.15 | 0.62 ± 0.08 | 0.26 ± 0.24 | 7.39 ± 1.13 |
| 11 | 25.0 | 15.0 | 5.1 | 37.2 | 8.2 | 0.20 ± 0.10 | 0.42 ± 0.12 | 0.01 ± 0.01 | 0.50 ± 0.36 | 5.26 ± 2.62 |
| 12 | 25.0 | 15.0 | 12.7 | 37.2 | 8.2 | 0.20 ± 0.04 | 0.47 ± 0.23 | 0.32 ± 0.19 | 0.37 ± 0.29 | 8.05 ± 1.26 |
| 13 | 25.0 | 15.0 | 25.4 | 37.2 | 8.2 | 0.18 ± 0.02 | 0.56 ± 0.14 | 0.45 ± 0.14 | 0.26 ± 0.19 | 7.55 ± 1.17 |
| 14 | 25.0 | 15.0 | 50.8 | 37.2 | 8.2 | 0.19 ± 0.01 | 0.92 ± 0.26 | 0.75 ± 0.11 | 0.61 ± 0.16 | 8.51 ± 1.10 |
| 15 | 25.0 | 15.0 | 127.0 | 37.2 | 8.2 | 0.16 ± 0.10 | 0.48 ± 0.06 | 0.39 ± 0.31 | 0.57 ± 0.36 | 8.20 ± 1.37 |
| 16 | 25.0 | 15.0 | 25.4 | 7.4 | 8.2 | 0.20 ± 0.06 | 2.05 ± 0.42 | 1.00 ± 0.28 | 0.46 ± 0.25 | 5.12 ± 2.97 |
| 17 | 25.0 | 15.0 | 25.4 | 18.6 | 8.2 | 0.15 ± 0.03 | 1.03 ± 0.13 | 0.55 ± 0.10 | 0.35 ± 0.18 | 7.47 ± 0.79 |
| 18 | 25.0 | 15.0 | 25.4 | 37.2 | 8.2 | 0.13 ± 0.02 | 0.71 ± 0.20 | 0.45 ± 0.14 | 0.34 ± 0.20 | 7.27 ± 0.90 |
| 19 | 25.0 | 15.0 | 25.4 | 74.3 | 8.2 | 0.12 ± 0.00 | 0.34 ± 0.07 | 0.16 ± 0.11 | 0.98 ± 0.75 | 10.14 ± 2.85 |
| 20 | 25.0 | 15.0 | 25.4 | 185.8 | 8.2 | 0.10 ± 0.02 | 0.23 ± 0.04 | 0.09 ± 0.07 | 1.15 ± 1.09 | 10.13 ± 3.86 |
| 21 | 25.0 | 15.0 | 25.4 | 37.2 | 1.6 | 0.22 ± 0.06 | 1.13 ± 0.50 | 0.77 ± 0.26 | 1.66 ± 0.55 | 7.86 ± 2.00 |
| 22 | 25.0 | 15.0 | 25.4 | 37.2 | 4.1 | 0.16 ± 0.09 | 0.53 ± 0.31 | 0.37 ± 0.21 | 0.44 ± 0.29 | 7.73 ± 1.24 |
| 23 | 25.0 | 15.0 | 25.4 | 37.2 | 8.2 | 0.13 ± 0.04 | 0.47 ± 0.29 | 0.28 ± 0.18 | 0.09 ± 0.07 | 7.07 ± 0.74 |
| 24 | 25.0 | 15.0 | 25.4 | 37.2 | 16.3 | 0.17 ± 0.01 | 0.75 ± 0.26 | 0.67 ± 0.09 | 0.42 ± 0.08 | 8.60 ± 1.61 |
| 25 | 25.0 | 15.0 | 25.4 | 37.2 | 40.8 | 0.13 ± 0.00 | 0.38 ± 0.00 | 0.50 ± 0.05 | 0.22 ± 0.03 | 7.53 ± 1.01 |

Metabolite Quantification using LC-MS/MS

Figure 17A:
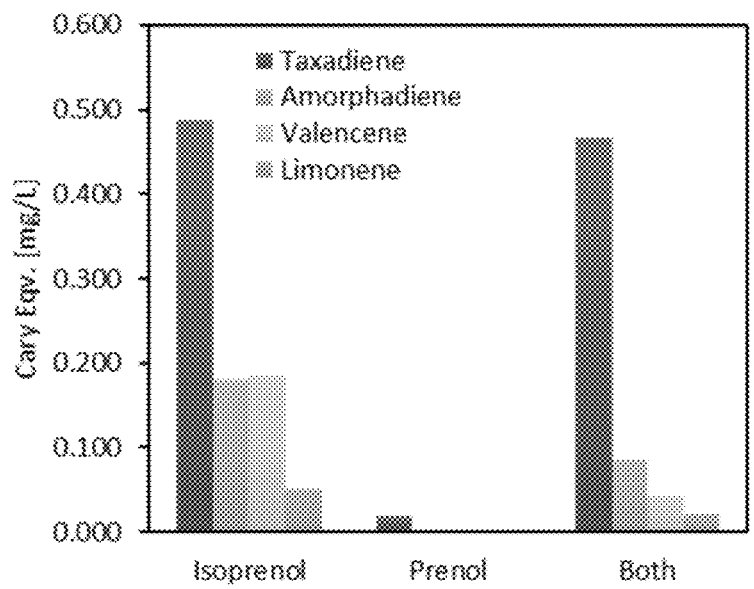
FIGS. 17A-17F. Proof of concept of the multi-enzyme system.
Figure 17B:
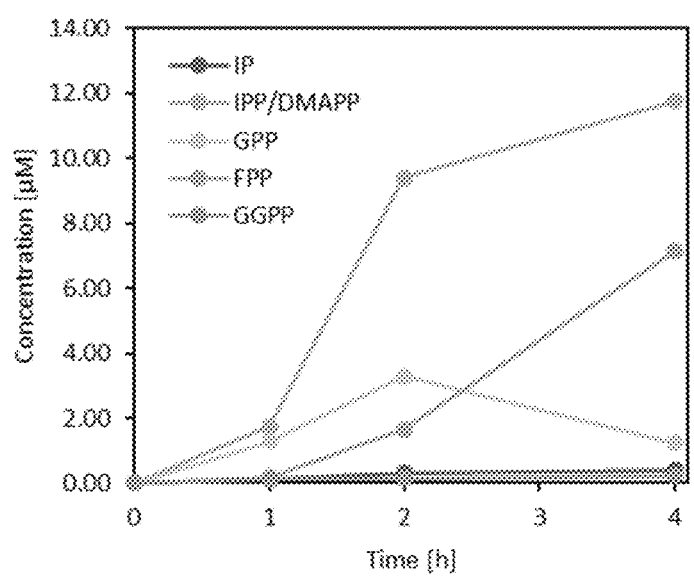
Figure 17C:
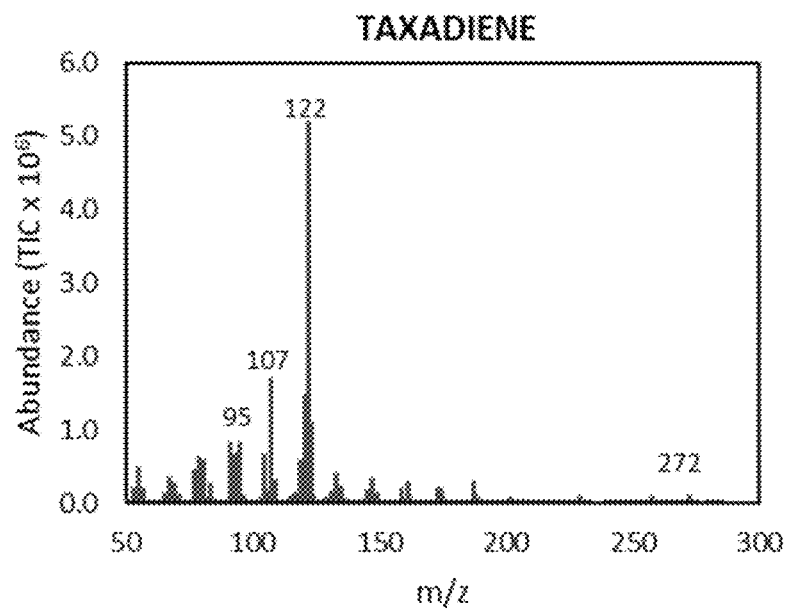
Figure 17D:
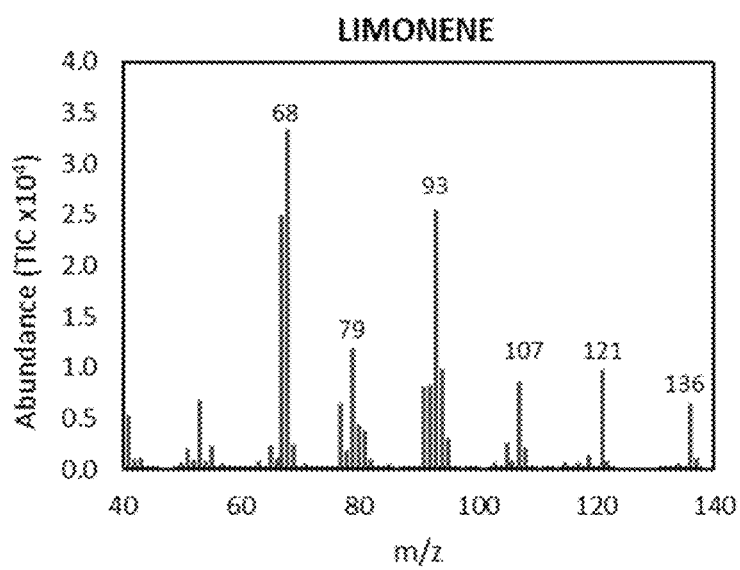
Figure 17E:
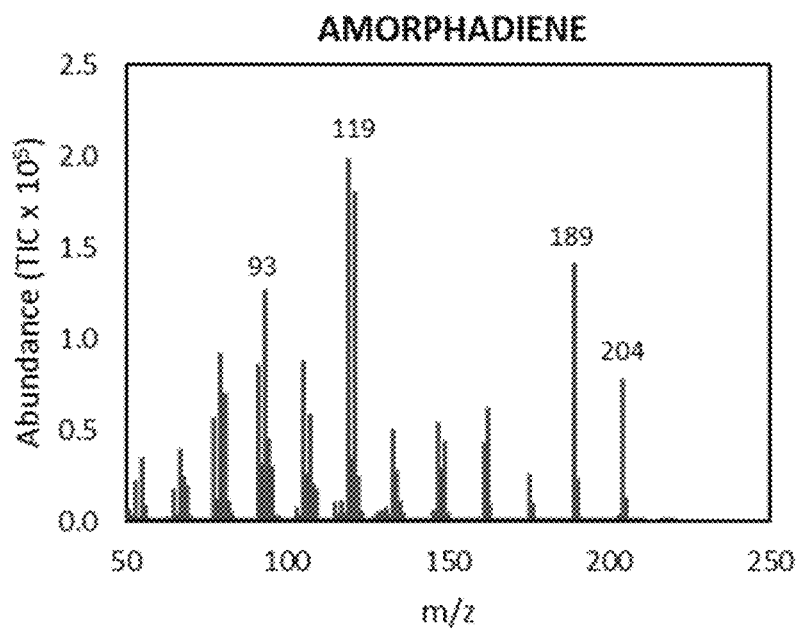
Figure 17F:
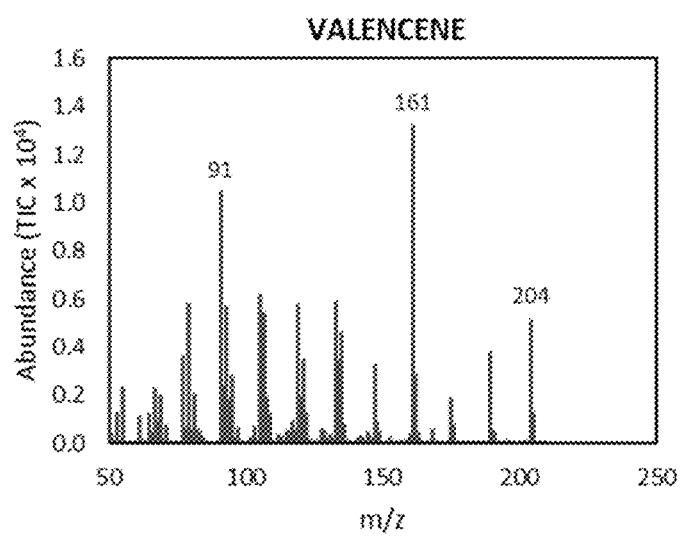
Figures 18A, 18B:
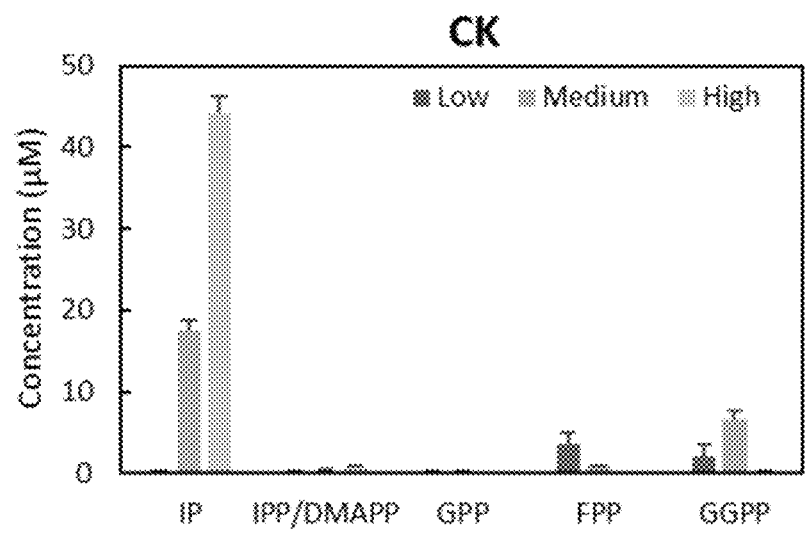
FIGS. 18A-18F. One-at-a-time modulation of each enzyme concentration for the multienzyme system: CK, IPK, IDI, IspA, and GGPPS. Each enzyme was modulated separately to high, low and medium levels indicated in panel A (FIG. 18A), while all other enzymes were kept at the midpoint concentration. Assays were conducted at 30° C., at pH 7.4 for 24 h with 10 mM ATP and 5 mM isoprenol. Error bars (1a) are presented for assays performed in triplicate.
Figure 18C:
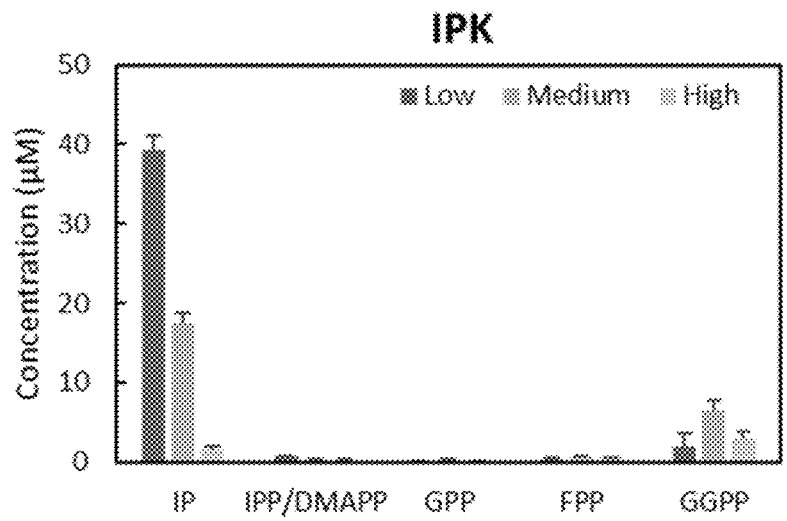
Figure 18D:
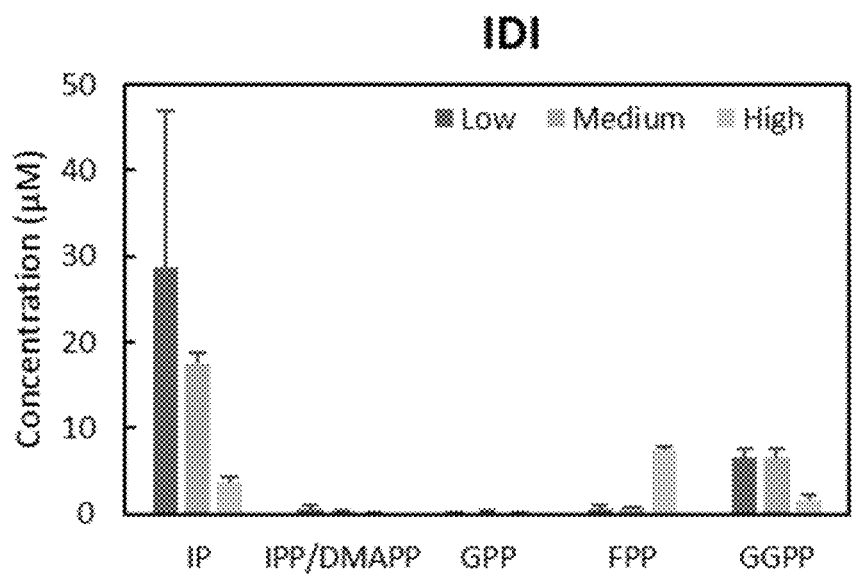
Figure 18E:
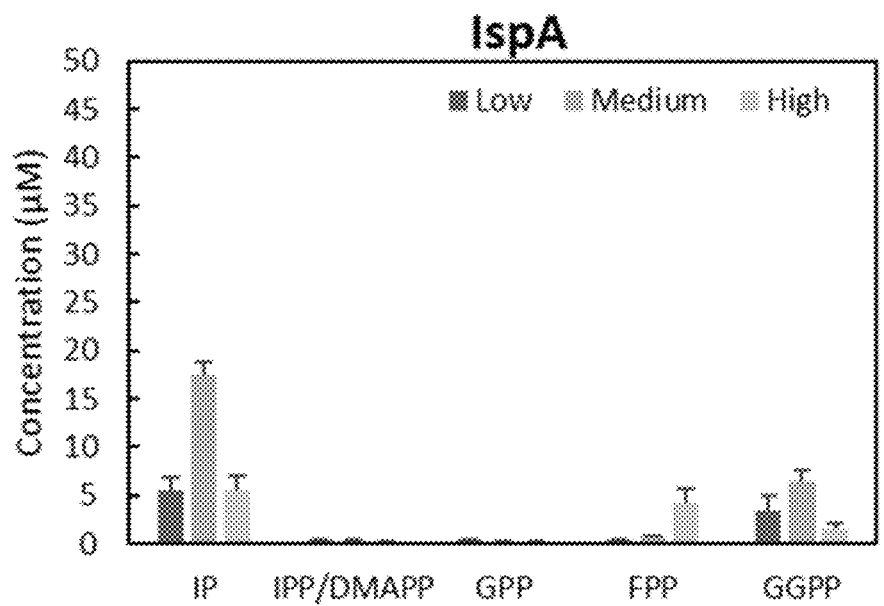
Figure 18F:
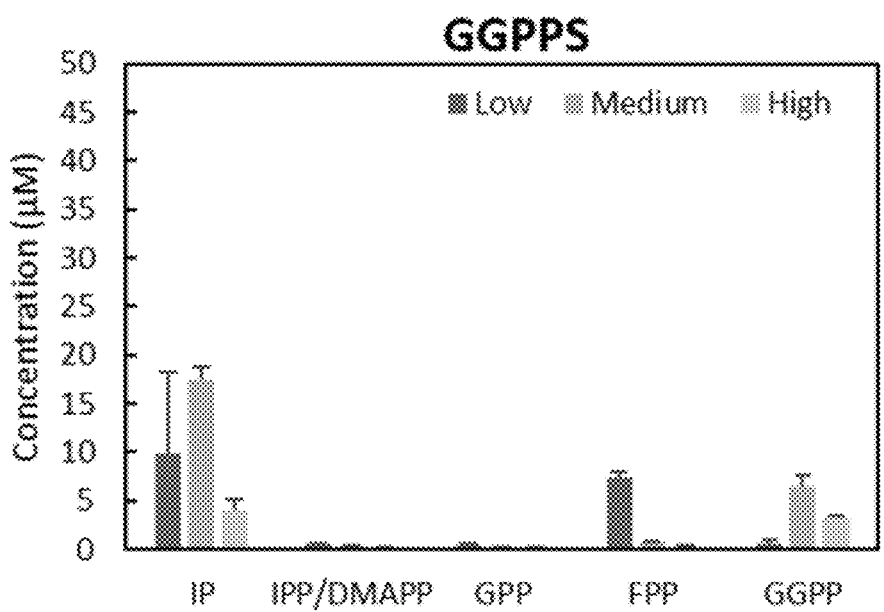
Figure 19:
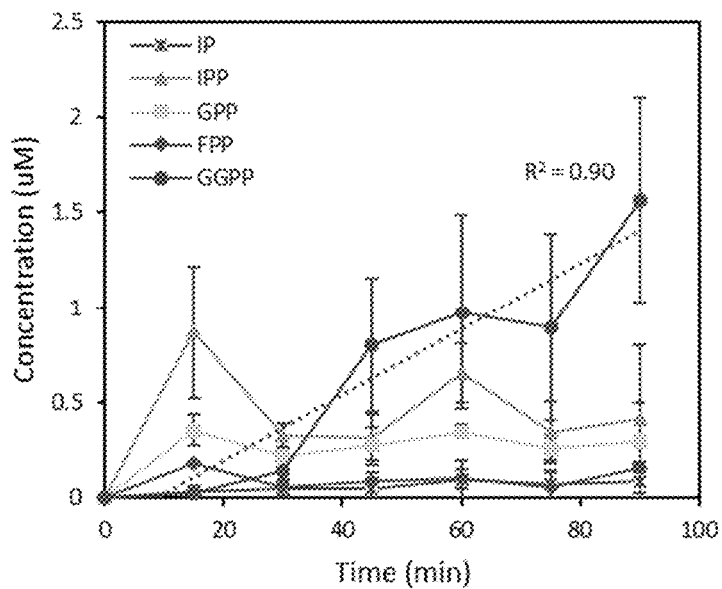
FIG. 19. Formation of a QSS in the CK, IPK, IDI, IspA, and GGPPS system. Samples were taken every 15 min for 1.5 h. Enzymes concentrations were as follows: CK (25 ug/mL), IPK (15 ug/mL), IDI (25.4 ug/mL), IspA (37.1 ug/mL) and GGPPS (8.15 g/mL). Assays were performed in triplicate at 30° C. at pH 7.4. Error bars are shown for experiments performed in triplicate (1a). Referencing the position at the 90 minute time point, the lines, from top to bottom, are: GGPP, IPP, GPP, FPP, and IP.

Liquid chromatography was performed using an Agilent 1100 Series HPLC (Agilent Technologies) and the MS/MS was conducted using an API 4000 triple quadrupole mass spectrometer (SCIEX) with ESI running in negative MRM mode as previously described. The LC-MS/MS was equipped with an Xbridge C18 column (150 mm, 3.5 um, 2.1 mm) from Waters and was operated using a mobile phase (A) of 0.1% v/v TBA, 0.12% v/v acetic acid, and titrated with ~0.5% v/v 5N NH$_4$OH until a pH of 8.5 was reached. The elutant, acetonitrile (B) was introduced using the following gradient: 0-5 min 0% B, 5-20 min 0-65% B, 20-25 min 65% B, 25-30 min 100% B, 30-35 min 100% B, 35-36 min 100-0% B, 0% B until 45 min. Standard curves were generated for a mixture of IP, DMAPP, GPP, FPP, and GGPP diluted in mobile phase A. Standards were purchased from Sigma-Aldrich and/or Cayman Chemicals, except IP which was synthesized as previously described. Metabolite specific ionization and fragmentation voltages determined from a 1 µM standard solution of each metabolite was obtained using the Analyst software (v 1.6) and monitored during chromatography. Peaks were integrated using the Analyst software (FIG. 17B, FIG. 19).

Quantification of Volatile Isoprenoids

Taxadiene, valencene, amorphadiene, and limonene were quantified by diluting the dodecane overlays into an appropriate range depending on analyte concentration with ethyl acetate containing 90 mg/L β-caryophyllene as an internal standard as previously described (FIGS. 17C-17F). The samples were separated using an HP-5 MS UI capillary until 200° C., hold 2 min, 30° C./min until 250° C., hold 1 min, and 30° C./min until 290° C., hold 2 min was used for determination of taxadiene, valencene, and amorphadiene. Limonene was separated using an oven program of 80° C., hold 3 min, 10° C./min until 140° C., hold 2 min, 45° C./min until 290° C., hold 1 min. The MS was operated at an ion source temperature of 280° C., and a quadrupole temperature of 180° C. Ions were scanned between a mass of 40 to 400 at 1.562 u/s. Taxadiene was quantified using a standard curve based on the m/z 122 ion which has the greatest abundance in unlabeled taxadiene. The remaining compounds were estimated by normalizing their area to that of the internal standard. The taxadiene standard was purified as previously described.

Enzyme Assays

Enzyme assays for IPK, GGPPS, and TDS were conducted for further kinetic information and future modeling. IPK exhibited only marginally greater affinity for IP with a $k_{cat}/K_m$ of 1.79 uM$^{-1}$s$^{-1}$ versus 1.30 uM$^{-1}$s$^{-1}$ for DMAP (FIGS. 16A and 16B). GGPPS (26.7 s$^{-1}$) and TDS (23.1 s$^{-1}$) showed catalytic rates on the same order as IPK (FIGS. 16C and 16D). A preliminary experiment was conducted since the activities of IDI and IspA were not confirmed by enzyme assays, the full enzyme systems with either pure isoprenol, pure prenol or a mixture of both enzymes were incubated overnight and analyzed for isoprenoid production (FIG. 17A). By supplying both isoprenol and prenol we hoped to still form a complete pathway with or without an active IDI, and be able to identify if either IDI or IspA were activity by LC-MS/MS of the intermediates (FIG. 17B). All of the assays produced isoprenoids and the products were identified by their electron ionization mass spectra (FIGS. 17C-17F).

An exploratory experiment was run using the rates determined empirically from the enzyme assays or in the literature to balance the rates of each step. That results in the data in FIG. 18. This data was used to numerically optimize for the highest flux towards GGPP. It was decided to optimize TDS separately since they used different types of sample prep and analysis. In order to study the control of the pathway, the pathway must be operating at a quasi steady state. Since it was unknown whether the exploratory study in FIG. 18 was at a steady state, a time profile was constructed for the intermediates from 0-90 min using the concentrations optimized from the smaller perturbation study (FIG. 18). It took approximately 30 min to see any formation of GGPP, after which there was a linear increase in production of GGPP (FIG. 19). Therefore, 60 min was chosen for the larger perturbation study as having formed the quasi-steady state. The full raw data is given in Table 5.

Optimization of Taxadiene Synthase and Operating Conditions

Figure 20A:
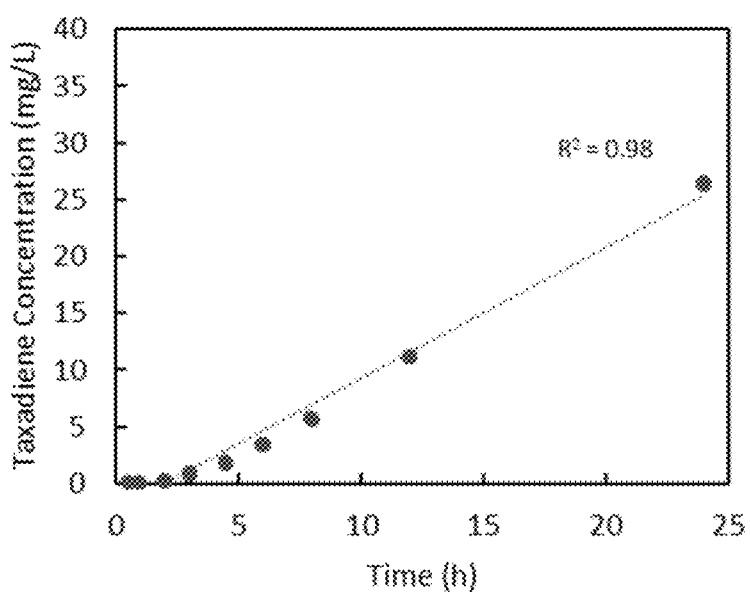
FIGS. 20A-20B. Time profile and TDS optimization for the multi-enzyme system: CH, IPK, IDI, IspA, GGPPS. Assays were conducted at 30° C. at pH 7.4. Error bars are shown for experiments performed in triplicate (1σ) FIG. 20A. The linear relationship between taxadiene concentration and time.
Figure 20B:
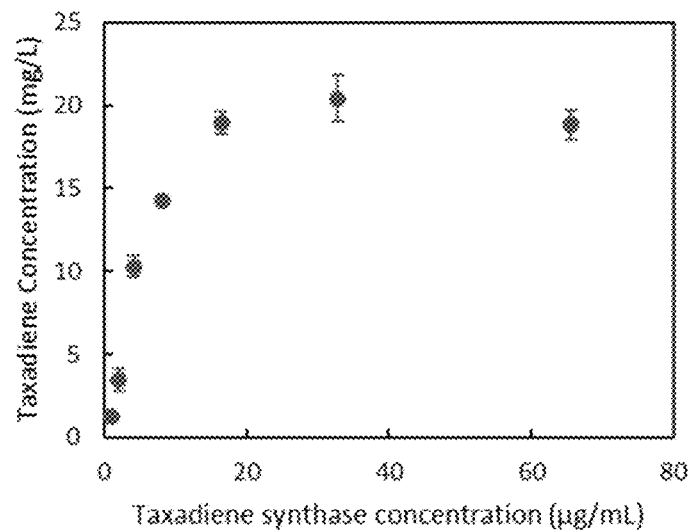
Figure 21A:
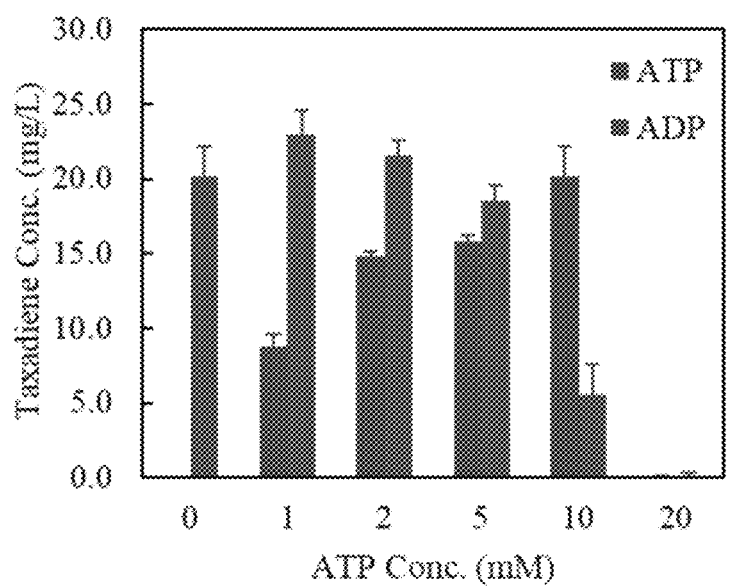
FIGS. 21A-21D. Titration of cofactors, potential inhibitors, and additives.
Figure 21B:
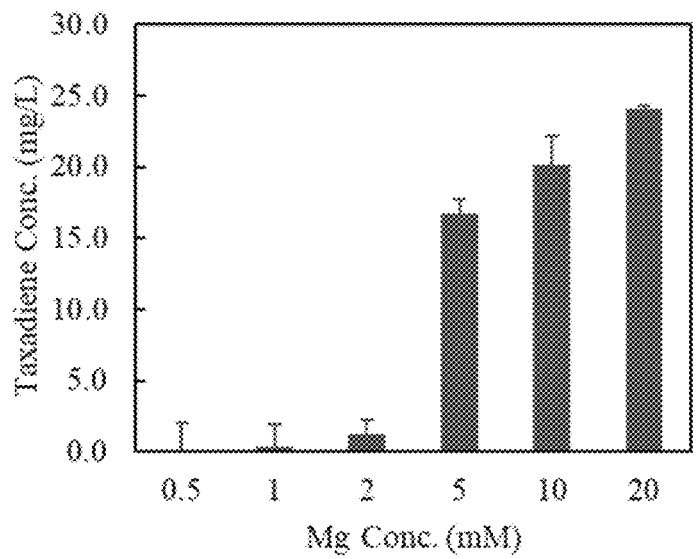
Figure 21C:
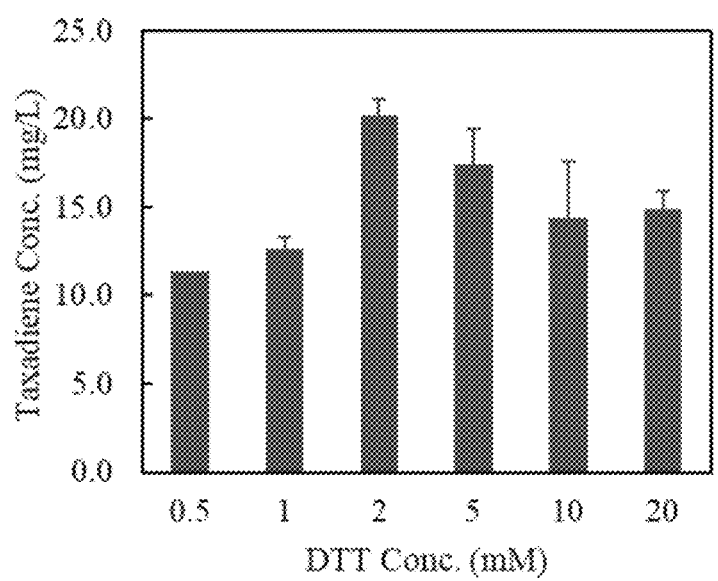
Figure 21D:
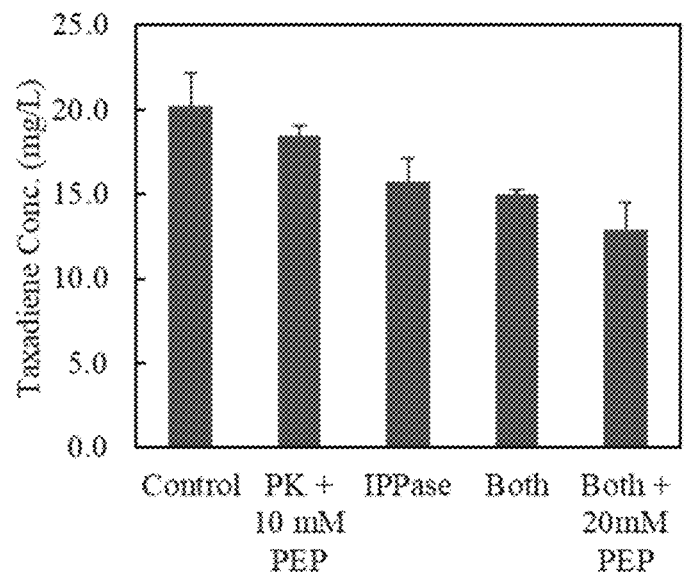
Figure 22A:
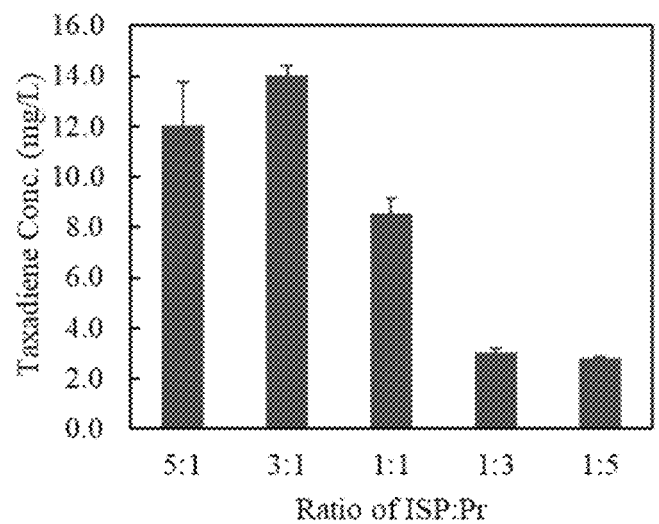
FIGS. 22A-22B. The production of taxadiene without IDI and the production of alternative isoprenoids using the optimized in vitro system.
Figure 22B:
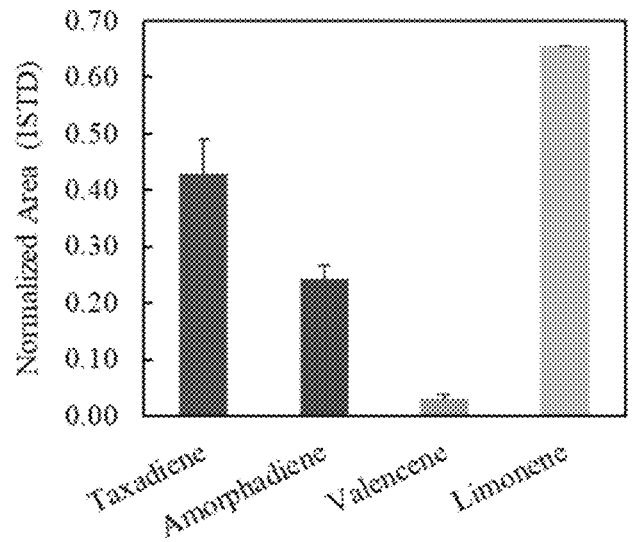
Figure 23A:
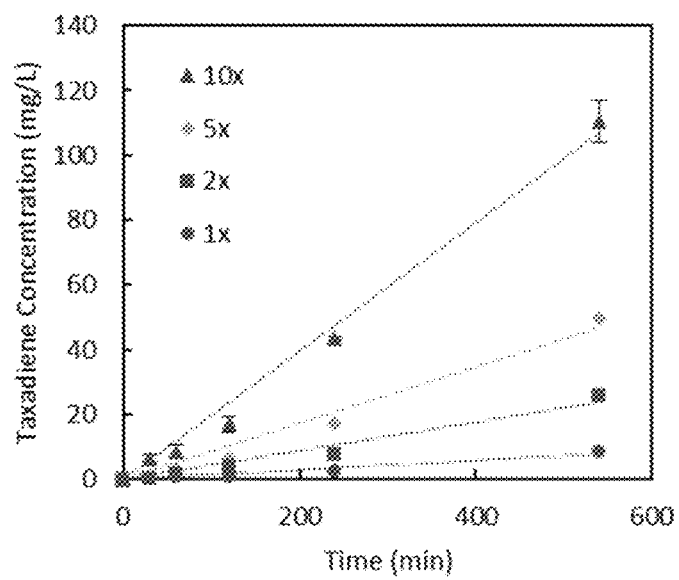
FIGS. 23A-23B. The effect of increasing enzyme concentration on the taxadiene flux.
Figure 23B:
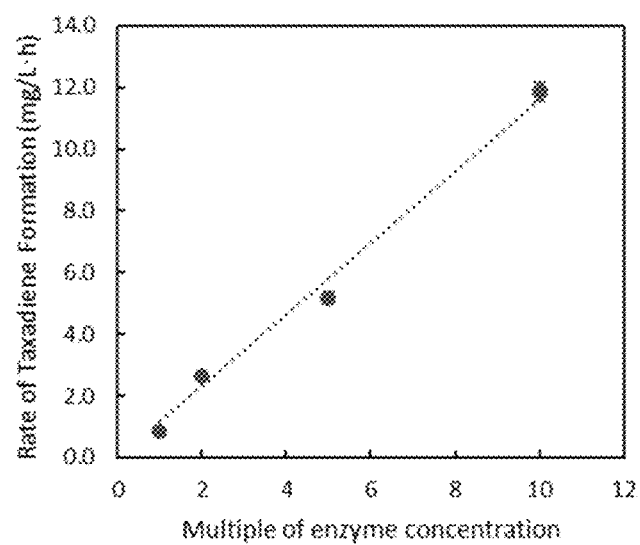

First taxadiene synthase was added in excess (100 μg/mL) and the rate of taxadiene formation was monitored for linearity (FIG. 20A). Since it was linear until 24 h, the concentration of taxadiene synthase was optimized using a 20 h incubation. (FIG. 20B). After selecting the optimal TDS concentration, the effects of ATP, ADP, DTT, $Mg^{2+}$, and the addition of pyruvate kinase or inorganic pyrophosphatase was assessed (FIG. 21). In order to prove IDI was not necessary for this in vitro system, a series of assays with the taxadiene producing multi-enzyme system without IDI was run with different ratios of isoprenol to prenol (FIG. 22A). This showed that isoprenoids can be produced with the in vitro IUP without IDI. In order to test the optimized enzyme system for the production of various isoprenoids, the multi-enzyme systems containing the relevant enzymes were run with only pure isoprenol and included IDI. Finally, to observe the relationship between enzyme concentration and rate of taxadiene formation, time profiles containing multiples of the concentrations of each enzyme (i.e., all enzyme concentrations were doubles in the 2×) were constructed over 9h (FIG. 23).

REFERENCES

1. S. S. Chandran, J. T. Kealey, C. D. Reeves, Microbial production of isoprenoids. *Process Biochem.* 46, 1703-1710 (2011).
2. J. Kirby, J. D. Keasling, Biosynthesis of plant isoprenoids: Perspectives for microbial engineering. *Annu. Rev. Plant Biol.* 60, 335-355 (2009).
3. D. A. Nagegowda, Plant volatile terpenoid metabolism: Biosynthetic genes, transcriptional regulation and subcellular compartmentation. *FEBS Lett.* 584, 2965-2973 (2010).
4. H. Liu et al., Combination of Entner-Doudoroff pathway with MEP increases isoprene production in engineered *Escherichia coli. PLoS One.* 8, e83290 (2013).
5. W. Chang, H. Song, H. Liu, P. Liu, Current development in isoprenoid precursor biosynthesis and regulation. *Curr. Opin. Chem. Biol.* 17, 571-579 (2013).
6. K. Zhou, R. Zou, G. Stephanopoulos, H.-P. Too, Metabolite Profiling Identified Methylerythritol Cyclodiphosphate Efflux as a Limiting Step in Microbial Isoprenoid Production. *PLoS One.* 7, e47513 (2012).
7. A. Banerjee et al., Feedback inhibition of deoxy-D-xylulose-5-phosphate synthase regulates the methylerythritol 4-phosphate pathway. *J. Biol. Chem.* 288, 16926-16936 (2013).
8. D. A. Nagegowda, T. J. Bach, M.-L. Chye, *Brassica juncea* 3-hydroxy-3-methylglutaryl (HMG)-CoA synthase 1: expression and characterization of recombinant wild-type and mutant enzymes. *Biochem. J.* 383, 517-27 (2004).
9. J. D. Brooker, D. W. Russell, Properties of microsomal 3-hydroxy-3-methylglutaryl coenzyme A reductase from *Pisum sativum* seedlings. *Arch. Biochem. Biophys.* 167, 723-729 (1975).
10. T. J. Bach, D. H. Rogers, H. Rudney, Detergent-solubilization, purification, and characterization of membrane-bound 3-hydroxy-3-methylglutaryl-coenzyme A reductase from radish seedlings. *Eur J Biochem.* 154, 103-111 (1986).
11. Y. A. Primak et al., Characterization of a feedback-resistant mevalonate kinase from the archaeon *Methanosarcina mazei. Appl. Environ. Microbiol.* 77, 7772-7778 (2011).
12. N. Dellas, S. T. Thomas, G. Manning, J. P. Noel, Discovery of a metabolic alternative to the classical mevalonate pathway. *Elife.* 2013, 1-18 (2013).
13. S. Gao et al., Substrate promiscuity of pyruvate kinase on various deoxynucleoside diphosphates for synthesis of deoxynucleoside triphosphates. *Enzyme Microb. Technol.* 43, 455-459(2008).
14. Y. Li et al., Substrate promiscuity of n-acetylhexosamine 1-kinases. *Molecules.* 16, 6396-6407(2011).
15. Y. Liu, Z. Yan, X. Lu, D. Xiao, H. Jiang, Improving the catalytic activity of isopentenyl phosphate kinase through protein coevolution analysis. *Sci. Rep.* 6, 24117 (2016).
16. J. C. VanNice et al., Identification in *Haloferax volcanii* of phosphomevalonate decarboxylase and isopentenyl phosphate kinase as catalysts of the terminal enzyme reactions in an archaeal alternate mevalonate pathway. *J. Bacteriol.* 196, 1055-1063 (2014).
17. J. A. Chemler, Y. Yan, M. A. G. Koffas, Biosynthesis of isoprenoids, polyunsaturated fatty acids and flavonoids in *Saccharomyces cerevisiae. Microb. Cell Fact.* 5, 1-9 (2006).
18. Y. Jiang et al., Multigene editing in the *Escherichia coli* genome using the CRISPR-Cas9 system. *Appl. Environ. Microbiol.* 81, 2506-2514 (2015).
19. V. J. J. Martin, D. J. Pitera, S. T. Withers, J. D. Newman, J. D. Keasling, Engineering a mevalonate pathway in *Escherichia coli* for production of terpenoids. *Nat. Biotechnol.* 21, 796-802(2003).
20. R. Silva-Rocha et al., The Standard European Vector Architecture (SEVA): A coherent platform for the analysis and deployment of complex prokaryotic phenotypes. *Nucleic Acids Res.* 41, 666-675 (2013).
21. J. H. Davis, A. J. Rubin, R. T. Sauer, Design, construction and characterization of a set of insulated bacterial promoters. *Nucleic Acids Res.* 39, 1131-1141 (2011).
22. T. S. Lee et al., BglBrick vectors and datasheets: A synthetic biology platform for gene expression. *J. Biol. Eng.* 5, 12 (2011).
23. M. Takehara et al., Characterization and Thermal Isomerization of (all-E)-Lycopene. *J. Agric. Food Chem.* 62, 264-269 (2014).
24. W. B. Davis, Preparation of Lycopene from Tomato Paste for Use as a Spectrophotometric Standard. *Anal. Chem.* 21, 1226-1228 (1949).

25. S. Srivastava, A. K. Srivastava, Lycopene; chemistry, biosynthesis, metabolism and degradation under various abiotic parameters. *J. Food Sci. Technol.* 52, 41-53 (2015).
26. F. X. Cunningham, H. Lee, E. Gantt, Carotenoid biosynthesis in the primitive red alga *Cyanidioschyzon merolae*. *Eukaryot. Cell.* 6, 533-545 (2007).
27. P. K. Ajikumar et al., Isoprenoid pathway optimization for Taxol precursor overproduction in *Escherichia coli*. *Science.* 330, 70-74 (2010).
28. H. Tsuruta et al., High-level production of amorpha-4, 11-diene, a precursor of the antimalarial agent artemisinin, in *Escherichia coli. PLoS One.* 4, e4489 (2009).
29. G. S. Wang, H. Grammel, K. Abou-Aisha, R. Sagesser, R. Ghosh, High-level production of the industrial product lycopene by the photosynthetic *Bacterium Rhodospirillum rubrum. Appl. Environ. Microbiol.* 78, 7205-7215 (2012).
30. H. M. Salis, E. A. Mirsky, C. A. Voigt, Automated Design of Synthetic Ribosome Binding Sites to Precisely Control Protein Expression. *Nat Biotechnol.* 27, 946-950 (2010).
31. A. Espah Borujeni, A. S. Channarasappa, H. M. Salis, Translation rate is controlled by coupled trade-offs between site accessibility, selective RNA unfolding and sliding at upstream standby sites. *Nucleic Acids Res.* 42, 2646-2659 (2014).
32. C. N. S. Santos, M. Koffas, G. Stephanopoulos, Optimization of a heterologous pathway for the production of flavonoids from glucose. *Metab. Eng.* 13, 392-400 (2011).
33. L. M. Lira, D. Vasilev, R. A. Pilli, L. A. Wessjohann, One-pot synthesis of organophosphate monoesters from alcohols. *Tetrahedron Lett.* 54, 1690-1692 (2013).
34. Y. Wang, H. Xu, M. K. Jones, R. H. White, Identification of the final two genes functioning in methanofuran biosynthesis in *Methanocaldococcus jannaschii. J. Bacteriol.* 197, 2850-2858(2015).
35. S. Edgar et al., Mechanistic Insights into Taxadiene Epoxidation by Taxadiene-5α-Hydroxylase. *ACS Chem. Biol.* 11, 460-469 (2016).
36. J. Alonso-Gutierrez et al., Metabolic engineering of *Escherichia coli* for limonene and perillyl alcohol production. *Metab. Eng.* 19, 33-41 (2013).
37. K. Zhou, K. Qiao, S. Edgar, G. Stephanopoulos, Distributing a metabolic pathway among a microbial consortium enhances production of natural products. *Nat. Biotechnol.* 33, 377-383(2015).

Example 8—Cell Free Biosynthesis of Isoprenoids from Isopentenol

Cell-free systems for biosynthesis is a growing strategy for the synthesis of complex molecules that combines the precision of traditional chemistry with the ingenuity of biological systems. Recently, a new synthetic pathways for the biosynthesis of isoprenoids using the substrate, isopentenol, dubbed the 'Isopentenol Utilization Pathway (IUP), was demonstrated to be a promising alternative to the native 2C-methyl-D-erythritol-4-phosphate (MEP) and mevalonate (MVA) pathways. This simplified pathway which contains a minimum of 4 enzymes to produce basic monoterpenes, and only depends on ATP and isopentenol as substrates, allows for a highly flexible and engineered approach to commercial synthesis of isoprenoids. In this work, we use metabolic reconstitution to characterize this new pathway in vitro and demonstrate the use of the IUP for cell-free synthesis of mono-, sesquit-, and diterpenoids. Metabolic control analysis was used to elucidate protein-level interactions within this pathway, which demonstrated that the IUP enzymes are not regulated by the metabolic intermediates of the isoprenoid biosynthesis pathway. This is a significant advantage over the natural MEP or MVA pathways and it greatly simplifies future metabolic engineering efforts both in vitro and in vivo. Finally, we used the insights gathered to demonstrate an in vitro IUP system that can produce 220 mg/L of the diterpene, taxadiene, in 9 h.

Isoprenoids are a large class of diverse molecules which encompasses high-value pharmaceuticals such as paclitaxel and low-value bulk chemicals like isoprene (Vickers et al., 2014). While isoprenoids are produced in all organisms, many of the compounds of greatest interest are made in small quantities in plants (Vickers et al., 2014). Due to the high cost of their recovery, high-level production of isoprenoids through metabolic engineering is highly desirable, however, attempts at engineering the methyl-D-erythritol-4-phosphate (MEP) and mevalonate (MVA) pathways in *Escherichia coli* and *Saccharomyces cerevisiae* have revealed significant challenges related to their strict regulation (Chen et al., 2015; Ward et al., 2018) and the toxicity caused by over-accumulation of pathway intermediates (George et al., 2018).

These challenges can be circumvented by using cell-free biocatalysis. Cell-free biosynthesis greatly simplifies the process by (i) eliminating the need for extensive strain engineering, (ii) removes competing metabolic pathways and the need to support cell growth and viability which erodes the maximum achievable yields, (iii) alleviating transcriptional and translational regulation present in the native isoprenoid pathways, and (iv) avoiding the effects of host toxicity caused by accumulation of pathway intermediates. In vitro biosynthesis of isoprenoids becomes particularly attractive when you contemplate our collective experience which has demonstrated that extensive engineering of central carbon metabolism is required to achieve even low isoprenoid titers (Meadows et al., 2016).

However, examples of cell-free systems used at scale is limited. This is primarily due to the high cost of enzyme production, but also many pathways require a number of expensive labile cofactors which, normally regenerated by complex metabolic systems in vivo, are no longer present in vitro. Fortunately, cofactor recycling systems have been demonstrated for ATP to sustain long-term cell-free protein synthesis using the low cost substrate polyphosphate (Andexer and Richter, 2015), however, the use of NADH and NADPH in cell-free systems remains a significant challenge (Zhang, 2011). The native MVA and MEP pathways both have multiple co-factor requirements including NAD(P)H and ATP/CTP. Furthermore, their direct precursors, acetyl-CoA, pyruvate, and glyceraldehyde-3-phosphate are not bulk chemicals making them unsuitable for cell-free synthesis on their own (Boronat and Rodriguex-Concepcion, 2015). In order to use a low cost substrate like glucose, glycolysis enzymes must also be included. This was demonstrated for the production of monoterpenes, which increased the number of required enzymes to 27 (Korman et al., 2017). While they were able to achieve high titers (>11 g/L over 7 days) of pinene, sabinene, and limonene, and mitigate the toxicity effects which limit monoterpene production in vivo, the high cost for the production, purification, and maintenance of so many enzymes would be prohibitive at scale.

Disclosed herein is a new synthetic pathway for the production of isoprenoids, the Isopentenol Utilization Pathway (IUP) (Chatzivasileiou et al., 2018). This pathway converts the substrates prenol or isoprenol to IPP and DMAPP respectively, through two subsequent phosphorylation reactions catalyzed by the enzymes choline kinase (CK) and isopentenyl phosphate kinase (IPK)—FIG. 24 This pathway was characterized in vivo and achieved high flux with very little optimization. Using the IUP for cell-free monoterpene biosynthesis would dramatically shorten the pathway to only 4 enzymes (CK, IPK, IspA, and a monoterpene synthase). Combined with the high price of complex isoprenoids, a cell-free IUP could have significant potential for commercial production of isoprenoids.

Finally, metabolic reconstitution can also be used to study pathway kinetics and elucidate rate-limiting steps using a systematic approach which can be used in turn for the optimization of metabolic pathways in vivo (Galloway et al., 2015; Guo et al., 2017). It can also be used to identify pathway regulatory mechanisms at the protein level (Guo et al., 2017). The metabolic reconstitution the MVA from mevalonate and acetyl-CoA for the production of amorphadiene (Chen et al., 2017) and farnesene (Zhu et al., 2014) have been studied, which identified previously unknown regulatory interactions and was subsequently used to guide in vivo engineering efforts.

After first determining kinetic constants for pathway enzymes and demonstrating that the IUP can be used for the in vitro biosynthesis of a range isoprenoids, the enzyme elasticity coefficients were calculated, i.e. the degree to which factors such as metabolic intermediate concentrations affect the reaction rates of specific enzymes, by introducing perturbations to individual enzyme concentrations. Lin-log kinetic combined with metabolic control analysis was used to understand the interactions between pathway intermediates and overall flux. This information was used to create an optimized enzyme system which was probed to further understand the importance of various process parameters such as ATP and magnesium concentration on productivity. The kinetic parameters for each enzyme were then used to create an Ordinary Differential Equation (ODE) model of the in vitro IUP system from isoprenol to taxadiene which can provide information on the dynamics of substrate consumption, product formation and the accumulation of intermediates. This model accurately predicts the productivity of the cell-free system at several scales which were experimentally verified. The cell-free IUP was found to be a linearly scalable in vitro biosynthesis system capable of producing high taxadiene titers with high productivity.

Example 9

Materials and Methods
Strains and Cultivation Conditions
The gene for choline kinase (ck) from *Saccharomyces cerevisiae* was previously codon-optimized for expression in *E. coli*, 6× his-tagged and cloned under the control of the $T7_{lacUV}$ promoter in pET28a(+) for overexpression in *E. coli* BL21 (DE3) (Chatzivasileiou et al., 2018). The following genes were also cloned into pET28a(+) and his-tagged for overexpression and purification: isopentenyl kinase (ipk) from *Arabidopsis thaliana*, isopentenyl pyrophosphate isomerase (idi) from *E. coli*, farnesyl pyrophosphate synthase (ispA) from *E. coli*, geranylgeranyl pyrophosphate synthase (ggpps) from *Taxus canadensis* (Ajikumar et al., 2010), a truncated taxadiene synthase (tds) from *Taxus brevifolia* (Ajikumar et al., 2010), a codon optimized amorphadiene synthase (ads) from *Artemisia annua* (Martin et al., 2003), a valencene synthase (vs) from *Callitropsis nootkatensis* (Yang et al., 2015), and a limonene synthase (ls) from *Mentha spicata* (Alonso-Gutierrez et al., 2013). All plasmids were constructed using a standard workflow for Gibson Assembly described in (Chatzivasileiou et al., 2018). Detailed information on plasmids and primers are given in the supplementary data (Table S1-2). Plasmids were constructed by amplifying the pET28a vector backbone and amplifying each enzyme sequence. Gibson assembly was used to assemble the vector backbone and each gene to create 9 separate plasmids encoding one enzyme each under the control of a $T7_{lacUV}$ promoter followed by a 6× his-tag and the T7 terminator region. Plasmids were confirmed by sequencing then were transformed by heat-shock into BL21 (DE3) according to manufacturer's recommendation (NEB) and plated on kanamycin plates (50 µg/L) overnight at 37° C.

Cultivation, Protein Expression, and Quantification
A single colony from each strain containing one plasmid for the expression of a single enzyme was inoculated into 5 mL of sterile LB media (BD Sciences) with kanamycin and grown overnight at 37° C. One milliliter was then inoculated into a 1 L flask containing 200 mL of sterile SOB media (AMRESCO, Inc.) with kanamycin. The culture was grown at 30° C. until an optical density (OD) of 0.4-0.6 ($\lambda$=600 nm). At this point protein production was induced by the addition of IPTG for a final concentration of 0.1 mM and continued at 30° C. for 3 h. Cells were harvested by centrifugation at 3750 rpm in an Allegra X-12R centrifuge (Beckman Coulter). The supernatant was removed and the cell pellets were frozen at −20° C. until purification. Proteins were visualized by SDS-PAGE performed according to the manufacturer's guidelines (Bio-rad). Gradient (4-20%) gels were purchased from Bio-rad, as were the Kalidescope pre-stained protein ladder, Laemelli 4× sample buffer, Tris-glycine-SDS buffer, and mini-protean electrophoresis chambers. Gels were stained using Instant-Blue (Expedeon). Protein concentrations were very roughly estimated from the gel using Image J (NIH) in order to determine an appropriate amount of resin for purification.

Protein Purification
All purification steps were performed in a single day on ice and in a cold room when possible. Cell pellets were thawed and resuspended in 30 mL of NPI-10 buffer (50 mM $NaH_2PO_4$, 300 mM NaCl, 10 mM imidazole, pH 8.0) and supplemented with 0.5 mM PMSF immediately prior to cell lysis. Cells were lysed by passaging 2-3 times through an EmulsiFlex-C5 high-pressure homogenizer (Avestin). Lysates were then centrifuged at 4° C. for 15 min to remove cellular debris. The clarified lysate was loaded onto a Ni-NTA resin (Gold Bio, capacity 50 mg/mL) which was housed in a gravity column (Thermofisher) and was pre-equilibrated with 10 column volumes (CV) of NPI-10 buffer. The column was then washed with 10 CV of NPI-20 buffer (20 mM imidazole). The enzyme was then eluted from the column by 3 CV using NPI-250 buffer (250 mM imidazole). Enzymes were exchanged into 50 mM Tris-HCl pH 7.5 using 10 kDa Microseps (Millipore) by centrifugation and repeated buffer exchanges until the imidazole was calculated to be under 1 mM. Buffer exchange of IDI was performed by using a 10 kDa Float-a-lyzer device (Spectrum Labs) for dialysis as the solution would not exchange through the Microsep. In this case, the IDI solution was added to the Float-a-lyzer and the solution was topped up to 10 mL using 50 mM Tris (pH 7.5). The device was placed fully submerged in a beaker of 50 mM Tris (pH 7.5) and the buffer was completely changed at 2, 6 and 16 h. Dialysis was allowed to proceed for 24 h. Enzyme concentration was determined using a bicinchoninic acid (BCA) assay kit from Pierce using bovine serum albumin as a standard (BSA). Proteins were then diluted in Tris buffer if necessary and aliquoted into microtubes which were flash frozen in liquid nitrogen and stored at −80° C. until use.

Individual Enzyme Assays

In order to estimate the best ratio of pathway enzymes, each enzyme was individually measured using a kinetic assay to determine the Michaelis-Menten constant and the specific velocity/catalytic constant ($K_{cat}$) of each enzyme. The kinetics for CK towards isoprenol and prenol were previously determined (Chatzivasileiou et al., 2018). The kinetics for IPK were determined by ATP consumption using a pyruvate kinase (PK) lactate dehydrogenase (LDH) coupled assay. The following components were added into a single solution then distributed into a 96 well microplate for continuous monitoring at 340 nm: 10 mM ATP, 10 mM $MgCl_2$, 50 mM ammonium bicarbonate pH 7.4, 10 mM phosphoenolpyruvate (pH 7.4), 0.6 mM NADH, and 1 U of PK, and 1.4 U LDH (PK-LDH solution from Sigma Aldrich), IPK (10 µg/mL). NADH was made fresh each time and the appropriate concentration was determined by constructing a standard curve using a SpectraMax M3 plate reader and selecting the highest value in the linear range. This curve was also used to determine the adsorption coefficient of NADH for calculation of the reaction rate. The reactions were monitored prior to the addition of the substrate to determine if any non-specific rate of ATP hydrolysis was present, however there was no non-specific ATP hydrolysis found for purified enzymes. Pyruvate and ADP (Sigma-Aldrich) were used to determine the appropriate amount of PK-LDH solution (Sigma-Aldrich) and to confirm the assay was working appropriately. No substrate/enzyme only and no enzyme/substrate only controls were also included but no activity was detected. The substrates (IP or DMAP) were diluted in a 2 log standard curve which were then added to the microplate using a multichannel pipette and NADH oxidation to NAD+ was monitored at 340 nm. Assays were done in triplicate. The rate of IPP or DMAPP formation was equivalent to the negative rate of ATP consumption. The activity of GGPPS was determined by the conversion of IPP and FPP to GFPP by monitoring pyrophosphate (PPi) formation using the EnzChek pyrophosphate assay kit (Invitrogen). The activity of TDS was also monitored using the PPi assay but only used GGPP as the substrate. The assays were performed as described for IPK using the same controls as above: TDS was added to 50 mM Tris-HCl pH 7.5, with 10 mM $MgCl_2$, 20 mM 2-amino-6-mercapto-7-pethylpurine (MESG), purine nucleoside phosphatase (PNP), and 0.03 U of inorganic pyrophosphatase (IPPase). The substrates for GGPPS, IPP and FPP, were each diluted in a microplate so that all combinations of each level were assayed in triplicate. The substrates were added to the appropriate well and the reaction was monitored for the fluorescence of MESG-phosphate. A standard curve was constructed using sodium pyrophosphate provided in the kit and was used to calculate the rate for each reaction. The rate of IDI was not determined as the isomerization of IPP to/from DMAPP cannot be measured using a kinetic assay and was not found to be a necessary component of the enzyme system. IspA kinetics were estimated from the literature (Ku et al., 2005; Weaver et al., 2015).

Multi-Enzyme Reactions in Solution

The multi-enzyme system reactions were carried out in 50 mM ammonium bicarbonate (pH 7.4) with 10 mM $MgCl_2$, 2 mM $MnCl_2$, 0.05% (w/v) Tween 20, 10 mM ATP, and 5 mM isoprenol at 30° C. unless otherwise stated. The solution in glass GC vials (Agilent) were overlaid with 1/10 volume of dodecane to entrap the volatile isoprenoids. The enzyme concentrations and raw data obtained in the large perturbation experiment are reported in Table 8. An initial estimated optimal concentration of each enzyme was calculated using the rates determined by individual enzyme assays. The final optimized enzyme concentrations were determined to be 25 µg/mL CK, 15 µg/mL IPK, 25.4 µg/mL IDI, 37.15 µg/mL IspA, 8.15 µg/mL GGPPS, and 25 µg/mL for TDS.

Time profiles were constructed by dividing up three separately prepared reaction master mixes into 100 µL aliquots in a deep-well microplate after the addition of ATP to start the reaction. The reactions were stopped at different times by the addition of 1 mL of −20° C. acetonitrile which was then transferred into a microtube and centrifuged at 16,000×g for 10 min to remove the precipitated enzymes. The supernatant was dried using a Reacti-Therm III with filtered air in glass test tubes. The dried precipitate was resuspended in 100 µL of LC-MS/MS mobile phases as described below. The samples were vortexed and then centrifuged at 16,000×g a second time. Samples were analyzed using LC-MS/MS and/or GC-MS.

Metabolite Quantification Using LC-MS/MS

Liquid chromatography was performed using an Agilent 1100 Series HPLC (Agilent Technologies) and the MS/MS was conducted using an API 4000 triple quadrupole mass spectrometer (SCIEX) with ESI running in negative MRM mode as previously described (Chatzivasileiou et al., 2018). The LC-MS/MS was equipped with an Xbridge C18 column (150 mm, 3.5 µm, 2.1 mm) from Waters and was operated using a mobile phase (A) of 0.1% v/v TBA, 0.12% v/v acetic acid, and titrated with ~0.5% v/v 5N $NH_4OH$ until a pH of 8.5 was reached. The elutant, acetonitrile (B) was introduced using the following gradient: 0-5 min 0% B, 5-20 min 0-65% B, 20-25 min 65% B, 25-30 min 100% B, 30-35 min 100% B, 35-36 min 100-0% B, 0% B until 45 min. Standard curves were generated for a mixture of IP, DMAPP, GPP, FPP, and GGPP diluted in mobile phase A. Standards were purchased from Sigma-Aldrich and/or Cayman Chemicals, except IP which was synthesized as previously described (Chatzivasileiou et al., 2018). The isomers IP and DMAP were determined together as total IP/DMAP as these isomers could not be resolved using this method. This also applied to the isomers IPP/DMAPP which eluted together and are indistinguishable by mass. Metabolite specific ionization and fragmentation voltages determined from a 1 µM standard solution of each metabolite was obtained using the Analyst software (v 1.6) and monitored during chromatography. Peaks were integrated using the Analyst software.

Quantification of Volatile Isoprenoids

Taxadiene, valencene, amorphadiene, and limonene were quantified by diluting the dodecane overlays into an appropriate range depending on analyte concentration with ethyl acetate containing 90 mg/L caryophyllene as an internal standard as previously described (Chatzivasileiou et al., 2018). The samples were separated using an HP-5 MS UI capillary column (30 m, 250 µm, 0.25 µm) (Agilent Technologies) using a 7890B Series GC and a 5977B MS. Chromatography was performed under the following conditions: 1 µL splitless injection, inlet temperature 280° C., constant inlet pressure 115.8 kPa, valve temperature 300° C., and MS transfer line 300° C. A oven program of 100° C., hold 1 min, 15° C./min until 200° C., hold 2 min, 30° C./min until 250° C., hold 1 min, and 30° C./min until 290° C., hold 2 min was used for determination of taxadiene, valencene, and amorphadiene. Limonene was separated using an oven program of 80° C., hold 3 min, 10° C./min until 140° C., hold 2 min, 45° C./min until 290° C., hold 1 min. The MS was operated at an ion source temperature of 280° C., and a quadrupole temperature of 180° C. Ions were scanned between a mass of 40 to 400 at 1.562 u/s. Taxadiene was quantified using a standard curve based on the m/z 122 ion which has the greatest abundance in unlabeled taxadiene. The remaining compounds were estimated by normalizing their area to that of the internal standard. The taxadiene standard was purified as previously described (Chatzivasileiou et al., 2018).

Example 10—Individual Enzyme Kinetics and ODE Model

Figure 30A:
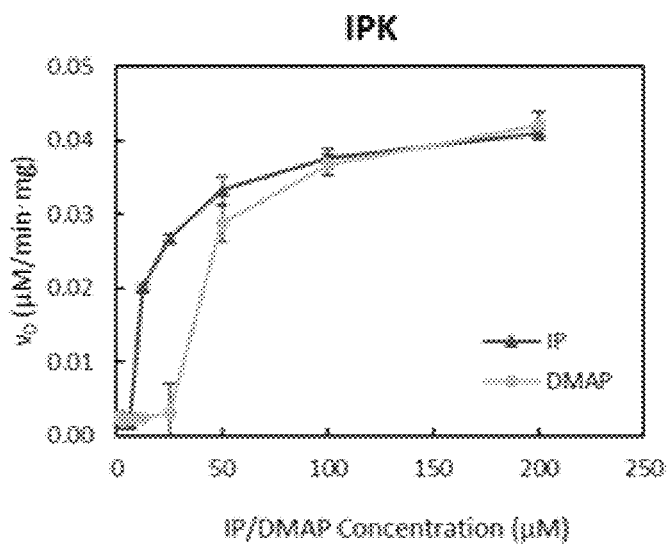
FIGS. 30A-30D. Michaelis-Menten profiles for IUP and terpenoid backbone biosynthesis enzymes. Enzyme assays were conducted at 30° C., at pH 7.4 in ammonium bicarbonate buffer with 10 mM $MgCl_2$, 2 mM $MnCl_2$, and 2 mM DTT.
Figure 30B:
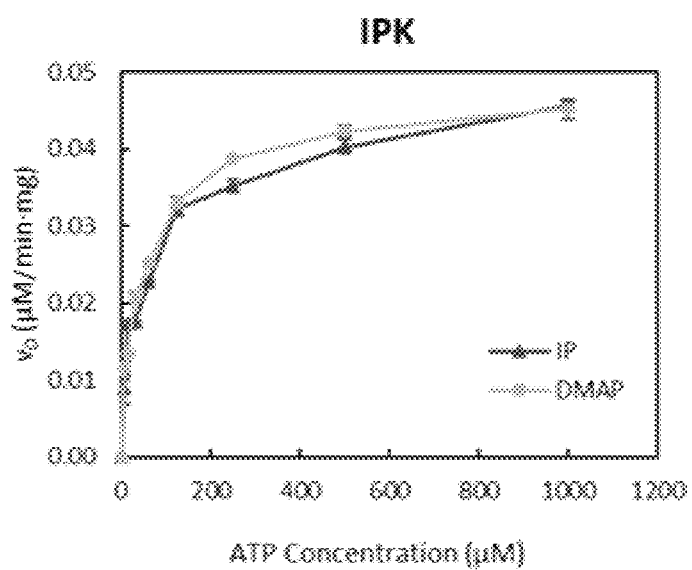

To guide the rational design of the in vitro enzyme system and aid in the creation of the kinetic model of the IUP, the Michaelis-Menten kinetics for each enzyme were determined (Table 6). As previously reported (Chatzivasileiou et al., 2018), choline kinase shows a distinct preference for isoprenol as a substrate rather than prenol with a three times greater specificity constant, $k_{cat}/K_m$ of 3.23 $mM^{-1}s^{-1}$ for isoprenol versus 1.01 $mM^{-1}s^{-1}$ for prenol. The Michaelis-Menten parameters for IPK were estimated for both IP and DMAP as substrates (FIG. 30A) assuming single substrate kinetics when ATP was well above 1 mM, and for ATP in combination with IP or DMAP at 100 μM (FIG. 30B). IPK exhibited only marginally greater affinity for IP with a $k_{cat}/K_m$ of 1.79 $uM^{-1}s^{-1}$ versus 1.30 $uM^{-1}s^{-1}$ for DMAP.

Figure 30C:
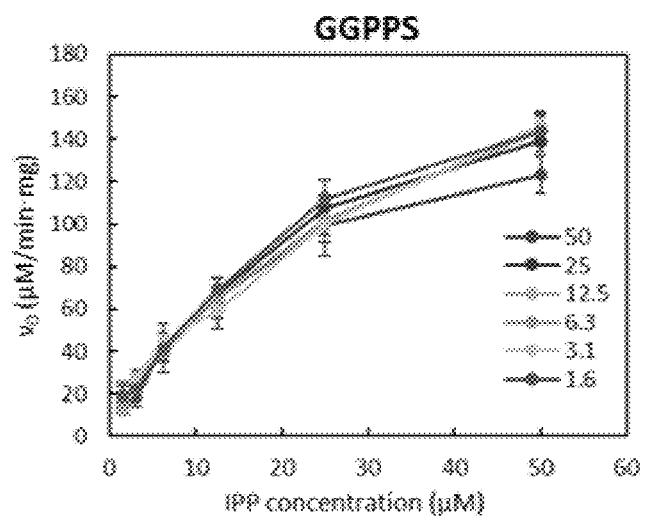
Figure 30D:
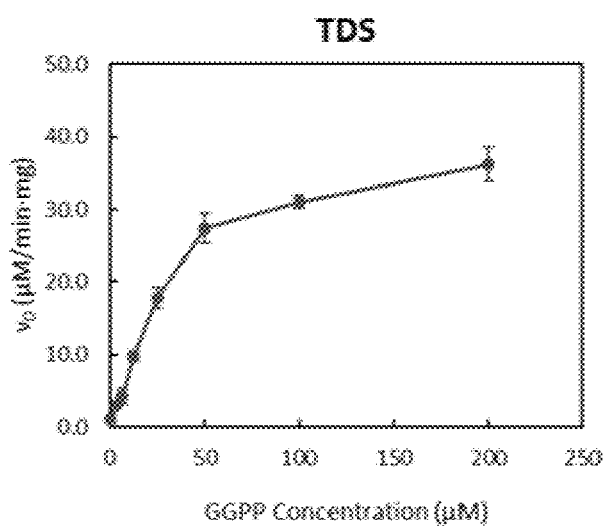

GGPPS exhibited Michaelis-Menten-like behavior for its substrate IPP when FPP was held at 100 μM (FIG. 30C), however, interestingly no substrate effect was detected for FPP concentrations in the range of 1-50 μM in the presence of 100 μM IPP. It has been reported elsewhere that the $K_M$ for IPP and FPP respectively were 6 and 7 μM for GGPPS from *Taxus canadensis* (Hefner et al., 1998), which is similar to the achieved results of 13.5 μM. GGPPS and TDS were found to have similar turnovers with a $k_{cat}$ of 23.1 $s^{-1}$ and 26.7 $s^{-1}$ respectively (FIG. 30D).

Example 11—Cell Free Isoprenoid Production Using the Multi-Enzyme System

Figure 31A:
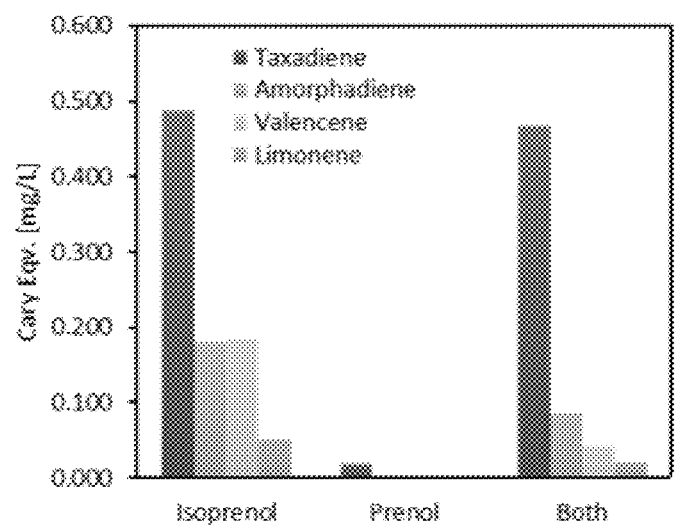
FIGS. 31A-31F. Proof of concept for the in vitro biosynthesis of isoprenoids using the IUP.
Figure 31B:
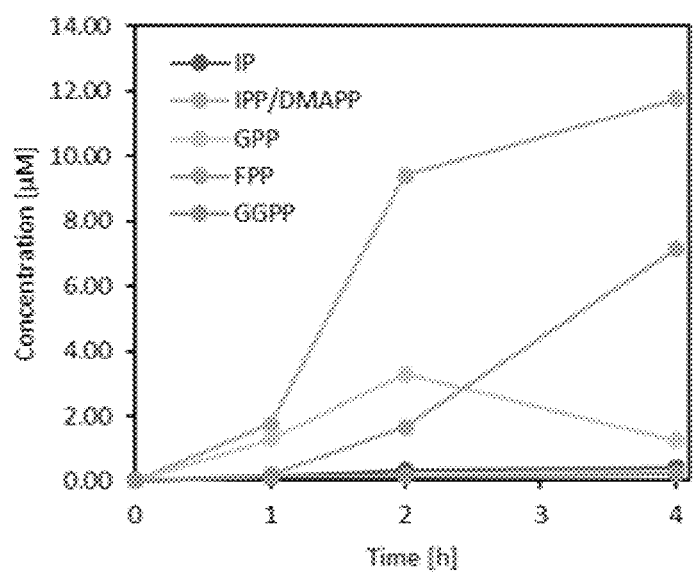
Figure 31C:
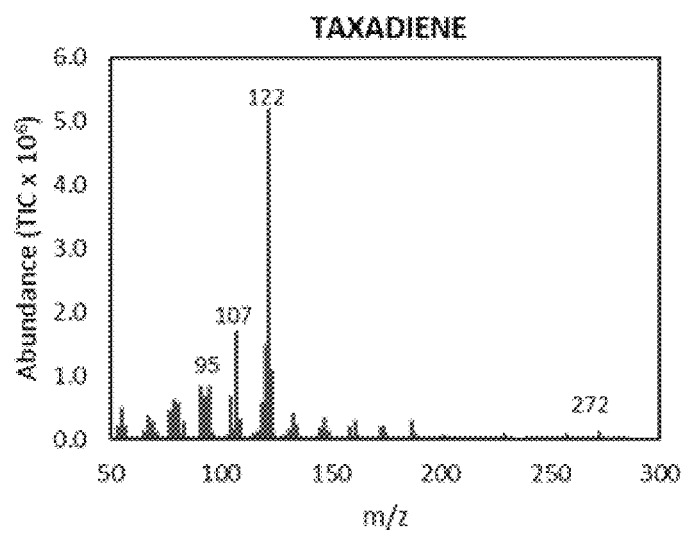
Figure 31D:
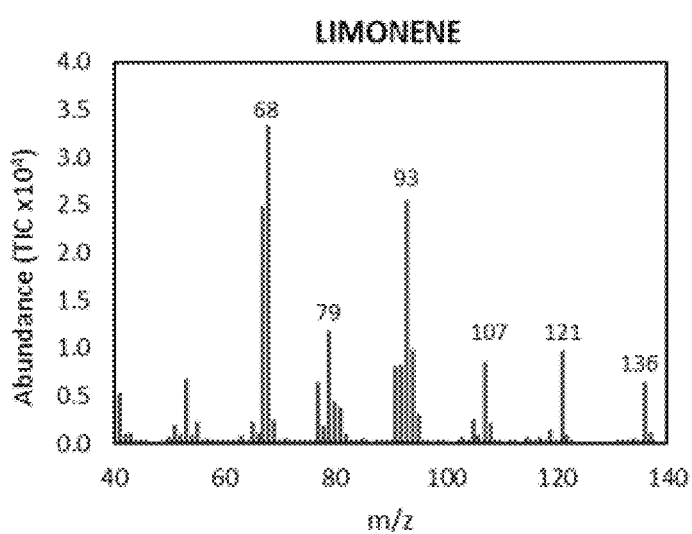
Figure 31E:
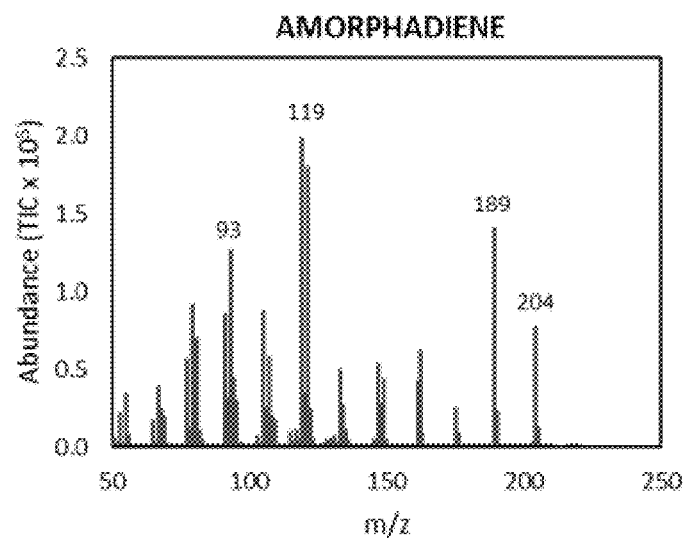
Figure 31F:
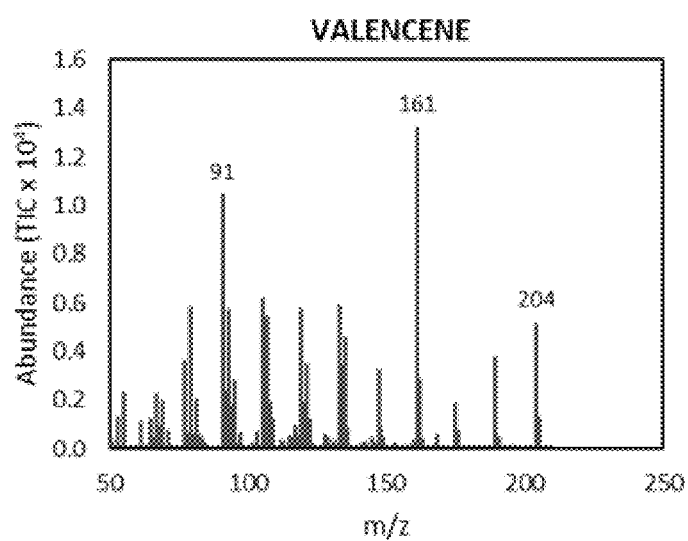

Since the substrates of the IUP, isoprenol and prenol, are alcohols which are often used in the laboratory for protein precipitation and purification, the functionality of the cell-free enzyme system in an aqueous/isopentenol system was confirmed. Furthermore, technical difficulties in assaying the kinetics of IspA and IDI prevented confirmation of the activity of these enzymes independently. Therefore, to provide an in vitro proof of concept, a preliminary experiment was conducted overnight by resuspending all enzymes at 50 μg/mL each, adding 10 mM ATP and 5 mM isoprenol, prenol, or both at a 3:1 molar ratio, and using different terpene synthases. By supplying both isoprenol and prenol, circumvention of the need for a functional IDI was sought, in case it was inactive. A dodecane layer was used to accumulate the isoprenoids, from which they were quantified using GC-MS (FIG. 31A). Additionally, the formation of the intermediates IP, IPP/DMAPP, GPP, FPP, and GGPP in the taxadiene based run was monitored to better understand the time scale of their production (FIG. 31B). All of the expected products were identified by their electron ionization (EI) mass spectra using purchased standards (valencene and limonene), a standard purified in-house (taxadiene), or from the literature (amorphadiene (Malhotra et al., 2016) (FIG. 31C-31F). At the concentrations used, protein precipitation was visible after 24 h, but was prevented by the addition of 0.025% Tween-20 (w/v) (data not shown) in subsequent experiments.

All the synthases used led to some product formation, however, limonene production was poor (FIG. 31A). This is likely due to the use of IspA, which is a farnesyl diphosphate synthase and converts one DMAPP and two IPPs into GPP then FPP in sequential reactions (Ku et al., 2005). Since the second reaction is known to proceed faster than the first (Table 6), some of the pathway flux would branch towards FPP rather than limonene. This could be corrected by using a more specific GPP synthase that only catalyzes the production of GPP rather than IspA which catalyzes both the GPP and FPP synthesis steps (Alonso-Gutierrez et al., 2013). Overall, isoprenol proved to be a better substrate than prenol or the 3:1 isoprenol:prenol molar mix (FIG. 31A) resulting in a focus on using isoprenol exclusively, in combination with IDI, for the following optimization work. By observing the formation of pathway intermediates (FIG. 31B), detectable levels of prenyl diphosphates were seen within 1-2 h. In this experiment, only isoprenol was used as a substrate, therefore it is assumed that all IP/DMAP detected was only in the form of IP since the isomers are indistinguishable by the chromatography method used. The lack of IP accumulation is likely due to the higher rate of IPK than CK, which was expected from results obtained when the enzymes were all incubated at the same concentration.

Example 12—Optimization of Enzyme Levels for Flux Maximization

Figures 25A, 25B:
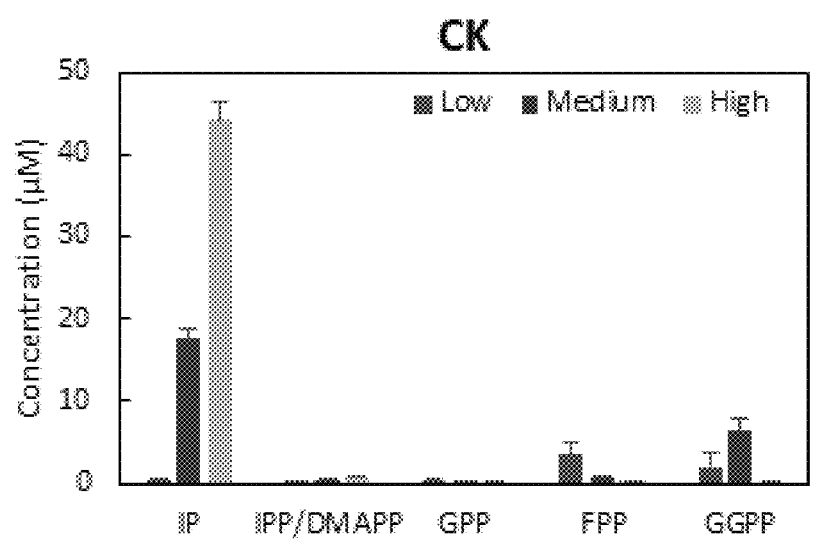
FIGS. 25A-25F. Monothetic modulation of each enzyme concentration for CK, IPK, IDI, IspA, and GGPPS. Each enzyme was modulated separately to high, low and medium levels while all other enzymes were kept at the midpoint. Assays were conducted at 30° C., at pH 7.4 for 24 h with 10 mM ATP and 5 mM isoprenol. All experiments were performed in triplicate (error bars 1σ).
Figure 25C:
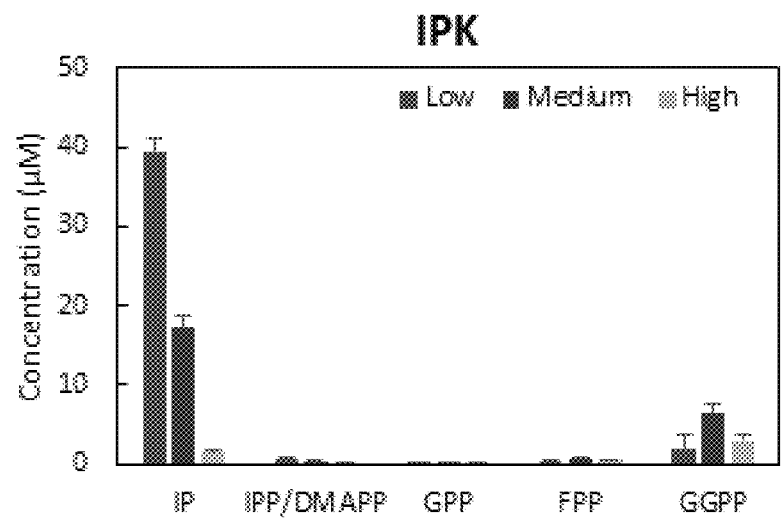
Figure 25D:
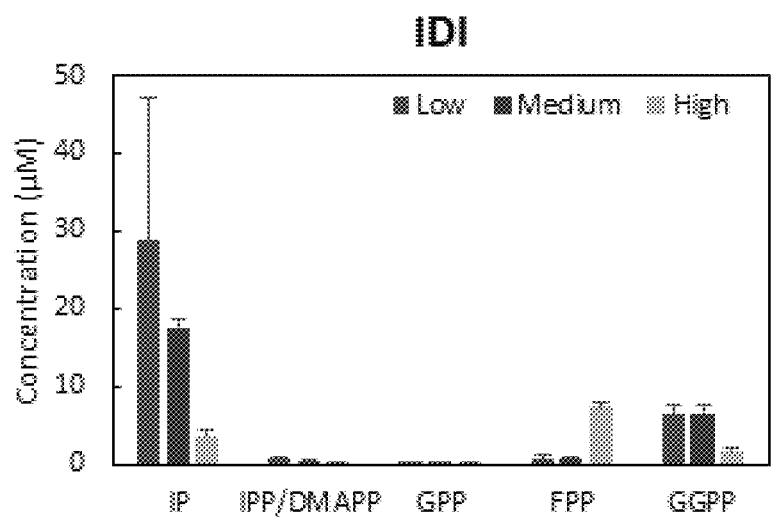
Figure 25E:
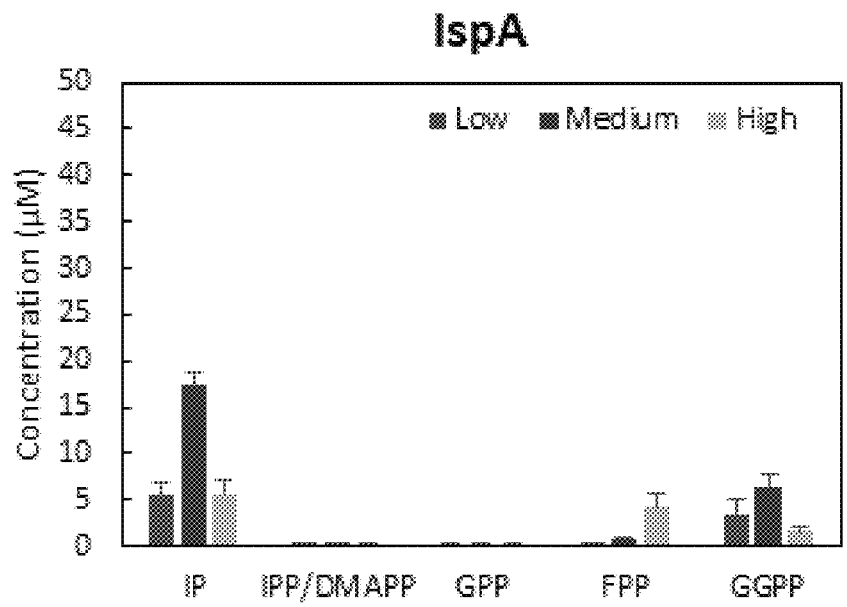
Figure 25F:
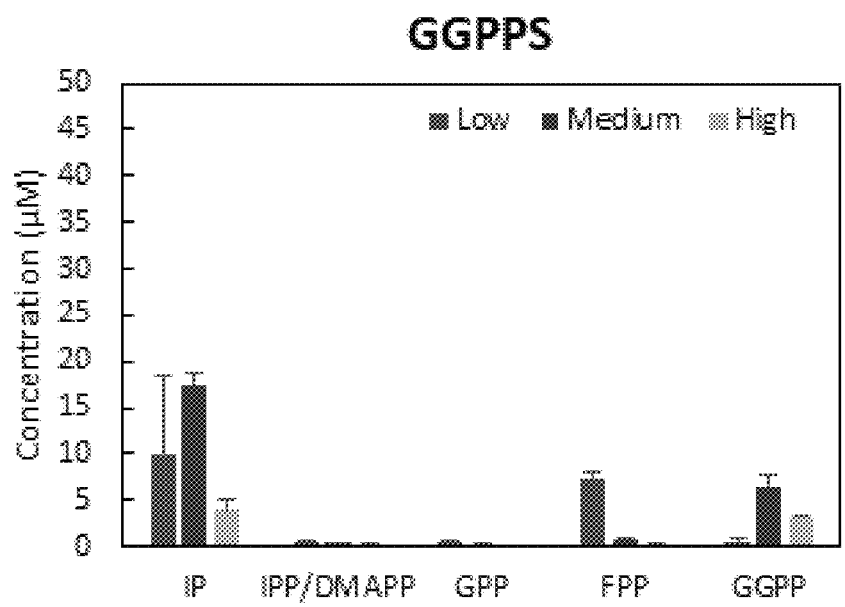

With a working system in hand, the concentrations of pathway intermediates from FIG. 31B and the kinetic parameters in Table 6 were used to estimate a reasonable starting point for optimization of the multi-enzyme system. Since taxadiene was more readily detected than the other isoprenoids in FIG. 31A, this system of enzymes was the focus for further study. In the first step, the flux towards GGPP was optimized using a perturbation experiment where each enzyme concentration was individually increased or decreased to a level 5 fold higher or lower than the estimated midpoint. Other enzymes were kept at the midpoint concentration indicated in FIG. 25A. The effects of changing each enzyme on the intermediate metabolites after 24 h are shown in FIG. 25B-25F. When the concentration of CK was increased, so did the concentration of its product (FIG. 25B). Similarly, decreasing the IPK concentration resulted in higher accumulation of IP (FIG. 25C). IDI also played a role in the accumulation of IP, which decreased as more IDI was added (FIG. 25D), which is expected as IspA requires DMAPP to proceed and consume IPP/DMAPP In every case, over addition of each enzyme reduced the overall flux towards GGPP, suggesting that substrate inhibition may play a role in balancing the overall flux (FIG. 25B-25F). In order to quantify these interactions using metabolic control analysis (MCA) and gather all the data required to calculate enzyme elasticities to optimize the system, this work was repeated with a greater number of perturbations.

Figure 32:
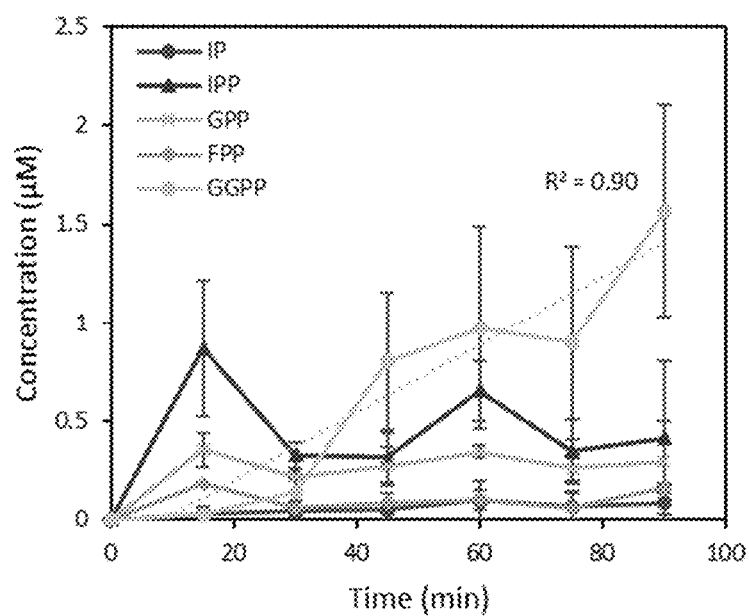
FIG. 32. Formation of a QSS in the CK, IPK, IDI, IspA, and GGPPS system. Samples were taken every 15 min for 1.5h. Enzymes concentrations were as follows: CK (25 µg/mL), IPK (15 µg/mL), IDI (25.4 µg/mL), IspA (37.1 µg/mL) and GGPPS (8.15 µg/mL). Assays were performed in triplicate at 30° C. at pH 7.4. All experiments were performed in triplicate (error bars 1σ).
Figure 33A:
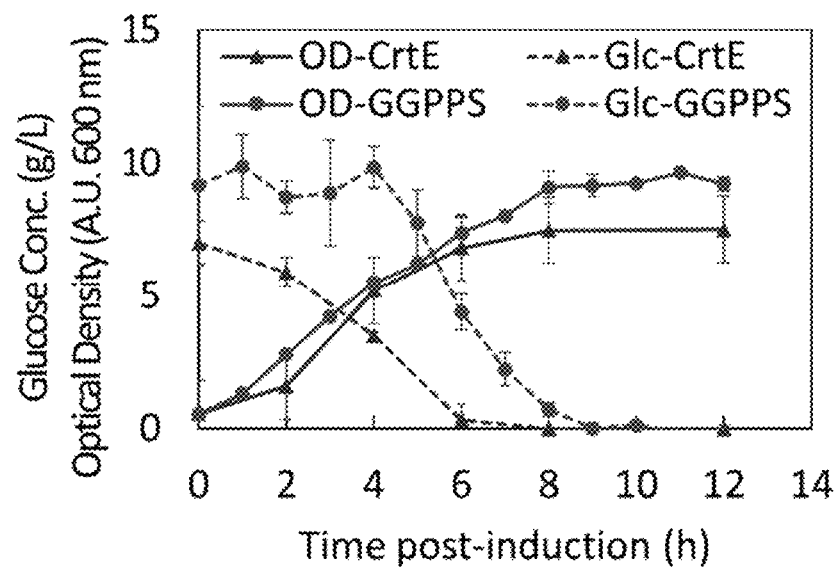
FIGS. 33A-33D. Batch bioreactor cultivation of lycopene production utilizing the IUP. The IUP was expressed under the control of the pro4 promoter along with a p5T7-LYC vector containing either crtE or ggpps.
Figure 33B:
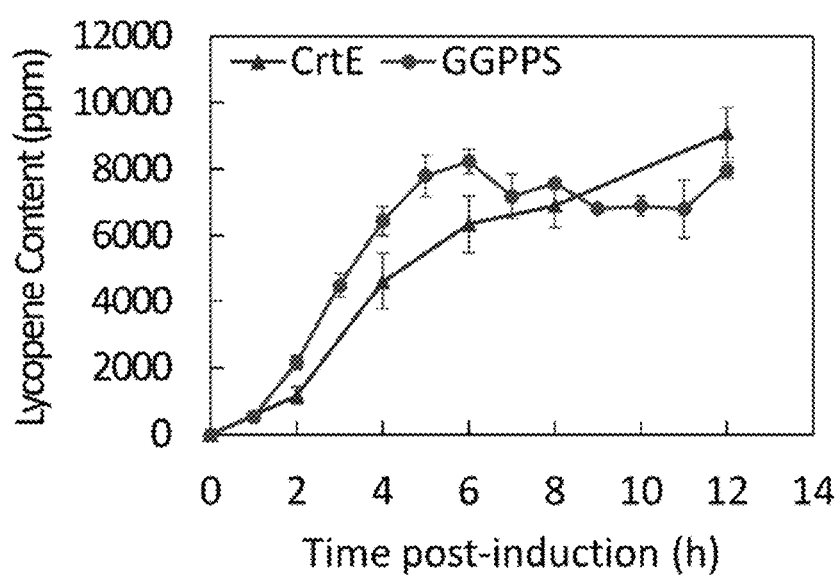
Figure 33C:
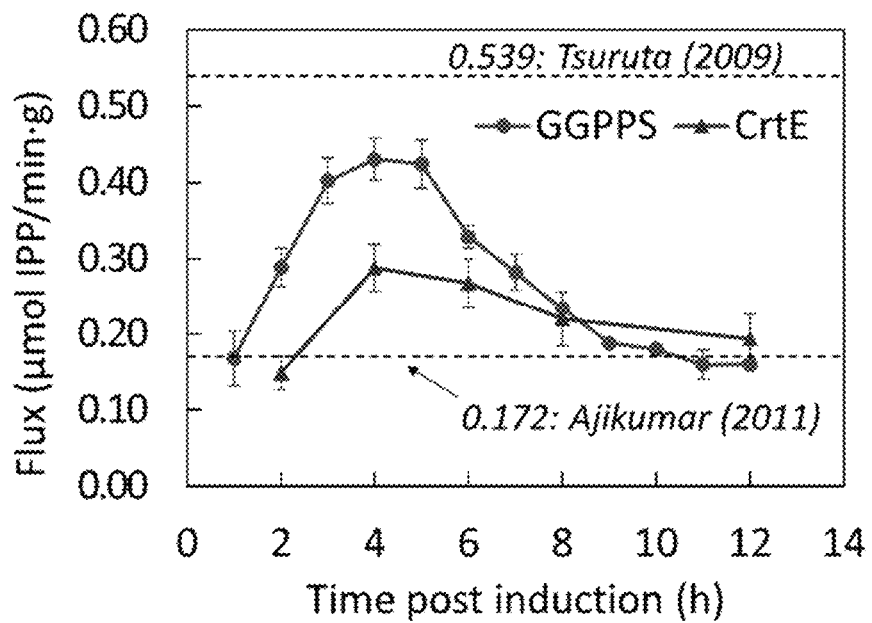
Figure 33D:
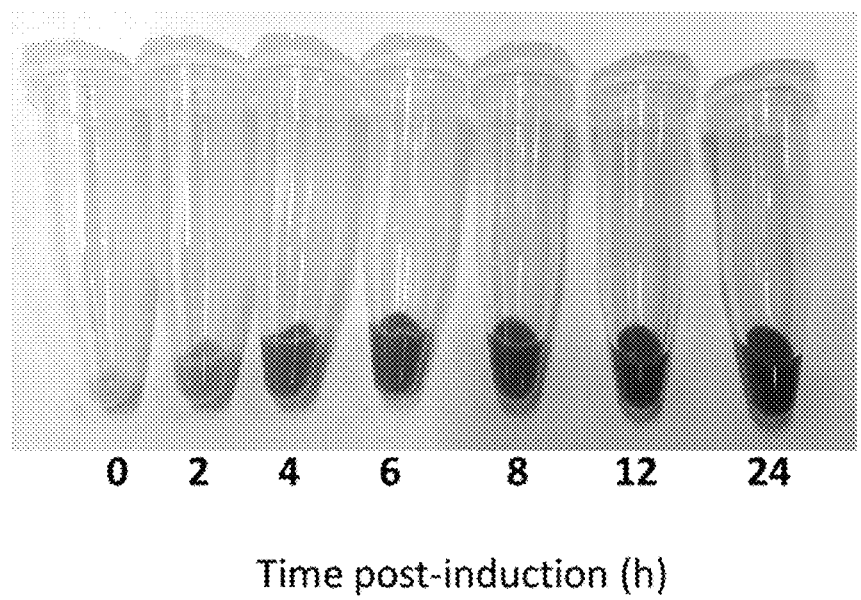
Figure 34:
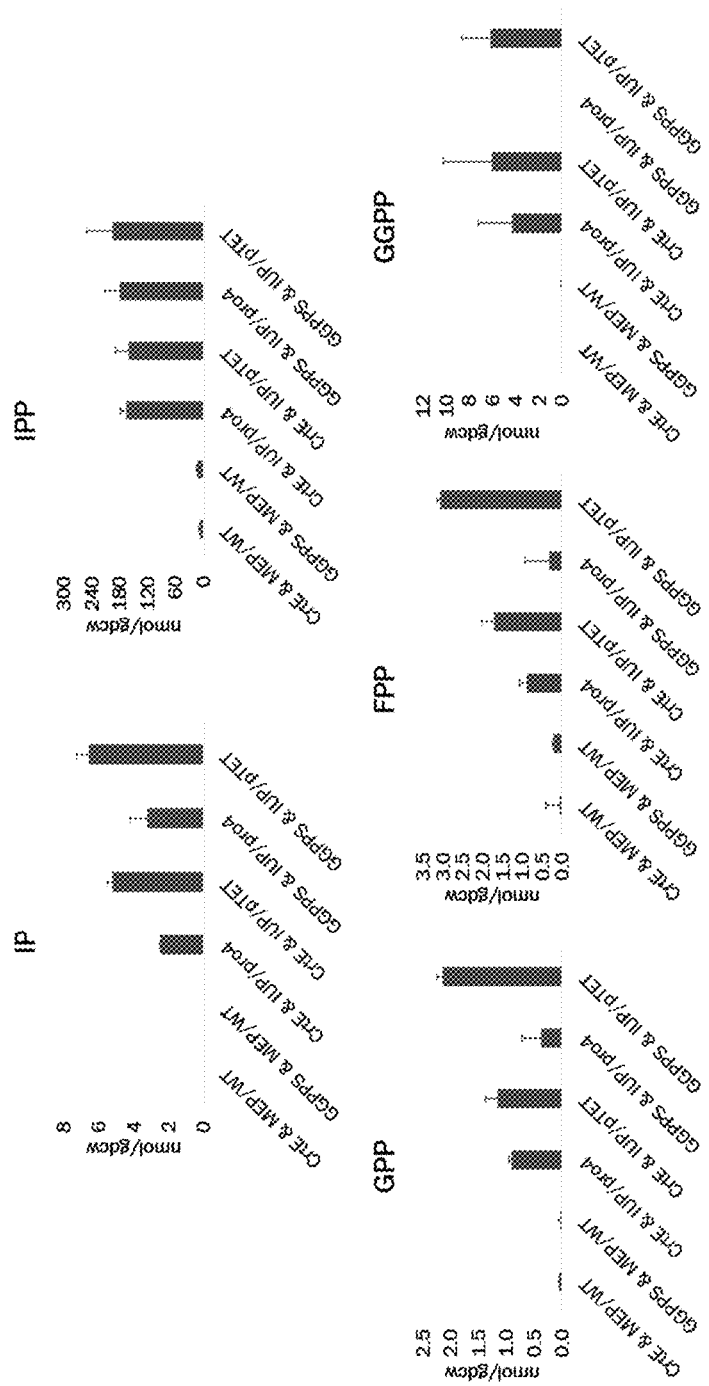
FIG. 34. Metabolite profiles in cultivation for lycopene production utilizing the IUP. Lycopene production was achieved through the use of a p5T7-LYC vector containing either crtE or ggpps, whereas the IUP was not utilized (WT) or was expressed under the control of the pro4 or pTET promoter.
Figure 35:
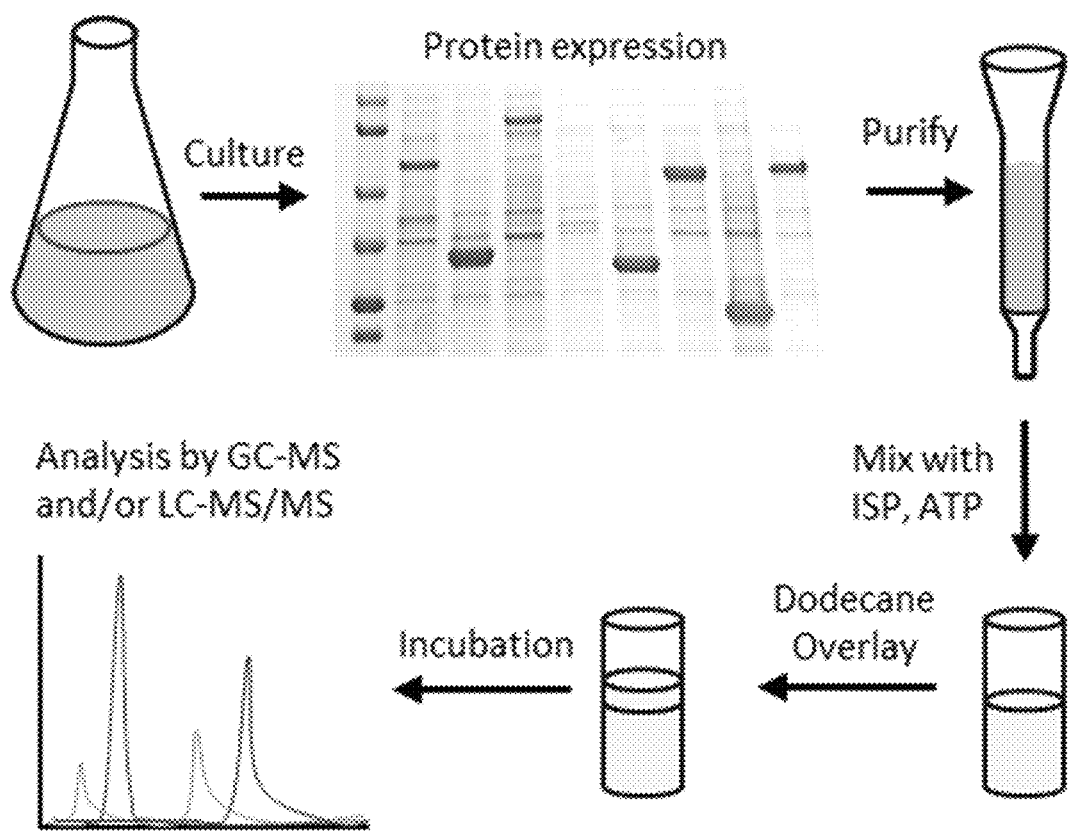
FIG. 35. Graphical abstract.

One of the underlying assumptions of MCA is the formation of a pseudo-steady state (PSS) (Wu et al., 2004). Typically, this requires the use of initial rates of reaction, however the end point used in FIG. 25 (24 h) was likely too late to adequately measure this, as intermediate metabolites could accumulate to much higher levels by this point. In order to identify a PSS, an in vitro reaction was run, using the optimal enzyme concentrations, as predicted from the initial perturbation study, using a "main interactions only" linear regression model. A time profile of metabolic intermediate concentrations was constructed (FIG. 32). Since the GGPPS concentration was linearly increasing and the remaining intermediate levels remained steady, a PSS was found to exist within the first 45-90 min (FIG. 32). The reaction was stopped at 60 min in the repeat experiment. The full dataset is available in Table 8. Lin-log kinetics were used to estimate the elasticities using the framework developed by Wu et al. (2004):

$$\frac{v}{J^0} = \left[\frac{e}{e^0}\right] \cdot \left(i + E^{x0} \cdot \ln\left(\frac{x}{x^0}\right)\right)$$

where i represents the unit vector, v represents the relative flux compared to the reference state flux $J^0$, $E^{x0}$ represents the elasticity matrix for the metabolic intermediate concentrations ($x^0$) in relation to the enzyme concentration compared to the reference state as designed by $e/e^0$ and the relative intermediate metabolic concentrations compared to the reference state ($x/x^0$).

This framework was developed to allow the application of MCA to data sets with large changes/fluctuations like those found in an in vitro metabolic pathway (Wu et al., 2004). By applying this model to the data generated in the large perturbation study and alternating the designated reference state, 25 sets of elasticities were generated, using the maximum connectivity assumption to calculate the elasticity of every enzyme for each measured metabolite. The adjusted coefficient of determination ($R^2$) was used to determine the best reference state. The results are shown in FIG. 26.

Figure 26A:
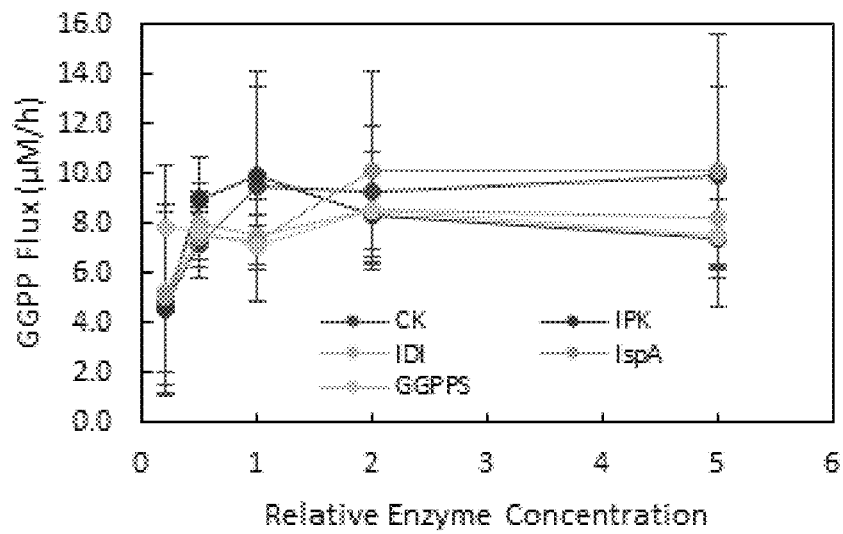
FIGS. 26A-26F.
Figure 26B:
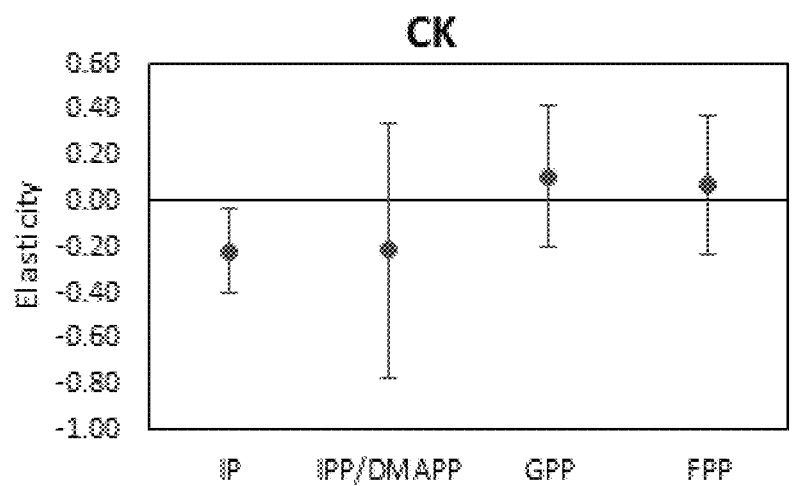
Figure 26C:
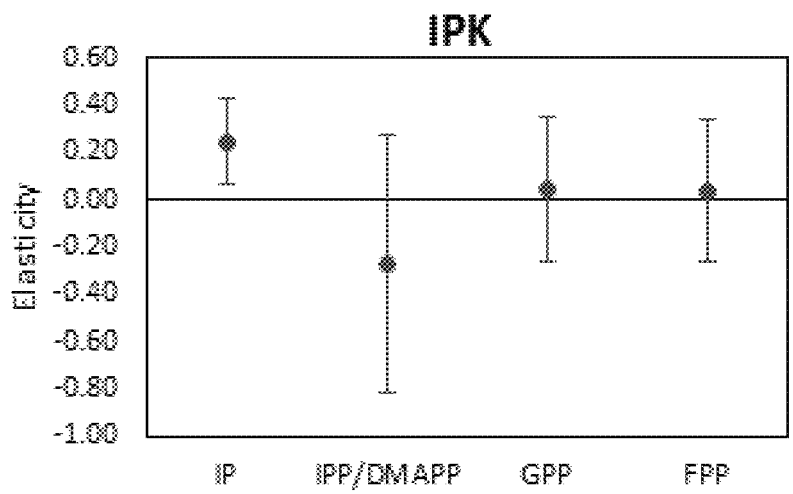
Figure 26D:
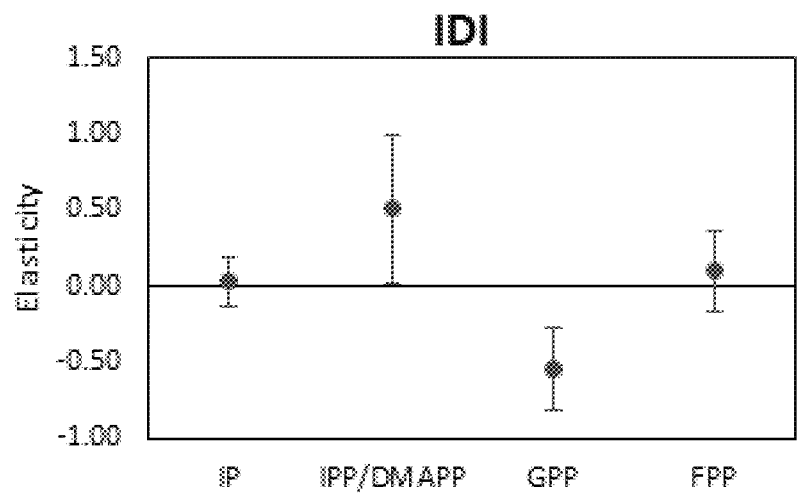
Figure 26E:
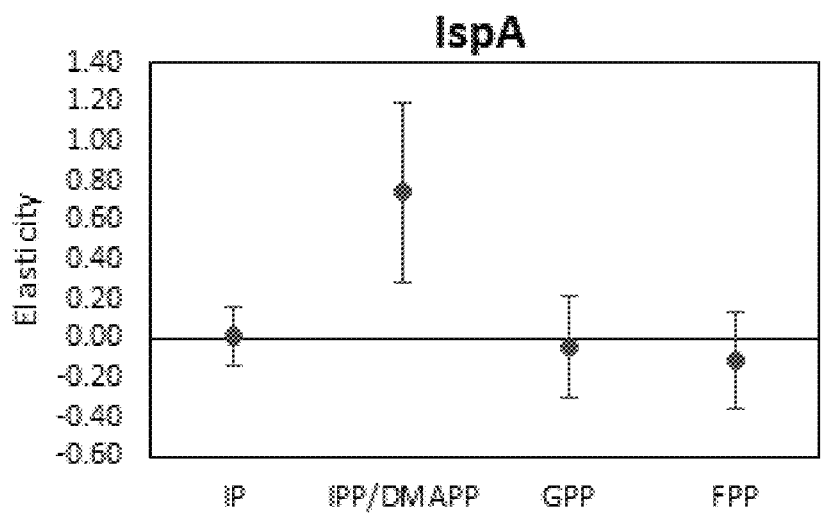
Figure 26F:
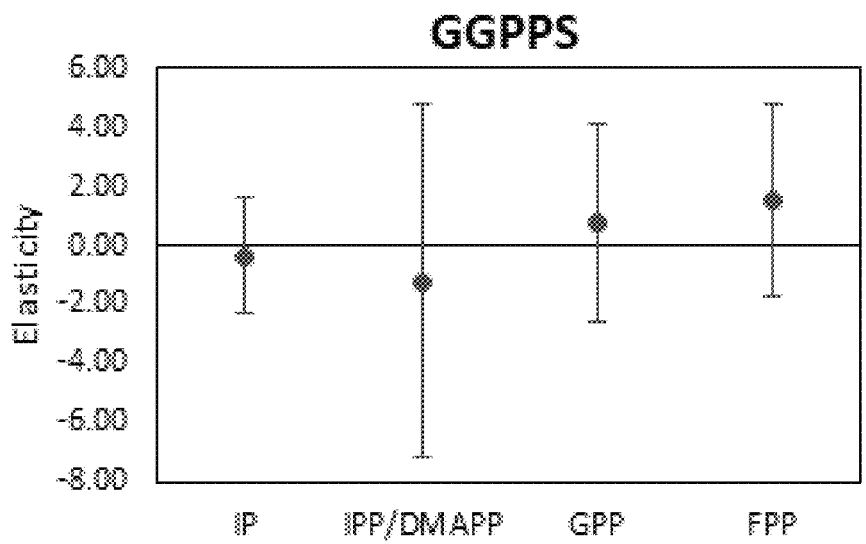

The overall steady-state flux towards GGPP of the multi-enzyme system is shown in FIG. 26A as a function of relative enzyme concentration for each enzyme. The most significant elasticities (p<0.05) included $\varepsilon_{CK}^{IP}$, $\varepsilon_{IPK}^{IP}$, $\varepsilon_{IDI}^{IPP}$, $\varepsilon_{IDI}^{GPP}$, and $\varepsilon_{IspA}^{IPP}$. IP was slightly inhibitory to CK activity (FIG. 26B) but stimulatory for IPK activity (FIG. 26C), which correlates well to its role as a product in one reaction and a reactant in the other. IPP/DMAPP was measured as a total sum of the two metabolites and had a positive effect on both IDI and IspA (FIG. 26D-26E). This slight sensitivity from IDI can be explained by the greater affinity of IDI for IPP conversion to DMAPP (Hahn et al., 1999). The sensitivity of IspA to IPP/DMAPP was found to be the most significant (p<6.9×10$^{-5}$) of all of the elasticities measured and had a positive effect on IspA. This is likely due to the higher stoichiometric needs of IspA for IPP/DMAPP which needs 2 IPP and 1 DMAPP molecule to make 1 FPP. GGPPS showed no effect on the overall pathway flux (FIG. 26A) and accordingly none of the elasticities calculated were significant (FIG. 26F). The concentration of GGPPS could therefore be decreased a least 5 fold without any effect on the pathway flux and thus this new concentration was used following experiments.

Example 13—Optimization of Process Parameters for Taxadiene Production

Figure 27A:
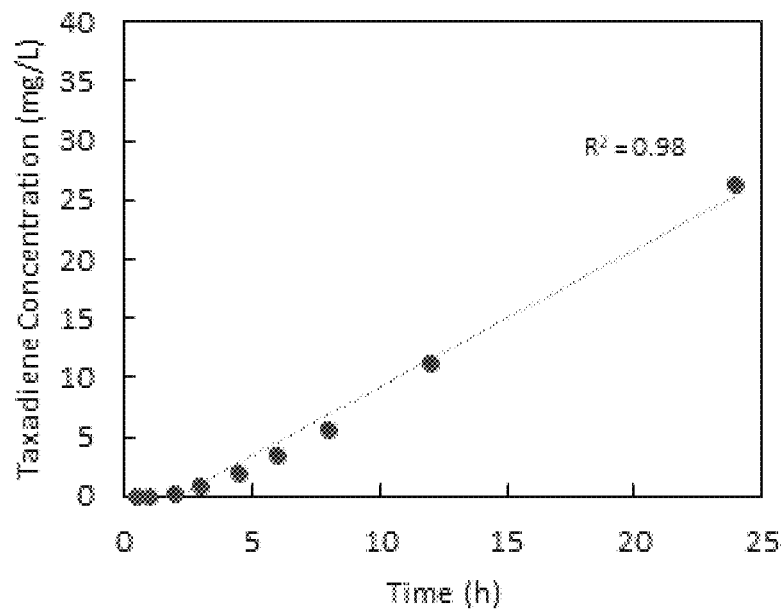
FIGS. 27A-27B. Time profile and TDS optimization for the multi-enzyme system. Assays were conducted at 30° C. at pH 7.4. Error bars are shown for experiments performed in triplicate (1σ) FIG. 27A. The linear relationship between taxadiene concentration and time.
Figure 27B:
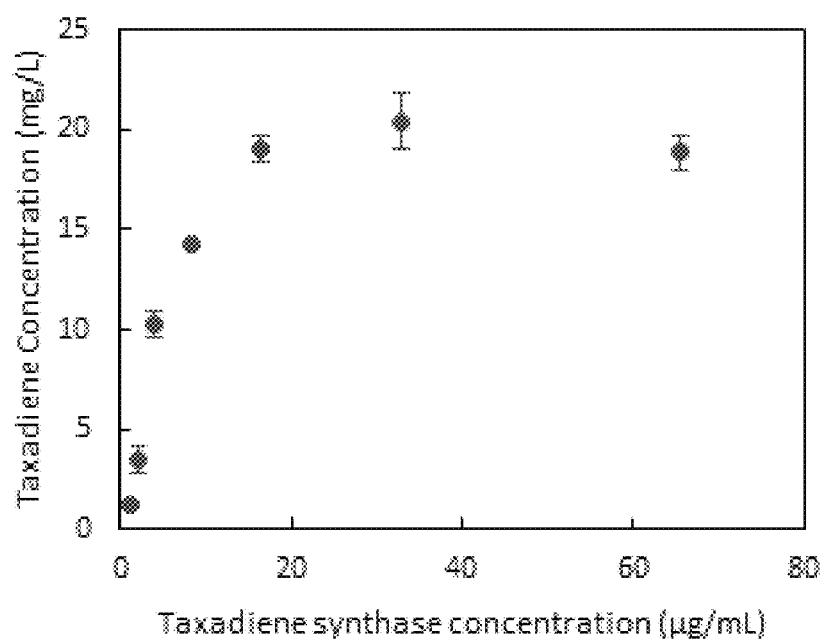

Having identified the optimal enzyme concentrations, operational limits of this process were probed by conducting the remaining experiments with the above optimized enzyme system, but now also including TDS. First, based on the determined $k_{cat}$ for TDS (Table 6), an excess of this enzyme (200 µg/mL) was added to the optimized multi-enzyme system and the reaction was monitored over time for linearity (FIG. 27). Since the reaction rate did not change in over 24 h (FIG. 27A), this suggested that not all of the available substrate was used in this period and it was decided that incubating the enzymes overnight (20 h) would allow us to optimize the TDS (FIG. 27B). The expectation was that taxadiene production should plateau when the concentration of TDS exceeded the amount needed to consume all of the GGPP being synthesized, and as expected, at concentrations of TDS greater than 20 µg/mL, taxadiene concentration was constant. Therefore, a TDS concentration of 25 µg/mL was selected for future experiments.

Next, the effect of several additional potential inhibitors and cofactors (FIG. 28 were investigated. First, increasing ATP and ADP concentrations both had a negative effect on the taxadiene production (FIG. 28A). With regards to ATP, the reaction did not proceed if ATP was not added, taxadiene production increased until 10 mM ATP. However, production was completely inhibited at 20 mM ATP. Chen et al. (2017) found that ATP levels above 5 mM completely inhibited IspA, however amorphadiene yields increased in their multi-enzyme system when ATP was between 5-15 mM. The addition of more IspA can be used to compensate for the inhibition of this enzyme by increasing the number of active sights per ATP molecule. Some inhibition by ADP was detected when it was added to the multi-enzyme system. A possible explanation for such inhibitions could be that the enzymes would salt out when a combined amount of >20 mM ATP+ADP (sodium salts) are added to the mixture. Attempts to increase ATP to 50 mM resulted in the formation of a visible protein precipitate and remained a major limiting factor in this system. Since 8 moles of ATP are necessary for the synthesis of 1 mole of taxadiene, salting out of proteins by high concentrations of ATP sodium salt limits that maximum titer of taxadiene that can be achieved using this system making ATP the limiting reagent. Therefore, the concentration of isoprenol was controlled at half of the ATP concentration (only 4 moles per mole of taxadiene) and concentration effects were not investigated since the reaction would not proceed at ATP concentrations above 10 mM. Furthermore, the consumption of isoprenol in this process could not be determined due to the high variability the utilized GC-FID assay which could not accurately measure such small changes in isoprenol concentration.

Figure 28A:
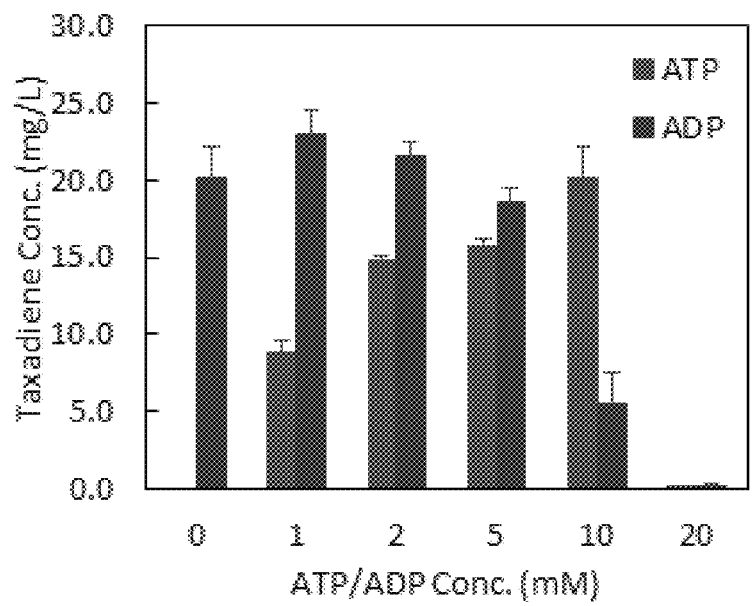
FIGS. 28A-28D. Titration of cofactors, potential inhibitors, and additives.
Figure 28B:
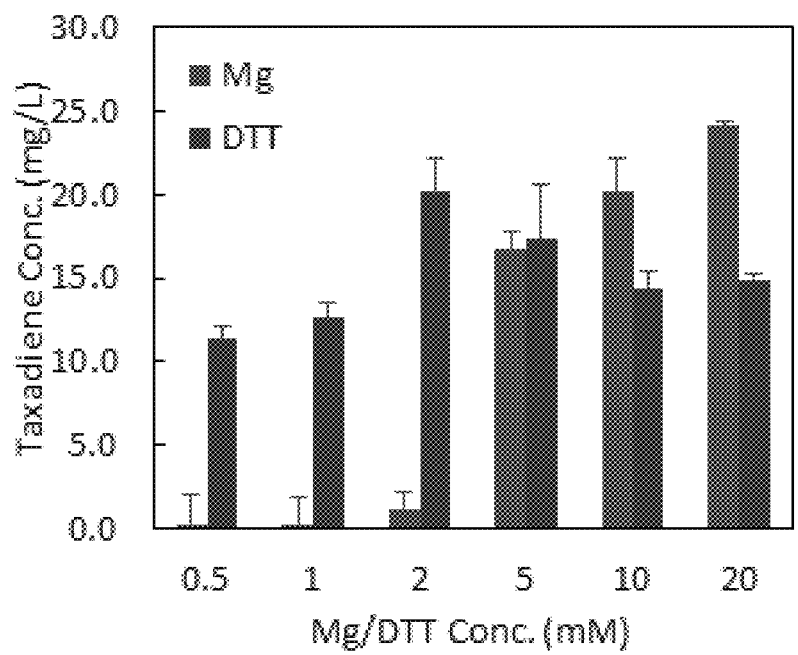
Figure 28C:
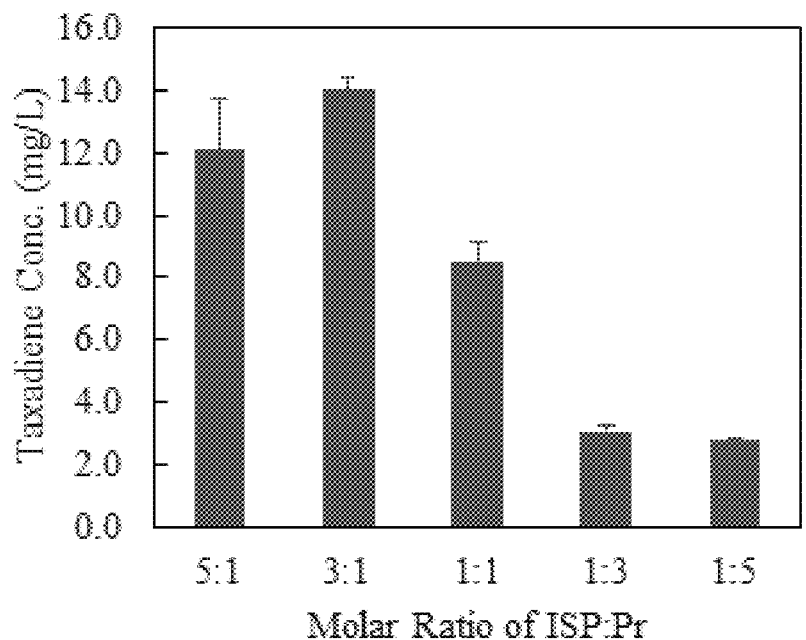

The dependence of the reaction on dithiothreitol (DTT) and magnesium was characterized by titrating each reagent (FIG. 28B). When magnesium was not added, very little taxadiene was detected. Presumably some residual enzyme bound magnesium from the cell was still present after purification. DTT also had a positive effect on the system's activity with an optimum around 2 mM. Since enzymes are a significant driver of production costs in biotransformation processes (Lima-ramos et al., 2011), the possibility of eliminating the need for the enzyme IDI in the multi-enzyme system through supplying the proper ratio of IPP and DMAPP precursors isoprenol and prenol was explored. Using the optimized enzyme ratio, multi-enzyme assays were conducted without the addition of IDI with various mixtures of isoprenol to prenol (FIG. 28C). Taxadiene production was maximized for ratios where isoprenol was in excess of prenol and decreased with increasing proportion of prenol added. This behavior is likely a due to both increased stoichiometric need for IPP over DMAPP for taxadiene production (3 IPP and 1 DMAPP) and also the preferences of CK and IPK for isoprenol/prenol or IP/DMAP.

Figure 28D:
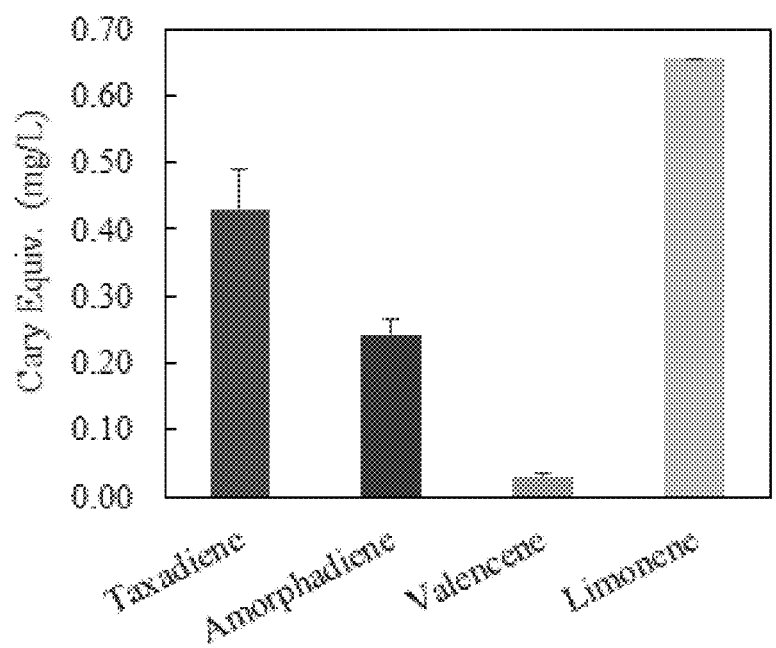

Using the minimized enzyme system without IDI, taxadiene (5 enzyme system), amorphadiene, valencene, and limonene (4 enzyme systems) could all be synthesized using a 3:1 substrate ratio (FIG. 28D).

Example 14—Optimized System is Scalable and Leads to High Taxadiene Titers

Figure 29A:
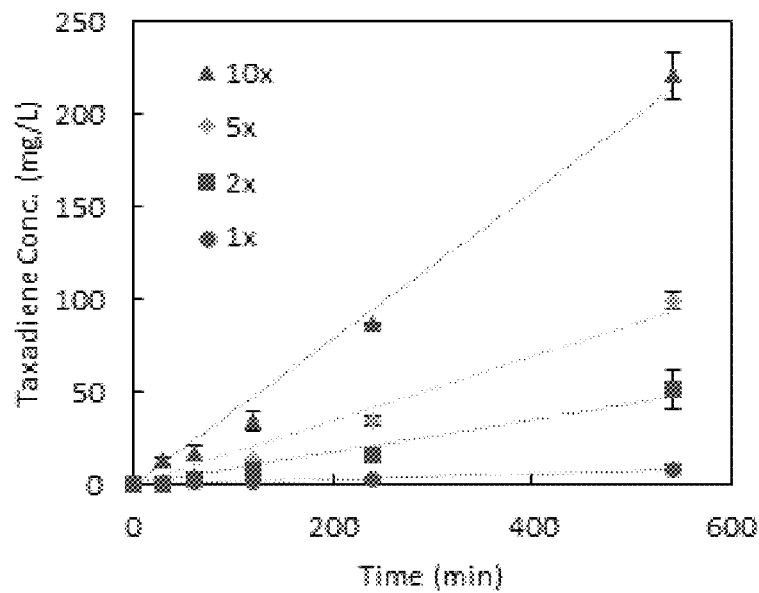
FIGS. 29A-29B. Scale-up of the optimized enzyme ratio.
Figure 29B:
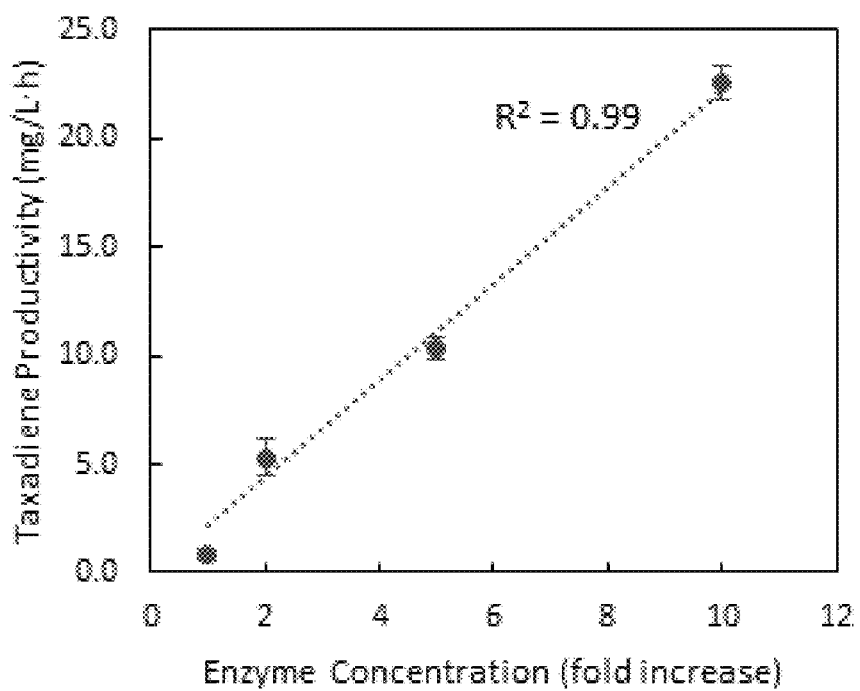

By combining the insights gathered from the preceding experiments, an optimized system using the optimized enzyme ratios, with IDI, as well as the appropriate ATP/ADP and salt concentrations was set up (See materials and methods for optimized ratio of enzymes and process parameters). To see if the flux was linearly scalable for the optimized enzyme system, the optimized ratio of enzyme was resuspended at 1, 2, 5, or 10 fold. The results are shown in FIG. 29. It was observed that that, under the conditions studied, the overall flux could be increased by increasing the amount of enzymes, and the in vitro IUP system was able to produce 220 mg/L of taxadiene in in 9 h which is a rate of approximately 24.4 mg/L·h, or a 2.9 fold increase over the highest reported in vivo system, which produced taxadiene at a rate of 8.5 mg/L·h (Ajikumar et al., 2010). Sixty-five percent of the available ATP was converted to taxadiene. The results and techniques used in this optimization study will be important in future studies of this simple in vitro isoprenoid production process and for future studies on the immobilization of this enzyme system.

Example 15—Perspective

Results show that a cyclic diterpenoid like taxadiene can be produced in vitro from the low cost feedstock isoprenol and/or prenol with as little as 5 enzymatic steps using the disclosed synthetic isoprenoid pathway. This system has several major advantages over in vivo isoprenoid production as there is no competition for flux to support biological functions, it uses an easily available low cost substrate is used (isoprenol), has simple enzyme kinetics, and it can be easily adapted to make any terpene if an active enzyme can be generated. This makes this system a powerful tool for the study of isoprenoid biosynthesis and the characterization of new terpene synthases, as well as a promising commercial method for the production of high value isoprenoids. Another major advantage for commercial synthesis is the ease of isoprenoid purification using this system which is often one of the major costs of a bioprocess. This may be particularly useful for synthesizing high purity reference standards for quantification purposes. Some limiting factors were identified, particularly that a robust ATP recycling system will be needed for diterpenoid production as high concentrations of ATP either precipitated proteins or inhibited the pathway. Using the IUP greatly simplified the pathway kinetics, however, diterpenes require 8 moles of ATP to synthesize a single molecule, meaning that at the 10 mM (disodium salt) concentration used in this study, the theoretical maximum taxadiene concentration attainable is only 340 mg/L. In order to achieve titers in the grams per liter range, an ATP regeneration system will have to be implemented. The economic viability of an in vitro IUP biotransformation process will be highly dependent on the cost of enzyme purification, the long-term stability of the enzymes and their possible immobilization, the recycling of ATP and unused isoprenol/prenol, and the costs of product recovery which should be pursued directly as the next steps in this line of investigation.

REFERENCES

Ajikumar P K, Xiao W H, Tyo K E J, Wang Y, Simeon F, Leonard E, Mucha O, Phon T H, Pfeifer B, Stephanopoulos G. 2010. Isoprenoid pathway optimization for Taxol precursor overproduction in *Escherichia coli*. *Science*. 330:70-74.

Alonso-Gutierrez J, Chan R, Batth T S, Adams P D, Keasling J D, Petzold C J, Lee T S. 2013. Metabolic engineering of *Escherichia coli* for limonene and perillyl alcohol production. *Metab. Eng.* 19:33-41.

Andexer J N, Richter M. 2015. Emerging enzymes for ATP regeneration in biocatalytic processes. *ChemBioChem* 16:380-386.

Boronat A, Rodriguex-Concepcion M. 2015. Terpenoid Biosynthesis in Prokaryotes. *Adv. Biochem. Eng. Biotechnol.* 148:3-18.

Chatzivasileiou A O, Ward V, Edgar S, Stephanopoulos G. 2018. A novel two-step pathway for isoprenoid synthesis. *Proc. Nat. Acad. Sci.* 116:506-511.

Chen X, Zhang C, Zou R, Stephanopoulos G, Too H P. 2017. In Vitro Metabolic Engineering of Amorpha-4,11-diene Biosynthesis at Enhanced Rate and Specific Yield of Production. *ACS Synth. Biol.* 6:1691-1700.

Chen Y, Zhou Y J, Siewers V, Nielsen J. 2015. Enabling Technologies to Advance Microbial Isoprenoid Production. *Adv. Biochem. Eng. Biotechnol.* 148:143-160.

Galloway D A, Laimins L A, Division B, Hutchinson F. 2015. In Vitro Reconstitution of Metabolic Pathways: Insights into Nature's Chemical Logic. *Synlett* 26:87-92.

George K W, Thompson M, Kim J, Baidoo E E K, Wang G, Benites V T, Petzold C J, Chan L J G, Yilmaz S, Turhanen P, Adams P D, Keasling J D, Lee T S. 2018. Integrated analysis of isopentenyl pyrophosphate (IPP) toxicity in isoprenoid-producing *Escherichia coli*. *Metab. Eng.* 47:60-72.

Guo W, Sheng J, Feng X. 2017. Mini-review: In vitro Metabolic Engineering for Biomanufacturing of High-value Products. *Comput. Struct. Biotechnol. J.* 15:161-167.

Hahn F M, Hurlburt A P, Poulter C D. 1999. *Escherichia coli* Open Reading Frame 696 Is idi, a Nonessential Gene Encoding Isopentenyl Diphosphate Isomerase. *J. Bacteriol.* 181:4499-4504.

Hefner J, Ketchum R E B, Croteau R. 1998. Cloning and functional expression of a cDNA encoding geranylgeranyl diphosphate synthase *Taxus canadensis* and assessment of the role of this prenyltransferase in cells induced for Taxol production. *Arch. Biochem. Biophys.* 360:62-74.

Korman T P, Opgenorth P H, Bowie J U. 2017. A synthetic biochemistry platform for cell free production of monoterpenes from glucose. *Nat. Commun.* 8:1-8.

Ku B, Jeong J C, Mijts B N, Schmidt-Dannert C, Dordick J S. 2005. Preparation, characterization, and optimization of an in vitro C30 carotenoid pathway. *Appl Env. Microbiol* 71:6578-6583.

Lima-ramos J, Nordblad M, Woodley J M. 2011. Guidelines and Cost Analysis for Catalyst Production in Biocatalytic Processes Pa Abstract: 15:266-274.

Malhotra K, Subramaniyan M, Rawat K, Kalamuddin M, Qureshi M I, Malhotra P, Mohmmed A, Cornish K, Daniell H, Kumar S. 2016. Compartmentalized Metabolic Engineering for Artemisinin Biosynthesis and Effective Malaria Treatment by Oral Delivery of Plant Cells. *Mol. Plant* 9:1464-1477.

Martin V J J, Pitera D J, Withers S T, Newman J D, Keasling J D. 2003. Engineering a mevalonate pathway in *Escherichia coli* for production of terpenoids. *Nat. Biotechnol.* 21:796-802.

Meadows A L, Hawkins K M, Tsegaye Y, Antipov E, Kim Y, Raetz L, Dahl R H, Tai A, Mahatdejkul-Meadows T, Xu L, Zhao L, Dasika M S, Murarka A, Lenihan J, Eng D, Leng J S, Liu C L, Wenger J W, Jiang H, Chao L, Westfall P, Lai J, Ganesan S, Jackson P, Mans R, Platt D, Reeves C D, Saija P R, Wichmann G, Holmes V F, Benjamin K, Hill P W, Gardner T S, Tsong A E. 2016. Rewriting yeast central carbon metabolism for industrial isoprenoid production. *Nature* 537:694-697. dx.doi.org/10.1038/nature19769.

Vickers C E, Bongers M, Liu Q, Delatte T, Bouwmeester H. 2014. Metabolic engineering of volatile isoprenoids in plants and microbes. *Plant, Cell Environ.* 37:1753-1775.

Vickers C E, Sabri S. 2015. Isoprene. *Adv Biochem Eng Biotechnol* 148:289-317.

Ward V C A, Chatzivasileiou A O, Stephanopoulos G. 2018. Metabolic engineering of *Escherichia coli* for the production of isoprenoids. *FEMS Microbiol. Lett.* 365:fny079.

Weaver L J, Sousa M M L, Wang G, Baidoo E, Petzold C J, Keasling J D. 2015. A kinetic-based approach to understanding heterologous mevalonate pathway function in *E. coli*. *Biotechnol. Bioeng.* 112:111-119.

Wu L, Wang W, Winden W a Van, Gulik W M Van, Heijnen J J. 2004. A new framework for the estimation of control parameters in metabolic pathways using lin-log kinetics. *Eur. J. Biochem.* 271:3348-3359.

Yang G, Sau C, Lai W, Cichon J, Li W. 2015. Distributing a metabolic pathway among a microbial consortium enhances production of natural products. *Nat Biotechnol.* 33(4):377-383.

Zhang Y H P. 2011. Simpler is better: High-yield and potential low-cost biofuels production through cell-free synthetic pathway biotransformation (SyPaB). *ACS Catal.* 1:998-1009.

Zhu F, Zhong X, Hu M, Lu L, Deng Z, Liu T. 2014. In vitro reconstitution of mevalonate pathway and targeted engineering of farnesene overproduction in *Escherichia coli*. *Biotechnol. Bioeng.* 111:1396-1405.

TABLE 7

Plasmids used in this study. Bolded genes were used as templates for cloning.

| Name | Description | Ref |
|---|---|---|
| pET28a | pBR322, KnR, PT7lacUV | Novagen |
| pSEVA228pro4IUP | RK2, KnR, Ppro4, ck, ipk, idi | [1] |
| p5T7tds-ggpps | pSC101, Sp$^R$, P$_{T7lacUV}$, tds, ggpps | [2] |
| pADS | pTrc99A derivative containing the ads gene; Ap$^R$ | [3] |
| JBEI-6409 | p15A, Cm$^R$, P$_{lacUV5}$, atoB, hmgs, hmgr, , P$_{lacUV5}$, mvk pmk, pmd, idi, P$_{trc}$, tr-gpps, ls | [4] |
| p5T7vs-ispA | pSC101, Sp$^R$, P$_{T7lacUV}$, vs, ispA | [5] |

TABLE 8

Primers used in this study

| Anneals | SEQ ID NO | Sequence |
|---|---|---|
| pET28a | 99 | CACCACCACCACCACCACTGAGATCCGGCTGCTAAC CGGTATATCTCCTTCTTAAAGTTAAACAAAATTATT TC |
| CK | 100 | TTTAAGAAGGAGATATACCGATGGTGCAGGAGTCCC GCTTGTTAGCAGCCGGATCTCAGTGGTGGTGGTGGT GGTGCAGGTAGCTGGTGTCGAGG |
| IPK | 101 | AAGAAGGAGATATACCGATGGAACTCAATATCAGCG GTTAGCAGCCGGATCTCAGTGGTGGTGGTGGTGGTG TTTGCTGAAGCGGATGATG |
| IDI | 102 | AAGAAGGAGATATACCGATGCAAACGGAACACGTCG TTAGCAGCCGGATCTCAGTGGTGGTGGTGGTGGTGT TAAGCTGGGTAAATGCAG |
| IspA | 103 | AAGAAGGAGATATACCGATGGACTTTCCGCAGCAAC GTTAGCAGCCGGATCTCAGTGGTGGTGGTGGTGGTG TTTATTACGCTGGATGATGTAGTC |
| GGPPS | 104 | AAGAAGGAGATATACCGATGTTCGACTTCAACGAGG TTAGCAGCCGGATCTCAGTGGTGGTGGTGGTGGTGG TTTTGACGAAAGGCAATATAATC |
| TDS | 105 | AAGAAGGAGATATACCGATGTCTAGCTCTACGGGTA |

TABLE 6

Michaelis-Menten kinetic parameters determined for the enzymes encompassing the IUP, terpenoid backbone synthesis pathway, and taxadiene synthase

| Enzyme | Origin | Substrate(s) | $k_{cat}$ (S$^{-1}$) | $K_m$ (μM) | Ref |
|---|---|---|---|---|---|
| Choline kinase (CK) | *S. cerevisiae* | Isoprenol | 14.7 | 4538 | (Chatzivasileiou et al., 2018) |
|  |  | Prenol | 1.13 | 1114 |  |
| Isopentenyl pyrophosphate kinase (IPK) | *A. thaliana* | IP | 45.5 | 21.7 | This study |
|  |  | DMAP | 53.1 | 35.5 |  |
|  |  | ATP | — | 43.5 |  |
| Isopentenyl delta isomerase (IDI) | *E. coli* | IPP/DMAPP | 0.33 | 7.9 | (Hahn et al., 1999; Weaver et al., 2015) |
| Farnesyl pyrophosphate synthase (IspA) | *E. coil* | IPP + DMAPP | 0.21 | DMAPP, 1.3 | (Ku et al., 2005; Weaver et al., 2015) |
|  |  |  |  | IPP, 29.3 |  |
|  |  | IPP +GPP | 0.47 | GPP, 10.3 |  |
|  |  |  |  | IPP, 5.5 |  |
| Geranylgeranyl pyrophosphate synthase (GGPPS) | *T. canadensis* | IPP +FPP | 26.7 | IPP, 13.5 FPP < 1 | This study |
| Taxadiene Synthase (TDS) | *T. brevolia* | GGPP | 23.1 | 43.0 | This study |

TABLE 8-continued

Primers used in this study

| Anneals | SEQ ID NO | Sequence |
|---|---|---|
| | | CGTTAGCAGCCGGATCTCAGTGGTGGTGGTGGTGGT GGACCTGGATTGGATCGATG |
| VS | 106 | AAGAAGGAGATATACCGATGGCCGAGATGTTCAACG GTTAGCAGCCGGATCTCAGTGGTGGTGGTGGTGGTG GGGGATGATGGGCTCGAC |
| LS | 107 | AAGAAGGAGATATACCGATGCGTCGCAGTGGTAATT ACGTTAGCAGCCGGATCTCAGTGGTGGTGGTGGTGG TGGGCGAAAGGTGCAAACAG |
| ADS | 108 | AAGAAGGAGATATACCGATGGCCCTGACCGAAGAGG TTAGCAGCCGGATCTCAGTGGTGGTGGTGGTGGTGG ATGGACATCGGGTAAACC |

TABLE 9

Full data set of perturbation experiments after 1 h incubation at 30° C., pH 7.4 with 5 mM isoprenol and 10 mM ATP.

| | Enzyme Concentration (µg/mL) | | | | | Metabolite Concentration (µM) | | | | Flux (µM/h) |
|---|---|---|---|---|---|---|---|---|---|---|
| Run | CK | IPK | IDI | ISPA | GGPPS | IP | IPP/DMAPP | GPP | FPP | GGPP |
| 1 | 5.0 | 15.0 | 25.4 | 37.2 | 8.2 | 0.03 ± 0.01 | 0.37 ± 0.15 | 0.24 ± 0.07 | 0.15 ± 0.09 | 4.77 ± 2.97 |
| 2 | 12.5 | 15.0 | 25.4 | 37.2 | 8.2 | 0.11 ± 0.02 | 0.62 ± 0.28 | 0.47 ± 0.16 | 0.26 ± 0.20 | 7.23 ± 1.18 |
| 3 | 25.0 | 15.0 | 25.4 | 37.2 | 8.2 | 0.21 ± 0.05 | 0.82 ± 0.21 | 0.48 ± 0.13 | 0.57 ± 0.59 | 9.48 ± 3.80 |
| 4 | 50.0 | 15.0 | 25.4 | 37.2 | 8.2 | 0.98 ± 0.04 | 1.36 ± 0.43 | 1.03 ± 0.09 | 0.99 ± 0.30 | 9.32 ± 1.87 |
| 5 | 125.0 | 15.0 | 25.4 | 37.2 | 8.2 | 7.82 ± 0.00 | 0.98 ± 0.50 | 0.76 ± 0.18 | 1.25 ± 0.74 | 9.95 ± 2.37 |
| 6 | 25.0 | 3.0 | 25.4 | 37.2 | 8.2 | 1.58 ± 0.24 | 0.36 ± 0.21 | 0.23 ± 0.16 | 0.17 ± 0.16 | 4.58 ± 2.77 |
| 7 | 25.0 | 7.5 | 25.4 | 37.2 | 8.2 | 0.34 ± 0.20 | 0.83 ± 0.53 | 0.28 ± 0.19 | 0.64 ± 0.42 | 8.93 ± 1.39 |
| 8 | 25.0 | 15.0 | 25.4 | 37.2 | 8.2 | 0.09 ± 0.07 | 0.70 ± 0.43 | 0.28 ± 0.26 | 0.86 ± 0.42 | 9.89 ± 2.91 |
| 9 | 25.0 | 30.0 | 25.4 | 37.2 | 8.2 | 0.04 ± 0.00 | 1.12 ± 0.01 | 0.73 ± 0.04 | 0.42 ± 0.12 | 8.30 ± 1.29 |
| 10 | 25.0 | 75.0 | 25.4 | 37.2 | 8.2 | 0.03 ± 0.00 | 0.89 ± 0.15 | 0.62 ± 0.08 | 0.26 ± 0.24 | 7.39 ± 1.13 |
| 11 | 25.0 | 15.0 | 5.1 | 37.2 | 8.2 | 0.20 ± 0.10 | 0.42 ± 0.12 | 0.01 ± 0.01 | 0.50 ± 0.36 | 5.26 ± 2.62 |
| 12 | 25.0 | 15.0 | 12.7 | 37.2 | 8.2 | 0.20 ± 0.04 | 0.47 ± 0.23 | 0.32 ± 0.19 | 0.37 ± 0.29 | 8.05 ± 1.26 |
| 13 | 25.0 | 15.0 | 25.4 | 37.2 | 8.2 | 0.18 ± 0.02 | 0.56 ± 0.14 | 0.45 ± 0.14 | 0.26 ± 0.19 | 7.55 ± 1.17 |
| 14 | 25.0 | 15.0 | 50.8 | 37.2 | 8.2 | 0.19 ± 0.01 | 0.92 ± 0.26 | 0.75 ± 0.11 | 0.61 ± 0.16 | 8.51 ± 1.10 |
| 15 | 25.0 | 15.0 | 127.0 | 37.2 | 8.2 | 0.16 ± 0.10 | 0.48 ± 0.06 | 0.39 ± 0.31 | 0.57 ± 0.36 | 8.20 ± 1.37 |
| 16 | 25.0 | 15.0 | 25.4 | 7.4 | 8.2 | 0.20 ± 0.06 | 2.05 ± 0.42 | 1.00 ± 0.28 | 0.46 ± 0.25 | 5.12 ± 2.97 |
| 17 | 25.0 | 15.0 | 25.4 | 18.6 | 8.2 | 0.15 ± 0.03 | 1.03 ± 0.13 | 0.55 ± 0.10 | 0.35 ± 0.18 | 7.47 ± 0.79 |
| 18 | 25.0 | 15.0 | 25.4 | 37.2 | 8.2 | 0.13 ± 0.02 | 0.71 ± 0.20 | 0.45 ± 0.14 | 0.34 ± 0.20 | 7.27 ± 0.90 |
| 19 | 25.0 | 15.0 | 25.4 | 74.3 | 8.2 | 0.12 ± 0.00 | 0.34 ± 0.07 | 0.16 ± 0.11 | 0.98 ± 0.75 | 10.14 ± 2.85 |
| 20 | 25.0 | 15.0 | 25.4 | 185.8 | 8.2 | 0.10 ± 0.02 | 0.23 ± 0.04 | 0.09 ± 0.07 | 1.15 ± 1.09 | 10.13 ± 3.86 |
| 21 | 25.0 | 15.0 | 25.4 | 37.2 | 1.6 | 0.22 ± 0.06 | 1.13 ± 0.50 | 0.77 ± 0.26 | 1.66 ± 0.55 | 7.86 ± 2.00 |
| 22 | 25.0 | 15.0 | 25.4 | 37.2 | 4.1 | 0.16 ± 0.09 | 0.53 ± 0.31 | 0.37 ± 0.21 | 0.44 ± 0.29 | 7.73 ± 1.24 |
| 23 | 25.0 | 15.0 | 25.4 | 37.2 | 8.2 | 0.13 ± 0.29 | 0.47 ± 0.04 | 0.28 ± 0.18 | 0.09 ± 0.07 | 7.07 ± 0.74 |
| 24 | 25.0 | 15.0 | 25.4 | 37.2 | 16.3 | 0.17 ± 0.01 | 0.75 ± 0.26 | 0.67 ± 0.09 | 0.42 ± 0.08 | 8.60 ± 1.61 |
| 25 | 25.0 | 15.0 | 25.4 | 37.2 | 40.8 | 0.13 ± 0.00 | 0.38 ± 0.00 | 0.50 ± 0.05 | 0.22 ± 0.03 | 7.53 ± 1.01 |

Example 16—Differential Equations

Figure 24:
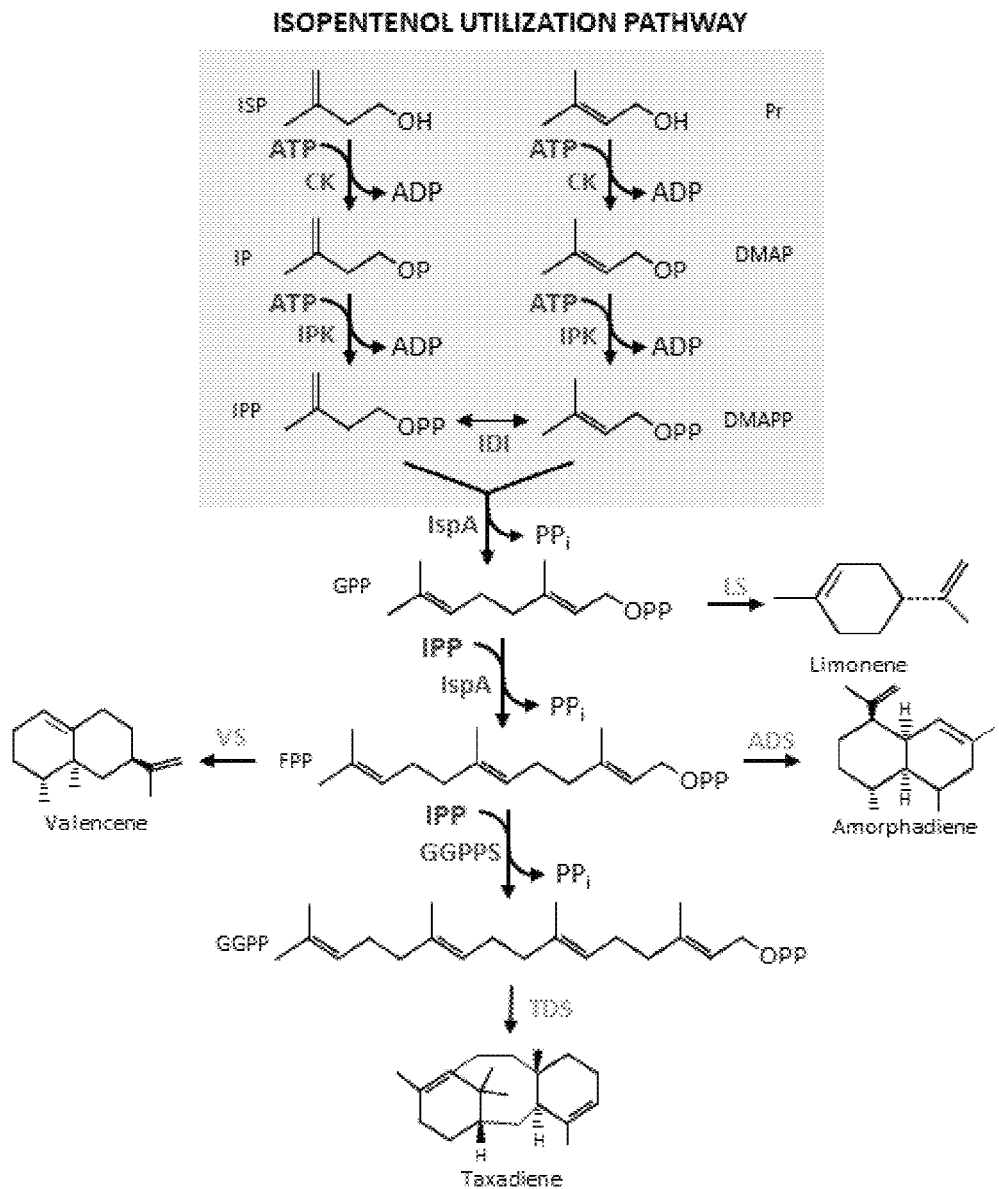
FIG. 24. Reaction scheme for the synthesis pathway for taxadiene, valencene, amorphadiene, and limonene starting from isoprenol or prenol. The box indicates the enzymes of the IUP. Enzymes involved in the IUP include choline kinase (CK), isopentenyl phosphate kinase (IPK), and isopentenyl pyrophosphate isomerase (IDI). Enzymes from the terpenoid backbone biosynthesis pathway used in this work include farnesyl pyrophosphate synthase (IspA), and geranylgeranyl pyrophosphate synthase (GGPPS). Terpene synthases used in this work include limonene synthase (LS), valencene synthase (VS), amorphadiene synthase (ADS), and taxadiene synthase (TDS). Metabolites structures include: isoprenol (ISP), prenol (Pr), adenosine triphosphate (ATP), adenosine diphosphate (ADP), isoprenyl phosphate (IP), dimethylallyl phosphate (DMAP), isoprenyl pyrophosphate (IPP), dimethylallyl pyrophosphate (DMAPP), geranyl pyrophosphate (GPP), farnesyl pyrophosphate (FPP), and geranylgeranyl pyrophosphate (GGPP).

The following equations (1-9) were derived using convenience rate laws for the IUP pathway (FIG. 24). Reactions were based on the BRENDA entries for each enzyme used in this work. Where possible, the kinetic coefficients determined in this study were used, otherwise they were sourced from the literature.

Rate Law for Choline Kinase (CK):

$$\frac{k_{cat}[CK_0]\frac{[ISP]}{K_{M,ISP}}\frac{[ATP]}{K_{M,ATP}}}{\left(1+\frac{[ISP]}{K_{M,ISP}}\right)\left(1+\frac{[ATP]}{K_{M,ATP}}\right)-1} \quad (1)$$

CK Rate Laws when Both Isoprenol and Prenol are Present:

$$\frac{k_{cat}[CK_0]\frac{[ISP]}{K_{M,ISP}}\frac{[ATP]}{K_{M,ATP}}}{\left(1+\frac{[ISP]}{K_{M,ISP}}\right)\left(1+\frac{[ATP]}{K_{M,ATP}}\right)-1}\left(\frac{K_i}{K_i+[Pr]}\right) \quad (1a)$$

$$\frac{k_{cat}[CK_0]\frac{[Pr]}{K_{M,Pr}}\frac{[ATP]}{K_{M,ATP}}}{\left(1+\frac{[ISP]}{K_{M,ISP}}\right)\left(1+\frac{[ATP]}{K_{M,ATP}}\right)-1}\left(\frac{K_i}{K_i}+[ISP]\right) \quad (1b)$$

Rate Law for Isopentenyl Kinase (IPK):

$$\frac{k_{cat}[IPK_0]\frac{[IP]}{K_{M,IP}}\frac{[ATP]}{K_{M,ATP}}}{\left(1+\frac{[IP]}{K_{M,IP}}\right)\left(1+\frac{[ATP]}{K_{M,ATP}}\right)-1} \quad (2)$$

IPK Rate Laws when Both IP and DMAP are Present:

$$\frac{k_{cat}[IPK_0]\frac{[IP]}{K_{M,IP}}\frac{[ATP]}{K_{M,ATP}}}{\left(1+\frac{[IP]}{K_{M,IP}}\right)\left(1+\frac{[ATP]}{K_{M,ATP}}\right)-1}\left(\frac{K_i}{K_i+[DMAP]}\right) \quad (2a)$$

-continued $$\frac{k_{cat}[IPK_0]\frac{[DMAP]}{K_{M,DMAP}}\frac{[ATP]}{K_{M,ATP}}}{\left(1+\frac{[DMAP]}{K_{M,DMAP}}\right)\left(1+\frac{[ATP]}{K_{M,ATP}}\right)-1}\left(\frac{K_i}{K_i+[IP]}\right) \quad (2b)$$

Rate Law for Isopentenyl Delta Isomerase (IDI):

$$\frac{k_{cat}^f[IDI_0]\frac{[IPP]}{K_{M,IPP}}-k_{cat}^r[IDI_0]\frac{[DMAPP]}{K_{M,DMAPP}}}{\left(1+\frac{[IP]}{K_{M,IP}}\right)\left(1+\frac{[ATP]}{K_{M,ATP}}\right)-1} \quad (3)$$

Rate Laws for Farnesyl Pyrophosphate Synthase (IspA):

$$\frac{k_{cat}[IspA_0]\frac{[IPP]}{K_{M,IPP}}\frac{[DMAPP]}{K_{M,DMAPP}}}{\left(1+\frac{[IPP]}{K_{M,IPP}}\right)\left(1+\frac{[DMAPP]}{K_{M,DMAPP}}\right)-1}\left(\frac{K_i}{K_i+[GPP]}\right) \quad (4)$$

$$\frac{k_{cat}[IspA_0]\frac{[IPP]}{K_{M,IPP}}\frac{[GPP]}{K_{M,GPP}}}{\left(1+\frac{[IPP]}{K_{M,IPP}}\right)\left(1+\frac{[GPP]}{K_{M,GPP}}\right)-1}\left(\frac{K_i}{K_i+[DMAPP]}\right) \quad (5)$$

Rate Laws for Geranylgeranylpyrophosphate Synthase (GGPPS):

$$\frac{k_{cat}[GGPPS_0]\frac{[FPP]}{K_{M,FPP}}\frac{[IPP]}{K_{MIPP}}}{\left(1+\frac{[FPP]}{K_{M,FPP}}\right)\left(1+\frac{[IPP]}{K_{M,IPP}}\right)-1} \quad (6)$$

$$\left(\frac{K_{i,GPP}}{K_{i,GPP}+[GPP]}\right)\left(\frac{K_{i,DMAPP}}{K_{i,DMAPP}+[DMAPP]}\right)$$

$$\frac{k_{cat}[GGPPS_0]\frac{[GPP]}{K_{M,GPP}}\left(\frac{[IPP]}{K_{M,IPP}}\right)^2}{\left(1+\frac{[GPP]}{K_{M,GPP}}\right)\left(1+\frac{[IPP]}{K_{M,IPP}}+\left(\frac{[IPP]}{K_{M,IPP}}\right)^2\right)-1} \quad (7)$$

$$\left(\frac{K_{i,FPP}}{K_{i,FPP}+[FPP]}\right)\left(\frac{K_{i,DMAPP}}{K_{i,DMAPP}+[DMAPP]}\right)$$

$$\frac{k_{cat}[GGPPS_0]\frac{[DMAPP]}{K_{M,DMAPP}}\left(\frac{[IPP]}{K_{M,IPP}}\right)^3}{\left(1+\frac{[DMAPP]}{K_{M,DMAPP}}\right)\left(1+\frac{[IPP]}{K_{M,IPP}}+\left(\frac{[IPP]}{K_{M,IPP}}\right)^2+\left(\frac{[IPP]}{K_{M,IPP}}\right)^3\right)-1} \quad (8)$$

$$\left(\frac{K_i}{K_i+[FPP]}\right)\left(\frac{K_i}{K_i+[GPP]}\right)$$

Rate Law for Taxadiene Synthase (TDS):

$$\frac{k_{cat}[TDS_0]\frac{[GGPP]}{K_{M,GGPP}}}{1+\frac{[GGPP]}{K_{M,GGPP}}} \quad (9)$$

REFERENCES

[1] A. O. Chatzivasileiou, V. Ward, S. Edgar, G. Stephanopoulos, A novel two-step pathway for isoprenoid synthesis, Revis. n.a (2018).
[2] P. K. Ajikumar, W. H. Xiao, K. E. J. Tyo, Y. Wang, F. Simeon, E. Leonard, O. Mucha, T. H. Phon, B. Pfeifer, G. Stephanopoulos, Isoprenoid pathway optimization for Taxol precursor overproduction in Escherichia coli, Science (80-. ). 330 (2010) 70-74. doi:10.1126/science.1191652.
[3] V. J. J. Martin, D. J. Pitera, S. T. Withers, J. D. Newman, J. D. Keasling, Engineering a mevalonate pathway in Escherichia coli for production of terpenoids, Nat. Biotechnol. 21 (2003) 796-802. doi:10.1038/nbt833.
[4] J. Alonso-Gutierrez, R. Chan, T. S. Batth, P. D. Adams, J. D. Keasling, C. J. Petzold, T. S. Lee, Metabolic engineering of Escherichia coli for limonene and perillyl alcohol production, Metab. Eng. 19 (2013) 33-41. doi:10.1016/j.ymben.2013.05.004.
[5] G. Yang, C. Sau, W. Lai, J. Cichon, W. Li, Distributing a metabolic pathway among a microbial consortium enhances production of natural products, Nat Biotechnol. 33(4) (2015) 377-383. doi:10.1126/science.1249098.Sleep.

Enzyme Sequences

The amino acid sequence of choline kinase is well known to one of ordinary skill in the art. An exemplary, representative amino acid sequence of choline kinase includes:

Amino acid sequence of Saccharomyces cerevisiae
choline kinase
GenBank: AAA34499.1
(SEQ ID NO: 96)
MVQESRPGSV RSYSVGYQAR SRSSSQRRHS LTRQRSSQRL

IRTISIESDV SNITDDDDLR AVNEGVAGVQ LDVSETANKG

PRRASATDVT DSLGSTSSEY IEIPFVKETL DASLPSDYLK

QDILNLIQSL KISKWYNNKK IQPVAQDMNL VKISGAMTNA

IFKVEYPKLP SLLLRIYGPN IDNIIDREYE LQILARLSLK

NIGPSLYGCF VNGRFEQFLE NSKTLTKDDI RNWKNSQRIA

RRMKELHVGV PLLSSERKNG SACWQKINQW LRTIEKVDQW

VGDPKNIENS LLCENWSKFM DIVDRYHKWL ISQEQGIEQV

NKNLIFCHND AQYGNLLFTA PVMNTPSLYT APSSTSLTSQ

SSSLFPSSSN VIVDDIINPP KQEQSQDSKL VVIDFEYAGA

NPAAYDLANH LSEWMYDYNN AKAPHQCHAD RYPDKEQVLN

FLYSYVSHLR GGAKEPIDEE VQRLYKSIIQ WRPTVQLFWS

LWAILQSGKL EKKEASTAIT REEIGPNGKK YIIKTEPESP

EEDFVENDDE PEAGVSIDTF DYMAYGRDKI AVFWGDLIGL

GIITEEECKN FSSFKFLDTS YL

The amino acid sequence of choline kinase from other species can be readily identified by one of ordinary skill in the art with tools available in the art, such as Basic Local Alignment Search Tool (BLAST), are also contemplated herein. Information on additional choline kinase isoforms is available in the art (see e.g., Aoyama et al., *Prog Lipid Res* (2004) 43(3):266-81, which is incorporated herein by reference in its entirety).

The amino acid sequence of isopentenyl phosphate kinase is well known to one of ordinary skill in the art. An exemplary, representative amino acid sequence of isopentenyl phosphate kinase includes:

```
Amino acid sequence of Arabidopsis thaliana
isopentenyl phosphate kinase
GenBank: AAN12957.1
                                        (SEQ ID NO: 97)
MELNISESRS RSIRCIVKLG GAAITCKNEL EKIHDENLEV

VACQLRQAML EGSAPSKVIG MDWSKRPGSS EISCDVDDIG

DQKSSEFSKF VVVHGAGSFG HFQASRSGVH KGGLEKPIVK

AGFVATRISV TNLNLEIVRA LAREGIPTIG MSPFSCGWST

SKRDVASADL ATVAKTIDSG FVPVLHGDAV LDNILGCTIL

SGDVIIRHLA DHLKPEYVVF LTDVLGVYDR PPSPSEPDAV

LLKEIAVGED GSWKVVNPLL EHTDKKVDYS VAAHDTTGGM

ETKISEAAMI AKLGVDVYIV KAATTHSQRA LNGDLRDSVP

EDWLGTIIRF SK
```

The amino acid sequence of isopentenyl phosphate kinase from other species can be readily identified by one of ordinary skill in the art with tools available in the art, such as Basic Local Alignment Search Tool (BLAST), are also contemplated herein. Also, information on additional isopentenyl phosphate kinases is available in the art (see e.g., Henry et al., *Proc Natl Acad Sci USA* (2015)112(32):10050-5, which is incorporated herein by reference in its entirety).

The amino acid sequence of isopentenyl pyrophosphate isomerase is well known to one of ordinary skill in the art. An exemplary, representative amino acid sequence of isopentenyl pyrophosphate isomerase includes:

```
Amino acid sequence of Escherichia coli
isopentenyl pyrophosphate isomerase
GenBank: AAD26812.1
                                        (SEQ ID NO: 98)
MQTEHVILLN AQGVPTGTLE KYAAHTADTR LHLAFSSWLF

NAKGQLLVTR RALSKKAWPG VWTNSVCGHP QLGESNEDAV

IRRCRYELGV EITPPESIYP DFRYRATDPS GIVENEVCPV

FAARTTSALQ INDDEVMDYQ WCDLADVLHG IDATPWAFSP

WMVMQATNRE ARKRLSAFTQ LK
```

The amino acid sequence of isopentenyl pyrophosphate isomerase from other species can be readily identified by one of ordinary skill in the art with tools available in the art, such as Basic Local Alignment Search Tool (BLAST), are also contemplated herein. Also, information on additional isopentenyl pyrophosphate isomerases is available in the art (see e.g., Kajiwara et al., *Biochem J* (1997) 324(Pt 2): 421-6, which is incorporated herein by reference in its entirety).

The amino acid sequence of farnesyl pyrophosphate synthase is well known to one or ordinary skill in the art. An exemplary, representative amino acid sequence of farnesyl pyrophosphate synthase includes:

```
Amino acid sequence of (2E,6E)-farnesyl
diphosphate synthase from Escherichia coli
GenBank: WP_097750737.1
                                        (SEQ ID NO: 109)
MDFPQQLEAC VKQANQALSR FIAPLPFQNT PVVETMQYGA

LLGGKRLRPF LVYATGHMFG VSTNTLDAPA AAVECIHAYS

LIHDDLPAMD DDDLRRGLPT CHVKFGEANA ILAGDALQTL

AFSILSDADM PEVSDRDRIS MISELASASG IAGMCGGQAL

DLDAEGKHVP LDALERIHRH KTGALIRAAV RLGALSAGDK

GRRALPVLDK YAESIGLAFQ VQDDILDVVG DTATLGKRQG

ADQQLGKSTY PALLGLEQAR KKARELIDDA RQSLKQLAEQ

SLDTSALEAL ADYIIQRNK
```

The amino acid sequence of farnesyl pyrophosphate synthase from other species can be readily identified by one of ordinary skill in the art with tools available in the art, such as Basic Local Alignment Search Tool (BLAST), and are also contemplated herein. Information on additional farnesyl pyrophosphate synthase isoforms is available in the art (see, e.g., NCBI Accession No. WP_128881036 (*Shigella dysenteriae*) at ncbi.nlm.nih.gov/protein/WP_128881036.1; NCBI Accession No. WP_095785303 (*Shigella boydii*) at ncbi.nlm.nih.gov/protein/WP_095785303.1; Gabelli, et al., *Proteins* (2006) 62(1):80-8 (*Trypanosoma cruzi*), and KEGG Enzyme EC 2.5.1.10 at genome.jp/dbget-bin/www_bget?ec:2.5.1.10; which are incorporated herein by reference in their entirety).

In some embodiments, the farnesyl pyrophosphate synthase is at least 55%, at least 60%, at least 65%, at least 70%, at least 75%, at least 76%, at least 77%, at least 70%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence of SEQ ID NO: 109. In some embodiments, the recombinant enzyme is at least 50% identical to the amino acid sequence of SEQ ID NO: 109.

In some embodiments, the farnesyl pyrophosphate synthase is a mutant farnesyl pyrophosphate synthase comprising one or more amino acid modifications that increase productivity for synthesis of IPP and DMAPP from IP and DMAP relative to a control cell in which farnesyl pyrophosphate synthase is not mutated, or relative to a corresponding wildtype cell. In some embodiments, the mutant farnesyl pyrophosphate synthase comprises from 1 to about 20 or from 1 to about 10 amino acid modifications with respect to SEQ ID NO: 109. In some embodiments, the farnesyl pyrophosphate synthase comprises from 1 to 5 amino acid modifications with respect to SEQ ID NO: 109. In some embodiments, the mutant farnesyl pyrophosphate synthase comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 35, 40, 45, 50, or more than 50 amino acid modifications with respect to the amino acid sequence of SEQ ID NO: 109. In some embodiments, the farnesyl pyrophosphate synthase comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 35, at least 40, or at least 45 amino acid modifications with respect to the amino acid sequence of SEQ ID NO: 109.

The amino acid sequence of geranylgeranyl pyrophosphate synthase is well known to one or ordinary skill in the art. An exemplary, representative amino acid sequence of farnesyl pyrophosphate synthase includes:

```
Amino acid sequence of geranylgeranyl diphosphate
synthase from Taxus canadensis
GenBank: AAD16018.1
                                        (SEQ ID NO: 110)
MAYTAMAAGT QSLQLRTVAS YQECNSMRSC FKLTPFKSFH

GVNFNVPSLG AANCEIMGHL KLGSLPYKQC SVSSKSTKTM

AQLVDLAETE KAEGKDIEFD FNEYMKSKAV AVDAALDKAI

PLEYPEKIHE SMRYSLLAGG KRVRPALCIA ACELVGGSQD

LAMPTACAME MIHTMSLIHD DLPCMDNDDF RRGKPTNHKV

FGEDTAVLAG DALLSFAFEH IAVATSKTVP SDRTLRVISE

LGKTIGSQGL VGGQVVDITS EGDANVDLKT LEWIHIHKTA

VLLECSVVSG GILGGATEDE IARIRRYARC VGLLFQVVDD

ILDVTKSSEE LGKTAGKDLL TDKATYPKLM GLEKAKEFAA

ELATRAKEEL SSFDQIKAAP LLGLADYIAF RQN
```

The amino acid sequence of geranylgeranyl pyrophosphate synthase from other species can be readily identified by one of ordinary skill in the art with tools available in the art, such as Basic Local Alignment Search Tool (BLAST), and are also contemplated herein. Information on additional farnesyl pyrophosphate synthase isoforms is available in the art (see, e.g., GenBank Accession No. ACA21461 (*Picea abies*) at ncbi.nlm.nih.gov/protein/ACA21461.1; GenBank Accession No. AAL17614.2 (*Abies grandis*) at ncbi.nlm.nih.gov/protein/AAL17614.2; GenBank Accession No. AGM53487 (*Cephalotaxus mannii*) at ncbi.nlm.nih.gov/protein/AGM53487.1; GenBank Accession No. AMX21442 (*Taxus chinensis*) at ncbi.nlm.nih.gov/protein/AMX21442.1; and GenBank Accession No. AAQ72786 (*Gingko biloba*) at ncbi.nlm.nih.gov/protein/AAQ72786.1, which are incorporated herein by reference in their entirety).

In some embodiments, the geranylgeranyl pyrophosphate synthase is at least 55%, at least 60%, at least 65%, at least 70%, at least 75%, at least 76%, at least 77%, at least 70%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence of SEQ ID NO: 110. In some embodiments, the geranylgeranyl pyrophosphate synthase is at least 50% identical to the amino acid sequence of SEQ ID NO: 110.

In some embodiments, the geranylgeranyl pyrophosphate synthase is a mutant geranylgeranyl pyrophosphate synthase comprising one or more amino acid modifications that increase productivity for synthesis of IPP and DMAPP from IP and DMAP relative to a control cell in which geranylgeranyl pyrophosphate synthase is not mutated, or relative to a corresponding wildtype cell. In some embodiments, the mutant geranylgeranyl pyrophosphate synthase comprises from 1 to about 20 or from 1 to about 10 amino acid modifications with respect to SEQ ID NO: 110. In some embodiments, the geranylgeranyl pyrophosphate synthase comprises from 1 to 5 amino acid modifications with respect to SEQ ID NO: 110. In some embodiments, the mutant geranylgeranyl pyrophosphate synthase comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 35, 40, 45, 50, or more than 50 amino acid modifications with respect to the amino acid sequence of SEQ ID NO: 110. In some embodiments, the geranylgeranyl pyrophosphate synthase comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 35, at least 40, or at least 45 amino acid modifications with respect to the amino acid sequence of SEQ ID NO: 110.

What is claimed is:

1. A host cell engineered to recombinantly express polynucleotides encoding Isopentenol Utilization Pathway (IUP) enzymes producing isoprenoid precursors isopentenyl diphosphate (IPP) and dimethylallyl diphosphate (DMAPP) from isoprenol and/or prenol, wherein the IUP enzymes comprise one or more heterologous enzymes, and the IUP enzymes comprise a *Saccharomyces cerevisiae* choline kinase, an isopentenyl phosphate kinase, and an isopentenyl pyrophosphate isomerase (IDI), and wherein when the host cell is *Saccharomyces cerevisiae*, the *Saccharomyces cerevisiae* host cell is transformed with an exogenous polynucleotide encoding the *Saccharomyces cerevisiae* choline kinase.

2. The host cell of claim 1, wherein the *S. cerevisiae* choline kinase is encoded by a nucleotide sequence having at least 90% sequence identity to the nucleotide sequence set forth in SEQ ID NO: 1.

3. The host cell of claim 1, wherein the isopentenyl phosphate kinase is an enzyme of *Haloferax volcanii, Methanothermobacter thermoautotrophicus, Methanocaldococcus janaschii, Arabidopsis thaliana*, or *Thermoplasma acidophilium*.

4. The host cell of claim 3, wherein the isopentenyl phosphate kinase is an enzyme of *Arabidopsis thaliana*.

5. The host cell of claim 1, wherein the IDI is from *Escherichia coli*.

6. The host cell of claim 1, wherein expression of the polynucleotides encoding the IUP enzymes is under the control of a constitutive promoter or a conditional promoter.

7. The host cell of claim 1, wherein the polynucleotides encoding the IUP enzymes are inserted on a plasmid.

8. The host cell of claim 1, wherein the polynucleotides encoding the IUP enzymes are integrated in the chromosome of the host cell.

9. The host cell of claim 1, wherein the host cell is capable of producing the IPP and/or the DMAPP from isoprenol or prenol.

10. The host cell of claim 1, wherein the host cell is a prokaryotic cell or a eukaryotic cell.

11. The host cell of claim 10 wherein the host cell is a fungal cell.

12. The host cell of claim 11, wherein the fungal cell is a yeast cell selected from the group consisting of *Saccharomyces* spp., *Schizosaccharomyces* spp., *Pichia* spp., *Paffia* spp., *Kluyveromyces* spp., *Candida* spp., *Talaromyces* spp.,

*Brettanomyces* spp., *Pachysolen* spp., *Debaryomyces* spp., *Yarrowia* spp., and an industrial polyploid yeast strain.

13. The host cell of claim 1 wherein the host cell is *Saccharomyces cerevisiae* or *Yarrowia lipolytica*.

14. The host cell of claim 1 further comprising an isoprenoid synthesis pathway that converts the IPP and/or the DMAPP to an isoprenoid product.

* * * * *